US006627746B1

(12) United States Patent
Doberstein et al.

(10) Patent No.: US 6,627,746 B1
(45) Date of Patent: Sep. 30, 2003

(54) NUCLEIC ACIDS AND PROTEINS OF *C. ELEGANS* INSULIN-LIKE GENES AND USES THEREOF

(75) Inventors: Stephen Kohl Doberstein, San Francisco, CA (US); Darren Mark Platt, San Francisco, CA (US); Kimberly Carr Ferguson, Pacifica, CA (US); Andrew Roy Buchman, Berkeley, CA (US); Sheila Akiko Homburger, Oakland, CA (US)

(73) Assignee: Exelixis, Inc., South San Francesco, CA (US)

( * ) Notice: Subject to any disclaimer, the term of this patent is extended or adjusted under 35 U.S.C. 154(b) by 0 days.

(21) Appl. No.: 09/084,303

(22) Filed: May 26, 1998

Related U.S. Application Data

(63) Continuation-in-part of application No. 09/074,984, filed on May 8, 1998, now abandoned, which is a continuation-in-part of application No. 09/062,580, filed on Apr. 17, 1998, now abandoned.

(51) Int. Cl.$^7$ .......................... C07H 21/04; A61K 38/28; C12P 21/06
(52) U.S. Cl. ..................... 536/23.5; 536/23.1; 530/303; 530/350; 435/69.1
(58) Field of Search ............................... 536/23.1, 23.5; 435/320.1, 691, 325, 455; 530/350, 303

(56) References Cited

U.S. PATENT DOCUMENTS

| | | | |
|---|---|---|---|
| 5,166,191 A | 11/1992 | Cronin et al. .................. | 514/12 |
| 5,256,644 A | 10/1993 | Antoniades et al. ........... | 514/2 |
| 5,478,807 A | 12/1995 | Cronin et al. .................. | 514/12 |
| 5,593,879 A | 1/1997 | Steller et al. ............. | 435/240.1 |

(List continued on next page.)

OTHER PUBLICATIONS

Genbank F13B12.
Genbank ZK75.
Genbank ZK84.
Genbank ZK1251.
Genbank C17C3.
Genbank M04D8.
Genbank F56F3.
Genbank T28B8.
Genbank ZC334.
Genbank T08G5.
Genbank F41G3.
Genbank U23181.
Swiss–Prot Q21507.
Swiss–Prot Q21508.
Swiss–Prot Q21506.
Swiss–Prot Q09626.
Swiss–Prot Q09627.
Swiss–Prot Q09628.
Swiss–Prot Q23430.
Swiss–Prot P56174.
Swiss–Prot P56173.
Swiss–Prot 18060.
Genbank 3220259.
Genbank 2648002.
Genbank 3122302.
Genbank 3122296.
Genbank 3122286.
Genbank 3122285.
Genbank 3122284.
Genbank 3122283.
Genbank 3122282.
Genbank 3122281.
Genbank 3122280.
Genbank 3122279.
Adham, I.M. et al., 1993, "Cloning of a cDNA for a Novel Insulin–like Peptides of the Testicular Leydig Cells", J. Biol. Chem. 268:26668–26672.
Adachi, T. et al., 1989, "cDNA Structure and Expression of Bombyxin, an Insulin–like Brain Secretory Peptide of the Silkmoth *Bombyx mori*", J. Biol. Chem. 264(13):7681–7865.
Bani, D., 1997, "Relaxin and breast cancer", Bull. Cancer 84(2):179–182.
Bani, D., 1997, "Relaxin: a pleiotropic hormone", Gen. Pharmacol. 28(1):13–22.
Bargmann, C.I. & Horvitz, H.R., 1991, "Control of larval development by chemosensory neurons in *Caenorhabditis elegans*", Science 251:1243–1246.
Becker, A. et al., 1996, "The regulation of trehalose metabolism in insects", Experientia 52(5):433–439.
Bell & Swain, 1979, "Nucleotide Sequence of a cDNA clone encoding human preproinsulin", Nature 29:525–527.

(List continued on next page.)

*Primary Examiner*—Scott D. Priebe
*Assistant Examiner*—Sumesh Kaushal
(74) *Attorney, Agent, or Firm*—Pennie & Edmonds LLP

(57) ABSTRACT

The present invention relates to *C. elegans* insulin-like genes and methods for identifying insulin-like genes. The methods provide nucleotide sequences of *C. elegans* insulin-like genes, amino acid sequences of their encoded proteins, and derivatives (e.g., fragments) and analogs thereof. The invention further relates to fragments (and derivatives and analogs thereof) of insulin-like proteins which comprise one or more domains of an insulin-like protein. Antibodies to an insulin-like protein, and derivatives and analogs thereof, are provided. Methods of production of an insulin-like protein (e.g., by recombinant means), and derivatives and analogs thereof, are provided. Further, methods to identify the biological function of a *C. elegans* insulin-like gene are provided, including various methods for the functional modification (e.g., overexpression, underexpression, mutation, knock-out) of one or more genes simultaneously. Still further, methods to identify a *C. elegans* gene which modifies the function of, and/or functions in a downstream pathway from, an insulin-like gene are provided.

2 Claims, 51 Drawing Sheets

U.S. PATENT DOCUMENTS

Figure 1:
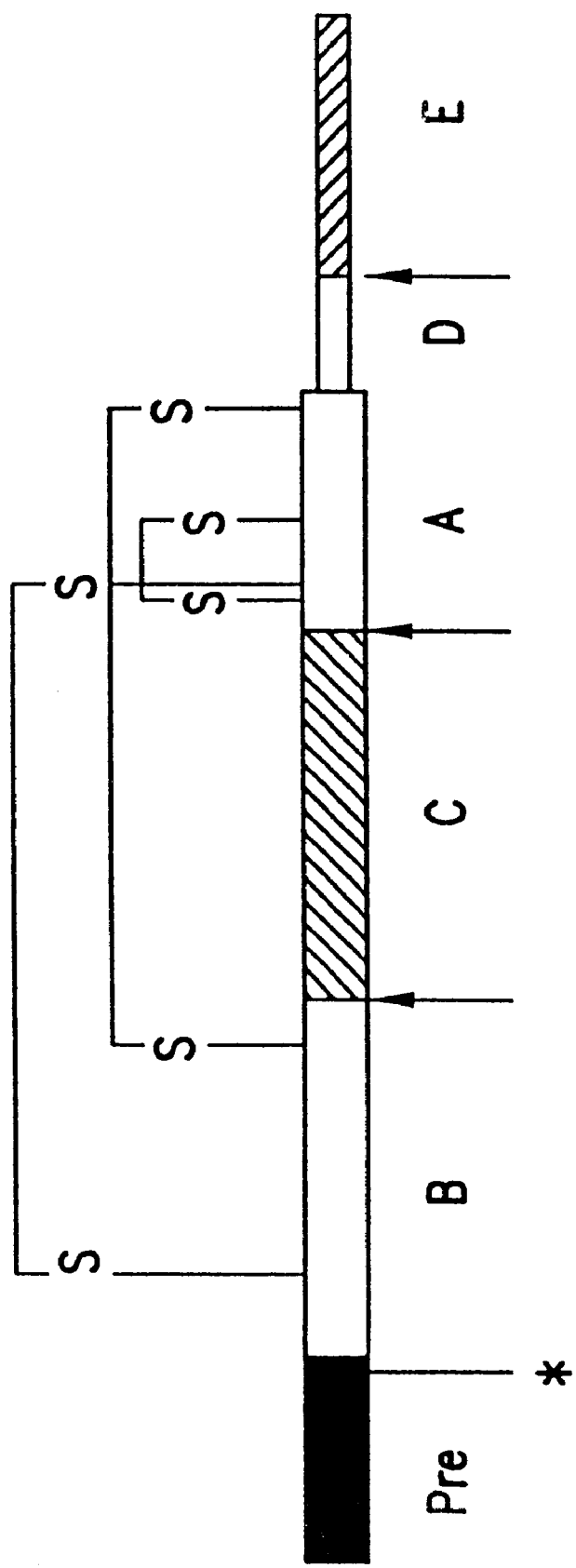

| | | | |
|---|---|---|---|
| 5,646,116 A | 7/1997 | Burk | 514/12 |
| 5,661,122 A | 8/1997 | Clark et al. | 514/2 |
| 5,674,845 A | 10/1997 | MacCuish et al. | 514/12 |
| 5,679,771 A | 10/1997 | Ballard et al. | 514/12 |
| 5,700,675 A | 12/1997 | Rubin et al. | 435/194 |
| 5,707,642 A | 1/1998 | Yue | 424/423 |
| 5,714,460 A | 2/1998 | Gluckman et al. | 514/3 |

OTHER PUBLICATIONS

Bermudez, I. et al., 1991, "Electrophysiological Activity of the C–peptide of the Locusta Insulin–Related Peptide. Effect on the Membrane Conductance of Locusta Neurones in Vitro", FEBS Lett. 293(1–2):137–141.

Swiss–Prot Q18060.

Blundell, T.L. & Dodson, 1972, "Insulin: the structure in the crystal and its reflectoin in chemistry and biology", Advan. Protein Chem. 26:279–402.

Blundell, T.L. & Humbel, R.E., 1980, "Hormone familes: pancreatic hormones and homologous growth factors", Nature 287:781–787.

Brange, J. & Langkjoer, L., 1993, "Insulin Structure and Stability", Pharm. Biotechnol. 5:315–350.

Brousseau et al., 1998, "An insulin–related gene family of unprecedented size and diversity in C.elegans", Early 1998 West Coast Worm Meeting abstract 18.

Brousseau et al., 1998, "A remarkably large and diverse group of insulin superfamily genes in C. elegans", Early 1998 Midwest Coast Worm Meeting abstract 7.

Brousseau et al., 1998, "An insulin–related gene family of unprecedented size and diversity in C.elegans", Early 1998 East Coast Worm Meeting abstract 20.

Bullesbach, E.E. et al., 1996, "Chemical Synthesis of a Zwitterhormon, Insulaxin, and of a Relaxin–like Bomboyxin Derivative", Biochemistry 35(30):9754–9760.

Bullesbach & Schwabe, 1988, "On the receptor binding site of relaxins", Int. J. Peptide Protein Res. 32:361–367.

Chalfie & Tu et al., 1994, "Green Fluorescent protein as a marker for gene expression", Science 263:802–805.

Chan, S.J. et al., 1990, "Evolution of the Insulin Superfamily: Cloning of a Hybrid Insulin/Insulin–like Growth Factor cDNA from Amphioxus", 87(23):9319–9323.

Chassin, D. et al., 1995, "Cloning of a New Member of the Insulin Gene Superfamily (INSL4) Expressed in Human Placenta", Genomics 29:465–470.

Chen, J.Y. et al., 1997, "Production of Biologically Active Recombinant Tilapia Insulin–like Growth Factor–II Polypeptides in *Escherichia coli* Cells and Characterization of the Genomic Structure of the Coding Region", DNA Cell Biol. 16(7):883–392.

Conlon, J.M. et al., 1997, "Primary Structure of Insulin from the African Lungfish, Protopterus Annectens", Gen. Comp. Endocrinol. 107(3):421–427.

Cooke & Harvey et al., 1991, "Solution structure of human insulin–like growth factor I: A nuclear magnetic resonance and restrained molecular dynamics study", Biochemistry 30:5484–5491.

Derwenda, U. et al., 1989, "Molecular Structure of Insulin: the Insulin Monomer and its Assembly", Br. Med. Bull. 45(1):4–18.

Dorman, J.B. et al., 1995, "The age–1 and daf–2 Genes Function in a Common Pathway to Control the Lifespan of Caenorhabditis elegans", 141(4):1399–1406.

Duret, L. et al., 1998, "New insulin–like proteins with atypical disulfide bond pattern characterized in *Caenorhabditis elegans* by comparative sequence analysis and homology modeling", Genome Res. 8:348–353.

Eigenbrot & Randal et al., 1991, "X–ray structure of human relaxin at 1.5 angstrom", J. Mol. Biol. 221:15–21.

Evans & Fowler et al., 1993, "The mouse relaxin gene: nucleotide sequence and expression", J. Mol. Endocrinol. 10:15–23.

Fernandez & Tabarini et al., 1995, "The Drosophilia insulin receptor hornologue: a gene essential for embryonic development encodes two receptor isoforms with different signaling potential", EMBO J. 14:3373–3384.

Fire, A. et al., 1998, "Potent and specific genetic interference by double–stranded RNA in *Caenorhabditis elegans*", Nature 391:806–811.

Foster, D., 1979, Diabetes Mellitus, Endocrinology and Metabolism, Part Thirteen, 337.

Fulbright, G. et al., 1997, "The prothoracicotropic hormone bombyxin has specific receptors on insect ovarian cells", Eur. J. Biochem. 245(3):774–780.

Gottlieb, S. & Ruvkin G., 1994, "daf–2, daf–16 and daf–23: genetically Interacting Genes Controlling Dauer Formation in *Caenorhabditis elegans*", Genetics 137(1):107–120.

Gregoire, F.M. et al., 1998, "Cloning and developmental regulation of a novel member of the insulin–like gene family in *caenorhabditis elegans*", Biochem. Biophys. Res. Commun. 249(2):385–390.

Hekimi, S. et al., 1998, "Molecular genetics of life span in C. elegans: how much does it teach us?", Trends in Genetics 14(1):1–20.

Hetru, C. et al., 1991, "Isolation and Structural Characterization of an Insulin–related Molecule, a Predominant Neuropeptide from *Locusta migratoria*", Eur. J. Biochem. 201(2):495–499.

Hietter, H. et al., 1990, "Isolation and Structure Elucidation of a Novel 5–kDa Peptide from Neurohaemal Lobes of the Corpora Cardiaca of *Locusta migratoria* (Insecta, Orthoptera)", Eur. J. Biochem. 187(1):241–247.

Hua, Q.X. et al., 1996, "Mapping the Functional Surface of Insulin by Design: Structure and Function of a Novel A–chain Analogue", J. Mol. Biol. 264(2):390–403.

Hua, Q.X. & Shoelson et al., 1991, "Receptor binding defined by a structural switch in a mutant human insulin", Nature 354:238–241.

Hudson & John et al., 1984, "Relaxin gene expression in human ovaries and the predicted structure of a human preprorelaxin by analysis of cDNA clones", EMBO J. 3:2333–2339.

Hudson & Haley et al., 1983, "Structure of a genomic clone encoding biologically active human relaxin", Nature 301:628–631.

Humbell, R.E., 1990, "Insulin–like growth factors I and II", Eur. J. Biochem. 190:445–462.

Hunter, T., 1985, "Cell–surface Proteins. At Last the Insulin Receptor", Nature 313(6005):740–741.

Ishizaki, H. & Suzuki, A., 1988, "An Insect Brain Peptide as a Member of Insulin Family", Horm. Metabl. Res. 20(7):426–429.

Ivell, R., 1997, "Biology of the relaxin–like factor (RFL)", Rev. Reprod., 2(3):133–138.

Iwami, M. et al., 1996, "Bombyxin–related Peptides: cDNA Structure and Expression in the Brain of the Hornworm *Agrius Convolvuli* [corrected]", Insect Biochem. Mol. Biol. 26(1):25–32.

Jansen & van Schaik et al., 1983, "Sequence of cDNA encoding human insulin–like growth factor I precursor", Nature 306:609–611.

Kahn, R.C. et al., 1996, "Genetics of Non–Insulin–Dependent (Type–II) diabetes Mellitus", Annu. Rev. Med. 47:509–531.

Kahn, R.C., 1988, "Type 2 Diabetes: when insulin secretion fails to compensate for insulin resistance", Cell 92:593–596.

Karim & Chang et al., 1996, "A screen for genes that function downstream of Rasi during Drosophilia eye–development", Genetics 143:315–329.

Kataoka, H. et al., 1987, "Isolation and Primary Structure of the Eclosion Hormone of the Tobacco Hornworm, *Manduca sexta*", Biochem. Biophys. Res. Commun. 146(2):746–750.

Kawakami, A. et al., 1989, "Structure and Organization of Four Clustered Genes that Encode bombyxin, an Insulin––related Brain Secretory Peptide of the Silkmoth *Bombyx mori*", PNAS USA 86(18):6843–6847.

Kawano, T. et al., 1998, "Insulin–like Peptides of *C. elegan*", Worm Breeder's Gazette 15(2):47 (abstract).

Kenyon, C. et al., 1993, "A *C. elegans* Mutant that Lives Twice as Long as Wild Type", Nature 366(6454):461–464.

Kimura, K.D. et al., 1997, "daf–2, an Insulin Receptor–Like Gene That Regulates Longevity and Diapause in *Caenorhabiditis elegans*", Science 277:942–946.

Kimura–Kawakami, M. et al., 1992, "Structure and Expression of Bombyxin–related Peptide Genes of the Moth *Samia cynthia ricini*", 86(2):257–268.

Kirishi & Nagasawa et al., 1992, "Comparison of the in vivo and in vitro effects of bombyxin and prothoracicotropic hormone on prothoracic glands of the silkworm, *Bombyx mori*", Zool. Sci. 9:149–155.

Kondo, H. et al., 1996, "Multiple Gene copies for Bombyxin, an insulin–related Peptide of the Silkmoth Bombyx mori:Structural Signs for Gene Rearrangement and Duplication Responsible for Generation of Multiple Molecular Forms of Bombyxin", J. Mol. Biol. 259(5):926–937.

Kornfeld & Horn et al., 1995, "The ksr–1 gene encodes a novel protein kinase involved in Ras–mediated signaling in *C. elegans*", Cell 83:903–913.

Kristenson & Kjeldson et al., 1997, "Alanine scanning mutagenesis of insulin", J. Biol. Chem. 272:12978–12983.

Kromer–Metzger, E. & Lageux, M., 1994, "Expression of the Gene Encoding an insulin–related Peptide in Locusta (Insecta, Orthoptera). Evidence for Alternative Promoter Usage", Eur. J. Biochem. 221(1):427–434.

Laguex, M. et al., 1990, "cDNAs form Neurosecretory Cells of Brains of *Locusta migratoria* (Insecta, Orthoptera) Encoding a Novel Member of the Superfamily of Insulins", Eur. Biochem. 187(1):249–254.

Lakowski, B, & Hekimi, S., 1996, "Determination of Life–span in *Caenorhabditis elegans* by Four Clock Genes", Science 272(5264):1010–1013.

Larsen, P.L. et al., 1995, "Genes that Regulate Both Development and Longevity in *Caenorhabditis elegans*", Genetics 139(4):1567–1583.

LeRoith, D. et al., 1988, "Insulin–related materials in the nervous system of vertebrates and non–vertebrates: possible extrapancreatic production", Horm. Metabol. 20:411–420.

Li, K.W. et al., 1992, "Purification and Sequencing of Molluscan Insulin–related Peptide I (MIP I) from the Neuroendrocrine Light Green Cells of *Lymnaea stagnalis*", Mol. Cell Endocrinol. 85(1–2):141–150.

Li, K.W. et al., 1992, "Purification and Sequencing of Molluscan Insulin–related Peptide II from the Neuroendocrine Light Green Cells in *Lymnaea stagnalis*", 130(6):3427–3432.

Li, K.W. & Geraerts, W.P., 1992, "Isolation and Chemical Characterization of a Novel Insulin–related Neuropeptide from the Freshwater Snail, *Lymnaea stagnalis*", Eur. J. Biochem. 205(2):675–678.

Lin, K. et al., 1997, "daf–16: An HNF–3/forkhead Family Member Can Function to Double the Life–Span of *Caenorhabditis elegans*", Science 278:1319–1322.

Lithgow, G.J. et al., 1995, "Thermotolerance and Extended Life–Span Conferred by Single–gene Mutations and Induced by Thermal Stress", PNAS USA 92(16):7540–7544.

Liu, K. et al., 1985, "Insulin–related genes expressed in human placenta from normal and diabetic pregnancies", PNAS USA 82:3868–3870.

Malone, E.A. et al., 1996, "Genetic Analysis of the Roles of daf–28 and age–1 in Regulated *Caenorhabditis elegans*-Dauer Formation", Genetics 143(3):1193–1205.

Malone, E.A. & Thomas, J.H., 1994, "A Screen for Nonconditional Dauer–constitutive Mutations in *Caenorhabditis elegans*", Genetics 136(3):879–886.

McRory, J.E. & Sherwood, N.M., 1997, "Ancient Divergence of Insulin and Insulin–Like Growth Factor", DNA and Cell Biol. 16(8):939–949.

Mello & Kramer et al., 1991, "Efficient gene transfer in *C. elegans*: Extrachromosomal maintenance and integration of transforming sequences", EMBO J. 10:3959–3970.

Miklos & Rubin, 1996, "The role of the genome project in determining gene fucntion: insights from model organisms", Cell 86:521–529.

Moller & Flier, 1991, "Insulin Resistance—Mechanisms, Syndromes, and Implications", N. Engl. J. Med. 325(13):938.

Morris, J.Z. et al., 1996, "A Phosphatidylinositol–3–OH Kinase Family Member Regulating Longevity and Diapause in *Caenorhabditis elegans*", Nature 382(6591):536–539.

Murray–Rust & Mcloeod et al., 1992, "Structure and evolution of insulins: Implications for receptor binding", BioEssays 14:325–331.

Nagata, K. et al., 1995, "Identification of the Receptor Recognition Surface of Bombyxin–II, an Insulin–like Peptide of the silkmoth *Bombyx mori:* Critical Importance of the B–chain Central Part", J. Mol. Biol. 253(5):759–770.

Nagata, K. et al., 1995, "Three–dimensional Solution Structure of Bombyxin–II an Insulin–like Peptide of the Silkmoth *Bombyx mori:* Structural Comparison with Insulin and Relaxin", J. Mol. Biol. 253(5):749–758.

Nagamatsu, S. et al., 1991, "Evolution of the Insulin Gene Superfamily. Sequence of a Preproinsulin–like Growth Factor cDNA from the Atlantic Hagfish", J. Biol. Chem. 266(4):2397–2402.

Nagasawa, H. et al., 1986, "Amino acid sequence of a prothoracicotropic hormone of the silkworm *Bombyx mori*", PNAS USA 83:5480–5483.

O'Brien & Noisin et al., 1995, "Hepatic nuclear factor 3– and hormone–regulated expression of the phosphoenolypyruvate carbokinase and insulin–like growth factor–binding protein I genes", Mol. Cell. Biol. 15:1747–1758.

Ogg, S. et al., 1997, "The Fork Head Transcription Factor DAF–16 Transduces Insulin–like Metabolic and Longevity Signals in *C. elegans*", Nature 389(6654):994–999.

Olsen, H.B. et al., 1996, "Solution Structure of an Engineered Insulin Monomer at Neutral pH", Biochemistry 35(27):8836–8845.

O'Riordan & Burnell, 1989, "Intermediary metabolism in the dauer larva of the nematode *C. elegans* I. Glucolysis, fluconeogenesis, oxidative phosphorylation and the tricarboxylic acid cycle", Comp. Biochem. Physiol. 92B:233–238.

O'Riordan & Burnell, 1990, "Intermediary metabolism in the dauer larva II. The glycoxylate cycle and fatty acid oxidation", Comp. Biochem. Physiol. 95B:125–130.

Paradis, S. et al., 1998, "*Caenorhabditis elegans* Akt/PKB transduces insulin receptor–like signals from AGE–1 P13 kinase to the DAF–16 transcription factor", Genes Dev. 12(16):2488–2498.

Partridge, L. & Harvey, P.H., 1993, "Gerontology. Methuselah among Nematodes", Nature 366(6454);404–405.

Patterson, G.I. et al., 1997, "The dAF–3 Smad Protein Antagonizes TGF–beta–related Receptor Signaling in the *Caenorhabditis elegans* Dauer Pathway", Genes Dev. 11(20):2679–2690.

Petruzzelli & Herrera et al., 1986, "Isolation of a Drosophilia genomic sequence homologous to the kinase domain to the human insulin receptor and detection of the phosphorylated Drosophilia receptor with an anti–peptide antibody", PNAS USA 83:4710–4714.

Pierce, S.B. & Ruvkun, G.B., 1998, "Identification of a Putative DAF–2 Insulin–Like Ligand", Early 1998 East Coast Worm Meeting abstract 150.

Rand, J.B & Johnson, C.D., 1995, "Genetic Pharmacology: Interactions Between Drugs and Gene Products in *Caenorhabditis elegans*", Methods Cell Biol. 48:187–204.

Rawitch & Moore et al., 1980, "Relaxin–insulin homology: predictions of secondary structure and lack of competitive binding", Int. J. Biochem. 11:357–362.

Riddle, D.L. & Albert, P.S., 1997, "Genetic and Environmental Regulation of Dauer Larva Development", Cold Spring Har. Lab. Press 28:739.

Robitzki, A. et al., 1989, "Demonstration of an endocrine signaling circuit for insulin in the sponge Geodia cydonium", EMBO J. 8:2905–2909.

Roovers, E. et al., 1995, "Characterization of a Putative Molluscan Insulin–related Peptide Receptor", Gene 162(2):181–188.

Roush, W., 1997, "Worm Longevity Gene Cloned", Science 277(5328):897–898.

Rotwein, P., 1986, "Human insulin–related DNA sequences map to chromosomes 2 and 11", Somatic. Cell and Molec. Gen. 12(6):625–631.

Ruan & Chen et al., 1995, "The Drosophilia insulin receptor contains a novel carboxyl–terminal extension likely to play an important role in signal transduction", J. Biol. Chem. 270:4236–4243.

Ruvkun Lab Homepage, 1997, Research in the Ruvkin Lab, Massachusetts General Hospital.

Satake, S. et al., 1997, "Bombyxin, an Insulin–Related Peptide of Insects, Reduces the Major Storage Carbohydrates in the Silkworm *Bombyx mori*", Comp. Biochem. Psysiol. B. Biochem. Mol. Biol. 118(2):349–357.

Scangos, 1997, "Drug discovery in the postgenomic era", Nat. Biotechnol. 15:1220–1221.

Schaffer, 1994, "A model for insulin binding to the receptor", Eur. J. Biochem. 221:1127–1132.

Schwabe, C. & Bullesbach, E.E., 1994, "Relaxin: structures, functions, promises, and nonevolution", FASEB J. 8(14):1152–1160.

Smit, A.B. et al., 1998, "Towards understanding the role of insulin in the brain: lessons from insulin–related signaling systems in the invertebrate brain", Prog. Neurobiol. 54:35–54.

Smit, A.B. & Van Kestem et al., 1998, "Towards understanding the role of insulin in the brain: lessons from the insulin–related signaling systems in the invertebrate brain", Prog. Neurobiol. 54:35–54.

Smit, A.B. et al., 1996, "Expression and Characterization of Molluscan Insulin–related Peptide VII from the Mollusc *Lymnaea stagnalis*", Neuroscience 70(2):589–596.

Smit, A.B. et al., 1993, "Evolutionary Conservation of the Insulin Gene Structure in Invertebrates: Cloning of the Gene Encoding Molluscan Insulin–related Peptide III from *Lymnaea stagnalis*", J. Mol. Endocrinol. 11(1):103–113.

Smit, A.B. et al., 1992, "Characterization of a cDNA Clone Encoding Molluscan Insulin–related Peptide V of *Lymnaea stagnalis*", Brain Res. Mol. Mol. Brain Res. 14(1–2):7–12.

Smit, A.B. et al., 1991, "Characterization of a cDNA Clone Encoding Molluscan Insulin–related Peptide II of *Lymnaea stagnalis*", Eur. J. Biochem. 199(3):699–703.

Smit, A.B. et al., 1998, "Growth–controlling molluscan neurons produce the precursor of an insulin–related peptide", Nature 331:535–538.

Steiner & Bell, 1989, Endocrinology, L. DeGroot. Philadelphia, Saunders: 1263–1289.

Taylor, S.I., 1994, "Insulin Resistance or Insulin Deficiency", Diabetes 43:735–740.

Taylor, S.I. et al., 1992, "Mutations in the Insulin Receptor Gene", Endocrin. Rev. 13(3):566–595.

Therrien & Chang et al., 1995, "KSR, a novel protein kinase required for RAS signal transduction", Cell 83:879–888.

Thomas, J.H. et al., 1998, "Methuselah meets diabetes", Bioessays 20(2):113–115.

Tissenbaum & Ruvkun, 1998, "An insulin–like signaling pathway affects both longevity and reproduction in *Caenorhabditis elegans*", Genetics 148:703–717.

Tsuzuki, S. et al., 1997, "Structure and Expression of Bombyxin E1 Gene: a Novel Family Gene that Encodes Bombyxin–IV, an Insect Insulin–related Neurosecretory Peptide", Comp. Biochem. Pysiol. B. Biochem. Mol. Biol. 117(3):409–416.

Ullrich & Bell et al., 1985, "Human insulin receptor and its relationship to the tyrosine kinase family of oncogenes", Nature 313:756–761.

Vanfleteren, J.R. & De Vreese, A., 1997, "Modulation of kinase activities in dauers and in long–lived mutants of *Caenorhabditis elegans*", J. Gerontol. A Biol. Sci. Med. Sci. 52(4):B212–B216.

Vanfleteren, J.R. & De Vreese, A., 1995, "The Gerontogenes age–1 and daf–2 Determine Metabolic Rate Potential in Aging *Caenorhabditis elegans*", FASEB J 9(13):1355–1361.

Villa–Komaroff et al., "Novel insulin–related sequences in fetal brain", *Gene Expression and Cell–Cell Interactions in the Developing Nervous System,* pp. 65–86.

Wade, J.D., 1997, "Relaxin", Methods Enzymol. 289:637–646.

Wadsworth & Riddle, 1989, "Developmental regulation of energy metabolism in *Caenorhabditis elegans*", Dev. Biol. 132:167–173.

Warram & Rich et al., 1995, "Epidemiology and genetics of diabetes mellitus",*Joslin's Diabetes Mellitus* C.R. Kahn and C.C. Weir. Philadelphia, Lea & Febiger: 201–215.

Waterson & Sulston, 1995, "The genome of *Caenorhabditis elegans*", PNAS USA 92:10836–10840.

Weiss, G., 1995, "Relaxin used to produce the cervical ripening of labor", Clin. Obstet. Gynecol. 38(2):293–300.

White, M.F. & Kahn, C.R., 1994, "The Insulin Signaling System", J. Biol. Chem. 269(1):1–4.

Wisotzkey, R. & Liu, L., 1998, "A Family of Insulin–like Genes in *C. elegans*", Early 1998 East Coast Worm Meeting abstract 206.

Yenushi, L. et al., 1996, "The Drosophila Insuiin Receptor Activates Multiple Signaling Pathways but Requres Insulin Receptor Substrate Proteins for DNA Synthesis", Molec. Cell. Biol. 16(5):2509–2517.

Yoshida, I. et al., 1997, "Bombyxin F1 Gene: Structure and Expression of a New Bombyxin Family Gene That Forms a Pair with Bombyxin B10 Gene", Zoolog. Sci. 14(4):615–622.

Yuan & Shaham et al., 1993, "The *C. elegans* cell death gene ced–3 encodes a protein similar to mammalian interleukin–1 beta–converting enzyme", Cell 75:641–652.

Zhu, J. & Kahn, C.R., 1997, "Analysis of a Peptide Hormone–receptor Interaction in the Yeast Two–Hybrid System", PNAS USA 94(24):13063–13068.

Gregoire et al, Biochem. Biophys. Res. Commun. 249(2):385–90, 1998.*

Kawano et al. Biochem Biophys. Res. Commun. 273(2):431–436, 2000.*

Duret et al, Genome Res. 8:348–353, 1998.*

Ogg et al., 1997, The fork head transcription factor DAF–16 transduces insulin–like metabolic and longevity signals in *C. elegans,* Nature 389, 994–999.

Lin et al., 1997, daf–16: an HNF–3/forkhead family member that can function to double the life–span of *Caenorhabditis elegans* Science, 278, 1319–1322.

* cited by examiner

FIG. 3A

| | | | | |
|---|---|---|---|---|
| M04D8.1 | SKSHSKKHVRFLC | ATKAVKHITRKMPD | MCLTGE | EVEVNEFCK | MGYSDSQIKYII CCPE |
| M04D8.2 | MDAHTDKYVRILC | GKTAIRNIANLCPPKPEMKGICSTGE | | YPSITEYCS | MGFSDSQIKFM CCDNQ |
| M04D8.3 | QVTDAHSELHVRRVC | GTATIKNIMRLCPG | VPACENGE | VPSPTEYCS | MGYSDSQVKYL CCPTSQ |
| ZK84.N | KEPKHHHHHHRHKGYC | GVKAVKKLKQICPD | LCSNVDD | NLLMEMCS | KNLTDDDILQR CCPE |
| ZC334.N | FLAPSTAAKRRC | GRRLIPYMYSICGG | PCENGD | IIIEHCF | SGTTPTIAEMQKA CCPELSEDPTFSS |
| ZC334.N2 | (+23)MGLIRANQGPQKAC | GRSMMKVQKLCAG | GCTIQNDD | LTIKSCS | TGYTDAGFISA CCPSGFVF |
| ZC334.N3 | KPEAQRRC | GRYLIRFLGELCNG | PCSGVSSVD | IATIACA | TAVPIEDLKNM CCPNL |
| ZC334.N4 | (+30)IGNHHGTKAGLITC | GMNIIERMDKLCNG | QCTRNYDA | LVIKSCH | RGVSDMEFMVA CCPTMKLFIH |
| ZC334.N5 | ASPTC | GRALHRIQSVCGL | CTIDAHHE | LIATACS | RGLGDKETIEM CCPI |
| ZC334.N6 | DFGAQRRC | GRHLVNFLEGLCGG | PCSEAPTVE | LASWACS | SAVSIQDLEKL CCPSNLA |
| ZC334.N7 | (+34)REPVVAAQGAKKIC | GRSLLIKIIQQLCHG | ICTVHADD | LHETACM | KGLTDSQLINS CCPPIPQTPFVF |

FIG.3B

F13B12.N

```
          10        20        30        40        50        60
ATGTACTGGTTTCGTCAAGTTTACAGACCCTCGTTCTTCTTTGGCTTTCTCGCGATCCTT
TACATGACCAAAGCAGTTCAAATGTCTGGGAGCAAGAAGAAACCGAAAGAGCGCTAGGAA
  M  Y  W  F  R  Q  V  Y  R  P  S  F  F  F  G  F  L  A  I  L>
  _____SIGNAL PEPTIDE_____>
  M  Y  W  F  R  Q  V  Y  R  P  S  F  F  F  G  F  L  A  I  L>
  _____CODING REGION_____>

70        80        90       100       110       120
CTCCTCTCGTCGCCGACGCCTTCAGACGCATCGATTCGACTATGTGGATCACGTCTCACA
GAGGAGAGCAGCGGCTGCGGAAGTCTGCGTAGCTAAGCTGATACACCTAGTGCAGAGTGT
                                S  I  R  L  C  G  S  R  L  T>
                                _____B PEPTIDE_____>
  L  L  S  S  P  T  P  S  D  A>
  _____SIGNAL PEPTIDE_____>
  L  L  S  S  P  T  P  S  D  A  S  I  R  L  C  G  S  R  L  T>
  _____CODING REGION_____>

130       140       150       160       170       180
ACAACCCTTTTAGCAGTATGCCGGAATCAGCTGTGCACTGGATTAACCGCTTTCAAACGT
TGTTGGGAAAATCGTCATACGGCCTTAGTCGACACGTGACCTAATTGGCGAAAGTTTGCA
                                                        K  R>
                                                        _____>
  T  T  L  L  A  V  C  R  N  Q  L  C  T  G  L  T  A  F>
  _____B PEPTIDE_____>
  T  T  L  L  A  V  C  R  N  Q  L  C  T  G  L  T  A  F  K  R>
  _____CODING REGION_____>
```

FIG. 4A

```
            190       200       210       220       230       240
      TCCGCCGACCAATCCTATGCACCAACAACTCGCGATCTTTTTCACATTCACCACCAACAA
      AGGCGGCTGGTTAGGATACGTGGTTGTTGAGCGCTAGAAAAAGTGTAAGTGGTGGTTGTT
        S  A  D  Q  S  Y  A  P  T  T  R  D  L  F  H  I  H  H  Q  Q>
      _____C PEPTIDE_____>
        S  A  D  Q  S  Y  A  P  T  T  R  D  L  F  H  I  H  H  Q  Q>
      _____CODING REGION_____>

250       260       270       280       290       300
      AAGCGAGGCGGAATTGCGACAGAATGTTGTGAGAAGCGATGTTCATTTGCATATCTCAAA
      TTCGCTCCGCCTTAACGCTGTCTTACAACACTCTTCGCTACAAGTAAACGTATAGAGTTT
           G  G  I  A  T  E  C  C  E  K  R  C  S  F  A  Y  L  K>
      _____A PEPTIDE_____>
       K  R>
      _____>
       K  R  G  G  I  A  T  E  C  C  E  K  R  C  S  F  A  Y  L  K>
      _____CODING REGION_____>

310       320       330
      ACATTCTGCTGCAATCAGGACGATAATTGA
      TGTAAGACGACGTTAGTCCTGCTATTAACT
        T  F  C  C  N  Q  D  D  N  *>
      _____A PEPTIDE_____>
        T  F  C  C  N  Q  D  D  N  *>
      _____CODING REGION_____>
```

FIG. 4B

ZK75.1

```
          10        20        30        40        50        60
ATGTTTTCATTCTTTACATATTTCCTTCTCTCCGCACTTCTTCTCTCCGCTTCATGTCGA
TACAAAAGTAAGAAATGTATAAAGGAAGAGAGGCGTGAAGAAGAGAGGCGAAGTACAGCT
                                                          R>
                                                         ___>
  M  F  S  F  F  T  Y  F  L  L  S  A  L  L  L  S  A  S  C>
  _____SIGNAL PEPTIDE _____>
  M  F  S  F  F  T  Y  F  L  L  S  A  L  L  L  S  A  S  C  R>
  _____CODING REGION _____>

70        80        90       100       110       120
CAACCTTCCATGGACACCAGCAAAGCCGATCGTATTCTACGAGAGATCGAAATGGAAACA
GTTGGAAGGTACCTGTGGTCGTTTCGGCTAGCATAAGATGCTCTCTAGCTTTACCTTTGT
   Q  P  S  M  D  T  S  K  A  D  R  I  L  R  E  I  E  M  E  T>
   _____PRO PEPTIDE _____>
   Q  P  S  M  D  T  S  K  A  D  R  I  L  R  E  I  E  M  E  T>
   _____CODING REGION _____>

130       140       150       160       170       180
GAACTCGAAAATCAACTCTCCCGAGCACGACGAGTCCCAGCTGGAGAGGTTCGTGCCTGT
CTTGAGCTTTTAGTTGAGAGGGCTCGTGCTGCTCAGGGTCGACCTCTCCAAGCACGGACA
   E  L  E  N  Q  L  S  R  A  R  R>
   _____PRO PEPTIDE _____>
                                    V  P  A  G  E  V  R  A  C>
                                    _____ B DOMAIN _____>
   E  L  E  N  Q  L  S  R  A  R  R  V  P  A  G  E  V  R  A  C>
   _____CODING REGION_____>
```

FIG. 5A

```
              190       200       210       220       230       240
       GGAAGACGACTTCTTCTCTTTGTCTGGTCAACCTGTGGAGAACCATGCACGCCACAAGAG
       CCTTCTGCTGAAGAAGAGAAACAGACCAGTTGGACACCTCTTGGTACGTGCGGTGTTCTC
                                                                 E>
                                                                 ___>
        G  R  R  L  L  L  F  V  W  S  T  C  G  E  P  C  T  P  Q>
       _____B DOMAIN_____>
        G  R  R  L  L  L  F  V  W  S  T  C  G  E  P  C  T  P  Q  E>
       _____CODING REGION_____>

250       260       270       280       290       300
       GACATGGACATTGCCACAGTTTGCTGCACAACACAGTGCACTCCATCATATATAAAACAA
       CTGTACCTGTAACGGTGTCAAACGACGTGTTGTGTCACGTGAGGTAGTATATATTTTGTT
        D  M  D  I  A  T  V  C  C  T  T  Q  C  T  P  S  Y  I  K  Q>
       _____A DOMAIN _____>
        D  M  D  I  A  T  V  C  C  T  T  Q  C  T  P  S  Y  I  K  Q>
       _____ CODING REGION_____>

310       320
       GCTTGCTGCCCAGAAAAGTAA
       CGAACGACGGGTCTTTTCATT
        A  C  C  P  E  K  *>
       _____A DOMAIN_____>
        A  C  C  P  E  K  *>
       ___CODING REGION_____>
```

FIG. 5B

ZK75.2

```
          10        20        30        40        50        60
ATGAACGCTATAATCTTCTGTCTCCTCTTCACAACTGTCACTGCCACTTATGAAGTTTTC
TACTTGCGATATTAGAAGACAGAGGAGAAGTGTTGACAGTGACGGTGAATACTTCAAAAG
                                                T  Y  E  V  F>
                                                __PRO PEPT___>
 M  N  A  I  I  F  C  L  L  F  T  T  V  T  A>
 _____SIGNAL PEPTIDE_____>
 M  N  A  I  I  F  C  L  L  F  T  T  V  T  A  T  Y  E  V  F>
 _____CODING REGION _____>

70        80        90       100       110       120
GGAAAAGGAATAGAACACAGAAATGAACATTTGATCATCAATCAACTTGATATCATACCA
CCTTTTCCTTATCTTGTGTCTTTACTTGTAAACTAGTAGTTAGTTGAACTATAGTATGGT
  G  K  G  I  E  H  R  N  E  H  L  I  I  N  Q  L  D  I  I  P>
 _____ PRO PEPTIDE _____>
  G  K  G  I  E  H  R  N  E  H  L  I  I  N  Q  L  D  I  I  P>
 _____ CODING REGION _____>

130       140       150       160       170       180
GTTGAGTCAACTCCAACTCCAAACCGTGCCTCAAGAGTCCAGAAACGTCTATGCGGAAGA
CAACTCAGTTGAGGTTGAGGTTTGGCACGGAGTTCTCAGGTCTTTGCAGATACGCCTTCT
  V  E  S  T  P  T  P  N  R  A  S  R>
 _____PRO PEPTIDE_____ >
                                         V  Q  K  R  L  C  G  R>
                                        _____ B DOMAIN _____>
  V  E  S  T  P  T  P  N  R  A  S  R  V  Q  K  R  L  C  G  R>
 _____ CODING REGION _____>
```

FIG. 6A

```
         190       200       210       220       230       240
CGTCTTATTTTATTCATGCTTGCAACATGTGGAGAATGTGATACAGATTCATCAGAAGAC
GCAGAATAAAATAAGTACGAACGTTGTACACCTCTTACACTATGTCTAAGTAGTCTTCTG
                                                 S  S  E  D>
                                                 _____>
  R  L  I  L  F  M  L  A  T  C  G  E  C  D  T  D>
  _____ B DOMAIN _____>
  R  L  I  L  F  M  L  A  T  C  G  E  C  D  T  D  S  S  E  D>
  _____ CODING REGION _____>

250       260       270       280       290       300
CTTTCGCATATTTGCTGCATAAAACAATGTGACGTTCAAGATATCATCAGAGTCTGCTGC
GAAAGCGTATAAACGACGTATTTTGTTACACTGCAAGTTCTATAGTAGTCTCAGACGACG
  L  S  H  I  C  C  I  K  Q  C  D  V  Q  D  I  I  R  V  C  C>
  _____ A DOMAIN _____>
  L  S  H  I  C  C  I  K  Q  C  D  V  Q  D  I  I  R  V  C  C>
  _____ CODING REGION _____>

310       320
CCGAATTCATTTAGAAAATAG
GGCTTAAGTAAATCTTTTATC
  P  N  S  F  R  K  *>
  ___A DOMAIN_____ >
  P  N  S  F  R  K  *>
  __CODING REGION__ >
```

FIG. 6B

ZK75.3

```
              10          20          30          40          50          60
       ATGAAACTCTCCGTTGTTCTTGCACTTTTCATTATTTTCCAACTTGGAGCTGCAAGTCTT
       TACTTTGAGAGGCAACAAGAACGTGAAAAGTAATAAAAGGTTGAACCTCGACGTTCAGAA
                                                           A   S   L>
```

```
                                                                          ———————>
       M   K   L   S   V   V   L   A   L   F   I   I   F   Q   L   G   A>
       ————————————————————— SIGNAL PEPTIDE ——————————————————————————————>
       M   K   L   S   V   V   L   A   L   F   I   I   F   Q   L   G   A   A   S   L>
       ————————————————————————— CODING REGION ———————————————————————————————————————>
```

```
              70          80          90         100         110         120
       ATGCGTAACTGGATGTTCGATTTTGAGAAAGAATTGGAACACGATTATGATGATTCGGAA
       TACGCATTGACCTACAAGCTAAAACTCTTTCTTAACCTTGTGCTAATACTACTAAGCCTT
       M   R   N   W   M   F   D   F   E   K   E   L   E   H   D   Y   D   D   S   E>
       ————————————————————————— PRO PEPTIDE ——————————————————————————————————————————>
       M   R   N   W   M   F   D   F   E   K   E   L   E   H   D   Y   D   D   S   E>
       ————————————————————————— CODING REGION ———————————————————————————————————————>
```

```
             130         140         150         160         170         180
       ATTGGATTCCATAACATTCACTCCCTGATGGCCAGATCAAGAAGAGGAGACAAAGTGAAG
       TAACCTAAGGTATTGTAAGTGAGGGACTACCGGTCTAGTTCTTCTCCTCTGTTTCACTTC
                                                           G   D   K   V   K>
                                                           ___B DOMAIN____>
       I   G   F   H   N   I   H   S   L   M   A   R   S   R   R>
       ————————————————————— PRO PEPTIDE ————————————————————————>
       I   G   F   H   N   I   H   S   L   M   A   R   S   R   R   G   D   K   V   K>
       ————————————————————————— CODING REGION ———————————————————————————————————————>
```

FIG. 7A

```
           190       200       210       220       230       240
ATTTGTGGTACAAAAGTTCTGAAAATGGTGATGGTAATGTGTGGAGGAGAATGTTCATCA
TAAACACCATGTTTTCAAGACTTTTACCACTACCATTACACACCTCCTCTTACAAGTAGT
 I   C   G   T   K   V   L   K   M   V   M   V   M   C   G   G   E   C   S   S>
 _____ B DOMAIN _____>
 I   C   G   T   K   V   L   K   M   V   M   V   M   C   G   G   E   C   S   S>
 _____ CODING REGION _____>

250       260       270       280       290       300
ACGAATGAGAACATCGCTACAGAATGCTGTGAAAAAATGTGCACAATGGAAGATATAACT
TGCTTACTCTTGTAGCGATGTCTTACGACACTTTTTTACACGTGTTACCTTCTATATTGA
 T   N   E   N   I   A   T   E   C   C   E   K   M   C   T   M   E   D   I   T>
 _____ A DOMAIN _____>
 T   N   E   N   I   A   T   E   C   C   E   K   M   C   T   M   E   D   I   T>
 _____ CODING REGION _____>

310       320
ACTAAGTGCTGCCCTTCAAGATGA
TGATTCACGACGGGAAGTTCTACT
 T   K   C   C   P   S   R   *>
 _____ A DOMAIN _____>
 T   K   C   C   P   S   R   *>
 _____ CODING REGION _____>
```

FIG. 7B

Zk84.6

```
              10        20        30        40        50        60
     ATGAACTCTGTCTTTACTATCATCTTCGTTTTGTGCGCACTCCAAGTCGCTGCAAGTTTC
     TACTTGAGACAGAAATGATAGTAGAAGCAAAACACGCGTGAGGTTCAGCGACGTTCAAAG
                                                                 F>
                                                              ___>
        M  N  S  V  F  T  I  I  F  V  L  C  A  L  Q  V  A  A  S>
        _____ SIGNAL PEPTIDE _____>
        M  N  S  V  F  T  I  I  F  V  L  C  A  L  Q  V  A  A  S  F>
        _____ CODING REGION _____>

70        80        90       100       110       120
     CGTCAATCCTTCGGTCCTTCAATGTCTGAAGAATCAGCAAGCATGCAACTTCTCCGTGAA
     GCAGTTAGGAAGCCAGGAAGTTACAGACTTCTTAGTCGTTCGTACGTTGAAGAGGCACTT
        R  Q  S  F  G  P  S  M  S  E  E  S  A  S  M  Q  L  L  R  E>
        _____ PRO PEPTIDE _____>
        R  Q  S  F  G  P  S  M  S  E  E  S  A  S  M  Q  L  L  R  E>
        _____ CODING REGION _____>

130       140       150       160       170       180
     CTTCAACACAACATGATGGAATCAGCTCACCGACCAATGCCACGAGCAAGACGTGTTCCA
     GAAGTTGTGTTGTACTACCTTAGTCGAGTGGCTGGTTACGGTGCTCGTTCTGCACAAGGT
                                                              V  P>
                                                           ___>
        L  Q  H  N  M  M  E  S  A  H  R  P  M  P  R  A  R  R>
        _____ PRO PEPTIDE _____>
        L  Q  H  N  M  M  E  S  A  H  R  P  M  P  R  A  R  R  V  P>
        _____ CODING REGION _____>
```

FIG. 8A

```
        190       200       210       220       230       240
GCACCAGGAGAAACTCGTGCCTGCGGAAGAAAACTCATCTCTTTAGTCATGGCTGTCTGT
CGTGGTCCTCTTTGAGCACGGACGCCTTCTTTTGAGTAGAGAAATCAGTACCGACAGACA
 A  P  G  E  T  R  A  C  G  R  K  L  I  S  L  V  M  A  V  C>
_____ B DOMAIN _____>
 A  P  G  E  T  R  A  C  G  R  K  L  I  S  L  V  M  A  V  C>
_____ CODING REGION _____>

250       260       270       280       290       300
GGAGATCTTTGCAACCCACAAGAAGGAAAGGACATTGCGACTGAATGCTGCGGAAATCAG
CCTCTAGAAACGTTGGGTGTTCTTCCTTTCCTGTAACGCTGACTTACGACGCCTTTAGTG
                   E  G  K  D  I  A  T  E  C  C  G  N  Q>
                  _____ A DOMAIN _____>
 G  D  L  C  N  P  Q>
 ____ B DOMAIN ____>
 G  D  L  C  N  P  Q  E  G  K  D  I  A  T  E  C  C  G  N  Q>
_____ CODING REGION _____>

310       320       330
TGTTCTGATGACTACATAAGATCTGCTTGTTGTCCATGA
ACAAGACTACTGATGTATTCTAGACGAACAACAGGTACT
 C  S  D  D  Y  I  R  S  A  C  C  P  *>
_____ A DOMAIN _____>
 C  S  D  D  Y  I  R  S  A  C  C  P  *>
_____ CODING REGION _____>
```

FIG. 8B

ZK84.N2

```
              10        20        30        40        50        60
    ATGCACTCGATCGTCGCCTTGATGCTCATCGGAACAATTCTCCCAATCGCTGCTCTTCAC
    TACGTGAGCTAGCAGCGGAACTACGAGTAGCCTTGTTAAGAGGGTTAGCGACGAGAAGTG
     M  H  S  I  V  A  L  M  L  I  G  T  I  L  P  I  A  A>
    ────────────── SIGNAL PEPTIDE ──────────────────────────>
     M  H  S  I  V  A  L  M  L  I  G  T  I  L  P  I  A  A  L  H>
    ────────────── CODING REGION ───────────────────────────────>
                                                            L  H>
                                                         ─────>

70        80        90       100       110       120
    CAGAAGCATCAAGGCTTCATCCTGTCGTCATCCGATTCAACCGGAAACCAACCAATGGAT
    GTCTTCGTAGTTCCGAAGTAGGACAGCAGTAGGCTAAGTTGGCCTTTGGTTGGTTACCTA
     Q  K  H  Q  G  F  I  L  S  S  S  D  S  T  G  N  Q  P  M  D>
    ────────────── CODING REGION ───────────────────────────────>
     Q  K  H  Q  G  F  I  L  S  S  S  D  S  T  G  N  Q  P  M  D>
    ────────────── PRO PEPTIDE ─────────────────────────────────>

130       140       150       160       170       180
    GCGATCTCAAGAGCCGACCGTCACACCAACTACCGATCATGCGCATTGCGGCTCATCCCG
    CGCTAGAGTTCTCGGCTGGCAGTGTGGTTGATGGCTAGTACGCGTAACGCCGAGTAGGGC
     A  I  S  R  A  D  R  H  T  N  Y  R  S  C  A  L  R  L  I  P>
    ────────────── CODING REGION ───────────────────────────────>

A  I  S  R>
    ──────────>
                 A  D  R  H  T  N  Y  R  S  C  A  L  R  L  I  P>
                ────────── B DOMAIN ────────────────────────────>
```

FIG. 9A

```
                190       200       210       220       230       240
         CATGTCTGGTCGGTGTGCGGTGACGCCTGCCAACCACAAAACGGAATCGATGTCGCTCAA
         GTACAGACCAGCCACACGCCACTGCGGACGGTTGGTGTTTTGCCTTAGCTACAGCGAGTT
                                                    N  G  I  D  V  A  Q>
                                                 ____ A DOMAIN _____>
          H  V  W  S  V  C  G  D  A  C  Q  P  Q  N  G  I  D  V  A  Q>
         _____ CODING REGION _____>
          H  V  W  S  V  C  G  D  A  C  Q  P  Q>
         _____ B DOMAIN _____>

250       260       270       280       290       300
         AAATGTTGCTCCACTGATTGCAGCTCCGATTACATCAAAGAAATCTGCTGCCCATTTGAC
         TTTACAACGAGGTGACTAACGTCGAGGCTAATGTAGTTTCTTTAGACGACGGGTAAACTG
          K  C  C  S  T  D  C  S  S  D  Y  I  K  E  I  C  C  P  F  D>
         _____ A DOMAIN _____>
          K  C  C  S  T  D  C  S  S  D  Y  I  K  E  I  C  C  P  F  D>
         _____ CODING REGION _____>

TAA
         ATT
          *>
          __>
          *>
          __>
```

FIG. 9B

ZK1251.2

```
             10        20        30        40        50        60
ATGCCACCAATAATTTTGGTTTTCTTTTTGGTTTTAATCCCTGCTTCTCAACAATATCCT
TACGGTGGTTATTAAAACCAAAAGAAAAACCAAAATTAGGGACGAAGAGTTGTTATAGGA
                                                           Y  P>
                                                      _____>
   M  P  P  I  I  L  V  F  F  L  V  L  I  P  A  S  Q  Q>
   _____ SIGNAL PEPTIDE _____>
   M  P  P  I  I  L  V  F  F  L  V  L  I  P  A  S  Q  Q  Y  P>
           _____ CODING REGION _____>

70        80        90       100       110       120
TTTTCACTGGAGTCCTTAAATGATCAAATAATCAATGAAGAAGTAATCGAATATATGCTT
AAAAGTGACCTCAGGAATTTACTAGTTTATTAGTTACTTCTTCATTAGCTTATATACGAA
  F  S  L  E  S  L  N  D  Q  I  I  N  E  E  V  I  E  Y  M  L>
  _____ PRO PEPTIDE _____>
  F  S  L  E  S  L  N  D  Q  I  I  N  E  E  V  I  E  Y  M  L>
  _____ CODING REGION _____>

130       140       150       160       170       180
GAAAATTCAATTAGGTCCAGCAGAACCAGAAGAGTCCCTGACGAGAAAAAAATTTATCGT
CTTTTAAGTTAATCCAGGTCGTCTTGGTCTTCTCAGGGACTGCTCTTTTTTTAAATAGCA
                                   V  P  D  E  K  K  I  Y  R>
                                   _____ B DOMAIN _____>
  E  N  S  I  R  S  S  R  T  R  R>
  _____ PRO PEPTIDE _____>
  E  N  S  I  R  S  S  R  T  R  R  V  P  D  E  K  K  I  Y  R>
  _____ CODING REGION _____>
```

FIG. 10A

```
          190        200        210        220        230        240
TGTGGAAGAAGAATACATTCGTATGTGTTTGCGGTTTGTGGAAAAGCATGCGAATCGAAT
ACACCTTCTTCTTATGTAAGCATACACAAACGCCAAACACCTTTTCGTACGCTTAGCTTA
  C  G  R  R  I  H  S  Y  V  F  A  V  C  G  K  A  C  E  S  N>
 ─────────────────────── B DOMAIN ───────────────────────────>
  C  G  R  R  I  H  S  Y  V  F  A  V  C  G  K  A  C  E  S  N>
 ─────────────────── CODING REGION ──────────────────────────>

250        260        270        280        290        300
ACTGAAGTTAATATTGCATCAAAATGTTGCCGTGAAGAATGCACCGACGACTTCATTCGA
TGACTTCAATTATAACGTAGTTTTACAACGGCACTTCTTACGTGGCTGCTGAAGTAAGCT
  T  E  V  N  I  A  S  K  C  C  R  E  E  C  T  D  D  F  I  R>
 ─────────────────────── A DOMAIN ───────────────────────────>
  T  E  V  N  I  A  S  K  C  C  R  E  E  C  T  D  D  F  I  R>
 ─────────────────── CODING REGION ──────────────────────────>

310
AAACAGTGCTGTCCTTAA
TTTGTCACGACAGGAATT
  K  Q  C  C  P  *>
 ─── A DOMAIN ────>
  K  Q  C  C  P  *>
 ── CODING REGI ──>
```

FIG. 10B

ZK1251.N

```
         10        20        30        40        50        60
ATGTCGCCAATCATTTTGATTTTCTTTTTGGTTTTCATTCCGTTTTCTCAACAACACACA
TACAGCGGTTAGTAAAACTAAAAGAAAAACCAAAAGTAAGGCAAAAGAGTTGTTGTGTGT
                                                          H  T>
                                                      ─────────>
   M   S   P   I   I   L   I   F   F   L   V   F   I   P   F   S   Q   Q>
   ──────────────────────── SIGNAL PEPTIDE ────────────────────────>
   M   S   P   I   I   L   I   F   F   L   V   F   I   P   F   S   Q   Q   H   T>
   ──────────────────────── CODING REGION ─────────────────────────>

70        80        90       100       110       120
TCTTTAGAGGAGTCCTTAAATGATCGAATAATCAGTGAAGAAGTAGTCGAAATGCTATCA
AGAAATCTCCTCAGGAATTTACTAGCTTATTAGTCACTTCTTCATCAGCTTTACGATAGT
   S   L   E   E   S   L   N   D   R   I   I   S   E   E   V   V   E   M   L   S>
   ──────────────────────── PRO PEPTIDE ───────────────────────────>
   S   L   E   E   S   L   N   D   R   I   I   S   E   E   V   V   E   M   L   S>
   ──────────────────────── CODING REGION ─────────────────────────>

130       140       150       160       170       180
GAGAAAGAAATTAGACCCAGCAGAGTAAGAAGAGTCCCTGAACAAAAAAATAAATTGTGC
CTCTTTCTTTAATCTGGGTCGTCTCATTCTTCTCAGGGACTTGTTTTTTTATTTAACACG
                                          V   P   E   Q   K   N   K   L   C>
                                          ────────── B DOMAIN ──────────>
   E   K   E   I   R   P   S   R   V   R   R>
   ────────── PRO PRPTIDE ──────────>
   E   K   E   I   R   P   S   R   V   R   R   V   P   E   Q   K   N   K   L   C>
   ──────────────────────── CODING REGION ─────────────────────────>
```

FIG. 11A

```
            190       200       210       220       230       240
GGAAAGCAAGTCTTATCCTACGTTATGGCACTTTGTGAAAAAGCATGCGATTCAAATACA
CCTTTCGTTCAGAATAGGATGCAATACCGTGAAACACTTTTTCGTACGCTAAGTTTATGT
                                                           T>
                                                          ─>
  G   K   Q   V   L   S   Y   V   M   A   L   C   E   K   A   C   D   S   N>
 ──────────────────────────────── B DOMAIN ────────────────────────────────
  G   K   Q   V   L   S   Y   V   M   A   L   C   E   K   A   C   D   S   N   T>
 ──────────────────────────── CODING REGION ───────────────────────────────>

250       260       270       280       290       300
AAAGTCGATATTGCGACAAAATGTTGCCGCGATGCATGCTCAGACGAATTCATTCGACAT
TTTCAGCTATAACGCTGTTTTACAACGGCGCTACGTACGAGTCTGCTTAAGTAAGCTGTA
  K   V   D   I   A   T   K   C   C   R   D   A   C   S   D   E   F   I   R   H>
 ──────────────────────────────── A DOMAIN ────────────────────────────────>
  K   V   D   I   A   T   K   C   C   R   D   A   C   S   D   E   F   I   R   H>
 ─────────────────────────────── CODING REGION ────────────────────────────>

310
CAATGTTGTCCTTAA
GTTACAACAGGAATT
  Q   C   C   P   *>
 ──── A DOMAIN ────>
  Q   C   C   P   *>
 ──── CODING R ────>
```

FIG. 11B

C06E2.N

```
                10        20        30        40        50        60
        ATGATCGTCACTTTGATTGTCTTTCTTGTCATTGGACTTCAAATGGCACACCTTTCTCAA
        TACTAGCAGTGAAACTAACAGAAAGAACAGTAACCTGAAGTTTACCGTGTGGAAAGAGTT
                                                                S  Q>
                                                                     ___>
         M  I  V  T  L  I  V  F  L  V  I  G  L  Q  M  A  H  L>
         _____SIGNAL PEPTIDE_____>
         M  I  V  T  L  I  V  F  L  V  I  G  L  Q  M  A  H  L  S  Q>
                         _____CODING REGION_____>

70        80        90        100       110       120
        GTATCTGGAAACAACGAAAATGGATTCTTAAATCCATTTGATTTGTCTCAATGGAGCGAA
        CATAGACCTTTGTTGCTTTTACCTAAGAATTTAGGTAAACTAAACAGAGTTACCTCGCTT
         V  S  G  N  N  E  N  G  F  L  N  P  F  D  L  S  Q  W  S  E>
         _____PRO PEPTIDE_____>
         V  S  G  N  N  E  N  G  F  L  N  P  F  D  L  S  Q  W  S  E>
         _____CODING REGION_____>

130       140       150       160       170       180
        GAAATCCTCCACCGTCAGTATCATCATCACCACCACCATCACCATGGAAATCGGGCGAGA
        CTTTAGGAGGTGGCAGTCATAGTAGTAGTGGTGGTGGTAGTGGTACCTTTAGCCCGCTCT
         E  I  L  H  R  Q  Y  H  H  H  H  H  H  H  G  N  R  A  R>
         _____PRO PEPTIDE_____>
         E  I  L  H  R  Q  Y  H  H  H  H  H  H  H  G  N  R  A  R>
         _____CODING REGION_____>
```

FIG. 12A

```
              190       200       210       220       230       240
     AGAACCTTGGAAACCGAAAAAATCTACCGCTGTGGAAGAAAACTCTACACTGATGTGCTA
     TCTTGGAACCTTTGGCTTTTTTAGATGGCGACACCTTCTTTTGAGATGTGACTACACGAT
       R>
       _>
          T  L  E  T  E  K  I  Y  R  C  G  R  K  L  Y  T  D  V  L>
                                  B DOMAIN                         >
       R  T  L  E  T  E  K  I  Y  R  C  G  R  K  L  Y  T  D  V  L>
                                  CODING REGION                    >

250       260       270       280       290       300
     TCAGCGTGCAACGGGCCATGTGAACCGGGTACGGAACAGGATCTCTCTAAGCTGTGCTGT
     AGTCGCACGTTGCCCGGTACACTTGGCCCATGCCTTGTCCTAGAGAGATTCGACACGACA
                                T  E  Q  D  L  S  K  L  C  C>
                                       A DOMAIN                    >
       S  A  C  N  G  P  C  E  P  G>
                  B DOMIAN              >
       S  A  C  N  G  P  C  E  P  G  T  E  Q  D  L  S  K  L  C  C>
                                  CODING REGION                    >

310       320       330       340       350
     GGAAACCAATGTACTTTCGTTGAAATCAGGAAAGCATGCTGTGCCGACAAATTGTAA
     CCTTTGGTTACATGAAAGCAACTTTAGTCCTTTCGTACGACACGGCTGTTTAACATT
       G  N  Q  C  T  F  V  E  I  R  K  A  C  C  A  D  K  L  *>
                                  A DOMAIN                      >
       G  N  Q  C  T  F  V  E  I  R  K  A  C  C  A  D  K  L  *>
                                  CODING REGION                 >
```

FIG. 12B

C17C3.4

```
           10        20        30        40        50        60
ATGTCTAGTTACCGTCAAACATTGTTCATTCTTATTATTCTTATTGTAATTATTCTCTTC
TACAGATCAATGGCAGTTTGTAACAAGTAAGAATAATAAGAATAACATTAATAAGAGAAG
 M  S  S  Y  R  Q  T  L  F  I  L  I  I  L  I  V  I  I  L  F>
 _____ SINGAL PEPTIDE _____>
 M  S  S  Y  R  Q  T  L  F  I  L  I  I  L  I  V  I  I  L  F>
 _____ CODING REGION _____>

70        80        90       100       110       120
GTCAATGAGGGTCAAGGAGCGCCTCACCATGACAAACGGCACACTGCATGCGTCCTAAAG
CAGTTACTCCCAGTTCCTCGCGGAGTGGTACTGTTTGCCGTGTGACGTACGCAGGATTTC
                         A  P  H  H  D  K  R  H  T  A  C  V  L  K>
                         _____ B DOMAIN _____>
 V  N  E  G  Q  G>
 __SINGAL PEPT__>
 V  N  E  G  Q  G  A  P  H  H  D  K  R  H  T  A  C  V  L  K>
 _____ CODING REGION _____>

130       140       150       160       170       180
ATTTTCAAGGCGCTAAACGTTATGTGTAATCATGAAGGTGATGCAGATGTTCTGAGGAGA
TAAAAGTTCCGCGATTTGCAATACACATTAGTACTTCCACTACGTCTACAAGACTCCTCT
                                              V  L  R  R>
                                              _____>
 I  F  K  A  L  N  V  M  C  N  H  E  G  D  A  D>
 _____ B DOMAIN _____>
 I  F  K  A  L  N  V  M  C  N  H  E  G  D  A  D  V  L  R  R>
 _____ CODING REGION _____>

190       200       210       220       230       240
ACAGCATCCGACTGCTGTCGGGAGAGCTGCTCGCTAACAGAAATGTTAGCGAGCTGCACC
TGTCGTAGGCTGACGACAGCCCTCTCGACGAGCGATTGTCTTTACAATCGCTCGACGTGG
 T  A  S  D  C  C  R  E  S  C  S  L  T  E  M  L  A  S  C  T>
 _____ A DOMAIN _____>
 T  A  S  D  C  C  R  E  S  C  S  L  T  E  M  L  A  S  C  T>
 _____ CODING REGION _____>

250       260       270
CTCACCAGCTCAGAAGAGTCAACTCGGGACATTTAA
GAGTGGTCGAGTCTTCTCAGTTGAGCCCTGTAAATT
 L  T  S  S  E  E  S  T  R  D  I  *>
 _____ A DOMAIN _____>
 L  T  S  S  E  E  S  T  R  D  I  *>
 _____CODING REGION _____>
```

FIG. 13

C17C3.N

```
         10        20        30        40        50        60
ATGCAATCAAACATCACCGCTTCATTATTCATAGCGTTGCTTATATTTGGAGTAATCAGT
TACGTTAGTTTGTAGTGGCGAAGTAATAAGTATCGCAACGAATATAAACCTCATTAGTCA
  M  Q  S  N  I  T  A  S  L  F  I  A  L  L  I  F  G  V  I  S>
_____SIGNAL PEPTIDE_____>
  M  Q  S  N  I  T  A  S  L  F  I  A  L  L  I  F  G  V  I  S>
_____CODING REGION_____>

70        80        90       100       110       120
GCAGCTCCATCTCATGAAAAAACACACAAAAAATGCTCTGATAAATTATATTTGGCCGATG
CGTCGAGGTAGAGTACTTTTTTGTGTGTTTTTTACGAGACTATTTAATATAAACCGCTAC
  A  P  S  H  E  K  T  H  K  K  C  S  D  K  L  Y  L  A  M>
_____B DOMAIN_____>
A>
__>
  A  A  P  S  H  E  K  T  H  K  K  C  S  D  K  L  Y  L  A  M>
_____CODING REGION_____>

130       140       150       160       170       180
AAGTCGTTGTGTAGTTATCGAGGTTATAGTGAATTCTTAAGAAATTCTGCAACTAAGTGT
TTCAGCAACACATCAATAGCTCCAATATCACTTAAGAATTCTTTAAGACGTTGATTCACA
                              F  L  R  N  S  A  T  K  C>
                         _____A DOMAIN_____>
  K  S  L  C  S  Y  R  G  Y  S  E>
_____B DOMAIN_____>
  K  S  L  C  S  Y  R  G  Y  S  E  F  L  R  N  S  A  T  K  C>
_____CODING REGION_____>

190       200       210       220       230       240
TGCCAAGACAATTGTGAGATTTCGGAAATGATGGCGTTGTGTGTTGTTGCTCCCAATTTT
ACGGTTCTGTTAACACTCTAAAGCCTTTACTACCGCAACACACAACAACGAGGGTTAAAA
  C  Q  D  N  C  E  I  S  E  M  M  A  L  C  V  V  A  P  N  F>
_____A DOMAIN_____>
  C  Q  D  N  C  E  I  S  E  M  M  A  L  C  V  V  A  P  N  F>
_____CODING REGION_____>

250       260
GACGACGATCTCCTTCATTAA
CTGCTGCTAGAGGAAGTAATT
  D  D  D  L  L  H  *>
____A DOMAIN____>
  D  D  D  L  L  H  *>
__CODING REGION____>
```

FIG. 14

M04D8.1

```
          10        20        30        40        50        60
ATGAAAAACCTACTCATTTTTCGTGCTTTTTATTGTATTCATCTTTTTTATTTCTTCATCA
TACTTTTGGATGAGTAAAAAGCACGAAAAATAACATAAGTAGAAAAAATAAAGAAGTAGT
                                                            S>
                                                         ___>
 M  K  T  Y  S  F  F  V  L  F  I  V  F  I  F  F  I  S  S>
 _____SIGNAL PEPTIDE_____>
 M  K  T  Y  S  F  F  V  L  F  I  V  F  I  F  F  I  S  S  S>
 _____ CODING REFION _____>

70        80        90       100       110       120
AAATCTCATTCAAAGAAACATGTTCGTTTCCTTTGTGCAACAAAAGCCGGTCAAACACATT
TTTAGAGTAAGTTTCTTTGTACAAGCAAAGGAAACACGTTGTTTTCGCCAGTTTGTGTAA
 K  S  H  S  K  K  H  V  R  F  L  C  A  T  K  A  V  K  H  I>
 _____ B DOMAIN _____>
 K  S  H  S  K  K  H  V  R  F  L  C  A  T  K  A  V  K  H  I>
 _____ CODING REGION _____>

130       140       150       160       170       180
CGGAAAGTATGCCCTGATATGTGTCTCACTGGAGAAGAAGTCGAAGTCAATGAGTTTTGC
GCCTTTCATACGGGACTATACACAGAGTGACCTCTTCTTCAGCTTCAGTTACTCAAAACG
                                     E  V  E  V  N  E  F  C>
                                     _____ A DOMAIN _____>
 R  K  V  C  P  D  M  C  L  T  G  E>
 _____ B DOMAIN _____>
 R  K  V  C  P  D  M  C  L  T  G  E  E  V  E  V  N  E  F  C>
 _____ CODING REGION _____>

190       200       210       220       230
AAGATGGGGTACTCGGATTCTCAAATCAAGTACATTTGCTGTCCCGAATAA
TTCTACCCCATGAGCCTAAGAGTTTAGTTCATGTAAACGACAGGGCTTATT
 K  M  G  Y  S  D  S  Q  I  K  Y  I  C  C  P  E  *>
 _____ A DOMAIN _____>
 K  M  G  Y  S  D  S  Q  I  K  Y  I  C  C  P  E  *>
 _____ CODING REGION _____>
```

FIG. 15

M04D8.2

```
         10        20        30        40        50        60
ATGCACACTACAACTATTCTCATATGCTTTTTCATCTTTCTTGTTCAAGTCTCCACAATG
TACGTGTGATGTTGATAAGAGTATACGAAAAAGTAGAAAGAACAAGTTCAGAGGTGTTAC
                                                           M>
                                                          ___>
  M  H  T  T  T  I  L  I  C  F  F  I  F  L  V  Q  V  S  T>
 _____ SIGNAL PEPTIDE _____>
  M  H  T  T  T  I  L  I  C  F  F  I  F  L  V  Q  V  S  T  M>
 _____ CODING REGION _____>

70        80        90       100       110       120
GATGCTCACACTGACAAATACGTCAGAACTCTGTGTGGAAAAACTGCAATCAGAAATATT
CTACGAGTGTGACTGTTTATGCAGTCTTGAGACACACCTTTTTGACGTTAGTCTTTATAA
  D  A  H  T  D  K  Y  V  R  T  L  C  G  K  T  A  I  R  N  I>
 _____ B DOMAIN _____>
  D  A  H  T  D  K  Y  V  R  T  L  C  G  K  T  A  I  R  N  I>
 _____ CODING REGION _____>

130       140       150       160       170       180
GCCAACCTTTGCCCCGCCAAAGCCAGAAATGAAGGGTATCTGTTCTACCGGAGAGTATCCA
CGGTTGGAAACGGGCGGTTTCGGTCTTTACTTCCCATAGACAAGATGGCCTCTCATAGGT
                                                         Y  P>
                                                         ___>
  A  N  L  C  P  P  K  P  E  M  K  G  I  C  S  T  G  E>
 _____ B DOMAIN _____>
  A  N  L  C  P  P  K  P  E  M  K  G  I  C  S  T  G  E  Y  P>
 _____ CODING REGION _____>

190       200       210       220       230       240
AGCATCACCGAATACTGTTCCATGGGATTTTCAGACTCTCAGATCAAGTTTATGTGCTGT
TCGTAGTGGCTTATGACAAGGTACCCTAAAAGTCTGAGAGTCTAGTTCAAATACACGACA
  S  I  T  E  Y  C  S  M  G  F  S  D  S  Q  I  K  F  M  C  C>
 _____ A DOMAIN _____>
  S  I  T  E  Y  C  S  M  G  F  S  D  S  Q  I  K  F  M  C  C>
 _____ CODING REGION _____>

250
GATAACCAATGA
CTATTGGTTACT
  D  N  Q  *>
 _____>
  D  N  Q  *>
 _____>
```

FIG. 16

M04D8.3

```
           10        20        30        40        50        60
ATGTTCGTTCTTCTTATTATTCTCTCTATCATTCTGGCTCAAGTCACTGATGCTCATTCA
TACAAGCAAGAAGAATAATAAGAGAGATAGTAAGACCGAGTTCAGTGACTACGAGTAAGT
                                        Q  V  T  D  A  H  S>
                                        _____ B DOMAIN _____>
 M  F  V  L  I  I  L  S  I  I  L  A>
 _____ SIGNAL PEPTIDE _____>
 M  F  V  L  I  I  L  S  I  I  L  A  Q  V  T  D  A  H  S>
 _____ CODING REGION _____>

70        80        90       100       110       120
GAGCTTCACGTTCGTAGGGTGTGCGGAACTGCTATCATAAAGAACATAATGCGATTGTGC
CTCGAAGTGCAAGCATCCCACACGCCTTGACGATAGTATTTCTTGTATTACGCTAACACG
 E  L  H  V  R  R  V  C  G  T  A  I  I  K  N  I  M  R  L  C>
 _____ B DOMAIN _____>
 E  L  H  V  R  R  V  C  G  T  A  I  I  K  N  I  M  R  L  C>
 _____ CODING REGION _____>

130       140       150       160       170       180
CCAGGGGTACCGGCTTGCGAAAATGGAGAAGTTCCAAGTCCAACCGAGTACTGTTCAATG
GGTCCCCATGGCCGAACGCTTTTACCTCTTCAAGGTTCAGGTTGGCTCATGACAAGTTAC
                                     V  P  S  P  T  E  Y  C  S  M>
                                     _____ A DOMAIN _____>
 P  G  V  P  A  C  E  N  G  E>
 _____ B DOMAIN _____>
 P  G  V  P  A  C  E  N  G  E  V  P  S  P  T  E  Y  C  S  M>
 _____ CODING REGION _____>

190       200       210       220       230
GGGTACTCAGACAGCCAGGTAAAATACCTATGCTGTCCAACTTCTCAGTGA
CCCATGAGTCTGTCGGTCCATTTTATGGATACGACAGGTTGAAGAGTCACT
 G  Y  S  D  S  Q  V  K  Y  L  C  C  P  T  S  Q  *>
 _____ A DOMAIN _____>
 G  Y  S  D  S  Q  V  K  Y  L  C  C  P  T  S  Q  *>
 _____ CODING REGION _____>
```

FIG. 17

```
ZK84.N
         10        20        30        40        50        60
ATGGACAAACCATCCTACCTGTCATCCAAAGAAGCATGGAAAATGCTAAATGAGCTGCTG
TACCTGTTTGGTAGGATGGACAGTAGGTTTCTTCGTACCTTTTACGATTTACTCGACGAC
 M  D  K  P  S  Y  L  S  S  K  E  A  W  K  M  L  N  E  L  L>
————————————— CODING REGION ——————————————————————>
 M  D  K  P  S  Y  L  S  S  K  E  A  W  K  M  L  N  E  L  L>
————————————— SIGNAL PEPTIDE ——————————————————————>

70        80        90       100       110       120
AAAGAGCCGAAACATCATCATCATCATCACAGGCACAAAGGATATTGTGGAGTTAAAGCT
TTTCTCGGCTTTGTAGTAGTAGTAGTAGTGTCCGTGTTTCCTATAACACCTCAATTTCGA
 K  E  P  K  H  H  H  H  H  H  R  H  K  G  Y  C  G  V  K  A>
————————————— B DOMAIN ——————————————————————>
 K  E  P  K  H  H  H  H  H  H  R  H  K  G  Y  C  G  V  K  A>
————————————— CODING REGION ——————————————————————>

130       140       150       160       170       180
GTAAAGAAATTAAAACAAATCTGTCCAGATCTTTGCTCGAATGTTGATGATAACCTTCTC
CATTTCTTTAATTTTGTTTAGACAGGTCTAGAAACGAGCTTACAACTACTATTGGAAGAG
                                                     N  L  L>
                                                     ————————>
 V  K  K  L  K  Q  I  C  P  D  L  C  S  N  V  D  D>
————————————— B DOMAIN ——————————————>
 V  K  K  L  K  Q  I  C  P  D  L  C  S  N  V  D  D  N  L  L>
————————————— CODING REGION ——————————————————————>

190       200       210       220       230       240
ATGGAAATGTGCTCAAAAAACCTGACGGATGATGATATTTTGCAACGGTGCTGTCCAGAA
TACCTTTACACGAGTTTTTTGGACTGCCTACTACTATAAAACGTTGCCACGACAGGTCTT
 M  E  M  C  S  K  N  L  T  D  D  D  I  L  Q  R  C  C  P  E>
————————————— A DOMAIN ——————————————————————>
 M  E  M  C  S  K  N  L  T  D  D  D  I  L  Q  R  C  C  P  E>
————————————— CODING REGION ——————————————————————>

TGA
ACT
 *>
 _>
 *>
 _>
```

FIG. 18

FS6F3.6
```
          10        20        30        40        50        60
ATGTTCTCGACCAGAGGGGTACTCCTTTTACTGTCTTTGATGGCTGCTGTAGCCGCATTC
TACAAGAGCTGGTCTCCCCATGAGGAAAATGACAGAAACTACCGACGACATCGGCGTAAG
                                                            F>
                                                          __>
  M  F  S  T  R  G  V  L  L  L  S  L  M  A  A  V  A  A>
  _____ SIGNAL PEPTIDE _____>
  M  F  S  T  R  G  V  L  L  L  S  L  M  A  A  V  A  A  F>
  _____ CODING REGION _____>

70        80        90       100       110       120
GGGCTGTTTTCTAGACCGGCTCCAATCACTCGGGACACTATCCGACCACCACGTGCCAAA
CCCGACAAAAGATCTGGCCGAGGTTAGTGAGCCCTGTGATAGGCTGGTGGTGCACGGTTT
  G  L  F  S  R  P  A  P  I  T  R  D  T  I  R  P  P  R  A  K>
  _____ PRO PEPTIDE _____>

G  L  F  S  R  P  A  P  I  T  R  D  T  I  R  P  P  R  A  K>
  _____ CODING REGION _____>

130       140       150       160       170       180
CACGGTTCGCTGAAATTATGCCCACCAGGTGGTGCCCTCATTCCTTGACGCTTTCAACTTG
GTGCCAAGCGACTTTAATACGGGTGGTCCACCACGGAGTAAGGAACTGCGAAAGTTGAAC
                                                            H>
                                                          __>
  H  G  S  L  K  L  C  P  P  G  G  A  S  F  L  D  A  F  N  L>
  _____ CODING REGION _____>
  _____ B DOMAIN _____>
```

FIG. 19A

```
          190       200       210       220       230       240
ATTTGCCCAATGCGCCGTCGACGCAGGAGTGTTTCAGAAAACTACAACGACGGCGGTGGC
TAAACGGGTTACGCGGCAGCTGCGTCCTCACAAAGTCTTTTGATGTTGCTGCCGCCACCG
    I  C  P  M  R  R  R  R  S  V  S  E  N  Y  N  D  G  G  G>
  ─────────────────── CODING REGION ──────────────────────────>
  ─────────── B DOMAIN ──────────────────>
                                              ──────────>

250       260       270       280       290       300
AGCCTTTTGGGACGGACAATGAATATGTGCTGTGAGACGGGATGTGAATTCACTGACATT
TCGGAAAACCCTGCCTGTTACTTATACACGACACTCTGCCCTACACTTAAGTGACTGTAA
    S  L  L  G  R  T  M  N  M  C  C  E  T  G  C  E  F  T  D  I>
  ─────────────────── CODING REGION ──────────────────────────>
          ──────────────── A DOMAIN ────────────────────────────>

310       320
TTCGCAATCTGCAATCCTTTTGGATAA
AAGCGTTAGACGTTAGGAAAACCTATT
    F  A  I  C  N  P  F  G  *>
  ──── CODING REGION ───────>
     ────── A DOMAIN ───────>
```

FIG. 19B

T28B8.N

```
              10        20        30        40        50        60
    ATGGTCCACCGACTTTTCATCGTCCTTATTGCAATTATTCTTGTCGCAAAATCAACTGCA
    TACCAGGTGGCTGAAAAGTAGCAGGAATAACGTTAATAAGAACAGCGTTTTAGTTGACGT
      M  V  H  R  L  F  I  V  L  I  A  I  I  L  V  A  K  S  T  A>
    _____ SIGNAL PEPTIDE _____>
      M  V  H  R  L  F  I  V  L  I  A  I  I  L  V  A  K  S  T  A>
    _____ CODING REGION _____>

70        80        90       100       110       120
    ATCTCACTTCAACAAGCTGACGGACGCATGAAAATGTGCCCCACCAGGTGGTTCAACATTC
    TAGAGTGAAGTTGTTCGACTGCCTGCGTACTTTTACACGGGTGGTCCACCAAGTTGTAAG
      I  S  L  Q  Q  A  D  G  R  M  K  M  C  P  P  G  G  S  T  F>
    _____ B DOMAIN _____>
      I  S  L  Q  Q  A  D  G  R  M  K  M  C  P  P  G  G  S  T  F>
    _____ CODING REGION _____>

130       140       150       160       170       180
    ACAATGGCATGGTCAATGTCGTGTTCGATGCGCAGGAGAAAACGAGATGTTGGACGATAT
    TGTTACCGTACCAGTTACAGCACAAGCTACGCGTCCTCTTTTGCTCTACAACCTGCTATA
      T  M  A  W  S  M  S  C  S  M  R  R  R  K  R  D  V  G  R  Y>
    _____ B DOMAIN _____>
      T  M  A  W  S  M  S  C  S  M  R  R  R  K  R  D  V  G  R  Y>
    _____ CODING REGION _____>

190       200       210       220       230       240
    TTCGAAAAACGTGCTCTGATCGCCCCATCAATCCGTCAACTTCAAACAATTTGCTGTCAA
    AAGCTTTTTGCACGAGACTAGCGGGGTAGTTAGGCAGTTGAAGTTTGTTAAACGACAGTT
      F  E>
    ____>
      F  E  K  R  A  L  I  A  P  S  I  R  Q  L  Q  T  I  C  C  Q>
    _____ CODING REGION _____>
            K  R  A  L  I  A  P  S  I  R  Q  L  Q  T  I  C  C  Q>
    _____ A DOMAIN _____>

250       260       270       280
    GTTGGTTGCAACGTGGAAGATCTTCTTGCCTACTGTGCCCCAATTTAA
    CAACCAACGTTGCACCTTCTAGAAGAACGGATGACACGGGGTTAAATT
      V  G  C  N  V  E  D  L  L  A  Y  C  A  P  I  *>
    _____ CODING REGION _____>
      V  G  C  N  V  E  D  L  L  A  Y  C  A  P  I  *>
    _____ A DOMAIN _____>
```

FIG. 20

ZC334.N

```
          10        20        30        40        50        60
ATGAAATTCTTCCGCTTAATGTTGCTCTGCGCCCTTGTCCTGACCACCATGGCTTTTTTG
TACTTTAAGAAGGCGAATTAGAACGAGACGCGGGAACAGGACTGGTGGTACCGAAAAAAC
  M  K  F  F  R  L  I  L  L  C  A  L  V  L  T  T  M  A>
  ─────────────────── SIGNAL PEPTIDE ───────────────────>
  M  K  F  F  R  L  I  L  L  C  A  L  V  L  T  T  M  A  F  L>
  ──────────────────── CODING REGION ────────────────────>
                                                    F  L>
                                                    ───>
```

```
          70        80        90       100       110       120
GCTCCAAGTACGGCAGCCAAGAGGCGTTGTGGCCGCCGCTTAATTCCCTATGTCTATTCA
CGAGGTTCATGCCGTCGGTTCTCCGCAACACCGGCGGCGAATTAAGGGATACAGATAAGT
  A  P  S  T  A  A  K  R  R  C  G  R  R  L  I  P  Y  V  Y  S>
  ──────────────────── CODING REGION ────────────────────>
  A  P  S  T  A  A  K  R  R  C  G  R  R  L  I  P  Y  V  Y  S>
  ──────────────────── B DOMAIN ────────────────────>
```

```
         130       140       150       160       170       180
ATATGCGGCGGCCCGTGCGAGAATGGAGATATTATCATCGAGCACTGCTTCTCCGGAACA
TATACGCCGCCGGGCACGCTCTTACCTCTATAATAGTAGCTCGTGACGAAGAGGCCTTGT
  I  C  G  G  P  C  E  N  G  D  I  I  I  E  H  C  F  S  G  T>
  ──────────────────── CODING REGION ────────────────────>
  I  C  G  G  P  C  E  N  G  D>
  ─────── B DOMAIN ─────>
                         I  I  I  E  H  C  F  S  G  T>
                         ─────── A DOMAIN ──────────>
```

```
         190       200       210       220       230       240
ACTCCCACCATTGCCGAAGTCCAAAAGGCTTGCTGTCCTGAACTATCTGAAGACCCAACT
TGAGGGTGGTAACGGCTTCAGGTTTTCCGAACGACAGGACTTGATAGACTTCTGGGTTGA
  T  P  T  I  A  E  V  Q  K  A  C  C  P  E  L  S  E  D  P  T>
  ──────────────────── CODING REGION ────────────────────>
  T  P  T  I  A  E  V  Q  K  A  C  C  P  E  L  S  E  D  P  T>
  ─────── A DOMAIN ──────────>
```

```
         250
TTCTCATCTTAA
AAGAGTAGAATT
  F  S  S  *>
  ──────>
  F  S  S  *>
  ──────>
```

FIG. 21

T08G5.N

```
         10        20        30        40        50        60
ATGTCACTGCATTTCTCCACTATTCAAAAAACAATTCTTCTAATCTCATTCTTGCTCCTC
TACAGTGACGTAAAGAGGTGATAAGTTTTTTGTTAAGAAGATTAGAGTAAGAACGAGGAC
 M  S  L  H  F  S  T  I  Q  K  T  I  L  L  I  S  F  L  L  L>
─────────────────── SIGNAL PEPTIDE ─────────────────────────>
 M  S  L  H  F  S  T  I  Q  K  T  I  L  L  I  S  F  L  L  L>
─────────────────── CODING REGION ──────────────────────────>

70        80        90       100       110       120
GTAACATTGGCTCCCAGAACAAGTGCAGCTTTTCCATTCCAAATTTGTGTCAAAAAAATG
CATTGTAACCGAGGGTCTTGTTCACGTCGAAAAGGTAAGGTTTAAACACAGTTTTTTTAC
 V  T  L  A  P  R  T  S  A>
____ SIGNAL PEPTIDE _____>
 V  T  L  A  P  R  T  S  A  A  F  P  F  Q  I  C  V  K  K  M>
─────────────── CODING REGION ──────────────────────────────>
                            A  F  P  F  Q  I  C  V  K  K  M>
                           ────────── B DOMAIN ─────────────>

130       140       150       160       170       180
GAAAAAATGTGCAGAATCATCAATCCAGAGCAGTGTGCACAAGTAAATAAAATCACTGAG
CTTTTTTACACGTCTTAGTAGTTAGGTCTCGTCACACGTGTTCATTTATTTTAGTGACTC
 E  K  M  C  R  I  I  N  P  E  Q  C  A  Q  V  N  K  I  T  E>
─────────────────── CODING REGION ──────────────────────────>
 E  K  M  C  R  I  I  N  P  E  Q  C  A  Q  V  N  K  I  T  E>
──────────────────────── B DOMAIN ──────────────────────────>

190       200       210       220       230       240
ATTGGAGCATTGACAGACTGTTGCACCGGACTGTGCTCCTGGGAAGAAATCCGGATCTCC
TAACCTCGTAACTGTCTGACAACGTGGCCTGACACGAGGACCCTTCTTTAGGCCTAGAGG
 I  G  A  L  T  D  C  C  T  G  L  C  S  W  E  E  I  R  I  S>
─────────────────── CODING REGION ──────────────────────────>
 I  G>
────>
       A  L  T  D  C  C  T  G  L  C  S  W  E  E  I  R  I  S>
     ──────────────── A DOMAIN ──────────────────────────────>

250
TGCTGCTCCGTTTTATAA
ACGACGAGGCAAAATATT
 C  C  S  V  L  *>
__CODING REGI___>
 C  C  S  V  L>
__A DOMAIN___ >
```

FIG. 22

F41G3.N

```
              10         20         30         40         50         60
     ATGCTCACACATCTGAAATTCTTGCTTCTAGTGAGCCTTTTTATCAACTTCGCCGTAAGC
     TACGAGTGTGTAGACTTTAAGAACGAAGATCACTCGGAAAAATAGTTGAAGCGGCATTCG
      M  L  T  H  L  K  F  L  L  L  V  S  L  F  I  N  F  A  V  S>
     _____ SIGNAL PEPTIDE _____>
      M  L  T  H  L  K  F  L  L  L  V  S  L  F  I  N  F  A  V  S>
     _____ CODING REGION _____>

70         80         90        100        110        120
     TCTGAAGACATCAAATGCGATGCAAAGTTCATTTCGAGAATCACGAAACTCTGTATTCAC
     AGACTTCTGTAGTTTACGCTACGTTTCAAGTAAAGCTCTTAGTGCTTTGAGACATAAGTG
      S  E  D  I  K  C  D  A  K  F  I  S  R  I  T  K  L  C  I  H>
     _____ B DOMAIN _____>
      S  E  D  I  K  C  D  A  K  F  I  S  R  I  T  K  L  C  I  H>
     _____ CODING REGION _____>

130        140        150        160        170        180
     GGAATTACTGAAGATAAACTTGTTCGTCTTCTCACAAGATGCTGCACATCTCACTGCTCC
     CCTTAATGACTTCTATTTGAACAAGCAGAAGAGTGTTCTACGACGTGTAGAGTGACGAGG
      G  I  T  E  D  K>
     ___ B DOMAIN _____>
                         L  V  R  L  L  T  R  C  C  T  S  H  C  S>
                        _____ A DOMAIN _____>
      G  I  T  E  D  K  L  V  R  L  L  T  R  C  C  T  S  H  C  S>
     _____ CODING REGION _____>

190        200        210        220        230        240
     AAAGCTCATCTGAAAATGTTCTGCACCCTGAAACCTCACGAAGAAGAACCACATCACGAA
     TTTCGAGTAGACTTTTACAAGACGTGGGACTTTGGAGTGCTTCTTCTTGGTGTAGTGCTT
      K  A  H  L  K  M  F  C  T  L  K  P  H  E  E  E  P  H  H  E>
     _____ A DOMAIN _____>
      K  A  H  L  K  M  F  C  T  L  K  P  H  E  E  E  P  H  H  E>
     _____ CODING REGION _____>
     ATCTAA
     TAGATT
      I>
     __>
      I *>
     ____>
```

FIG. 23

F41G3.N2

```
            10        20        30        40        50        60
   ATGAAGCTTCTTCCTCTCATTGTGGTTTTTGCTCTTTTGGCAGTCATATCAGAATCATAT
   TACTTCGAAGAAGGAGAGTAACACCAAAAACGAGAAAACCGTCAGTATAGTCTTAGTATA
     M  K  L  L  P  L  I  V  V  F  A  L  L  A  V  I  S  E  S  Y>
   ───────────────────── SIGNAL PEPTIDE ──────────────────────>
     M  K  L  L  P  L  I  V  V  F  A  L  L  A  V  I  S  E  S  Y>
   ───────────────────── CODING REGION ───────────────────────>

70        80        90       100       110       120
   TCTGGAAATGACTTCCAACCTCGTGACAATAAACATCATTCCTATCGTTCATGTGGGGAA
   AGACCTTTACTGAAGGTTGGAGCACTGTTATTTGTAGTAAGGATAGCAAGTACACCCCTT
     G  N  D  F  Q  P  R  D  N  K  H  H  S  Y  R  S  C  G  E>
   ──────────────────────── B DOMAIN ─────────────────────────>
   S>
   ─>
   S  G  N  D  F  Q  P  R  D  N  K  H  H  S  Y  R  S  C  G  E>
   ─────────────────────── CODING REGION ─────────────────────>

130       140       150       160       170       180
   TCGTTGAGCCGACGAGTTGCATTTCTGTGTAATGGTGGAGCTATTCAAACAGAAATACTA
   AGCAACTCGGCTGCTCAACGTAAAGACACATTACCACCTCGATAAGTTTGTCTTTATGAT
     S  L  S  R  R  V  A  F  L  C  N  G  G  A  I  Q  T>
   ────────────── B DOMAIN ──────────────>
                                                          E  I  L>
                                                         ────────>
     S  L  S  R  R  V  A  F  L  C  N  G  G  A  I  Q  T  E  I  L>
   ──────────────────── CODING REGION ────────────────────────>

190       200       210       220       230       240
   AGAGCTCTGGATTGTTGTTCCACTGGTTGTACGGACAAACAGATCTTTTCTTGGTGTGAT
   TCTCGAGACCTAACAACAAGGTGACCAACATGCCTGTTTGTCTAGAAAAGAACCACACTA
     R  A  L  D  C  C  S  T  G  C  T  D  K  Q  I  F  S  W  C  D>
   ────────────────────────── A DOMAIN ───────────────────────>
     R  A  L  D  C  C  S  T  G  C  T  D  K  Q  I  F  S  W  C  D>
   ───────────────────── CODING REGION ───────────────────────>

250
   TTTCAAATTTGA
   AAAGTTTAAACT
     F  Q  I>
   ──────────>
     F  Q  I  *>
   ──────────────>
```

FIG. 24

C17C3.N2

```
            10        20        30        40        50        60
     ATGAAGCTTTTACATATTTTTATTATTTTTCTGTTATTCCAATCGTGCTCTAATAAAATG
     TACTTCGAAAATGTATAAAAATAATAAAAAGACAATAAGGTTAGCACGAGATTATTTTAC
                                                              N  K  M>
                                                              ─────────>
      M  K  L  L  H  I  F  I  I  F  L  L  F  Q  S  C  S>
      ────────────────────── SIGNAL PEPTIDE ──────────────────────>
      M  K  L  L  H  I  F  I  I  F  L  L  F  Q  S  C  S  N  K  M>
      ────────────────────── CODING REGION ───────────────────────────>

70        80        90       100       110       120
     TGTCAATATTCAAAGAAAAAGTACAAGATTTGTGGAGTTAGAGCTCTTAAGCATATGAAA
     ACAGTTATAAGTTTCTTTTTCATGTTCTAAACACCTCAATCTCGAGAATTCGTATACTTT
      C  Q  Y  S  K  K  K  Y  K  I  C  G  V  R  A  L  K  H  M  K>
      ──────────────────────── B DOMAIN ──────────────────────────>
      C  Q  Y  S  K  K  K  Y  K  I  C  G  V  R  A  L  K  H  M  K>
      ─────────────────────── CODING REGION ──────────────────────>

130       140       150       160       170       180
     GTCTATTGTACACGTGGAATGACAAGAGATTATGGAAAATTACTCGTGACTTGTTGTTCG
     CAGATAACATGTGCACCTTACTGTTCTCTAATACCTTTTAATGAGCACTGAACAACAAGC
      V  Y  C  T  R  G  M  T  R  D>
      ────────── B DOMAIN ──────────>
                                    Y  G  K  L  L  V  T  C  C  S>
                                    ────────── A DOMAIN ──────────>
      V  Y  C  T  R  G  M  T  R  D  Y  G  K  L  L  V  T  C  C  S>
      ─────────────────────── CODING REGION ──────────────────────>

190       200       210       220
     AAAGGATGTAATGCAATAGATATCCAACGTATTTGTTTATGA
     TTTCCTACATTACGTTATCTATAGGTTGCATAAACAAATACT
      K  G  C  N  A  I  D  I  Q  R  I  C  L>
      ─────────────── A DOMAIN ───────────────>
      K  G  C  N  A  I  D  I  Q  R  I  C  L *>
      ─────────────── CODING REGION ──────────>
```

FIG. 25

ZC334.N2

```
           10        20        30        40        50        60
ATGAGATCTCCCACCTTGTTTCTTCTTCTGCTCCTAGTGCCCCTGGCACTATGCCATGTC
TACTCTAGAGGGTGGAACAAAGAAGAAGACGAGGATCACGGGGACCGTGATACGGTACAG
  M   R   S   P   T   L   F   L   L   L   L   L   V   P   L   A   L   C   H   V>
  _____CODING REGION_____>
  M   R   S   P   T   L   F   L   L   L   L   L   V   P   L   A   L   C>
  _____SIGNAL PEPTIDE_____>
                                                                      H   V>
                                                                      _____>

70        80        90       100       110       120
TTCTCGGAGCCCGCGGATTTGGAGCTCAAAAGCTACCAAGCGCTTGAAAAAAGCCTCAAG
AAGAGCCTCGGGCGCCTAAACCTCGAGTTTTCGATGGTTCGCGAACTTTTTTCGGAGTTC
  F   S   E   P   A   D   L   E   L   K   S   Y   Q   A   L   E   K   S   L   K>
  _____CODING REGION_____>
  F   S   E   P   A   D   L   E   L   K   S   Y   Q   A   L   E   K   S   L   K>
  _____B DOMAIN_____>

130       140       150       160       170       180
GAGATGGGACTCATTCGAGCCAACCAGGGACCTCAAAAAGCGTGCGGACGATCAATGATG
CTCTACCCTGAGTAAGCTCGGTTGGTCCCTGGAGTTTTTCGCACGCCTGCTAGTTACTAC
  E   M   G   L   I   R   A   N   Q   G   P   Q   K   A   C   G   R   S   M   M>
  _____CODING REGION_____>
  E   M   G   L   I   R   A   N   Q   G   P   Q   K   A   C   G   R   S   M   M>
  _____B DOMAIN_____>
```

FIG. 26A

```
              190       200       210       220       230       240
       ATGAAGGTGCAGAAGCTTTGCGCGGGCGGATGCACAATTCAGAACGACGATCTTACCATC
       TACTTCCACGTCTTCGAAACGCGCCCGCCTACGTGTTAAGTCTTGCTGCTAGAATGGTAG
        M  K  V  Q  K  L  C  A  G  G  C  T  I  Q  N  D  D  L  T  I>
       _____CODING REGION_____>
        M  K  V  Q  K  L  C  A  G  G  C  T  I  Q  N. D  D>
       _____ B DOMAIN _____>
                                                        L  T  I>
                                                        _____>

250       260       270       280       290       300
       AAATCCTGCAGTACTGGGTACACCGATGCCGGCTTCATCTCGGCCTGCTGCCCATCTGGC
       TTTAGGACGTCATGACCCATGTGGCTACGGCCGAAGTAGAGCCGGACGACGGGTAGACCG
        K  S  C  S  T  G  Y  T  D  A  G  F  I  S  A  C  C  P  S  G>
       _____CODING REGION_____>
        K  S  C  S  T  G  Y  T  D  A  G  F  I  S  A  C  C  P  S  G>
       _____ A DOMAIN _____>

310
       TTCGTTTTCTAA
       AAGCAAAAGATT
        F  V  F  *>
       _____>
        F  V  F>
       _____>
```

FIG. 26B

ZC334.N3

```
            10        20        30        40        50        60
ATGTTGTTCAAAATCATCATTTTATTTTTCCTGCTCCTCCAGCTTTCTGAAGCCAAACCG
TACAACAAGTTTTAGTAGTAAAATAAAAAGGACGAGGAGGTCGAAAGACTTCGGTTTGGC
 M  L  F  K  I  I  I  L  F  F  L  L  L  Q  L  S  E  A  K  P>
_____ CODING REGION _____>
 M  L  F  K  I  I  I  L  F  F  L  L  L  Q  L  S  E  A>
_____ SIGNAL PEPTIDE _____>
                                                          K  P>
                                                         _____>

70        80        90       100       110       120
GAAGCCCAGAGGCGCTGCGGCCGGTATTTAATTCGTTTTTTGGGGGAACTGTGTAATGGT
CTTCGGGTCTCCGCGACGCCGGCCATAAATTAAGCAAAAAACCCCCTTGACACATTACCA
 E  A  Q  R  R  C  G  R  Y  L  I  R  F  L  G  E  L  C  N  G>
_____ CODING REGION _____>
 E  A  Q  R  R  C  G  R  Y  L  I  R  F  L  G  E  L  C  N  G>
_____ B DOMAIN _____>

130       140       150       160       170       180
CCCTGCTCAGGAGTTTCAAGCGTTGACATTGCCACAATTGCCTGTGCAACCGCCGTCCCA
GGGACGAGTCCTCAAAGTTCGCAAGTGTAACGGTGTTAACGGACACGTTGGCGGCAGGGT
 P  C  S  G  V  S  S  V  D  I  A  T  I  A  C  A  T  A  V  P>
_____ CODING REGION _____>
 P  C  S  G  V  S  S  V  D>
_____ B DOMAIN _____>
                             I  A  T  I  A  C  A  T  A  V  P>
                            _____ A DOMAIN _____>

190       200       210
ATCGAAGATCTGAAGAATATGTGTTGCCCAAATTTGTGA
TAGCTTCTAGACTTCTTATACACAACGGGTTTAAACACT
 I  E  D  L  K  N  M  C  C  P  N  L  *>
_____ CODING REGION _____>
 I  E  D  L  K  N  M  C  C  P  N  L>
_____ A DOMAIN _____>
```

FIG. 27

ZC334.N4

```
         10        20        30        40        50        60
ATGAGAGCTCTCGTCGCTATTCTCTGCCTTATGGCACTATGCCATGCAGCAATGCTCGAT
TACTCTCGAGAGCAGCGATAAGAGACGGAATACCGTGATACGGTACGTCGTTACGAGCTA
  M  R  A  L  V  A  I  L  C  L  M  A  L  C  H  A  A  M  L  D>
  ─────────────────────────── CODING REGION ───────────────────>
  M  R  A  L  V  A  I  L  C  L  M  A  L  C  H  A>
  ────────────────── SIGNAL PEPTIDE ──────────────>
                                                   A  M  L  D>
                                                   ───────────>

70        80        90       100       110       120
GAGCTGGAGATGCAGAAGGAGGTTCAGGAGTTCCATCACATGAACGGCATGCTCCAAGAG
CTCGACCTCTACGTCTTCCTCCAAGTCCTCAAGGTAGTGTACTTGCCGTACGAGGTTCTC
  E  L  E  M  Q  K  E  V  Q  E  F  H  H  M  N  G  M  L  Q  E>
  ─────────────────────────── CODING REGION ───────────────────>
  E  L  E  M  Q  K  E  V  Q  E  F  H  H  M  N  G  M  L  Q  E>
  ─────────────────────────── B DOMAIN ────────────────────────>

130       140       150       160       170       180
TTCATGAATAAGGGGCTCATCGGGAATCATCACCATGGTACCAAGGCCGGCCTCACCTGC
AAGTACTTATTCCCCGAGTAGCCCTTAGTAGTGGTACCATGGTTCCGGCCGGAGTGGACG
  F  M  N  K  G  L  I  G  N  H  H  H  G  T  K  A  G  L  T  C>
  ─────────────────────────── CODING REGION ───────────────────>
  F  M  N  K  G  L  I  G  N  H  H  H  G  T  K  A  G  L  T  C>
  ─────────────────────────── B DOMAIN ────────────────────────>
```

FIG. 28A

```
         190       200       210       220       230       240
GGGATGAACATCATCGAGAGAGTCGACAAGCTGTGCAATGGGCAGTGCACTCGGAACTAT
CCCTACTTGTAGTAGCTCTCTCAGCTGTTCGACACGTTACCCGTCACGTGAGCCTTGATA
  G  M  N  I  I  E  R  V  D  K  L  C  N  G  Q  C  T  R  N  Y>
 ─────────────────────── CODING REGION ──────────────────────>
  G  M  N  I  I  E  R  V  D  K  L  C  N  G  Q  C  T  R  N  Y>
 ─────────────────────── B DOMAIN ───────────────────────────>

250       260       270       280       290       300
GATGCACTCGTCATCAAGTCCTGCCACCGCGGAGTCTCGGACATGGAGTTCATGGTGGCA
CTACGTGAGCAGTAGTTCAGGACGGTGGCGCCTCAGAGCCTGTACCTCAAGTACCACCGT
  D  A  L  V  I  K  S  C  H  R  G  V  S  D  M  E  F  M  V  A>
 ─────────────────────── CODING REGION ──────────────────────>
  D              A>
 ─────>
        L  V  I  K  S  C  H  R  G  V  S  D  M  E  F  M  V  A>
 ─────────────────── A DOMAIN ───────────────────────────────>

310       320       330
TGCTGCCCAACCATGAAGCTATTCATTCACTAA
ACGACGGGTTGGTACTTCGATAAGTAAGTGATT
  C  C  P  T  M  K  L  F  I  H  *>
 ─────── CODING REGION ──────────>
  C  C  P  T  M  K  L  F  I  H>
 ─────── A DOMAIN ───────────────>
```

FIG. 28B

ZC334.N5

```
          10        20        30        40        50        60
ATGATGCGCTCATTCTTTGTGCTCTTGGCTCTGCTCGCAATAGTCACCAGCACCGCTAGT
TACTACGCGAGTAAGAAACACGAGAACCGAGACGAGCGTTATCAGTGGTCGTGGCGATCA
  M  M  R  S  F  F  V  L  L  A  L  L  A  I  V  T  S  T  A  S>
_____ CODING REGION _____>
  M  M  R  S  F  F  V  L  L  A  L  L  A  I  V  T  S  T>
_____ SIGNAL PEPTIDE _____>
                                                        A  S>
                                                        ____>

70        80        90       100       110       120
CCCACTTGTGGCAGGGCTCTTCTACACCGGATCCAGTCGGTTTGCGGTCTCTGTACCATC
GGGTGAACACCGTCCCGAGAAGATGTGGCCTAGGTCAGCCAAACGCCAGAGACATGGTAG
  P  T  C  G  R  A  L  L  H  R  I  Q  S  V  C  G  L  C  T  I>
_____ CODING REGION _____>
  P  T  C  G  R  A  L  L  H  R  I  Q  S  V  C  G  L  C  T  I>
_____ B DOMAIN _____>

130       140       150       160       170       180
GACGCTCACCACGAACTGATTGCCATTGCCTGCTCAAGGGGACTGGGCGATAAGGAAATC
CTGCGAGTGGTGCTTGACTAACGGTAACGGACGAGTTCCCCTGACCCGCTATTCCTTTAG
  D  A  H  H  E  L  I  A  I  A  C  S  R  G  L  G  D  K  E  I>
_____ CODING REGION _____>
  D  A  H  H  E>
_ B DOMAIN ___>
                 L  I  A  I  A  C  S  R  G  L  G  D  K  E  I>
                 _____ A DOMAIN _____>

190       200
ATTGAAATGTGCTGTCCAATCTAA
TAACTTTACACGACAGGTTAGATT
  I  E  M  C  C  P  I  *>
 ___ CODING REGION ____>
  I  E  M  C  C  P  I>
  ____ A DOMAIN _____>
```

FIG. 29

ZC334.N6

```
             10         20         30         40         50
     ATGTTCTGTAAATTTGTATTCCTGATCTTTCTACTCATCTCTCTGTCAGT
     TACAAGACATTTAAACATAAGGACTAGAAAGATGAGTAGAGAGACAGTCA
      M  F  C  K  F  V  F  L  I  F  L  L  I  S  L  S  V>
     ─────────────── CODING REGION ──────────────────>
      M  F  C  K  F  V  F  L  I  F  L  L  I  S  L  S  V>
     ─────────────── SIGNAL PEPTIDE ─────────────────>

60         70         80         90        100
     GGCCACCGCTGACTTTGGCGCCCAGCGCCGTTGTGGGCGCCACTTGGTGA
     CCGGTGGCGACTGAAACCGCGGGTCGCGGCAACACCCGCGGTGAACCACT
      A  T  A  D  F  G  A  Q  R  R  C  G  R  H  L  V>
     ─────────────── CODING REGION ──────────────────>
      A  T  A>
     ─────────>
             D  F  G  A  Q  R  R  C  G  R  H  L  V>
             ─────────── B DOMAIN ──────────────────>

110        120        130        140        150
     ACTTCCTCGAGGGACTCTGCGGTGGCCCGTGCTCTGAAGCTCCGACTGTT
     TGAAGGAGCTCCCTGAGACGCCACCGGGCACGAGACTTCGAGGCTGACAA
      N  F  L  E  G  L  C  G  G  P  C  S  E  A  P  T  V>
     ─────────────── CODING REGION ──────────────────>
      N  F  L  E  G  L  C  G  G  P  C  S  E  A  P  T  V>
     ─────────────── B DOMAIN ───────────────────────>

160        170        180        190        200
     GAACTAGCTTCGTGGGCATGTTCATCAGCAGTCTCAATTCAGGATCTCGA
     CTTGATCGAAGCACCCGTACAAGTAGTCGTCAGAGTTAAGTCCTAGAGCT
      E  L  A  S  W  A  C  S  S  A  V  S  I  Q  D  L  E>
     ─────────────── CODING REGION ──────────────────>
      E>
     ──>
         L  A  S  W  A  C  S  S  A  V  S  I  Q  D  L  E>
         ─────────────── A DOMAIN ──────────────────>

210        220        230
     AAAATTGTGCTGTCCTTCAAATCTTGCTTGA
     TTTTAACACGACAGGAAGTTTAGAACGAACT
      K  L  C  C  P  S  N  L  A  *>
     ─────────── CODING REGION ──────>
      K  L  C  C  P  S  N  L  A>
     ─────── A DOMAIN ───────────>
```

FIG. 30

ZC334.N7

```
            10        20        30        40        50        60
ATGAGTTCTCACGCCCTGGTTCTTTTCCTTCTCCTTTTCCTCCTACCAGTGGCAGTGGGC
TACTCAAGAGTGCGGGACCAAGAAAAGGAAGAGGAAAAGGAGGATGGTCACCGTGACCCG
  M  S  S  H  A  L  V  L  F  L  L  L  F  L  L  P  V  A  L  G>
  _____CODING REGION_____>
  M  S  S  H  A  L  V  L  F  L  L  L  F  L  L  P  V  A  L  G>
  _____SIGNAL PEPTIDE_____>

70        80        90       100       110       120
CACTTCCTCTCCAAGCCTGCACCGGATCCAAGGATCACATTCAACCGTAAGCTTGCGGAG
GTGAAGGAGAGGTTCGGACGTGGCCTAGGTTCCTAGTGTAAGTTGGCATTCGAACGCCTC
  H  F  L  S  K  P  A  P  D  P  R  I  T  F  N  R  K  L  A  E>
  _____CODING REGION_____>
  H  F  L  S  K  P  A  P  D  P  R  I  T  F  N  R  K  L  A  E>
  _____B DOMAIN_____>

130       140       150       160       170       180
ACACTCAAGGAGCTTCAGGACATGGGACTCATCCAGGCCCCCCGTGAGCCGGTAGTGGCG
TGTGAGTTCCTCGAAGTCCTGTACCCTGAGTAGGTCCGGGGGGCACTCGGCCATCACCGC
  T  L  K  E  L  Q  D  M  G  L  I  Q  A  P  R  E  P  V  V  A>
  _____CODING REGION_____>
  T  L  K  E  L  Q  D  M  G  L  I  Q  A  P  R  E  P  V  V  A>
  _____B DOMAIN_____>
```

FIG. 31A

```
              190       200       210       220       230       240
GCTCAGGGAGCCAAGAAGACTTGCGGAAGGAGTTTGTTGATAAAGATCCAACAACTCTGC
CGAGTCCCTCGGTTCTTCTGAACGCCTTCCTCAAACAACTATTTCTAGGTTGTTGAGACG
  A  Q  G  A  K  K  T  C  G  R  S  L  L  I  K  I  Q  Q  L  C>
_____ CODING REGION _____>
  A  Q  G  A  K  K  T  C  G  R  S  L  L  I  K  I  Q  Q  L  C>
_____ B DOMAIN _____>

250       260       270       280       290       300
CATGGAATCTGCACAGTTCACGCTGATGACCTCCACGAAACGGCATGCATGAAAGGTCTC
GTACCTTAGACGTGTCAAGTGCGACTACTGGAGGTGCTTTGCCGTACGTACTTTCCAGAG
  H  G  I  C  T  V  H  A  D  D  L  H  E  T  A  C  M  K  G  L>
_____ CODING REGION _____>
  H  G  I  C  T  V  H  A  D  D>
_____ B DOMAIN _____>
                              L  H  E  T  A  C  M  K  G  L>
                           _____ A DOMAIN _____>

310       320       330       340       350       360
ACCGACTCTCAGCTGATCAACTCCTGCTGCCCACCAATCCCCCAGACACCATTCGTCTTC
TGGCTGAGAGTCGACTAGTTGAGGACGACGGGTGGTTAGGGGGTCTGTGGTAAGCAGAAG
  T  D  S  Q  L  I  N  S  C  C  P  P  I  P  Q  T  P  F  V  F>
_____ CODING REGION _____>
  T  D  S  Q  L  I  N  S  C  C  P  P  I  P  Q  T  P  F  V  F>
_____ A DOMAIN _____>
TGA
ACT
 *>
___>
```

FIG. 31B

T10D4.N

```
        10         20         30         40         50
ATGAAGATGCCCTTGATCTTGCTGCTTCTCGTCGCCGCCGCATCGGCCGTT
TACTTCTACGGGAACTAGAACGACGAAGAGCAGCGGCGGCGTAGCCGCAA
  M  K  M  P  L  I  L  L  L  V  A  A  A  S  A>
  _____ SIGNAL PEPTIDE _____>
                                              F>
                                              _>
  M  K  M  P  L  I  L  L  L  V  A  A  A  S  A  F>
  _____ CODING REGION _____>

60         70         80         90        100
CGTCCACCACTTTGACCATTCAATGTTTGCCAGACCGGAGAAAAACGTGTG
GCAGGTGGTGAAACTGGTAAGTTACAAACGGTCTGGCCTCTTTTGCACAC
  V  H  H  F  D  H  S  M  F  A  R  P  E  K  T  C>
  _____ B DOMAIN 1 _____>
  V  H  H  F  D  H  S  M  F  A  R  P  E  K  T  C>
  _____ CODING REGION _____>

110        120        130        140        150
GAGGACTACTCATTCGTCGTGTCGATAGAATTTGCCCGAATCTAAATTAT
CTCCTGATGAGTAAGCAGCACAGCTATCTTAAACGGGCTTAGATTTAATA
  G  G  L  L  I  R  R  V  D  R  I  C  P  N  L  N  Y>
  _____ B DOMAIN 1 _____>
  G  G  L  L  I  R  R  V  D  R  I  C  P  N  L  N  Y>
  _____ CODING REGION _____>

160        170        180        190        200
ACATATAAAATTGAGTGGGAACTTATGGACAACTGTTGCGAAGTGGTTTG
TGTATATTTTAACTCACCCTTGAATACCTGTTGACAACGCTTCACCAAAC
  T  Y  K  I  E  W  E  L  M  D  N  C  C  E  V  V  C>
  _____ A DOMAIN 1 _____>
  T  Y  K  I  E  W  E  L  M  D  N  C  C  E  V  V  C>
  _____ CODING REGION _____>

210        220        230        240        250
CGAGGACCAGTGGATTAAGGAAACCTTTTGCAGAGCGCCCAGGTTCAACT
GCTCCTGGTCACCTAATTCCTTTGGAAAACGTCTCGCGGGTCCAAGTTGA
  E  D  Q  W  I  K  E  T  F  C  R  A  P  R  F  N>
  _____ A DOMAIN 1 _____>
  E  D  Q  W  I  K  E  T  F  C  R  A  P  R  F  N>
  _____ CODING REGION _____>
```

FIG. 32A

```
         260       270       280       290       300
TTTTCGGACCTTCATTCAAAGCCCTTGAAAGATCGTGTGGACCAAAACTG
AAAAGCCTGGAAGTAAGTTTCGGGAACTTTCTAGCACACCTGGTTTTGAC
  F  F  G  P  S  F>
  __A DOMAIN 1___>
                   K  A  L  E  R  S  C  G  P  K  L>
                   _____ B DOMAIN 2_____>
  F  F  G  P  S  F  K  A  L  E  R  S  C  G  P  K  L>
  _____ CODING REGION_____>

310       320       330       340       350
TTCACAAGGGTTAAAACTGTGTGCGGTGAAGACATCAATGTTGATAATAA
AAGTGTTCCCAATTTTGACACACGCCACTTCTGTAGTTACAACTATTATT
    F  T  R  V  K  T  V  C  G  E>
    _____B DOMAIN 2 _____>
                            D  I  N  V  D  N  K>
                            ___A DOMAIN 2____>
    F  T  R  V  K  T  V  C  G  E  D  I  N  V  D  N  K>
    _____ CODING REGION_____>

360       370       380       390       400
AGTCAAGATTTCGGATCACTGCTGCACACCAGAGGGAGGATGCACAGACG
TCAGTTCTAAAGCCTAGTGACGACGTGTGGTCTCCCTCCTACGTGTCTGC
  V  K  I  S  D  H  C  C  T  P  E  G  G  C  T  D>
  _____ A DOMAIN 2 _____>
  V  K  I  S  D  H  C  C  T  P  E  G  G  C  T  D>
  _____ CODING REGION_____>

410       420       430       440       450
ACTGGATCAAGGAGAACGTCTGCAAACAGACCAGATTCAACTTTTTCCGA
TGACCTAGTTCCTCTTGCAGACGTTTGTCTGGTCTAAGTTGAAAAAGGCT
  D  W  I  K  E  N  V  C  K  Q  T  R  F  N  F  F  R>
  _____ A DOMAIN 2 _____>
  D  W  I  K  E  N  V  C  K  Q  T  R  F  N  F  F  R>
  _____ CODING REGION _____>
```

FIG. 32B

```
                460       470       480       490       500
          CAATTTCTCGATTCCCCTCAAAGATCATGTGGACCCCAGTTGTTCAAAAG
          GTTAAAGAGCTAAGGGGAGTTTCTAGTACACCTGGGGTCAACAAGTTTTC
           Q   F   L>
          _____>
                    D   S   P   Q   R   S   C   G   P   Q   L   F   K   R>
                    _____ B DOMAIN 3 _____>
           Q   F   L   D   S   P   Q   R   S   C   G   P   Q   L   F   K   R>
          _____ CODING REGION _____>

510       520       530       540       550
          AGTGAATACTTTGTGTAATGAAAATATCAATGTTGAAAATAATGTAAGCG
          TCACTTATGAAACACATTACTTTTATAGTTACAACTTTTATTACATTCGC
           V   N   T   L   C   N   E>
          _____ B DOMAIN 2 _____>
                               N   I   N   V   E   N   N   V   S>
                              _____ A DOMAIN 3 _____
           V   N   T   L   C   N   E   I   N   V   E   N   N   V   S>
          _____ CODING REGION _____

560       570       580       590       600
          TGTCGAAAAGCTGTTGCGAATCAGCGGCAGGATGCACGGATGATTGGATT
          ACAGCTTTTCGACAACGCTTAGTCGCCGTCCTACGTGCCTACTAACCTAA
           V   S   K   S   C   C   E   S   A   A   G   C   T   D   D   W   I>
          _____ A DOMAIN 3 _____>
           V   S   K   S   C   C   E   S   A   A   G   C   T   D   D   W   I>
          _____ CODING REGION _____>

610       620       630       640       650
          AAGAAGAATGTCTGCACACAGCATAAGCCTTTTGTTTTCCGTCCAGGCTT
          TTCTTCTTACAGACGTGTGTCGTATTCGGAAAACAAAAGGCAGGTCCGAA
           K   K   N   V   C   T   Q   H   K   P   F   V   F   R   P   G   F>
          _____ A DOMAIN 3 _____>
           K   K   N   V   C   T   Q   H   K   P   F   V   F   R   P   G   F>
          _____ CODING REGION _____>

TTACTGA
          AATGACT
           Y>
          ___>
           Y  *>
          _____>
```

FIG. 32C

T10D4.N2

```
           10         20         30         40         50
  ATGATTTTCTATCTGACAACCTACCTAGTAACTATGTCACCTCTCTTCCT
  TACTAAAAGATAGACTGTTGGATGGATCATTGATACAGTGGAGAGAAGGA
    M  I  F  Y  L  T  T  Y  L  V  T  M  S  P  L  F  L>
  _____ SIGNAL PEPTIDE _____>
    M  I  F  Y  L  T  T  Y  L  V  T  M  S  P  L  F  L>
  _____ CODING REGION _____>

60         70         80         90        100
  GATCCTGTTGCTTCTAGTCTCTACCACTTACCCTTACATCATTGACTCTT
  CTAGGACAACGAAGATCAGAGATGGTGAATGGGAATGTAGTAACTGAGAA
     I  L  L  L  V  S  T  T  Y  P>
  _____ SIGNAL PEPTIDE _____>
     I  L  L  L  V  S  T  T  Y  P  Y  I  I  D  S>
  _____ CODING REGION _____>
                              Y  I  I  D  S>
                           __ B DOMAIN ____>

110        120        130        140        150
  CGGAGAGTTATGAAGTTCTAATGCTATTCGGGTATAAGAGAACATGTGGA
  GCCTCTCAATACTTCAAGATTACGATAAGCCCATATTCTCTTGTACACCT
    S  E  S  Y  E  V  L  M  L  F  G  Y  K  R  T  C  G>
  _____ CODING REGION _____>
    S  E  S  Y  E  V  L  M  L  F  G  Y  K  R  T  C  G>
  _____ B DOMAIN _____>

160        170        180        190        200
  CGACGCTTGATGAACAGGATTAATAGAGTATGCGTGAAGGATATAGATCC
  GCTGCGAACTACTTGTCCTAATTATCTCATACGCACTTCCTATATCTAGG
    R  R  L  M  N  R  I  N  R  V  C  V  K  D  I  D  P>
  _____ CODING REGION _____>
    R  R  L  M  N  R  I  N  R  V  C  V  K  D  I  D>
  _____ B DOMAIN _____>
                                                    P>
                                                   ___>
```

FIG. 33A

```
          210         220         230         240         250
AGCAGATATCGATCCGAAGATCAAATTATCGGAGCACTGTTGTATCAAGG
TCGTCTATAGCTAGGCTTCTAGTTTAATAGCCTCGTGACAACATAGTTCC
  A  D  I  D  P  K  I  K  L  S  E  H  C  C  I  K>
 _____ CODING REGION _____>
  A  D  I  D  P  K  I  K  L  S  E  H  C  C  I  K>
 _____ A DOMAIN _____>

260         270         280         290         300
GATGCACAGATGGATGGATCAAGAAGCATATTTGCAGTGAGGAAGTTCTG
CTACGTGTCTACCTACCTAGTTCTTCGTATAAACGTCACTCCTTCAAGAC
  G  C  T  D  G  W  I  K  K  H  I  C  S  E  E  V  L>
 _____ CODING REGION _____>
  G  C  T  D  G  W  I  K  K  H  I  C  S  E  E  V  L>
 _____ A DOMAIN _____>

310         320
AATTTTGGATTTTTTGAAAATTGA
TTAAAACCTAAAAAACTTTTAACT
  N  F  G  F  F  E  N  *>
 ____ CODING REGION ____>
  N  F  G  F  F  E  N>
 _____ A DOMAIN _____>
```

FIG. 33B

Y522A1.N

```
              10        20        30        40        50        60
     ATGCAAAGCCTACCAATTCTTGCCTGCCTCCTCACACTGTCAGTTTTTGCGCCGGAAATT
     TACGTTTCGGATGGTTAAGAACGGACGGAGGAGTGTGACAGTCAAAAACGCGGCCTTTAA
       M  Q  S  L  P  I  L  A  C  L  L  T  L  S  V  F  A  P  E  I>
     ───────────────────────── SIGNAL PEPTIDE ──────────────────────>
       M  Q  S  L  P  I  L  A  C  L  L  T  L  S  V  F  A  P  E  I>
     ──────────────────────── CODING REGION ────────────────────────>

70        80        90       100       110       120
     CATGGCCGGGAGCTCAAACGTTGTTCTGTGAAACTTTTTGATATTCTAAGCGTAATTTGT
     GTACCGGCCCTCGAGTTTGCAACAAGACACTTTGAAAAACTATAAGATTCGCATTAAACA
       H  G>
     ──────>
       H  G  R  E  L  K  R  C  S  V  K  L  F  D  I  L  S  V  I  C>
     ──────────────────────── CODING REGION ────────────────────────>
             R  E  L  K  R  C  S  V  K  L  F  D  I  L  S  V  I  C>
     ─────────────────────────── B DOMAIN ──────────────────────────>

130       140       150       160       170       180
     GGAACTGAAAGTGATGCAGAAATTCTACAAAAAGTCGCAGTGAAATGCTGCCAGGAGCAG
     CCTTGACTTTCACTACGTCTTTAAGATGTTTTTCAGCGTCACTTTACGACGGTCCTCGTC
       G  T  E  S  D  A  E  I  L  Q  K  V  A  V  K  C  C  Q  E  Q>
     ──────────────────────── CODING REGION ────────────────────────>
       G  T  E  S  D  A  E>
     ──────── B DOMAIN ────>
                         I  L  Q  K  V  A  V  K  C  C  Q  E  Q>
                       ─────────────── A DOMAIN ───────────────>

190       200       210       220       230
     TGTGGGTTTGAGGAAATGTGCCAGCATGCCAACTTGAAAATCGACAAAATTTAA
     ACACCCAAACTCCTTTACACGGTCGTACGGTTGAACTTTTAGCTGTTTTAAATT
       C  G  F  E  E  M  C  Q  H  A  N  L  K  I  D  K  I  *>
     ──────────────────────── CODING REGION ──────────────────>
       C  G  F  E  E  M  C  Q  H  A  N  L  K  I  D  K  I>
     ─────────────────────── A DOMAIN ────────────────────────>
```

FIG. 34

NUCLEIC ACIDS AND PROTEINS OF C. ELEGANS INSULIN-LIKE GENES AND USES THEREOF

This application is a continuation-in-part of U.S. patent application Ser. No. 09/074,984 filed May 8, 1998, now abandoned entitled "NUCLEIC ACIDS AND PROTEINS OF C. ELEGANS INSULIN-LIKE GENES AND USES THEREOF" by Buchman et al., which is a continuation-in-part of U.S. patent application Ser. No. 09/062,580 filed Apr. 17, 1998, now abandoned entitled "NUCLEIC ACIDS AND PROTEINS OF C. ELEGANS INSULIN-LIKE GENES AND USES THEREOF" by Homburger et al., each of which is incorporated herein by reference in its entirety.

1. INTRODUCTION

The present invention relates to C. elegans insulin-like genes and methods for identifying insulin-like genes. The methods provide nucleotide sequences of C. elegans insulin-like genes, amino acid sequences of their encoded proteins, and derivatives (e.g., fragments) and analogs thereof. The invention further relates to fragments (and derivatives and analogs thereof) of insulin-like proteins which comprise one or more domains of an insulin-like protein. Antibodies to an insulin-like protein, and derivatives and analogs thereof, are provided. Methods of production of an insulin-like protein (e.g., by recombinant means), and derivatives and analogs thereof, are provided. Methods to identify the biological function of a C. elegans insulin-like gene are provided, including various methods for the functional modification (e.g., overexpression, underexpression, mutation, knock-out) of one gene, or of two or more genes simultaneously. Methods to identify a C. elegans gene which modifies the function of, and/or functions in a downstream pathway from, an insulin-like gene are provided.

2. BACKGROUND OF THE INVENTION

Citation of references herein shall not be construed as an admission that such references are prior art to the present invention.

2.1. The Insulin Superfamily

Insulin-like proteins are a large and widely-distributed group of structurally-related peptide hormones that have pivotal roles in controlling animal growth, development, reproduction, and metabolism (Blundell and Humbel, 1980, "Hormone families: pancreatic hormones and homologous growth factors", Nature 287:781–787). Consequently, the insulin superfamily has become one of the most intensively investigated classes of peptide hormones. Such hormones have a vast array of uses including, for example, clinical applications in human disease, management of fish and livestock, and the control of agriculturally-important animal pests. At least five different subfamilies of insulin-like proteins have been identified in vertebrates, represented by insulin (Steiner et al., 1989, in Endocrinology, DeGroot, ed., Philadelphia, Saunders, pp. 1263–1289), insulin-like growth factor (IGF, previously termed somatomedin) (Humbel, 1990, "Insulin-like growth factors I and II", Eur. J. Biochem. 190:445–462), relaxin (Schwabe and Bullesback, 1994, "Relaxin: structures, functions, promises, and nonevolution", FASEB J. 8:1152–1160), relaxin-like factor (RLF, previously called Leydig cell-specific insulin-like peptide) (Adham al., 1993, "Cloning of a cDNA for a novel insulin-like peptide of the testicular Leydig cells", J. Biol. Chem. 268:26668–26672; Ivell, 1997, "Biology of the relaxin-like factor (RLF)", Reviews of Reproduction 2:133–138), and placentin (also known as early placenta insulin-like peptide, or ELIP) (Chassin et al., 1995, "Cloning of a new member of the insulin gene superfamily (INSL4) expressed in human placenta", Genomics 29:465–470).

Insulin superfamily members in invertebrates have been less extensively analyzed than in vertebrates, but a number of different subgroups have been defined. Such subgroups include molluscan insulin-related peptides (MIP-I to MIP-VII) (Smit et al., 1988, "Growth-controlling molluscan neurons produce the precursor of an insulin-related peptide", Nature 331:535–538; Smit et al., 1995, "Expression and characterization of molluscan insulin-related peptide VII from the mollusc Lymnaea stagnalis", Neuroscience 70:589–596), the bombyxins of lepidoptera (originally referred to as prothoracicotropic hormone or PTTH) (Kondo et al., 1996, "Multiple gene copies for bombyxin, an insulin-related peptide of the silkmoth Bombyx mori: structural signs for gene rearrangement and duplication responsible for generation of multiple molecular forms of bombyxin", J Mol. Biol. 259:926–937), and the locust insulin-related peptide (LIRP) (Lagueux et al., 1990, "cDNAs from neurosecretory cells of brains of Locusta migratoria (Insecta, Orthoptera) encoding a novel member of the superfamily of insulins", Eur. J. Biochem. 187:249–254). Most recently, putative orthologs of both vertebrate insulin and IGF have been identified in a tunicate (McRory and Sherwood, 1997, "Ancient divergence of insulin and insulin-like growth factor", DNA and Cell Biology 116:939–949). This is of significance since tunicates are thought to be the closest living invertebrate relative to the progenitor from which vertebrates evolved (Id.).

Comparison of the primary sequence of insulin superfamily peptides, cDNAs, and genes, as well as the overall conservation of functional and structural domains of insulin-like genes and proteins, lead to the conclusion that existing members of the insulin superfamily evolved from a common ancestral gene (Blundell and Humbel, 1980, Id.). From the extensive sequence divergence evident among known subfamilies of insulin-like proteins, it is assumed that this is an ancient family of regulatory hormones that evolved to control growth, reproduction and metabolism in early metazoans. However, the precise evolutionary origins of this important family remain unclear. Indeed, until now, no bona fide insulin-like proteins or genes had been identified in metazoan orders more primitive than insecta.

2.1.1. Common Structural Themes

There are common structural themes that unite the insulin superfamily of proteins. All insulin-like peptide hormones are synthesized in vivo as precursor proteins having structures that are variations of the structure schematically represented in FIG. 1. Most precursor forms of the insulin superfamily can be divided into four domains, termed Pre, B, C, and A domains, extending in order from the N-terminus to the C-terminus of a precursor polypeptide (see FIG. 1). Precursors of the IGF subfamily are distinguished by having two additional domains at the C-terminal end, termed D and E domains. The N-terminal Pre domain typically contains a hydrophobic signal sequence which directs secretion of the hormone from cells and is removed by the enzymatic action of a signal peptidase during transit into the endoplasmic reticulum (see the asterisk in FIG. 1). Upon folding, the prohormone undergoes additional processing which, in most cases, involves proteolytic cleavage at two sites that excise the C peptide from the mature hormone (see the left-hand and middle arrows illustrated in FIG. 1). These processing steps are mediated by prohormone convertases that cleave at specific positions next to basic residues in the C peptide sequence. As a result, most forms of mature insulin superfamily hormones consist of two polypeptide chains, the A and B peptides, which are covalently joined by disulfide linkages (S—S) between Cys residues (see S—S linkages illustrated in FIG. 1). The precise arrangement of Cys residues and disulfide linkages, both between and within the A and B peptides, is highly characteristic of the insulin superfamily of hormones. Nearly all known insulin superfamily members contain six precisely-positioned Cys residues, two in the B chain and four in the A chain, which participate in the formation of three disulfide bonds. Two of these disulfide linkages covalently join the B and A chains (i.e., they form inter-chain bonds), whereas the third disulfide linkage occurs within the A peptide (i.e., as an intra-chain bond) and appears to stabilize a bend in the A chain fold.

The IGF subfamily of hormones has a unique processing pathway. In this subfamily, the connecting C peptide is not removed by processing of the prohormone. Instead, a single proteolytic cleavage event removes the C-terminal E domain (see the right-hand arrow illustrated in FIG. 1). Consequently, mature hormones of the IGF subfamily contain a single polypeptide chain with contiguous B, C, A, and D domains. Despite this difference in proteolytic processing, the disulfide bonding pattern between Cys residues in the IGF subfamily is identical to that of other superfamily members.

In summary, FIG. 1 illustrates the structural organization of precursor forms of the insulin superfamily of hormones. The different domains that make up precursor forms of insulin-like hormones are represented as boxes labeled Pre, B, C, A, D, and E, extending from the N-terminus (left) to the C-terminus (right) of the nascent polypeptide chain, respectively. Domains that may remain in a mature hormone are represented as unshaded boxes (the B, A, and D peptide domains) or as lightly hatched (the C or "connecting" peptide domain). By contrast, domains that are removed during proteolytic processing are represented as shaded (the Pre peptide domain) or as hatched (the E peptide domain). IGF hormones are unique in having D and E peptide domains; these domains are represented as smaller boxes in FIG. 1. Cleavage sites utilized by proteases during proteolytic processing (i.e., protein maturation) are indicated below the boxes. The asterisk marks the position of cleavage by signal peptidase. Arrows indicate cleavage sites by prohormone convertases. Disulfide bonds (S—S) are represented above the boxes with lines indicating connections between covalently-bonded Cys residues.

Figure 2:
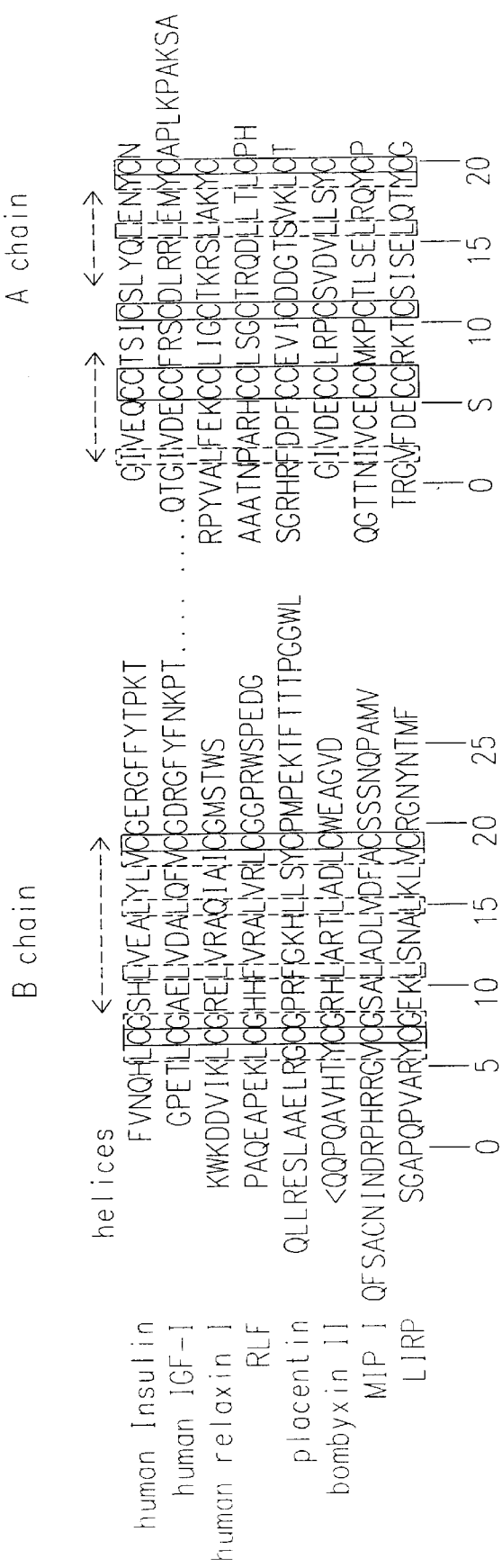

Since the A and B peptide domains constitute common structural segments among all mature insulin superfamily hormones, it is not surprising that these domains are the most highly conserved at the primary sequence level. Even among closely-related members of this superfamily, the domains removed by proteolytic processing (i.e., Pre, C and E domains) can differ extensively in amino acid sequence composition (McRory and Sherwood, 1997, Id.); Murray-Rust et al., 1992, "Structure and evolution of insulins: Implications for receptor binding", BioEssays 14:325–331), in marked contrast to the A and B peptides. Much of the amino acid sequence conservation within the A and B peptide domains reflects residues that play key roles in forming the secondary and tertiary structural elements that are characteristic of the insulin superfamily fold. Aligned sequences of A and B peptide domains from diverse insulin superfamily members are depicted in FIG. 2. This alignment serves to highlight the arrangement of conserved amino acid positions and their relationship to the overall folding pattern of the protein. The three dimensional structures of a number of different insulin superfamily proteins have been determined. Such superfamily proteins include insulin (Hua et al., 1991, "Receptor binding defined by a structural switch in a mutant human insulin", Nature 354:238–241), relaxin (Eigenbrot et al., 1991, "X-ray structure of human relaxin at 1.5 angstroms", J. Mol. Biol. 221:15–21), IGF (Cooke et al., 1991, "Solution structure of human insulin-like growth factor I: a nuclear magnetic resonance and restrained molecular dynamics study", Biochemistry 30:5484–5491), and bombyxin (Nagata et al., 1995, "Three-dimensional solution structure of bombyxin-II, an insulin-like peptide of the silkmoth *Bombyx mori*: structural comparison with insulin and relaxin", J. Mol. Biol. 253:749–758). The detailed geometry of amino acid side chains in these structures, as well as common secondary and tertiary structural themes, have provided valuable clues about the forces that promote the formation of the characteristic insulin fold. Common features of the main chain fold of insulin-like structures consist of the following: (1) two helices within the A chain joined by a loop; (2) an extended, N-terminal coil within the B chain followed by a tight turn and a central helix; (3) a hydrophobic cluster or "core" that forms an interface between juxtaposed surfaces of the A and B chains; and (4) three disulfide bonds. The common helical regions found in the A and B chains are illustrated in FIG. 2 above the alignment (see "<--->" symbols in FIG. 2).

Beyond the above-described general features of insulin-like structures, there are an number of specific features that are unique to the various subfamilies of insulin-like proteins. Notably, in insulin and IGFs, the main chain following the B peptide central helix forms a tight turn and an extended beta-strand. By contrast, the B chain in both relaxin and bombyxin adopts a fold comprising an extended central helix followed by a coil.

2.1.2. Number and Spacing of CYS Residues

The stereotypical arrangement of Cys residues which participate in disulfide linkages within the A and B chains was noted above. It is striking that the exact number and spacing of Cys residues is nearly invariant among insulin-like proteins (see positions B7, B19, A6, A7, A11 and A20, with respect to the human insulin sequence in FIG. 2). Among over 140 sequenced members of the insulin superfamily, only a few show deviations from the canonical arrangement of Cys residues. Further, when differences in the arrangement do occur, they tend to be relatively minor. For example, in the case of murine relaxin, the last two Cys residues of the A chain are separated by a spacer of 9 amino acids instead of the canonical 8 amino acids (Evans et al., 1993, "The mouse relaxin gene: nucleotide sequence and expression", J. Mol. Endocrinol. 10:15–23). Another interesting variation occurs in the molluscan insulin-like protein (MIP-I). MIP-I appears to have two extra Cys residues, one located N-terminal to the conserved Cys residues within the A chain and the other located N-terminal to the conserved Cys residues of the B chain (see FIG. 2) (Smit et al., 1988, "Growth-controlling molluscan neurons produce the precursor of an insulin-related peptide", Nature 331:535–538). It has been proposed that this extra pair of Cys residues within MIP-I forms an additional disulfide bond between the A and B chains, thus providing further stability to the folded structure of MIP-I (Id.).

The characteristic insulin core that makes up the interface between the A and B chains is composed of a set of side chains whose conserved hydrophobic nature helps stabilize a tight association. The side chains that participate in the core structure correspond to positions A2, A16, A19, B6, B11, B15, and B18 (see FIG. 2). In addition, the A6–A11 and B19–A20 disulfide bonds are enveloped within the core structure. One other highly-conserved residue within the insulin superfamily is that at B8, which is almost always Gly. The unique flexibility of Gly in this position allows the formation of a tight turn between the extended N-terminus of the B chain and the central helix that immediately follows. Gly residues appear to play a similar role in other positions that promote unique structural features of different insulin subfamily folding patterns. For instance, the Gly at position B20 in insulin and IGF appears important in allowing the formation of a tight turn between the central helix and the following beta-strand of the B chain, a hallmark of this subfamily of structures (Blundell et al., 1972, "Insulin: the structure in the crystal and its reflection in chemistry and biology", Adv. Protein Chem. 26:279–402). Similarly, a Gly at position A10 in relaxins has been shown to be important for the formation of an exceptionally tight turn between the two A chain helices within the folding pattern of this subfamily (Schwabe and Bullesback, 1994, "Relaxin: structures, functions, promises, and nonevolution", FASEB J. 8:1152–1160).

2.1.3. Receptor-LIGAND Recognition

An intriguing feature of this diverse family of peptide hormones is the nature of receptor-ligand recognition and the structural basis of its specificity. Although no structures have yet been solved for insulin superfamily receptor-ligand complexes, the issue has been explored through mutational analysis and structure-activity studies of a number of insulin superfamily hormones. The collected results of studies of insulin, relaxin and bombyxin have led to the hypothesis that a common surface is employed by these hormones for receptor-ligand interaction, composed of the central portion of the B chain and the A chain N- and C-termini (Hua et al., 1991, Id.; Blundell et al., 1972, Id.; Murray-Rust et al., 1992, Id.; Nagata et al., 1995, Id.; Bullesbach et al., 1996, "Chemical synthesis of a zwitterhormon, insulaxin, and of a relaxin-like bombyxin derivative", Biochemistry 35: 9754–9760; Kristensen et al., 1997, "Alanine scanning mutagenesis of insulin", J. Biol. Chem. 272:12978–12983; Schaffer, 1994, "A model for insulin binding to the receptor", Eur. J. Biochem. 221:1127–1132).

It appears that insulin and relaxin utilize other structural features for receptor recognition beyond these common elements, specifically, the C-terminus of the B chain in insulin and IGF, and the extended A chain N-terminal helix in relaxin (Nagata et al., 1995, Id.; Bullesbach et al., 1996, Id.; Kristensen et al., 1997, Id.). Clearly, it is the precise nature of specific amino acid side chains within the receptor recognition surface that contribute to the affinity and specificity of receptor binding. In this regard, a comparison of the residues implicated in receptor recognition for insulin versus relaxin is informative since these two hormones associate with distinct receptor molecules with no evidence for cross-recognition (Rawitch et al., 1980, "Relaxin-insulin homology: predictions of secondary structure and lack of competitive binding", Int. J. Biochem. 11:357–362).

Residues implicated in insulin receptor recognition include GlyA1, IleA2, ValA3, LeuA13, TyrA19 and AsnA21 on the A chain and ValB12, TyrB16, LeuB17, PheB24, PheB25, and TyrB26 on the B chain (see FIG. 2). A striking feature of this constellation of side chains is that they are largely hydrophobic in character, particularly through the B chain central helix and beta-strand. It is significant that, within the IGF-I sequence, most of the same positions are occupied by either identical or closely-related amino acids to those found in insulin (see FIG. 2). This is consistent with the observation that, although insulin and IGF-I preferentially associate with distinct receptor molecules, there is still measurable cross-recognition by the receptors. Such cross-recognition is believed to be of physiological significance in vivo, perhaps permitting crosstalk between signals controlling growth and metabolism (Humbel, 1990, Id.).

In relaxin, by marked contrast, two hydrophilic basic residues have been shown to be critical for receptor recognition. These relaxin residues, ArgB9 and ArgB13 (see FIG. 2), protrude one turn apart from the central B helix (Eigenbrot et al., 1991. Id.). Not surprisingly, this pair of Arg residues at positions B9 and B13 are rather distinctive for the relaxin subfamily hormones within vertebrates. Other residues implicated in human relaxin II-receptor recognition include TyrA(-1), PheA19, ValB12, GlnB15 and IleB16 (Bullesbach and Schwabe, 1988, "On the receptor binding site of relaxins", Int. J. Peptide Protein Res. 32:361–367).

In summary, FIG. 2 illustrates conserved structural features of known insulin superfamily members. The aligned sequences of the B and A chain peptide domains are shown for representative insulin superfamily hormones from the following vertebrates and invertebrates: human insulin (Bell et al., 1979, "Nucleotide sequence of a cDNA clone encoding human preproinsulin", Nature 29:525–527), human IGF-I (Jansen et al., 1983, "Sequence of cDNA encoding human insulin-like growth factor I precursor", Nature 306:609–611), human relaxin 1 (Hudson et al., 1983, "Structure of a genomic clone encoding biologically active human relaxin", Nature 301:628–631, RLF from human (Adham al., 1993, "Cloning of a cDNA for a novel insulin-like peptide of the testicular Leydig cells", J. Biol. Chem. 268:26668–26672), placentin from human (Chassin et al., 1995, "Cloning of a new member of the insulin gene superfamily (INSL4) expressed in human placenta", Genomics 29:465–470), bombyxin II from silkworm (Nagasawa et al., 1986, "Amino acid sequence of a protho-racicotropic hormone of the silkworm *Bombyx mori*", Proc. Natl. Acad. Sci. U.S.A. 83:5840–5843), MIP from freshwater snail (Smit et al., 1988, "Growth-controlling molluscan neurons produce the precursor of an insulin-related peptide", Nature 331:535–538), and LIRP from locust (Lagueux et al., 1990, "cDNAs from neurosecretory cells of brains of *Locusta migratoria* (Insecta, Orthoptera) encoding a novel member of the superfamily of insulins", Eur. J. Biochem. 187:249–254). The numbering scheme shown at the bottom of the figure is for residues of the A and B chains relative to residue numbers for human insulin peptide domains. The nearly invariant positions of the six Cys residues that participate in disulfide bonds are boxed. MIP-I is unique in having two extra Cys residues which are also individually boxed in that sequence. Other conserved amino acid positions that play important roles in promoting the common insulin superfamily fold are highlighted by shading of the following residue positions: B6, B8, B11, B15, B18, A2, A16, and A19. Three helical regions that comprise the common insulin fold are marked above the alignments using a "<--->" symbol.

2.2. Human Insulin-like Proteins and Therapeutic Applications

As noted above, five different subfamilies of insulin-like hormones are now recognized in humans: insulin, IGF, relaxin, RLF, and placentin. Two of these subfamilies (i.e., RLF and placentin) have been discovered relatively recently and their actual biological roles and corresponding clinical applications remain to be determined. The other three subfamilies (i.e., insulin, IGF and relaxin) have been studied much more extensively and their roles in regulating growth, differentiation, and metabolism has yielded clinical applications of profound and well-known importance, as described briefly below.

2.2.1. Insulin

Insulin is the central hormone governing metabolism in vertebrates (reviewed in Steiner et al., 1989, Id.). In humans, insulin is secreted by the beta cells of the pancreas in response to elevated blood glucose levels which normally occur following a meal. The immediate effect of insulin secretion is to induce the uptake of glucose by muscle, adipose tissue, and the liver. A longer term effect of insulin is to increase the activity of enzymes that synthesize glycogen in the liver and triglycerides in adipose tissue. Insulin can exert other actions beyond these "classic" metabolic activities, including increasing potassium transport in muscle, promoting cellular differentiation of adipocytes, increasing renal-retention of sodium, and promoting production of androgens by the ovary. Defects in the secretion and/or response to insulin are responsible for the disease diabetes mellitus, which is of enormous economic significance. Within the United States, diabetes mellitus is the fourth most common reason for physician visits by patients; it is the leading cause of end-stage renal disease, non-traumatic limb amputations, and blindness in individuals of working age (Warram et al., 1995, "Epidemiology and genetics of diabetes mellitus", In *Joslin's Diabetes Mellitus*, Kahn and Weir, eds., Philadelphia, Lea & Febiger, pp. 201–215; Kahn et al., 1996, "Genetics of non-insulin dependent (type-II) diabetes mellitus", Annu. Rev. Med. 47:509–531; Kahn, 1998, "Type 2 diabetes: when insulin secretion fails to compensate for insulin resistance", Cell 92:593–596). Two basic forms of diabetes mellitus occur in humans: type I or insulin-dependent diabetes, and type II or non-insulin-dependent diabetes. A critical problem in managing diabetic patients comes from the phenomenon of insulin resistance, as well as the compounding long term effects of abnormal insulin levels in these individuals. Beyond its role in diabetes mellitus, the phenomenon of insulin resistance has been linked to other pathogenic disorders including obesity, ovarian hyperandrogenism, and hypertension.

The physiologic effects of insulin are mediated by specific association of the peptide hormone with a cell surface receptor, the insulin receptor (IR), with concomitant activation of a signal transduction pathway in responding tissues. The IR has been well-characterized at the molecular level; it is a member of a large family of tyrosine kinase receptors (Ullrich et al., 1985, "Human insulin receptor and its relationship to the tyrosine kinase family of oncogenes", Nature 313:756–761). IR signaling has been shown to involve a number of intracellular participants (White and Kahn, 1994, "The insulin signalling system", J. Biol. Chem. 269:1–4; Kahn et al., 1998, Id.). These participants include the so-called insulin receptor substrate, or IRS-1, which is phosphorylated by an activated insulin receptor kinase. IRS-1 in turn associates with phosphatidyl-inositol-3-kinase (PI3K). A number of other protein kinases and signaling proteins have been implicated in this signal transduction mechanism and presumably participate in a "kinase cascade" that leads to the modification and regulation of a host of intracellular enzymes, structural proteins, and transcription factors. Nonetheless, the precise choreography of events involved in insulin signaling remains vague, and a deeper understanding of such events is likely to have application in surmounting the major clinical problem of insulin resistance. In summary, while clinical issues associated with abnormal insulin levels have raised interest in factors regulating the synthesis, secretion and turnover of insulin, many of the underlying regulatory mechanisms remain to be clarified.

2.2.2. IGF

Humans express two forms of the IGF subfamily of insulin-like hormones, termed IGF-I and IGF-II (Humbel, 1990, Id.). These proteins have been found to exert powerful mitogenic effects on a variety of cells and tissues, reflecting their normal physiologic role of promoting growth in developing animals. IGF-I is apparently the primary mediator of growth hormone signaling and, as such, is a major mediator of growth of the skeletal system following birth. IGF-II may have a significant role in fetal growth. Detailed studies with IGF-I, in particular, have led to a variety of significant clinical applications in humans which relate to its growth-promoting and mitogenic properties, including treatment of injuries to the central nervous system, peripheral neuropathy, disorders of the gut, osteoporosis, and congestive heart failure, as well as the acceleration of wound-healing (Gluckman and Nikolics, 1988, "IGF-1 to improve neural outcome", U.S. Pat. No. 5,714,460; Ballard and Read, 1997, "Method for treating intestinal diseases", U.S. Pat. No. 5,679,771; Clark et al., 1997, Treatment of congestive heart failure", U.S. Pat. No. 5,661,122; Lewis et al., 1997, "Prevention and treatment of peripheral neuropathy", U.S. Pat. Nos. 5,420,112, 5,633,228 and 5,648,335; Burk, 1997, "Composition and method for the treatment of osteoporosis in mammals", U.S. Pat. No. 5,646,116; Antoniades and Lynch, 1993, "Wound healing using IGF-II and TGF", U.S. Pat. No. 5,256,644). Since administration of IGF-I has been shown to increase the growth and size of animals, there are possible applications of this hormone in animal husbandry (Humbel, 1990, Id.). As mentioned above, IGFs can elicit insulin-like effects in muscle and adipose tissue, and there is evidence that IGF-I administration may be useful when administered together with insulin in the treatment of diabetes (MacCuish, 1997, "Treatment of insulin-resistant diabetes", U.S. Pat. No. 5,674,845).

2.2.3. Relaxin

The peptide hormone relaxin was first identified as an active substance in extracts of corpora lutea that induced the separation and relaxation of the pubic symphysis in guinea pigs (Schwabe and Bullesback, 1994, Id.). Thus, it was originally believed that the primary physiologic role of relaxin was one associated with promoting parturition during pregnancy. Subsequent studies have confirmed this role in pregnancy for rodents and ruminants. However, the importance of relaxin to the physiology of normal pregnancy in humans is still somewhat in question (Bani, 1997, "Relaxin: a pleiotropic hormone", Gen. Pharmacol. 28:13–22). Recent studies of relaxin have revealed a more complicated and interesting picture of the spectrum of activities of this peptide hormone. Specifically, relaxin has been found to control growth and differentiation of breast cancer cells in vitro, promote blood vessel dilation, have a chronotropic action on the heart, inhibit histamine release by mast cells, affect pituitary hormone secretion, and regulate fluid balance. Given this array of physiologic effects, it is not surprising that a number of clinical applications of relaxin have been pursued. These therapeutic applications of relaxin in humans have included the treatment of intractable pain caused by the swelling or dislocation of tissues, as well as the treatment of congestive heart failure, bradycardia, and neurodegenerative diseases (Cronin et al., 1992, "Use of relaxin in cardiovascular therapy", U.S. Pat. No. 5,166,191; Cronin et al., 1995, "Use of relaxin in the treatment of bradycardia", U.S. Pat. No. 5,478,807; Yue, 1998, "Method of treating fibromyalgia with relaxin", U.S. Pat. No. 5,707,642). Two forms of relaxin, which are encoded by separate genes, have been identified in humans (Hudson et al., 1983, "Structure of a genomic clone encoding biologically active human relaxin", Nature 301:628–631; Hudson et al., 1984, "Relaxin gene expression in human ovaries and the predicted structure of a human preprorelaxin by analysis of cDNA clones", EMBO J. 3:2333–2339). In contrast to insulin and the IGFs, the specific receptor protein(s) for the relaxins have yet to be characterized at either the DNA or protein sequence level.

2.3. Invertebrate Insulin-like Proteins and Applications to Pest Control

Studies of insulin-like molecules in invertebrates have been motivated by the desire to identify proteins which play analogous roles to the well-characterized activities of insulin and IGF in mammals. If such hormone activity existed in invertebrates, it would provide an avenue to target the growth, feeding and reproduction of agriculturally-important pest species. The first invertebrate insulin-like proteins to be discovered were the bombyxins of lepidoptera, and they remain the best characterized (Nagasawa et al., 1986, "Amino acid sequence of a prothoracicotropic hormone of the silkworm *Bombyx mori*", Proc. Natl. Acad. Sci. U.S.A. 83:5840–5843). Bombyxin, as the name implies, was first identified in extracts of adult heads of the silkworm *Bombyx mori*. Curiously, it was found that bombyxin stimulated prothoracic glands of the heterologous moth *Samia cynthia ricini* to synthesize and secrete ecdysteroid hormone. However, no prothoracicotropic activity was observed when bombyxin was injected into *Bombyx mori*, raising questions about its normal function in this organism (Kiriishi et al., 1992, "Comparison of the in vivo and in vitro effects of bombyxin and prothoracicotropic hormone on prothoracic glands of the silkworm, *Bombyx mori*", Zool. Sci. 9:149–155). Bombyxin is produced by neurosecretory cells within the brain of the silkworm and released into the hemolymph. Recent studies with synthetic bombyxin have suggested a role in regulating carbohydrate metabolism with some similarities to the function of insulin in mammals. When injected into neck-ligated larvae, bombyxin reduced the concentration of the major hemolymph sugar, trehalose, and caused elevated activity of trehalase in the midgut and muscle (Satake et al., 1997, "Bombyxin, an insulin-related peptide of insects, reduces the major storage carbohydrates in the silkworm *Bombyx mori*", Comp. Biochem. Physiol. 188B:349–357). Additional studies have revealed a remarkable array of bombyxin genes—over 30 separate bombyxin genes have now been identified in the haploid genome of the silkworm (Kondo et al., 1996, Id.). The bombyxin genes are organized in clusters, and sequence comparisons have led to the categorization of six different gene subtypes. Thus far, all of the bombyxin genes appear to be specifically expressed within four pairs of medial neurosecretory cells in the brain of the silkworm.

DNA-based approaches have been used to isolate insulin-like genes from other invertebrate species, including the LIRP gene from the locust and the MIP-I through MIP-VII series of genes from the freshwater snail (Smit et al., 1998, "Towards understanding the role of insulin in the brain: lessons from the insulin-related signaling systems in the invertebrate brain", Prog. Neurobiol. 54:35–54). The biological function of these other invertebrate superfamily members remains largely uncharacterized. One common theme is that the major site of expression of locust and snail invertebrate insulin-like hormones is in the central nervous system, particularly neurosecretory cells, as has also been observed for the bombyxins of lepidoptera. In the freshwater snail, the cerebral light-green cells, which are the main cells that express the MIP proteins, have been associated with endocrine functions that control glycogen metabolism and the regulation of growth of soft body parts and the shell (Smit et al., 1988, Id.).

2.4. Insulin Signaling in Invertebrate Genetic Model Organisms

Important issues raised in the preceding discussion regarding the biological function, regulation, and signaling mechanisms of insulin superfamily hormones could best be addressed if these pathways could be analyzed using model genetic organisms. In particular, the facile genetic tools currently available in two model organisms, the fruit fly *Drosophila melanogaster* and the nematode *Caenorhabditis elegans*, have proven to be of enormous utility in defining the biological function of genes through mutational analysis, as well as for identifying the components of biochemical pathways conserved during evolution with large-scale, systematic genetic screens (Scangos, 1997, "Drug discovery in the postgenomic era", Nature Biotechnol. 15:1220–1221; Miklos and Rubin, 1996, "The role of the genome project in determining gene function: insights from model organisms", Cell 86:521–529). Key discoveries regarding constituents of a number of important human disease pathways, such as the Ras pathway and the pathway controlling programmed cell death, first came from genetic analysis of pathways known to have an evolutionary relation in Drosophila and *C. elegans*, and later shown to have direct relevance to human biology (Yuan et al., 1993, "The *C. elegans* cell death gene ced-3 encodes a protein similar to mammalian interleukin-1 beta-converting enzyme", Cell 75:641–652; Therrien et al., 1995, "KSR, a novel protein kinase required for RAS signal transduction", Cell 83:879–888; Karim et al., 1996, "A screen for genes that function downstream of Ras1 during Drosophila eye development", Genetics 143:315–329; Kornfeld et al., 1995, "The ksr-1 gene encodes a novel protein kinase involved in Ras-mediated signaling in *C. elegans*", Cell 83:903–913; Rubin et al., 1997, "Protein kinase required for Ras signal transduction", U.S. Pat. No. 5,700,675; Steller et al., 1997, "Cell death genes of *Drosophila melanogaster* and vertebrate homologs", U.S. Pat. No. 5,593,879).

Accordingly, it can be anticipated that genetic analysis of pathways involving insulin superfamily hormones in Drosophila and/or *C. elegans* may yield results of similar importance to human disease. For example, systematic identification of participants in intracellular signaling by insulin-like hormones, or components regulating secretion and turnover of insulin-like hormones, could lead to the identification of drug targets, therapeutic proteins, diagnostics, or prognostics useful for treatment or management of insulin resistance in diabetics. In the realm of applications for the control of agriculturally-important pests, mutational analysis of genes encoding insulin-like hormones in *C. elegans* or Drosophila could provide the first clear evidence of the precise biological function of this class of hormones in invertebrates, and provide a means to validate potential pesticide targets that are constituents of these signaling pathways.

2.4.1. Apparent Insulin Receptor Homologs

Evidence for evolutionary conservation of insulin-like signaling pathways in invertebrates has come from the identification of apparent homologs of the insulin receptor in both the fruit fly and the nematode (Petruzzelli et al., 1986, "Isolation of a Drosophila genomic sequence homologous to the kinase domain for the human insulin receptor and detection of the phosphorylated Drosophila receptor with an anti-peptide antibody", Proc. Natl. Acad. Sci. U.S.A. 83:4710–4714; Kimura et al., 1997, "daf-2, an insulin receptor-like gene that regulates longevity and diapause in *Caenorhabditis elegans*", Science 277:942–946). One insulin receptor homolog has been characterized thus far in Drosophila, termed DIR (Drosophila insulin receptor) (Ruan et al., 1995, "The Drosophila insulin receptor contains a novel carboxyl-terminal extension likely to play an important role in signal transduction", J. Biol. Chem. 270:4236–4243), which exhibits extensive homology with vertebrate insulin and IGF receptors in both the extracellular ligand-binding domain and the intracellular tyrosine kinase domain. DIR is larger than the human insulin receptor protein due to extensions at both the N- and C-termini of the polypeptide chain. It is interesting that the additional C-terminal segment of the DIR shares sequence features with IRS-1, one of the substrates of the insulin receptor tyrosine kinase in mammals. Genetic analysis of DIR function in Drosophila has revealed that it is an essential gene with an apparent role in the development of the epidermis and nervous system (Fernandez et al., 1995, "The Drosophila insulin receptor homologue: a gene essential for embryonic development encodes two receptor isoforms with different signaling potential", EMBO J. 14:3373–3384). The role, if any, that DIR may play in metabolic regulation in Drosophila remains unclear.

Recent discoveries from studies of *C. elegans* have also led to the identification of components involved in a presumptive insulin signaling pathway. Furthermore, in *C. elegans*, unlike Drosophila, there are clear connections of this pathway to important aspects of metabolic regulation. This realization has emerged from genetic dissection of the process of dauer larvae formation in the-nematode (reviewed in Riddle and Albert, 1997, "Genetic and environmental regulation of dauer larva development", In *C. elegans* II, Riddle et al., eds., Cold Spring Harbor Press, Plainview, N.Y., pp. 739–768), as described further below.

2.4.2. The Dauer Stage

The dauer stage is an alterative developmental stage that is induced when environmental factors are not adequate to promote successful reproduction in *C. elegans*. There are a number of behavioral, morphologic and metabolic changes that characterize the dauer stage which promote survival of the organism under unfavorable conditions. For example, dauer larvae remain relatively motionless, stop feeding, remain small in size and are reproductively immature. Further, there is increased deposition of fat, a reduction of TCA cycle flux, increased phosphofructokinase activity and increased flux through the glyoxylate cycle in dauer larvae, indicating increased reliance on glycogen and lipid stores as energy reserves in the dauer state (O'Riordan and Burnell, 1989, "Intermediary metabolism in the dauer larva of the nematode *C. elegans* I. Glycolysis, gluconeogenesis, oxidative phosphorylation and the tricarboxylic acid cycle", Comp. Biochem. Physiol. 92B:233–238; O'Riordan and Burnell, 1990, "Intermediary metabolism in the dauer larva II. The glyoxylate cycle and fatty acid oxidation", Comp. Biochem. Physiol. 95B:125–130; Wadsworth and Riddle, 1989, "Developmental regulation of energy metabolism in *Caenorhabditis elegans*", Devel. Biol. 132:167–173). Dauer larvae are relatively resistant to detergent, high temperature and oxygen deprivation as compared to normal adults. Remarkably, dauer larvae can live more than four times as long as the normal life span of *C. elegans*.

The main environmental cues that control entry into the dauer state are pheromone, food, and temperature. High levels of pheromone (indicative of high population density), low levels of food, and high temperature all favor entry into the dauer stage; reversal of these conditions can induce exit from the dauer stage with resumption of normal organismal development. Clearly, the decision to enter either the dauer pathway or pursue normal development is a major milestone in the life cycle of *C. elegans*. As such, it likely involves a complex and precise integration of many different physiologic signals. Laser microsurgery has been used to investigate. the role of specific cells and tissues in regulating entry into the dauer state (Bargmann and Horvitz, 1991, "Control of larval development by chemosensory neurons in *Caenorhabditis elegans*", Science 251:1243–1246). These cell-killing experiments point to a prominent role for amphid neurons which comprise a pair of chemosensory organs on either side of the head. Killing of specific neurons in the amphid causes a dauer constitutive phenotype, implying that the amphids are responsible for producing a dauer-inhibiting neuronal signal during normal development.

The connection between dauer formation in the nematode and insulin signaling has come from the molecular characterization of the daf-2 gene of *C. elegans*. A daf-2 mutant animal exhibits a dauer constitutive phenotype, and molecular cloning of this gene has revealed that it is a nematode homolog of vertebrate insulin receptors. The physiologic analogy with insulin signaling in vertebrates is that activation of the daf-2 receptor in the nematode corresponds to a fed state, with the activated daf-2 receptor generating a dauer-inhibiting signal that promotes normal development. Conversely, lack of daf-2 receptor activity corresponds to a starved state, with the lack of inhibitory signal in this pathway favoring entry into the dauer stage. Indeed, studies of other components in the daf-2 signaling pathway have revealed further similarities with insulin signaling in humans. Two other genes, age-1 and daf-16, have been placed in the same pathway as daf-2 based on analysis of genetic interactions (Morris et al., 1996, "A phosphatidyl-inositol-3-OH kinase family member regulating longevity and diapause in *Caenorhabditis elegans*", Nature 382:536–539; Ogg et al., 1997, "The Forkhead transcription factor DAF-16 transduces insulin-like metabolic and longevity signals in *C. elegans*", Nature 389:994–999; Lin et al., 1997, "daf-16: An HNF-3/forkhead family member that can function to double the life-span of *Caenorhabditis elegans*", Science 278:1319–1322). The age-1 gene encodes a nematode homolog of PI3K, and the action of age-1 is required for the propagation of a daf-2 signal, in keeping with the role of PI3K in insulin signaling. Conversely, genetic analysis has shown that the normal role of daf-16 is one of blocking a signal generated by activated daf-2, and daf-16 has been found to encode a homolog of the HNF-3/forkhead family of transcription factors. In this respect, it is relevant that, in humans, there is the suggestion that insulin mediates some of its effects in target cells by blocking the action of HNF-3 (O'Brien et al., 1995, "Hepatic nuclear factor 3- and hormone-regulated expression of the phosphoenolpyruvate carboxykinase and insulin-like growth factor-binding protein I genes", Mol. Cell. Biol. 15:1747–1758).

There is another intriguing aspect to the phenotype of nematodes defective in components of the daf-2 pathway with respect to effects on the life-span of the organism (normally about 14 days). Mutations in daf-2 and age-1 can more than double the life-span of animals, even under conditions that do not induce the formation of dauer larvae, and the extension of life-span caused by daf-2 or age-1 mutations requires the activity of the daf-16 gene (Lin et al., 1997, Id.; Tissenbaum and Ruvkun, 1998, "An insulin-like signaling pathway affects both longevity and reproduction in *Caenorhabditis elegans*", Genetics 148:703–717; Larsen et al., 1995, "Genes that regulate both development and longevity in *Caenorhabditis elegans*", Genetics 139:1567–1583). These findings raise the interesting possibility that detailed genetic analysis of the daf-2 signaling pathway in nematodes, including identification of daf-2 ligands and their regulation, could reveal new therapeutic approaches with application to aging and longevity in humans.

2.4.3. Unanswered Questions

The structural homologies of components of the daf-2 pathway with those involved in insulin signaling in mammals, as well as the function of the daf-2 pathway in controlling metabolism and aging, raise critical questions with respect to further analysis of this pathway and its potential applications. For example, are there, in fact, insulin superfamily hormones in *C. elegans*? If so, how diverse is the insulin superfamily in *C. elegans* in terms of structure and function? Further, what specific *C. elegans* insulin-like protein(s) interact with the daf-2 receptor, or otherwise affect dauer formation or longevity? Finally, how are the synthesis, activity and turnover of insulin-like proteins regulated in *C. elegans*?

Accordingly, in an effort to answer such questions, an extensive search for insulin-like genes in the genome of *C. elegans* has been conducted. Further, certain aspects of *C. elegans* insulin-like gene function have now been characterized herein. The results of this search have revealed a surprisingly large and diverse family of insulin-like genes. Such a large, diverse family is quite unexpected in such a small, morphologically simple organism. Although all of the nematode insulin-like genes identified herein share structural features that are characteristic of the insulin superfamily, there are novel and significant structural elements of the *C. elegans* insulin-like proteins that have not been found in any previously-characterized members of the superfamily. These new insulin-like genes in *C. elegans* constitute very useful tools for probing the function and regulation of their corresponding pathways. Systematic genetic analysis of signaling pathways involving insulin-like proteins in *C. elegans* can be expected to lead to the discovery of new drug targets, therapeutic proteins, diagnostics and prognostics useful in the treatment of diseases and clinical problems associated with the function of insulin superfamily hormones in humans and other animals, as well as clinical problems associated with aging and senescence. Furthermore, analysis of these same pathways using *C. elegans* insulin-like proteins as tools will have utility for identification and validation of pesticide targets in invertebrate pests that are components of these signaling pathways.

2.4.4. Advantages of Insulin-LIKE Ligand Analysis

Use of *C. elegans* insulin-like genes for such purposes has advantages over manipulation of other known components of the nematode daf-2 pathway, such as daf-2, daf-16, and age-1. Use of ligand-encoding *C. elegans* insulin-like genes will provide a superior approach for identifying factors that are upstream of the receptor in the signal transduction pathway. Specifically, components involved in the synthesis, activation and turnover of insulin-like proteins may be identified. Furthermore, the large number of different insulin-like hormones could provide a means to separate components involved in response to different, specific environmental signals which may not be technically feasible with manipulation of downstream components of the pathway found in target tissues. Further, the diversity of different insulin-like hormones may provide a means to identify new receptor and/or signal transduction systems for insulin superfamily hormones that are structurally different than those that have been characterized to date in either vertebrates or invertebrates. Finally, use of *C. elegans* as a system for analyzing the function and regulation of insulin-like genes has great advantages over approaches in other organisms due to the ability to rapidly carry out large-scale, systematic genetic screens as well as the ability to screen small molecule libraries directly on whole organisms for possible therapeutic or pesticide use.

3. SUMMARY OF THE INVENTION

The present invention relates to nucleotide sequences of *C. elegans* insulin-like genes, amino acid sequences of their encoded proteins, and derivatives (e.g., fragments) and analogs thereof. Nucleic acids capable of hybridizing to or complementary to the foregoing nucleotide sequences are also provided. The invention also relates to a method of identifying genes that are modified by, or that participate in signal transduction with, *C. elegans* insulin-like genes. The invention also relates to derivatives and analogs of *C. elegans* insulin-like genes which are functionally active, i.e., which are capable of displaying one or more known functional activities associated with a full-length (wild-type) insulin-like protein. Such functional activities include but are not limited to antigenicity (ability to bind, or to compete for binding, to an anti-insulin antibody), immunogenicity (ability to generate antibody which binds to insulin), and ability to bind (or compete for binding) to a receptor for insulin (e.g., *C. elegans* insulin receptor-like gene daf-2). The invention further relates to fragments (and derivatives and analogs thereof) of an insulin-like protein which comprise one or more domains of an insulin-like protein. Antibodies to an insulin-like protein, derivatives and analogs of an insulin-like protein, are additionally provided. Methods of production of the insulin-like proteins, derivatives and analogs, e.g., by recombinant means, are also provided.

This invention provides a purified *C. elegans* insulin-like protein comprising an amino acid sequence of SEQ ID NO:198. In one embodiment, the protein comprises amino acid numbers 19 through 103 of SEQ ID NO:198.

This invention provides a purified *C. elegans* insulin-like protein comprising an amino acid sequence of SEQ ID NO:199. In another embodiment, the protein comprises amino acid numbers 19 through 72 of SEQ ID NO:199.

This invention provides a purified *C. elegans* insulin-like protein comprising an amino acid sequence of SEQ ID NO:200. In another embodiment, the protein comprises amino acid numbers 17 through 110 of SEQ ID NO:200.

This invention provides a purified *C. elegans* insulin-like protein comprising amino acid sequence of SEQ ID NO:201. In another embodiment, the protein comprises amino acid numbers 19 through 67 of SEQ ID NO:201.

This invention provides a purified *C. elegans* insulin-like protein comprising an amino acid sequence of SEQ ID NO:202. In another embodiment, the protein comprises amino acid numbers 20 through 76 of SEQ ID NO:202.

This invention provides a purified *C. elegans* insulin-like protein comprising an amino acid sequence of SEQ ID NO:203. In another embodiment, the protein comprises amino acid numbers 21 through 120 of SEQ ID NO:203.

This invention provides a purified *C. elegans* insulin-like protein comprising an amino acid sequence of SEQ ID NO:204. In another embodiment, the protein comprises amino acid numbers 16 through 218 of SEQ ID NO:204.

This invention provides a purified *C. elegans* insulin-like protein comprising amino acid sequence of SEQ ID NO:205. In another embodiment, the protein comprises amino acid numbers 29 through 107 of SEQ ID NO:205.

This invention provides a purified *C. elegans* insulin-like protein comprising amino acid sequence of SEQ ID NO:206. In another embodiment, the protein comprises amino acid numbers 23 through 77 of SEQ ID NO:206.

This invention provides a purified derivative of the protein of the above-listed proteins, which derivative is capable of immunospecific binding to an anti-insulin-like protein antibody.

This invention provides a purified derivative of the protein of the above-listed proteins, which derivative displays one or more functional activities of the *C. elegans* insulin-like protein.

This invention provides a purified fragment of the protein of the above-listed proteins, which fragment displays one or more functional activities of the *C. elegans* insulin-like protein.

This invention provides a purified fragment of the protein of the above-listed proteins, comprising a domain of the *C. elegans* insulin-like protein selected from the group consisting of a B peptide domain and an A peptide domain.

This invention provides a chimeric protein comprising the fragment of the above-listed proteins, consisting of at least 6 amino acids fused by a covalent bond to an amino acid sequence of a second protein, which second protein is not a *C. elegans* insulin-like protein.

This invention provides a chimeric protein comprising the fragment of the above-listed proteins, consisting of at least 6 amino acids fused by a covalent bond to an amino acid sequence of a second protein, which second protein is not a *C. elegans* insulin-like protein.

This invention provides a chimeric protein of the above-listed proteins, wherein the fragment of the *C. elegans* insulin-like protein is a fragment capable of immunospecific binding to an anti-insulin-like protein antibody.

This invention provides a chimeric protein of the above-listed proteins, wherein the fragment of the *C. elegans* insulin-like protein is a fragment capable of immunospecific binding to an anti-insulin-like protein antibody.

This invention provides a purified antibody or an antigen-binding derivative thereof capable of immunospecific binding to the protein of any one of the above-listed proteins and not to an insulin-like protein of another species.

In one embodiment, the antibody is polyclonal. In another embodiment, the antibody is monoclonal.

This invention provides an isolated nucleic acid comprising a nucleotide sequence selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215.

This invention provides an isolated nucleic acid comprising a nucleotide sequence encoding an amino acid sequence selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206. In one embodiment, the nucleic acid is cDNA. In another embodiment, the nucleic acid is mRNA.

This invention provides an isolated nucleic acid which hybridizes under conditions of high stringency to a second nucleic acid consisting of nucleotide sequence of the nucleic acid of the above-listed nucleotide sequences.

This invention provides a nucleic acid of the above-listed nucleotide sequences which encodes a *C. elegans* insulin-like protein or a functional derivative thereof.

This invention provides an isolated nucleic acid comprising a nucleotide sequence encoding a functional derivative of an amino acid sequence selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206.

This invention provides an isolated nucleic acid comprising a nucleotide sequence that is antisense to a nucleotide sequence selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215.

This invention provides an isolated nucleic acid comprising a nucleotide sequence that is antisense to a nucleotide sequence encoding an amino acid sequence selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206.

This invention provides a method of producing a *C. elegans* insulin-like protein comprising: (a) growing recombinant cell containing a nucleic acid comprising a nucleotide sequence selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215 such that the encoded *C. elegans* insulin-like protein is expressed by the cell; and (b) recovering the expressed *C. elegans* insulin-like protein. In one embodiment, invention provides a purified *C. elegans* insulin-like protein produced by this method.

This invention provides a method of producing a *C. elegans* insulin-like protein comprising: (a) growing a recombinant cell containing a nucleic acid comprising a nucleotide sequence encoding a *C. elegans* insulin-like protein comprising an amino acid sequence selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206 such that the encoded *C. elegans* insulin-like protein is expressed by the cell; and (b) recovering the expressed *C. elegans* insulin-like protein. This invention provides a purified *C. elegans* insulin-like protein produced by the method.

This invention provides a method of identifying a phenotype associated with mutation or abnormal expression of a *C. elegans* insulin-like protein comprising identifying the effect of a mutated or abnormally expressed *C. elegans* insulin-like gene which encodes a *C. elegans* insulin-like protein selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206 in a *C. elegans* animal. In one embodiment, the effect is determined by an assay selected from the group consisting of a dauer formation assay, a developmental assay, an energy metabolism assay, a growth rate assay and a reproductive capacity assay.

This invention provides a method of identifying a phenotype associated with mutation or abnormal expression of a *C. elegans* insulin-like protein comprising: (a) mutating or abnormally expressing a *C. elegans* insulin-like gene which encodes a *C. elegans* insulin-like protein selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206 in a *C. elegans* (b) identifying an effect of the gene mutated or abnormally expressed. In one embodiment, the effect is identified by an assay selected from the group consisting of a dauer formation assay, a developmental assay, an energy metabolism assay, a growth rate assay and a reproductive capacity assay. In another embodiment, the above phenotype gene is mutated or abnormally expressed using a technique selected from the group consisting of EMS chemical deletion mutagenesis, transposon insertion mutagenesis and double-stranded RNA interference.

This invention provides a recombinant cell containing a recombinant nucleic acid comprising a nucleotide sequence selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215.

This invention provides a vector comprising (a) a nucleotide sequence selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215, and (b) an origin of replication. In one embodiment, the vector in which the nucleotide sequence is operably linked to a heterologous promoter.

This invention provides a purified *C. elegans* insulin-like protein encoded by a nucleic acid capable of hybridizing under conditions of high stringency to a nucleic acid comprising a nucleotide sequence selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215.

This invention provides a purified protein consisting of a B peptide domain defined by amino acid numbers 19–77 of SEQ ID NO:198 linked by one or more disulfide bonds to an A peptide domain defined by amino acid numbers 78–103 of SEQ ID NO:198.

This invention provides a purified protein consisting of a B peptide domain defined by amino acid numbers 19–49 of SEQ ID NO:199 linked by one or more disulfide bonds to an A peptide domain:defined by amino acid numbers 50–72 of SEQ ID NO:199.

This invention provides a purified protein consisting of a B peptide domain defined by amino acid numbers 17–82 of SEQ ID NO:200 linked by one or more disulfide bonds to an A peptide domain defined by amino acid numbers 83–110 of SEQ ID NO:200.

This invention provides a purified protein consisting of a B peptide domain defined by amino acid numbers 19–45 of SEQ ID NO:201 linked by one or more disulfide bonds to an A peptide domain defined by amino acid numbers 46–67 of SEQ ID NO:201.

This invention provides a purified protein consisting of a B peptide domain defined by amino acid numbers 21–51 of SEQ ID NO:202 linked by one or more disulfide bonds to an A peptide domain defined by amino acid numbers 52–76 of SEQ ID NO:202.

This invention provides purified protein consisting of a B peptide domain defined by amino acid numbers 21–90 of SEQ ID NO:203 linked by one or more disulfide bonds to an A peptide domain defined by amino acid numbers 91–120 of SEQ ID NO:203.

This invention provides a purified protein consisting of a first B peptide domain defined by amino acid numbers 16–50 of SEQ ID NO:204 linked by one or more disulfide bonds to a first A peptide domain defined by amino acid numbers 51–89 of SEQ ID NO:204, a second B peptide domain defined by amino acid numbers 90–110 of SEQ ID NO:204 linked by one or more disulfide bonds to a second A peptide domain defined by amino acid numbers 111–153 of SEQ ID NO:204, and a third B peptide domain defined by amino acid numbers 154–174 of SEQ ID NO:204 linked by one or more disulfide bonds to a third A peptide domain defined by amino acid numbers 175–218 of SEQ ID NO:204.

This invention provides a purified protein consisting of a B peptide domain defined by amino acid numbers 29–66 of SEQ ID NO:205 linked by one or more disulfide bonds to an A peptide domain defined by amino acid numbers 67–107 of SEQ ID NO:205.

This invention provides a purified protein consisting of a B peptide domain defined by amino acid numbers 23–47 of SEQ ID NO:206 linked by one or more disulfide bonds to an A peptide domain defined by amino acid numbers 48–77 of SEQ ID NO:206.

This invention provides a method of identifying a gene-of-interest as capable of modifying a function of a *C. elegans* insulin-like gene comprising: (a) constructing a first mutant nematode having a first mutation in the *C. elegans* insulin-like gene which encodes a *C. elegans* insulin-like protein selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206 and a second mutation in the gene-of-interest; and (b) determining whether the phenotype displayed by the first mutant nematode is different from the phenotype of a second mutant nematode having said first mutation but not said second mutation, in which the displaying of a phenotype by the first mutant nematode that is different from said second mutant nematode identifies the gene-of-interest as capable of modifying the function of the *C. elegans* insulin-like gene. In one embodiment, the first mutant nematode is produced using a technique selected from the group consisting of EMS chemical deletion mutagenesis, transposon insertion mutagenesis and double-stranded RNA interference. In another embodiment, the phenotype is selected from the group consisting of an altered body shape phenotype, an altered body size phenotype, an altered chemotaxis phenotype, an altered brood size phenotype, an altered egg-laying phenotype, an altered life span phenotype, an altered lipid accumulation phenotype, an altered locomotion phenotype, an altered organ morphogenesis phenotype, an altered thermotaxis phenotype, a dauer constitutive phenotype, a dauer defective phenotype, a lethal phenotype and a sterile phenotype. In yet another embodiment, the altered organ morphogenesis phenotype involves an organ selected from the group consisting of vulva, nervous system, gut and musculature. In fourth embodiment, a nematode having the altered body size phenotype is assayed for activity of a gene affecting body size selected from the group consisting of daf-4, sma-2 and sma-3. In a fifth embodiment, the gene-of-interest is a homolog of an insulin signaling pathway gene from vertebrates. In a sixth embodiment, the gene-of-interest is selected from the group consisting of daf-2, daf-16 and age-1.

This invention provides a C. elegans animal having a first mutation in a C. elegans insulin-like gene comprising a cDNA selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215, and a second mutation in a different gene that is a homolog of an insulin signaling pathway gene from vertebrates.

This invention provides a method of studying a function of a C. elegans insulin-like gene comprising: (a) mis-expressing a wild-type or mutant C. elegans insulin-like gene which encodes a C. elegans insulin-like protein selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206 in a transgenic nematode by driving expression with a homologous or heterologous promoter; and (b) detecting a phenotype in said transgenic nematode, so as to study the function of the C. elegans insulin-like gene. In one embodiment, the heterologous promoter driving mis-expression is selected from the group consisting of an hsp 16-2 promoter, an hsp 16-41 promoter, a myo-2 promoter, an hlh-1 promoter and a mec-3 promoter. In another embodiment, the transgenic nematode mis-expressing the C. elegans insulin-like gene further has a mutation in daf-2. In yet another embodiment, the transgenic nematode mis-expressing the C. elegans insulin-like gene is assayed for a change in a phenotype selected from the group consisting of dauer formation and life span.

This invention provides a method of detecting the effect of expression of a C. elegans insulin-like gene on an insulin signaling pathway which encodes a C. elegans insulin-like protein selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206 comprising: (a) mutating or abnormally expressing a wild-type C. elegans insulin-like gene in a nematode already having a mutation in the insulin signaling pathway that displays a phenotype-of-interest; and (b) detecting the effect of step (a) on the phenotype-of-interest, so as to detect the effect of expression of the C. elegans insulin-like gene. In one embodiment, the mutation in the insulin signaling pathway is in a gene selected from the group consisting of daf-2, daf-16 and age-1.

This invention provides a method of identifying a molecule that specifically binds to a ligand selected from the group consisting of (i) a C. elegans insulin-like protein selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206, (ii) a fragment of the C. elegans insulin-like protein comprising a domain of the protein, and (iii) a nucleic acid encoding the C. elegans insulin-like protein or fragment, the method comprising: (a) contacting the ligand with a plurality of molecules under conditions conducive to binding between the ligand and the molecules; and (b) identifying a molecule within the plurality specifically that binds to the ligand. In one embodiment, the C. elegans insulin-like protein is selected from the group consisting from a signal peptide domain, a pre peptide domain, a pro peptide domain, a B peptide domain, a C peptide domain and an A peptide domain.

This invention provides a recombinant non-human animal in which a C. elegans insulin-like gene which encodes a C. elegans insulin-like protein selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206 has been deleted or inactivated by recombinant methods, or a progeny thereof containing the deleted or inactivated gene. In one embodiment, the recombinant non-human animal C. elegans insulin-like gene has been deleted or inactivated by a method selected from the group consisting of EMS chemical deletion mutagenesis, transposon insertion mutagenesis and double-stranded RNA interference.

This invention provides a recombinant non-human animal containing a C. elegans insulin-like transgene which encodes a C. elegans insulin-like protein selected from the group consisting of SEQ ID NO:198, SEQ ID NO:199, SEQ ID NO:200, SEQ ID NO:201, SEQ ID NO:202, SEQ ID NO:203, SEQ ID NO:204, SEQ ID NO:205 and SEQ ID NO:206. In one embodiment, the recombinant non-human animal of C. elegans insulin-like transgene is under the control of a promoter that is not the native promoter of the transgene.

This invention provides a purified protein encoded by a first nucleic acid which hybridizes under conditions of high stringency to a second nucleic acid, which second nucleic acid comprises a nucleotide sequence selected from the group consisting of SEQ ID NO:28, SEQ ID NO:29, SEQ ID NO:34, SEQ ID NO:35, SEQ ID NO:163, SEQ ID NO:164, SEQ ID NO:165, SEQ ID NO:213, SEQ ID NO:214, and SEQ ID NO:215, wherein the protein is characterized as lacking a cleavable C peptide and as having the same number and relative spacing of Cys residues as found in vertebrate insulin-like proteins.

This invention provides a purified protein encoded by a first nucleic acid which hybridizes under conditions of high stringency to a second nucleic acid, which second nucleic acid comprises a nucleotide sequence selected from the group consisting of SEQ ID NO:30, SEQ ID NO:31, SEQ ID NO:32 and SEQ ID NO:33, SEQ ID NO:36, SEQ ID NO:207, SEQ ID NO:208, SEQ ID NO:209, SEQ ID NO:210, SEQ ID NO:211 and SEQ ID NO:212 wherein the protein is characterized as (a) lacking a cleavable C peptide separating the B and A chains, (b) lacking an intra-chain disulfide bond in the A domain, and (c) having an extra pair of Cys residues relative to vertebrate insulin-like proteins.

This invention provides a purified C. elegans insulin-like protein which the B and A chain domains of the protein are not proteolytically cleaved into separate chains.

This invention provides a method of identifying a molecule that alters the expression level of a C. elegans insulin-like gene corresponding to a cDNA selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215, which method comprises: (a) contacting a transgenic nematode with one or more molecules, said transgenic nematode having a transgene comprising a promoter or enhancer region of genomic DNA from 1 base to 6 kilobases upstream of the start codon of the cDNA operably linked to a reporter gene; and (b) determining whether the level of expression of the reporter gene is altered relative to the level of expression of the reporter gene in the absence of the one or more molecules.

This invention provides a method of identifying a molecule that binds to a promoter or enhancer of a *C. elegans* insulin-like gene corresponding to a cDNA selected from the group consisting of SEQ ID NO:207, SEQ ID NO:208, SEQ ID NO:209, SEQ ID NO:210, SEQ ID NO:211, SEQ ID NO:212, SEQ ID NO:213, SEQ ID NO:214 and SEQ ID NO:215, which method comprises: (a) contacting a transgenic nematode with one or more molecules, said transgenic nematode having a transgene comprising a promoter or enhancer region of genomic DNA from 1 base to 6 kilobases upstream of the start codon of the cDNA operably linked to a reporter gene; (b) determining whether the level of expression of the reporter gene is altered relative to the level of expression of the reporter gene in the absence of the one or more molecules; (c) contacting the one or more molecules with the promoter or enhancer region of genomic DNA; and (d) identifying the molecule contacted in step (c) that binds to the promoter or enhancer. In one embodiment, the reporter gene encodes green fluorescent protein.

This invention provides a purified *C. elegans* insulin-like protein comprising an amino acid sequence of SEQ ID NO:158. In one embodiment, the protein of comprises amino acid numbers 30 through 85 of SEQ ID NO:158. This invention provides a purified *C. elegans* insulin-like protein comprising an amino acid sequence of SEQ ID NO:159. In another embodiment, the protein comprises amino acid numbers 21 through 81 of SEQ ID NO:159. The invention provides a purified *C. elegans* insulin-like protein comprising an amino acid sequence of SEQ ID NO:160. In another embodiment, the protein comprises amino acid numbers 22 through 83 of SEQ ID NO:160. The invention provides a purified *C. elegans* insulin-like protein comprising amino acid sequence of SEQ ID NO:161. In another embodiment, the protein comprises amino acid numbers 18 through 73 of SEQ ID NO:161. In another embodiment, the protein comprises a purified derivative of the protein of the above-listed proteins, which derivative is capable of immunospecific binding to an anti-insulin-like protein antibody. In another embodiment, the protein comprises a purified derivative of the above-listed proteins, which derivative displays one or more functional activities of the *C. elegans* insulin-like protein.

This invention provides a purified fragment of the above-listed proteins, which fragment displays one or more functional activities of the *C. elegans* insulin-like protein.

This invention provides a purified fragment of the above-listed proteins, comprising a domain of the *C. elegans* insulin-like protein selected from the group consisting of a B peptide domain and an A peptide domain.

This invention provides a chimeric protein comprising the fragment of the above-listed protein, consisting of at least 6 amino acids fused by a covalent bond to an amino acid sequence of a second protein, which second protein is not a *C. elegans* insulin-like protein.

This invention provides a chimeric protein comprising the fragment of the above-listed proteins, consisting of at least 6 amino acids fused by a covalent bond to an amino acid sequence of a second protein, which second protein is not a *C. elegans* insulin-like protein.

This invention provides a chimeric protein of the above-listed proteins, wherein the fragment of the *C. elegans* insulin-like protein is a fragment capable of immunospecific binding to an anti-insulin-like protein antibody.

This invention provides a chimeric protein of the above-listed proteins, wherein the fragment capable of immunospecific binding to an anti-insulin-like protein antibody further lacks one or more domains of the insulin-like protein.

This invention provides a purified antibody or an antigen-binding derivative thereof capable of immunospecific binding to the above-listed proteins and not to an insulin-like protein of another species. In one embodiment, the antibody is polyclonal. In another embodiment, the antibody is monoclonal.

This invention provides an isolated nucleic acid comprising a nucleotide sequence selected from the group consisting of SEQ ID NO:162, SEQ ID NO:163, SEQ ID NO:164 and SEQ ID NO:165.

This invention provides an isolated nucleic acid comprising a nucleotide sequence encoding an amino acid sequence selected from the group consisting of SEQ ID NO:158, SEQ ID NO:159, SEQ ID NO:160 and SEQ ID NO:161. In one embodiment, the nucleic acid is cDNA. In another embodiment, the nucleic acid is mRNA. In yet another embodiment, the invention provides an isolated nucleic acid which hybridizes under conditions of high stringency to the above-listed nucleic acids.

This invention provides an isolated nucleic acid comprising a nucleotide sequence encoding a functional derivative of the above-listed nucleic acids.

This invention provides an isolated nucleic acid comprising a nucleotide sequence encoding a functional derivative of an amino acid sequence selected from the group consisting of SEQ ID NO:158, SEQ ID NO:159, SEQ ID NO:160 and SEQ ID NO:161.

This invention provides an isolated nucleic acid comprising a nucleotide sequence that is antisense to a nucleotide sequence selected from the group consisting of SEQ ID NO:162, SEQ ID NO:163, SEQ ID NO:164 and SEQ ID NO:165.

This invention provides an isolated nucleic acid comprising a nucleotide sequence that is antisense to a nucleotide sequence encoding an amino acid sequence selected from the group consisting of SEQ ID NO:158, SEQ ID NO:159, SEQ ID NO:160 and SEQ ID NO:161.

This invention provides a method of producing a *C. elegans* insulin-like protein comprising: (a) growing a recombinant cell containing a nucleic acid comprising a nucleotide sequence selected from the group consisting of SEQ ID NO:162, SEQ ID NO:163, SEQ ID NO:164 and SEQ ID NO:165 such that the encoded *C. elegans* insulin-like protein is expressed by the cell; and (b) recovering the expressed *C. elegans* insulin-like protein. In another embodiment, this invention provides a *C. elegans* insulin-like protein produced by this method.

This invention provides a method of producing a *C. elegans* insulin-like protein comprising: (a) growing a recombinant cell containing a nucleic acid comprising a nucleotide sequence encoding a *C. elegans* insulin-like protein comprising an amino acid sequence selected from the group consisting of SEQ ID NO:158, SEQ ID NO:159, SEQ ID NO:160 and SEQ ID NO:161 such that the encoded *C. elegans* insulin-like protein is expressed by the cell; and (b) recovering the expressed *C. elegans* insulin-like protein. This invention provides a purified *C. elegans* insulin-like protein produced by this method.

This invention provides a method of identifying a phenotype associated with mutation or abnormal expression of a *C. elegans* insulin-like protein comprising identifying the effect of a mutated or abnormally expressed *C. elegans* insulin-like gene which encodes a *C. elegans* insulin-like protein selected from the group consisting of SEQ ID NO:158, SEQ ID NO:159, SEQ ID NO:160 and SEQ ID NO:161 in a *C. elegans* animal. In one embodiment, the effect is determined by an assay selected from the group consisting of a dauer formation assay, a developmental assay, an energy metabolism assay, a growth rate assay and a reproductive capacity assay.

This invention provides a method of identifying a phenotype associated with mutation or abnormal expression of a *C. elegans* insulin-like protein comprising: (a) mutating or abnormally expressing a *C. elegans* insulin-like gene which encodes a *C. elegans* insulin-like protein selected from the group consisting of SEQ ID NO:158, SEQ ID NO:159, SEQ ID NO:160 and SEQ ID NO:161 in a *C. elegans* animal; and (b) identifying an effect of the gene mutated or abnormally expressed. In one embodiment, the effect is identified by an assay selected from the group consisting of a dauer formation assay, a developmental assay, an energy metabolism assay, a growth rate assay and a reproductive capacity assay. In another embodiment of the above phenotype identification methods, the gene is mutated or abnormally expressed using a technique selected from the group consisting of EMS chemical deletion mutagenesis, transposon insertion mutagenesis and double-stranded RNA interference.

This invention provides a recombinant cell containing a recombinant nucleic acid containing a nucleotide sequence selected from the group consisting of SEQ ID NO:162, SEQ ID NO:163, SEQ ID NO:164 and SEQ ID NO:165.

This invention provides a vector comprising (a) a nucleotide sequence selected from the group consisting of SEQ ID NO:162, SEQ ID NO:163, SEQ ID NO:164 and SEQ ID NO:165, and (b) an origin of replication. In one embodiment, the nucleotide sequence is operably linked to a heterologous promoter.

This invention provides a purified *C. elegans* insulin-like protein encoded by a nucleic acid capable of hybridizing under conditions of high stringency to a nucleic acid comprising a nucleotide sequence selected from the group consisting of SEQ ID NO:162, SEQ ID NO:163, SEQ ID NO:164 and SEQ ID NO:165.

This invention provides a purified protein consisting of a B peptide domain defined by amino acid numbers 30–62 of SEQ ID NO:158 linked by one or more disulfide bonds to an A peptide domain defined by amino acid numbers 63–85 of SEQ ID NO:158.

This invention provides a purified protein consisting of a B peptide domain defined by amino acid numbers 21–46 of SEQ ID NO:159 linked by one or more disulfide bonds to an A peptide domain defined by amino acid numbers 47–81 of SEQ ID NO:159.

This invention provides a purified protein consisting of a B peptide domain defined by amino acid numbers 22–57 of SEQ ID NO:160 linked by one or more disulfide bonds to an A peptide domain defined by amino acid numbers 58–83 of SEQ ID NO:160.

This invention provides a purified protein consisting of a B peptide domain defined by amino acid numbers 18–50 of SEQ ID NO:161 linked by one or more disulfide bonds to an A peptide domain defined by amino acid numbers 51–73 of SEQ ID NO:161.

This invention provides a method of identifying a gene-of-interest as capable of modifying a function of a *C. elegans* insulin-like gene comprising: (a) constructing a first mutant nematode having a first mutation in the *C. elegans* insulin-like gene which encodes a *C. elegans* insulin-like protein selected from the group consisting of SEQ ID NO:158, SEQ ID NO:159, SEQ ID NO:160 and SEQ ID NO:161 and a second mutation in the gene-of-interest; and (b) determining whether the phenotype displayed by the first mutant nematode is different from the phenotype of a second mutant nematode having said first mutation but not said second mutation, in which the displaying of a phenotype by the first mutant nematode that is different from said second mutant nematode identifies the gene-of-interest as capable of modifying the function of the *C. elegans* insulin-like gene. In one embodiment, the first mutant nematode is produced using a technique selected from the group consisting of EMS chemical deletion mutagenesis, transposon insertion mutagenesis and double-stranded RNA interference. In another embodiment, the phenotype is selected from the group consisting of an altered body shape phenotype, an altered body size phenotype, an altered chemotaxis phenotype, an altered brood size phenotype, an altered egg-laying phenotype, an altered life span phenotype, an altered lipid accumulation phenotype, an altered locomotion phenotype, an altered organ morphogenesis phenotype, an altered thermotaxis phenotype, a dauer constitutive phenotype, a dauer defective phenotype, a lethal phenotype and a sterile phenotype. In another embodiment, the altered organ morphogenesis phenotype involves an organ selected from the group consisting of vulva, nervous system, gut and musculature. In yet still another embodiment, a nematode having the altered body size phenotype is assayed for activity of a gene affecting body size selected from the group consisting of daf-4, sma-2 and sma-3. In a fifth embodiment, the gene-of-interest is a homolog of an insulin signaling pathway gene from vertebrates. In a sixth embodiment, the gene-of-interest is selected from the group consisting of daf-2, daf-16 and age-1.

This invention provides a *C. elegans* animal having a first mutation in a *C. elegans* insulin-like gene comprising a cDNA selected from the group consisting of SEQ ID NO:162, SEQ ID NO:163, SEQ ID NO:164 and SEQ ID NO:165, and a second mutation in a different gene that is a homolog of an insulin signaling pathway gene from vertebrates.

This invention provides a method of studying a function of a *C. elegans* insulin-like gene comprising: (a) mis-expressing a wild-type or mutant *C. elegans* insulin-like gene which encodes a *C. elegans* insulin-like protein selected from the group consisting of SEQ ID NO:158, SEQ ID NO:159, SEQ ID NO:160 and SEQ ID NO:161 in a transgenic nematode by driving expression with a homologous or heterologous promoter; and (b) detecting a phenotype in said transgenic nematode, so as to study the function of the *C. elegans* insulin-like gene. In one embodiment, the heterologous promoter driving mis-expression is selected from the group consisting of an hsp 16-2 promoter, an hsp 16-41 promoter, a myo-2 promoter, an hlh-1 promoter and a mec-3 promoter. In one embodiment, the transgenic nematode mis-expressing the *C. elegans* insulin-like gene further has a mutation in daf-2. In yet another embodiment, the transgenic nematode mis-expressing the *C. elegans* insulin-like gene is assayed for a change in a phenotype selected from the group consisting of dauer formation and life span.

This invention provides a method of detecting the effect of expression of a *C. elegans* insulin-like gene on an insulin signaling pathway comprising: (a) mutating or abnormally expressing a wild-type *C. elegans* insulin-like gene in a nematode already having a mutation in the insulin signaling pathway that displays a phenotype-of-interest; and (b) detecting the effect of step (a) on the phenotype-of-interest, so as to detect the effect of expression of the *C. elegans* insulin-like gene. In one embodiment, the mutation in the insulin signaling pathway is in a gene selected from the group consisting of daf-2, daf-16 and age-1.

This invention provides a method of identifying a molecule that specifically binds to a ligand selected from the group consisting of (i) a *C. elegans* insulin-like protein selected from the group consisting of SEQ ID NO:158, SEQ ID NO:159, SEQ ID NO:160 and SEQ ID NO:161, (ii) a fragment of the *C. elegans* insulin-like protein comprising a domain of the protein, and (iii) a nucleic acid encoding the *C. elegans* insulin-like protein or fragment, the method comprising: (a) contacting the ligand with a plurality of molecules under conditions conducive to binding between the ligand and the molecules; and (b) identifying a molecule within the plurality that specifically binds to the ligand. In one embodiment, the domain of the *C. elegans* insulin-like protein is selected from the group consisting of a signal peptide domain, a pre peptide domain, a pro peptide domain, a B peptide domain, a C peptide domain and an A peptide domain.

This invention provides-a recombinant non-human animal in which a *C. elegans* insulin-like gene which encodes a *C. elegans* insulin-like protein selected from the group consisting of SEQ ID NO:158, SEQ ID NO:159, SEQ ID NO:160 and SEQ ID NO:161 has been deleted or inactivated by recombinant methods, or a progeny thereof containing the deleted or inactivated gene. In one embodiment, the recombinant non-human animal encoding the *C. elegans* insulin-like gene has been deleted or inactivated by a method selected from the group consisting of EMS chemical deletion mutagenesis, transposon insertion mutagenesis and double-stranded RNA interference.

This invention provides a recombinant non-human animal containing a *C. elegans* insulin-like transgene which encodes a *C. elegans* insulin-like protein selected from the group consisting of SEQ ID NO:158, SEQ ID NO:159, SEQ ID NO:160 and SEQ ID NO:161. In one embodiment, the recombinant non-human animal encoding the *C. elegans* insulin-like transgene is under the control of a promoter that is not the native promoter of the transgene.

This invention provides a purified protein encoded by a first nucleic acid which hybridizes under conditions of high stringency to a second nucleic acid, which second nucleic acid comprises a nucleotide sequence selected from the group consisting of SEQ ID NO:20, SEQ ID NO:21, SEQ ID NO:22, SEQ ID NO:23, SEQ ID NO:24, SEQ ID NO:25, SEQ ID NO:26, SEQ ID NO:27 and SEQ ID NO:162, wherein the protein is characterized as lacking a cleavable C peptide separating the B and A chains and as having an extra pair of Cys residues relative to vertebrate insulin-like proteins.

This invention provides a purified protein-encoded by a first nucleic acid which hybridizes under conditions of high stringency to a second nucleic acid, which second nucleic acid comprises a nucleotide sequence selected from the group consisting of SEQ ID NO:28, SEQ ID NO:29, SEQ ID NO:34, SEQ ID NO:35, SEQ ID NO:163, SEQ ID NO:164 and SEQ ID NO:165, which the protein is characterized as lacking a cleavable C peptide and as having the same number and relative spacing of Cys residues as found in vertebrate insulin-like proteins.

This invention provides a purified protein encoded by a first nucleic acid which hybridizes under conditions of high stringency to a second nucleic acid, which second nucleic acid comprises a nucleotide sequence selected from the group consisting of SEQ ID NO:30, SEQ ID NO:31, SEQ ID NO:32 and SEQ ID NO:33 and SEQ ID NO:36, which the protein is characterized as (a) lacking a cleavable C peptide separating the B and A chains, (b) lacking an intra-chain disulfide bond in the A domain, and (c) having an extra pair of Cys residues relative to vertebrate insulin-like proteins.

This invention provides a purified *C. elegans* insulin-like protein which the B and A chain domains of the protein are not proteolytically cleaved into separate chains.

This invention provides a method of identifying a molecule that alters the expression level of a *C. elegans* insulin-like gene corresponding to a cDNA selected from the group consisting of SEQ ID NO:162, SEQ ID NO:163, SEQ ID NO:164 and SEQ ID NO:165, which method comprises: (a) contacting a transgenic nematode with one or more molecules, said transgenic nematode having a transgene comprising a promoter or enhancer region of genomic DNA from 1 base to 6 kilobases upstream of the start codon of the cDNA operably linked to a reporter gene; and (b) determining whether the level of expression of the reporter gene is altered relative to the level of expression of the reporter gene in the absence of the one or more molecules.

This invention provides a method of identifying a molecule that binds to a promoter or enhancer of a *C. elegans* insulin-like gene corresponding to a cDNA selected from the group consisting of SEQ ID NO:162, SEQ ID NO:163, SEQ ID NO:164 and SEQ ID NO:165, which method comprises: (a) contacting a transgenic nematode with one or more molecules, said transgenic nematode having a transgene comprising a promoter or enhancer region of genomic DNA from 1 base to 6 kilobases upstream of the start codon of the cDNA operably linked to a reporter gene; (b) determining whether the level of expression of the reporter gene is altered relative to the level of expression of the reporter gene in the absence of the one or more molecules; (c) contacting the one or more molecules with the promoter or enhancer region of genomic DNA; and (d) identifying the molecule contacted in step (c) that binds to the promoter or enhancer. In one embodiment, the reporter gene encodes green fluorescent protein.

This invention provides a purified *C. elegans* insulin-like protein. In one embodiment, the protein comprises an amino acid sequence of SEQ ID NO:1. In another embodiment, the protein comprises an amino acid sequence comprising amino acid numbers 31 through 109 of SEQ ID NO:1. In another embodiment, the protein comprises an amino acid sequence of SEQ ID NO:6. In another embodiment, the protein comprises an amino acid sequence comprising residue numbers 18 through 100 of SEQ ID NO:6. In another embodiment, the protein comprises an amino acid sequence of SEQ ID NO:8. In another embodiment, the protein comprises an amino acid sequence comprising residue numbers 19 through 104 of SEQ ID NO:8. In another embodiment, the protein comprises an amino acid sequence of SEQ ID NO:9. In another embodiment, the protein comprises an amino acid sequence comprising residue numbers 19 through 118 of SEQ ID NO:9. In another embodiment, the protein comprises an amino acid sequence of SEQ ID NO:11. In another embodiment, the protein comprises an amino acid sequence comprising residue numbers 22 through 86 of SEQ ID NO:11. In another embodiment, the protein comprises an amino acid sequence of SEQ ID NO:12. In another embodiment, the protein comprises an amino acid sequence comprising residue numbers 20 through 76 of SEQ ID NO:12. In another embodiment, the protein comprises an amino acid sequence of SEQ ID NO:15. In another embodiment, the protein comprises an amino acid sequence comprising residue numbers through 80 of SEQ ID NO:15. In another embodiment, the protein comprises an amino acid sequence of SEQ ID NO:17. In another embodiment, the protein comprises an amino acid sequence comprising residue numbers 20 through 95 of SEQ ID NO:17. In another embodiment, the protein comprises an amino acid sequence of SEQ ID NO:18. In another embodiment, the protein comprises an amino acid sequence comprising residue numbers 19 through 83 of SEQ ID NO:18. In another embodiment, the protein comprises a purified derivative of the above-listed proteins, which derivative is capable of immunospecific binding to an anti-insulin-like protein antibody. In another embodiment, the protein comprises a purified derivative of the above-listed proteins, which derivative displays one or more functional activities of a C. elegans insulin-like protein.

This invention provides a purified fragment of a C. elegans insulin-like protein, which fragment displays one or more functional activities of the C. elegans insulin-like protein.

This invention provides a purified fragment of a C. elegans insulin-like protein comprising a domain of the C. elegans insulin-like protein selected from the group consisting of a B peptide domain and an A peptide domain. In one embodiment, a molecule comprising the fragment is provided.

This invention provides a chimeric protein comprising a fragment of a C. elegans insulin-like protein consisting of at least 6 amino acids fused by a covalent bond to an amino acid sequence of a second protein, which second protein is not a C. elegans insulin-like protein. In one embodiment, the fragment of the C. elegans insulin-like protein is a fragment capable of immunospecific binding to an anti-insulin-like protein antibody. In another embodiment, the fragment capable of immunospecific binding to an anti-insulin-like protein antibody further lacks one or more domains of the insulin-like protein.

This invention provides a. purified antibody or an antigen-binding derivative thereof capable of immunospecific binding to a C. elegans insulin-like protein and not to an insulin-like protein of another species. In one embodiment, the antibody is polyclonal. In another embodiment, the antibody is monoclonal.

This invention provides an isolated nucleic acid comprising a nucleotide sequence selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36.

This invention provides an isolated nucleic acid comprising a nucleotide sequence encoding an amino acid sequence selected from the group consisting of SEQ ID NO:1, SEQ ID NO:6, SEQ ID NO:8, SEQ ID NO:9, SEQ ID NO:11, SEQ ID NO:12, SEQ ID NO:15, SEQ ID NO:17 and SEQ ID NO:18. In one embodiment, the nucleic acid is cDNA. In another embodiment, the nucleic acid is mRNA. In yet another embodiment, this invention provides an isolated nucleic acid which hybridizes under conditions of high stringency to the above-listed nucleic acids. In yet still another embodiment, the nucleic acid encodes a C. elegans insulin-like protein or a functional derivative thereof.

This invention provides an isolated nucleic acid comprising a nucleotide sequence encoding a functional derivative of an amino acid sequence selected from the group consisting of SEQ ID NO:1, SEQ ID NO:6, SEQ ID NO:8, SEQ ID NO:9, SEQ ID NO:11, SEQ ID NO:12, SEQ ID NO:15, SEQ ID NO:17 and SEQ ID NO:18.

This invention provides an isolated nucleic acid comprising a nucleotide sequence that is antisense to a nucleotide sequence selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36.

This invention provides an isolated nucleic acid comprising a nucleotide sequence that is antisense to a nucleotide sequence encoding an amino acid sequence selected from the group consisting of SEQ ID NO:1, SEQ ID NO:6, SEQ ID NO:8, SEQ ID NO:9, SEQ ID NO:11, SEQ ID NO:12, SEQ ID NO:15, SEQ ID NO:17 and SEQ ID NO:18.

This invention provides a method of producing a C. elegans insulin-like protein comprising: (a) growing a recombinant cell containing a nucleic acid comprising a nucleotide sequence selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36 such that the encoded C. elegans insulin-like protein is expressed by the cell; and (b) recovering the expressed C. elegans insulin-like protein. This invention provides a C. elegans insulin-like protein produced by this method.

This invention provides a method of producing a C. elegans insulin-like protein comprising: (a) growing a recombinant cell containing a nucleic acid comprising a nucleotide sequence encoding a C. elegans insulin-like protein selected from the group consisting of SEQ ID NO:1, SEQ ID NO:6, SEQ ID NO:8, SEQ ID NO:9, SEQ ID NO:11, SEQ ID NO:12, SEQ ID NO:15, SEQ ID NO:17 and SEQ ID NO:18 such that the encoded C. elegans insulin-like protein is expressed by the cell; and (b) recovering the expressed C. elegans insulin-like protein. This invention provides a C. elegans insulin-like protein produced by this method.

This invention provides a method of identifying a phenotype associated with mutation or abnormal expression of a C. elegans insulin-like protein comprising identifying the effect of a mutated or abnormally expressed C. elegans insulin-like gene in a C. elegans animal. In one embodiment, the effect is determined by an assay selected from the group consisting of a dauer formation assay, a developmental assay, an energy metabolism assay, a growth rate assay and a reproductive capacity assay.

This invention provides a method of identifying a phenotype associated with mutation or abnormal expression of a C. elegans insulin-like protein comprising: (a) mutating or abnormally expressing a C. elegans insulin-like gene in a C. elegans animal; and (b) identifying an effect of the gene mutated or abnormally expressed. In one embodiment, the effect is identified by an assay selected from the group consisting of a dauer formation assay, a developmental assay, an energy metabolism assay, a growth rate assay and a reproductive capacity assay. In another embodiment of the above phenotype identification methods, the gene is mutated or abnormally expressed using a technique selected from the group consisting of EMS chemical deletion mutagenesis, transposon insertion mutagenesis and double-stranded RNA interference.

This invention provides a recombinant cell containing a recombinant nucleic acid comprising a nucleotide sequence selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36.

This invention provides a vector comprising a nucleotide sequence selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36, and an origin of replication. In one embodiment, the nucleotide sequence is operably linked to a heterologous promoter.

This invention provides a purified C. elegans insulin-like protein encoded by a nucleic acid capable of hybridizing under conditions of high stringency to a nucleic acid comprising a nucleotide sequence selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36.

This invention provides a purified protein consisting of a B peptide domain defined by residue numbers 31–58 linked by one or more disulfide bonds to an A peptide domain defined by residue numbers 83–109 of SEQ ID NO:1.

This invention provides a purified protein consisting of a B peptide domain defined by residue numbers 52–79 linked by one or more disulfide bonds to an A peptide domain defined by residue numbers 80–106 of SEQ ID NO:2.

This invention provides a purified protein consisting of a B peptide domain defined by residue numbers 53–76 linked by one or more disulfide bonds to an A peptide domain defined by residue numbers 77–106 of SEQ ID NO:3.

This invention provides a purified protein consisting of a B peptide domain defined by residue numbers 56–80 linked by one or more disulfide bonds to an A peptide domain defined by residue numbers 81–107 of SEQ ID NO:4.

This invention provides a purified protein consisting of a B peptide domain defined by residue numbers 59–87 linked by one or more disulfide bonds to an A peptide domain defined by residue numbers 88–112 of SEQ ID NO:5.

This invention provides a purified protein consisting of a B peptide domain defined by residue numbers 45–73 linked by one or more disulfide bonds to an A peptide domain defined by residue numbers 74–100 of SEQ ID NO:6.

This invention provides a purified protein consisting of a B peptide domain defined by residue numbers 52–80 linked by one or more disulfide bonds to an A peptide domain defined by residue numbers 81–105 of SEQ ID NO:7.

This invention provides a purified protein consisting of a B peptide domain defined by residue numbers 52–79 linked by one or more disulfide bonds to an A peptide domain defined by residue numbers 80–104 of SEQ ID NO:8.

This invention provides a purified protein consisting of a B peptide domain defined by residue numbers 62–90 linked by one or more disulfide bonds to an A peptide domain defined by residue numbers 91–118 of SEQ ID NO:9.

This invention provides a purified protein consisting of a B peptide domain defined by residue numbers 27–56 linked by one or more disulfide bonds to an A peptide domain defined by residue numbers 57–91 of SEQ ID NO:10.

This invention provides a purified protein consisting of a B peptide domain defined by residue numbers 22–51 linked by one or more disulfide bonds to an A peptide domain defined by residue numbers 52–86 of SEQ ID NO:11.

This invention provides a purified protein consisting of a B peptide domain defined by residue numbers 20–52 linked by one or more disulfide bonds to an A peptide domain defined by residue numbers 53–76 of SEQ ID NO:12.

This invention provides a purified protein consisting of a B peptide domain defined by residue numbers 20–58 linked by one or more disulfide bonds to an A peptide domain defined by residue numbers 59–83 of SEQ ID NO:13.

This invention provides a purified protein consisting of a B peptide domain defined by residue numbers 14–50 linked by one or more disulfide bonds to an A peptide domain defined by residue numbers 51–76 of SEQ ID NO:14.

This invention provides a purified protein consisting of a B peptide domain defined by residue numbers 20–57 linked by one or more disulfide bonds to an A peptide domain defined by residue numbers 58–80 of SEQ ID NO:15.

This invention provides a purified protein consisting of a B peptide domain defined by residue numbers 42–76 linked by one or more disulfide bonds to an A peptide domain defined by residue numbers 77–108 of SEQ ID NO:16.

This invention provides a purified protein consisting of a B peptide domain defined by residue numbers 20–62 linked by one or more disulfide bonds to an A peptide domain defined by residue numbers 63–95 of SEQ ID NO:17.

This invention provides a purified protein consisting of a B peptide domain defined by residue numbers 19–50 linked by one or more disulfide bonds to an A peptide domain defined by residue numbers 51–83 of SEQ ID NO:18.

This invention provides a method of identifying a gene-of-interest as capable of modifying a function of a C. elegans insulin-like gene comprising: (a) constructing a double mutant nematode having a first mutation in the C. elegans insulin-like gene which encodes a C. elegans insulin-like protein selected from the group consisting of SEQ ID NO:1, SEQ ID NO:6, SEQ ID NO:8, SEQ ID NO:9, SEQ ID NO:11, SEQ ID NO:12, SEQ ID NO:15, SEQ ID NO:17 and SEQ ID NO:18 and a second mutation in the gene-of-interest; and (b) determining whether the phenotype displayed by the double mutant nematode is different from the phenotype of a single mutant nematode having said first mutation but not said second mutation, in which the displaying of a phenotype by the double mutant nematode that is different from said single mutant nematode identifies the gene-of-interest as capable of modifying the function of the C. elegans insulin-like gene. In one embodiment, the double mutant nematode is produced using a technique selected from the group consisting of EMS chemical deletion mutagenesis, transposon insertion mutagenesis and double-stranded RNA interference. In another embodiment, the phenotype is selected from the group consisting of an altered body shape phenotype, an altered body size phenotype, an altered chemotaxis phenotype, an altered brood size phenotype, an altered egg-laying phenotype, an altered life span phenotype, an altered lipid accumulation phenotype, an altered locomotion phenotype, an altered organ morphogenesis phenotype, an altered thermotaxis phenotype, a dauer constitutive phenotype, a dauer defective phenotype, a lethal phenotype and a sterile phenotype. In yet another embodiment, the altered organ morphogenesis phenotype comprises an organ selected from the group consisting of vulva, nervous system, gut and musculature. In yet still another embodiment, the nematode having the altered body size phenotype is assayed for activity of a gene affecting body size selected from the group consisting of daf-4, sma-2 and sma-3. In a fifth embodiment the gene-of-interest displays nucleotide or amino acid sequence similarity to an insulin signaling pathway gene from vertebrates. In a sixth embodiment, the gene-of-interest is selected from the group consisting of daf-2, daf-16 and age-1.

This invention provides a C. elegans animal having a first mutation in a gene encoding a C. elegans insulin-like protein selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36, and a second mutation in a different gene that is the homolog of an insulin signaling pathway gene from vertebrates.

This invention provides a method of studying a function of a *C. elegans* insulin-like gene comprising: (a) mis-expressing a wild-type or mutant *C. elegans* insulin-like gene by driving expression with a homologous or heterologous promoter; and (b) detecting a phenotype in a transgenic nematode having the mis-expressed gene, so as to identify the function of the *C. elegans* insulin-like gene. In one embodiment, the heterologous promoter driving mis-expression is selected from the group consisting of an hsp 16-2 promoter, an hsp 16-41 promoter, a myo-2 promoter, an hlh-1 promoter and a mec-3 promoter. In another embodiment, transgenic animals mis-expressing *C. elegans* insulin-like genes further carry mutations in daf-2. In yet another embodiment, transgenic animals mis-expressing *C. elegans* insulin-like genes are assayed for changes in a phenotype selected from the group consisting of dauer formation and life span.

This invention provides a method of detecting the effect of expression of a *C. elegans* insulin-like gene on an insulin signaling pathway comprising: (a) mutating or abnormally expressing a wild-type *C. elegans* insulin-like gene in a nematode already having a mutation in the insulin signaling pathway that displays a phenotype-of-interest; and (b) detecting the effect of step (a) on the phenotype-of-interest, so as to detect the effect of expression of the *C. elegans* insulin-like gene. In one embodiment, the mutation in the insulin signaling pathway is in a gene selected from the group consisting of daf-2, daf-16 and age-1.

This invention provides a method of identifying a molecule that specifically binds to a ligand selected from the group consisting of a *C. elegans* insulin-like protein, a fragment of the *C. elegans* insulin-like protein comprising a domain of the protein, and a nucleic acid encoding the *C. elegans* insulin-like protein or fragment comprising: (a) contacting the ligand with a plurality of molecules under conditions conducive to binding between the ligand and the molecules; and (b) identifying a molecule within the plurality that specifically binds to the ligand. In one embodiment, the domain of the *C. elegans* insulin-like protein is selected from the group consisting from a signal peptide domain, a pre peptide domain, a pro peptide domain, a B peptide domain, a C peptide domain and an A peptide domain.

This invention provides a recombinant non-human animal in which a *C. elegans* insulin-like gene has been deleted or inactivated by recombinant methods or a progeny thereof containing the deleted or inactivated gene.

In one embodiment, the *C. elegans* insulin-like gene has been deleted or inactivated by a method selected from the group consisting of EMS chemical deletion mutagenesis, transposon insertion mutagenesis and double-stranded RNA interference. This invention provides a recombinant non-human animal containing a *C. elegans* insulin-like transgene.

In one embodiment, the *C. elegans* insulin-like transgene is under the control of a promoter that is not the native promoter of the transgene.

This invention provides a purified protein encoded by a first nucleic acid which hybridizes under conditions of high stringency to a second nucleic acid, which second nucleic acid comprises a nucleotide sequence of SEQ ID NO:1, wherein the protein is characterized as having a cleavable C peptide separating the B and A chains and an extra pair of Cys residues relative to vertebrate insulin-like proteins.

This invention provides a purified protein encoded by a first nucleic acid which hybridizes under conditions of high stringency to a second nucleic acid, which second nucleic acid comprises a nucleotide sequence selected from the group consisting of SEQ ID NO:20, SEQ ID NO:21, SEQ ID NO:22, SEQ ID NO:23, SEQ ID NO:24, SEQ ID NO:25, SEQ ID NO:26 and SEQ ID NO:27, wherein the protein is characterized as lacking a cleavable C peptide separating the B and A chains and as having an extra pair of Cys residues relative to vertebrate insulin-like proteins.

This invention provides a purified protein encoded by a first nucleic acid which hybridizes under conditions of high stringency to a second nucleic acid, which second nucleic acid comprises a nucleotide sequence selected from the group consisting of SEQ ID NO:28 and SEQ ID NO:29, wherein the protein is characterized as lacking a cleavable C peptide and as having the same number and relative spacing of Cys residues as found in vertebrate insulin-like proteins.

This invention provides a purified protein encoded by a first nucleic acid which hybridizes under conditions of high stringency to a second nucleic acid, which second nucleic acid comprises a nucleotide sequence selected from the group consisting of SEQ ID NO:30, SEQ ID NO:31, SEQ ID NO:32 and SEQ ID NO:33, wherein the protein is characterized as (a) lacking a cleavable C peptide separating the B and A chains, (b) lacking an intra-chain disulfide bond in the A domain which is characteristic of vertebrate insulin-like proteins, and (c) having an extra pair of Cys residues relative to vertebrate insulin-like proteins.

This invention provides a purified protein encoded by a first nucleic acid which hybridizes under conditions of high stringency to a second nucleic acid, which second nucleic acid comprises a nucleotide sequence selected from the group consisting of SEQ ID NO:34, SEQ ID NO:35 and SEQ ID NO:36, wherein the protein is characterized as lacking a cleavable C peptide separating the B and A chains and as having uncharacteristic spacing between Cys residues as compared to vertebrate insulin-like proteins.

In one embodiment of the above proteins lacking a cleavable C peptide, the B and A chain domains of the protein are not proteolytically cleaved into separate chains.

This invention provides a method of identifying a molecule that alters the expression level of a *C. elegans* insulin-like gene corresponding to a cDNA selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36, which method comprises: (a) contacting a transgenic nematode with one or more molecules, said transgenic nematode having a transgene comprising a promoter or enhancer region of genomic DNA from 1 base to 6 kilobases upstream of the start codon of the cDNA operably linked to a reporter gene; and (b) determining whether the level of expression of the reporter gene is altered relative to the level of expression of the reporter gene in the absence of the one or more molecules. Further, this invention provides a method of identifying a molecule that binds to a promoter or enhancer of a *C. elegans* insulin-like gene corresponding to a cDNA selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36, which method comprises: (a) contacting a transgenic nematode with one or more molecules, said transgenic nematode having a transgene comprising a promoter or enhancer region of genomic DNA from 1 base to 6 kilobases upstream of the start codon of the cDNA operably linked to a reporter gene; (b) determining whether the level of expression of the reporter gene is altered relative to the level of expression of the reporter gene in the absence of the one or more molecules; (c) contacting the one or more molecules with the promoter or enhancer region of genomic DNA; and (d) identifying the molecule contacted in step (c) that binds to the promoter or enhancer. In one embodiment, of the above methods, the reporter gene encodes green fluorescent protein.

This invention provides a purified *C. elegans* insulin-like protein. In one embodiment, the protein has an amino acid sequence substantially as set forth in SEQ ID NO:1. In another embodiment, the protein has an amino acid sequence substantially as set forth in SEQ ID NO:1 beginning with residue number 31 and ending with residue number 109. In another embodiment, the protein has an amino acid sequence substantially as set forth in SEQ ID NO:2. In another embodiment, the protein has an amino acid sequence substantially as set forth in SEQ ID NO:2 beginning with residue number 20 and ending with residue number 106. In another embodiment, the protein has an amino acid sequence substantially as set forth in SEQ ID NO:3. In another embodiment, the protein has an amino acid sequence substantially as set forth in SEQ ID NO:3 beginning with residue number 16 and ending with residue number 106. In another embodiment, the protein has an amino acid sequence substantially as set forth in SEQ ID NO:4. In another embodiment, the protein has an amino acid sequence substantially as set forth in SEQ ID NO:4 beginning with residue number 18 and ending with residue number 107. In another embodiment, the protein has an amino acid sequence substantially as set forth in SEQ ID NO:5. In another embodiment, the protein has an amino acid sequence substantially as set forth in SEQ ID NO:5 beginning with residue number 20 and ending with residue number 112. In another embodiment, the protein has an amino acid sequence substantially as set forth in SEQ ID NO:6. In another embodiment, the protein has an amino acid sequence substantially as set forth in SEQ ID NO:6 beginning with residue number 18 and ending with residue number 100. In another embodiment, the protein has an amino acid sequence substantially as set forth in SEQ ID NO:7. In another embodiment, the protein has an amino acid sequence substantially as set forth in SEQ ID NO:7 beginning with residue number 19 and ending with residue number 105. In another embodiment, the protein has an amino acid sequence substantially as set forth in SEQ ID NO:8. In another embodiment, the protein has an amino acid sequence substantially as set forth in SEQ ID NO:8 beginning with residue number 19 and ending with residue number 104. In another embodiment, the protein has an amino acid sequence substantially as set forth in SEQ ID NO:9. In another embodiment, the protein has an amino acid sequence substantially as set forth in SEQ ID NO:9 beginning with residue number 19 and ending with residue number 118. In another embodiment, the protein has an amino acid sequence substantially as set forth in SEQ ID NO:10. In another embodiment, the protein has an amino acid sequence substantially as set forth in SEQ ID NO:10 beginning with residue number 27 and ending with residue number 91. In another embodiment, the protein has an amino acid sequence substantially as set forth in SEQ ID NO:11. In another embodiment, the protein has an amino acid sequence substantially as set forth in SEQ ID NO:11 beginning with residue number 22 and ending with residue number 86. In another embodiment, the protein has an amino acid sequence substantially as set forth in SEQ ID NO:12. In another embodiment, the protein has an amino acid sequence substantially as set forth in SEQ ID NO:12 beginning with residue number 20 and ending with residue number 76. In another embodiment, the protein has an amino acid sequence substantially as set forth in SEQ ID NO:13. In another embodiment, the protein has an amino acid sequence substantially as set forth in SEQ ID NO:13 beginning with residue number 20 and ending with residue number 83. In another embodiment, the protein has an amino acid sequence substantially as set forth in SEQ ID NO:14. In another embodiment, the protein has an amino acid sequence substantially as set forth in SEQ ID NO:14 beginning with residue number 14 and ending with residue number 76. In another embodiment, the protein has an amino acid sequence substantially as set forth in SEQ ID NO:15. In another embodiment, the protein has an amino acid sequence substantially as set forth in SEQ ID NO:15 beginning with residue number 20 and ending with residue number 80. In another embodiment, the protein has an amino acid sequence substantially as set forth in SEQ ID NO:16. In another embodiment, the protein has an amino acid sequence substantially as set forth in SEQ ID NO:16 beginning with residue number 20 and ending with residue number 108. In another embodiment, the protein has an amino acid sequence substantially as set forth in SEQ ID NO:17. In another embodiment, the protein has an amino acid sequence substantially as set forth in SEQ ID NO:17 beginning with residue number 20 and ending with residue number 95. In another embodiment, the protein has an amino acid sequence substantially as set forth in SEQ ID NO:18. In another embodiment, the protein has an amino acid sequence substantially as set forth in SEQ ID NO:18 beginning with residue number 19 and ending with residue number 83.

This invention provides a purified *C. elegans* insulin-like protein. This invention provides a purified *C. elegans* insulin-like protein having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and SEQ ID NO:18. This invention provides a purified *C. elegans* insulin-like protein encoded by a nucleic acid capable of hybridizing under conditions of high stringency to a nucleic acid comprising a nucleotide sequence selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36.

This invention provides a purified derivative or analog of the above-listed proteins. In one embodiment, the purified derivative or analog displays one or more functional activities of an insulin-like protein. In another embodiment, the purified derivative or analog is capable of immunospecific binding to an anti-insulin-like protein antibody.

This invention provides a purified fragment of a *C. elegans* insulin-like protein comprising a domain of the *C. elegans* insulin-like protein selected from the group consisting of a B peptide domain and an A peptide domain. In a preferred embodiment, a molecule comprising the purified fragment is provided.

This invention provides a chimeric protein comprising a fragment of a *C. elegans* insulin-like protein consisting of at least 6 amino acids fused by covalent bond to an amino acid sequence of a second protein, which second protein is not an insulin-like protein. In one embodiment, the fragment of the C. elegans insulin-like protein is a fragment capable of immunospecific binding to an anti-insulin-like protein antibody. In another embodiment, the fragment capable of immunospecific binding to an anti-insulin-like protein antibody further lacks one or more domains of the insulin-like protein.

This invention provides a purified antibody capable of immunospecific binding to a C. elegans insulin-like protein. In one embodiment, the antibody is polyclonal. In another embodiment, the antibody is monoclonal.

This invention provides an isolated nucleic acid comprising a nucleotide sequence encoding a C. elegans insulin-like protein selected from the group consisting of SEQ ID NO:24 and SEQ ID NO:30 (i.e., ZK84.N2 and M04D8.1, respectively; see Table 1). In one embodiment, the nucleic acid is cDNA. In another embodiment, the nucleic acid is genomic DNA. In still another embodiment, the isolated nucleic acid comprises a nucleotide sequence complementary to a nucleotide sequence selected from the group consisting of SEQ ID NO:24 and SEQ ID NO:30 (i.e., ZK84.N2 and M04D8.1, respectively; see Table 1). In yet still another embodiment, the isolated nucleic acid comprises a nucleotide sequence capable of hybridizing under conditions of high stringency to a nucleotide sequence selected from the group consisting of SEQ ID NO:24 and SEQ ID NO:30 (i.e., ZK84.N2 and M04D8.1, respectively; see Table 1).

This invention provides a method of producing a C. elegans insulin-like protein comprising: (a) growing a recombinant cell containing a nucleic acid comprising a nucleotide sequence selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36 such that the encoded C. elegans insulin-like protein is expressed by the cell; and (b) recovering the expressed C. elegans insulin-like protein from the cell.

This invention provides a method of identifying a C. elegans insulin-like protein signaling pathway comprising: (a) disrupting a C. elegans insulin-like gene; and (b) identifying the effect of the gene disrupted in step (a) in an assay selected from the group consisting of a dauer formation assay, a developmental assay, an energy metabolism assay, a growth rate assay and a reproductive capacity assay. In one embodiment, the gene is disrupted using EMS chemical deletion mutagenesis. In another embodiment, the gene is disrupted using transposon insertion mutagenesis.

This invention provides an isolated nucleic acid comprising a nucleotide sequence encoding a C. elegans insulin-like protein selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36, corresponding to F13B12.N, ZK84.N2, ZK1251.N, C06E2.N, C17C3.N, M04D8.1, ZK84.N, T28B8.N and ZC334.N, respectively. In one embodiment, the nucleic acid is cDNA. In another embodiment, the nucleic acid is mRNA. In yet another embodiment, the nucleic acid comprises a nucleotide sequence complementary to the above nucleotide sequences. In yet still another embodiment, the nucleic acid is capable of hybridizing under conditions of high stringency to the above-listed nucleic acids.

This invention provides a method of producing a C. elegans insulin-like protein comprising: (a) growing a recombinant cell containing a nucleic acid comprising a nucleotide sequence selected from the group consisting of SEQ ID NO:19, SEQ ID NO:24, SEQ ID NO:26, SEQ ID NO:27, :SEQ ID NO:29, SEQ ID NO:30, SEQ ID NO:33, SEQ ID NO:35 and SEQ ID NO:36 such that the encoded C. elegans insulin-like protein is expressed by the cell; and (b) recovering the expressed C. elegans insulin-like protein from the cell. In another embodiment, this invention provides a C. elegans insulin-like protein produced by the above method.

This invention provides a method of identifying a phenotype associated with mutation or inactivation of a C. elegans insulin-like protein comprising identifying the effect of an inactivated or mutated insulin-like gene in a C. elegans animal in an assay selected from the group consisting of a dauer formation assay, a developmental assay, an energy metabolism assay, a growth rate assay and a reproductive capacity assay. Further, this invention provides a method of identifying a phenotype associated with mutation or inactivation of a C. elegans insulin-like protein comprising: (a) inactivating or mutating an insulin-like gene in a C. elegans animal; and (b) identifying the effect of the gene inactivated or mutated in step (a) in an assay selected from the group consisting of a dauer formation assay, a developmental assay, an energy metabolism assay, a growth rate assay and a reproductive capacity assay. In one embodiment of these methods, the gene is inactivated or mutated using EMS chemical deletion mutagenesis. In another embodiment of these methods, the gene is inactivated or mutated using transposon insertion mutagenesis. In yet another embodiment of these methods, the gene is inactivated or mutated using double-stranded RNA interference.

This invention provides a recombinant cell containing a nucleic acid comprising a nucleotide sequence selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36, corresponding to F13B12.N, ZK84.N2, ZK1251.N, C06E2.N, C17C3.N, M04D8.1, ZK84.N, T28B8.N and ZC334.N, respectively.

This invention provides a vector containing a nucleic acid comprising a nucleotide sequence selected from the group consisting of SEQ ID NO:19, SEQ ID NO:24, SEQ ID NO:26, SEQ ID NO:27, SEQ ID NO:29, SEQ ID NO:30, SEQ ID NO:33, SEQ ID NO:35 and SEQ ID NO:36, corresponding to F13B12.N, ZK84.N2, ZK1251.N, C06E2.N, C17C3.N, M04D8.1, ZK84.N, T28B8.N and ZC334.N, respectively.

This invention provides a purified C. elegans insulin-like protein encoded by a nucleic acid capable of hybridizing under conditions of high stringency to a nucleic acid comprising a nucleotide sequence selected from the group consisting of SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 and SEQ ID NO:36.

This invention provides a purified C. elegans insulin-like protein having an amino acid sequence substantially as set forth in SEQ ID NO:1, which protein consists of a B peptide domain defined by residue numbers 31–58 linked by one or more disulfide bonds to an A peptide domain defined by residue numbers 83–109.

This invention provides a purified C. elegans insulin-like protein having an amino acid sequence substantially as set forth in SEQ ID NO:2, which protein consists of a B peptide domain defined by residue numbers 52–79 linked by one or more disulfide bonds to an A peptide domain defined by residue numbers 80–106.

This invention provides a purified *C. elegans* insulin-like protein having an amino acid sequence substantially as set forth in SEQ ID NO:3, which protein consists of a B peptide domain defined by residue numbers 53–76 linked by one or more disulfide bonds to an A peptide domain defined by residue numbers 77–106.

This invention provides a purified *C. elegans* insulin-like protein having an amino acid sequence substantially as set forth in SEQ ID NO:4, which protein consists of a B peptide domain defined by residue numbers 56–80 linked by one or more disulfide bonds to an A peptide domain defined by residue numbers 81–107.

This invention provides a purified *C. elegans* insulin-like protein having an amino acid sequence substantially as set forth in SEQ ID NO:5, which protein consists of a B peptide domain defined by residue numbers 59–87 linked by one or more disulfide bonds to an A peptide domain defined by residue numbers 88–112.

This invention provides a purified *C. elegans* insulin-like protein having an amino acid sequence substantially as set forth in SEQ ID NO:6, which protein consists of a B peptide domain defined by residue numbers 45–73 linked by one or more disulfide bonds to an A peptide domain defined by residue numbers 74–100.

This invention provides a purified *C. elegans* insulin-like protein having an amino acid sequence substantially as set forth in SEQ ID NO:7, which protein consists of a B peptide domain defined by residue numbers 52–80 linked by one or more disulfide bonds to an A peptide domain defined by residue numbers 81–105.

This invention provides a purified *C. elegans* insulin-like protein having an amino acid sequence substantially as set forth in SEQ ID NO:8, which protein consists of a B peptide domain defined by residue numbers 52–79 linked by one or more disulfide bonds to an A peptide domain defined by residue numbers 80–104.

This invention provides a purified *C. elegans* insulin-like protein having an amino acid sequence substantially as set forth in SEQ ID NO:9, which protein consists of a B peptide domain defined by residue numbers 62–90 linked by one or more disulfide bonds to an A peptide domain defined by residue numbers 91–118.

This invention provides a purified *C. elegans* insulin-like protein having an amino acid sequence substantially as set forth in SEQ ID NO:10, which protein consists of a B peptide domain defined by residue numbers 27–56 linked by one or more disulfide bonds to an A peptide domain defined by residue numbers 57–91.

This invention provides a purified *C. elegans* insulin-like protein having an amino acid sequence substantially as set forth in SEQ ID NO:11, which protein consists of a B peptide domain defined by residue numbers 22–51 linked by one or more disulfide bonds to an A peptide domain defined by residue numbers 52–86.

This invention provides a purified *C. elegans* insulin-like protein having an amino acid sequence substantially as set forth in SEQ ID NO:12, which protein consists of a B peptide domain defined by residue numbers 20–52 linked by one or more disulfide bonds to an A peptide domain defined by residue numbers 53–76.

This invention provides a purified *C. elegans* insulin-like protein having an amino acid sequence substantially as set forth in SEQ ID NO:13, which protein consists of a B peptide domain defined by residue numbers 20–58 linked by one or more disulfide bonds to an A peptide domain defined by residue numbers 59–83.

This invention provides a purified *C. elegans* insulin-like protein having an amino acid sequence substantially as set forth in SEQ ID NO:14, which protein consists of a B peptide domain defined by residue numbers 14–50 linked by one or more disulfide bonds to an A peptide domain defined by residue numbers 51–76.

This invention provides a purified *C. elegans* insulin-like protein having an amino acid sequence substantially as set forth in SEQ ID NO:15, which protein consists of a B peptide domain defined by residue numbers 20–57 linked by one or more disulfide bonds to an A peptide domain defined by residue numbers 58–80.

This invention provides a purified *C. elegans* insulin-like protein having an amino acid sequence substantially as set forth in SEQ ID NO:16, which protein consists of a B peptide domain defined by residue numbers 42–76 linked by one or more disulfide bonds to an A peptide domain defined by residue numbers 77–108.

This invention provides a purified *C. elegans* insulin-like protein having an amino acid sequence substantially as set forth in SEQ ID NO:17, which protein consists of a B peptide domain defined by residue numbers 20–62 linked by one or more disulfide bonds to an A peptide domain defined by residue numbers 63–95.

This invention provides a purified *C. elegans* insulin-like protein having an amino acid sequence substantially as set forth in SEQ ID NO:18, which protein consists of a B peptide domain defined by residue numbers 19–50 linked by one or more disulfide bonds to an A peptide domain defined by residue numbers 51–83.

This invention provides a method of identifying functional redundancy of a *C. elegans* insulin-like gene in contributing to a phenotype comprising: (a) knocking-out function of more than one insulin-like gene simultaneously; and (b) detecting no change in the phenotype. In one embodiment, knocking-out function is carried out by simultaneous injection of more than one double-stranded RNA derived from each gene using the method of double-stranded RNA interference.

This invention provides a method identifying a gene-of-interest as capable of modifying a function of an insulin-like gene comprising: (a) constructing a double mutant nematode having a mutation in the insulin-like gene and the gene-of-interest; and (b) detecting a phenotype in the double mutant nematode which is different from the phenotype of a single mutant nematode in the insulin-like gene, so as to identify the gene-of-interest as capable of modifying the function of the *C. elegans* insulin-like gene. the double mutant nematode is produced using a technique selected from the group consisting of EMS chemical deletion mutagenesis, transposon insertion mutagenesis and double-stranded RNA interference. In one embodiment, the phenotype is selected from the group consisting of an altered body shape phenotype, an altered body size phenotype, an altered chemotaxis phenotype, an altered brood size. phenotype, an altered egg-laying phenotype, an altered life span phenotype, an altered lipid accumulation phenotype, an altered locomotion phenotype, an altered organ morphogenesis phenotype, an altered thermotaxis phenotype, a dauer constitutive phenotype, a dauer defective phenotype, a lethal phenotype and a sterile phenotype. In another embodiment, the altered organ morphogenesis phenotype comprises an organ selected from the group consisting of vulva, nervous system, gut and musculature. In yet another embodiment, a nematode having the altered body size phenotype is assayed for activity of a gene affecting body size selected from the group consisting of daf-4, sma-2 and sma-3. In yet still another embodiment, the gene-of-interest displays nucleotide or amino acid sequence similarity to an insulin signaling pathway gene from vertebrates. In yet still another embodiment, the gene-of-interest is selected from the group consisting of daf-2, daf-16 and age-1.

This invention provides a method of identifying a function of an insulin-like gene comprising: (a)mis-expressing a wild-type or mutant insulin-like gene by driving expression with a promoter; and (b) detecting a phenotype in a transgenic nematode having the mis-expressed gene, so as to identify the function of the insulin-like gene. in one embodiment, the promoter driving mis-expression is selected from the group consisting of an hsp 16-2 promoter, an hsp 16-41 promoter, a myo-2 promoter, an hlh-1 promoter and a mec-3 promoter. In another embodiment, transgenic animals mis-expressing insulin-like genes further carry mutations in daf-2. In yet another embodiment, transgenic animals mis-expressing insulin-like genes are assayed for changes in a phenotype selected from the group consisting of dauer formation and life span.

This invention provides a method of detecting the effect of expression of a C. elegans insulin-like gene on an insulin signaling pathway comprising: (a) over-expressing, inactivating or mutating a wild-type C. elegans insulin-like gene; and (b) detecting the effect of step (a) on a phenotype exhibited by a nematode already having a mutation in the insulin signaling pathway, so as to detect the effect of expression of the C. elegans insulin-like gene. In one embodiment, the mutation in the insulin signaling pathway occurs in a gene selected from the group consisting of daf-2, daf-16 and age-1.

This invention provides a method of identifying a molecule that specifically binds to a ligand selected from the group consisting of a C. elegans insulin-like protein, a fragment of the C. elegans insulin-like protein comprising a domain of the protein, and a nucleic acid encoding the C. elegans insulin-like protein or fragment comprising: (a) contacting the ligand with a plurality of molecules under conditions conducive to binding between the ligand and the molecules; and (b) identifying a molecule within the plurality that specifically binds to the ligand. In one embodiment, the domain of the C. elegans insulin-like protein is selected from the group consisting from a signal peptide, a pro peptide, a B peptide domain, a C peptide domain and an A peptide domain.

This invention provides a recombinant non-human animal or an ancestor thereof in which a C. elegans insulin-like gene has been deleted or inactivated. In one embodiment, the C. elegans insulin-like gene has been deleted or inactivated by a method selected from the group consisting of EMS chemical deletion mutagenesis, transposon insertion mutagenesis and double-stranded RNA interference.

This invention provides a recombinant non-human animal containing a C. elegans insulin-like transgene. In one embodiment, the C. elegans insulin-like transgene is under the control of a promoter that is not the natural promoter of the transgene (i.e., the promoter is a heterologous promoter).

This invention provides a C. elegans insulin-like protein (SEQ ID NO:1), wherein the mature protein is characterized as having a cleavable C peptide separating the B and A chains and an extra pair of Cys residues (e.g., F13B12.N).

This invention provides a C. elegans insulin-like protein selected from the group consisting of SEQ ID NO:2, SEQ ID NO:3, SEQ ID NO:4, SEQ ID NO:5, SEQ ID NO:6, SEQ ID NO:7, SEQ ID NO:8 and SEQ ID NO:9, wherein the mature protein is characterized as lacking a cleavable C peptide separating the B and A chains and as having an extra pair of Cys residues (e.g., ZK75.1, ZK75.2, ZK75.3, ZK84.6, ZK84.N2, ZK1251.2, ZK1251.N and C06E2.N).

This invention provides a C. elegans insulin-like protein selected from the group consisting of SEQ ID NO:10 and SEQ ID NO:11, wherein the mature protein is characterized as lacking a cleavable C peptide and as having the same number and relative spacing of Cys residues as found in vertebrate insulin-like proteins (e.g., C17C3.4 and C17C3.N).

This invention provides a C. elegans insulin-like protein selected from the group consisting of SEQ ID NO:12, SEQ ID NO:13, SEQ ID NO:14 and SEQ ID NO:15, wherein the mature protein is characterized as lacking a cleavable C peptide separating the B and A chains and as having an extra pair of Cys residues and as lacking the intra-chain disulfide bond in the A domain which is characteristic of vertebrate insulin-like proteins (e.g., M04D8.1, M04D8.2, M04D8.3 and ZK84.N).

This invention provides a C. elegans insulin-like protein selected from the group consisting of SEQ ID NO:16, SEQ ID NO:17 and SEQ ID NO:18, wherein the mature protein is characterized as lacking a cleavable C peptide separating the B and A chains and as having uncharacteristic spacing between Cys residues as compared to vertebrate insulin-like proteins (e.g., F56F3.6, T28B8.2 and ZC334.N).

This invention provides a C. elegans insulin-like protein, wherein the B and A chain domains of the protein are not cleaved into separate chains (e.g., ZK75.1, ZK75.2, ZK75.3, ZK84.6, ZK84.N2, ZK1251.2, ZK1251.N, C06E2.N, C17C3.4, C17C3.N, M04D8.1, M04D8.2, M04D8.3, ZK84.N, F56F3.6, T28B8.2 and ZC334.N).

This invention provides a C. elegans insulin-like protein (SEQ ID NO:1), wherein the mature protein is characterized as having an excised C peptide and an interchain disulfide bond between Cys residue 52 in the B chain and Cys residue 104 in the A chain (e.g., F13B12.N).

4. BRIEF DESCRIPTION OF THE DRAWINGS

FIG. 1. Structural organization of precursor forms of the insulin superfamily of hormones.

FIG. 2. Conserved structural features of insulin superfamily members (human Insulin SEQ ID NOs: 216 and 217, human IGF-1 SEQ ID NO: 218, human relaxin 1 SEQ ID NOs: 219 and 220, RLP SEQ ID NOs: 221 and 222, placentin SEQ ID NOs: 223 and 224, bombyxin II SEQ ID NOs: 225 and 226, MIP I, SEQ ID NOs: 227 and 228, and LIRP SEQ ID NOs: 229 and 230).

Figure 3A:
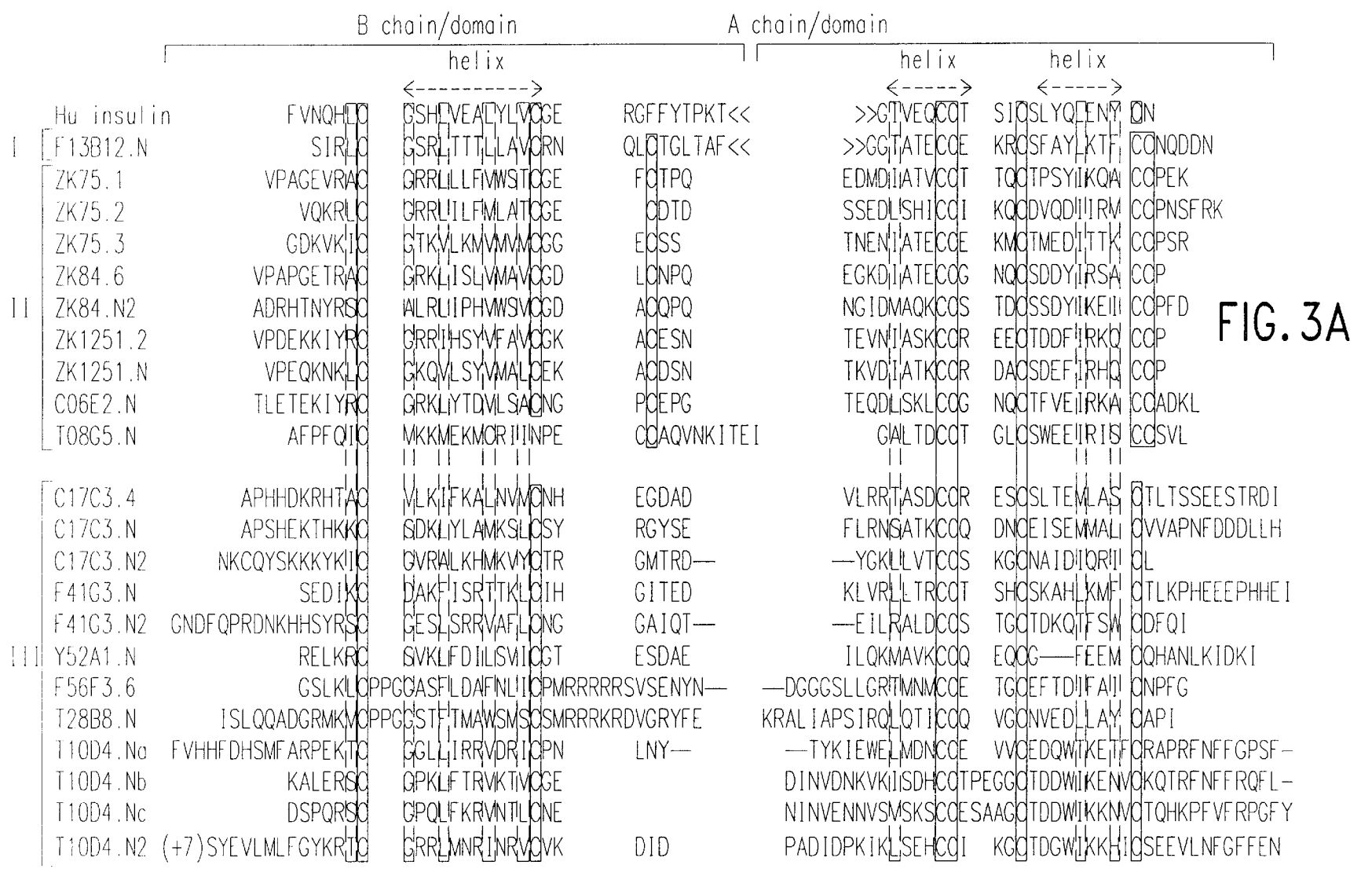

FIGS. 3A–3B. Alignment of the C elegans insulin-like protein family (SEQ ID NOS:1–18, 158–161 and 198–206).

FIGS. 4A–4B. Annotated sequence of C. elegans insulin-like protein F13B12.N and corresponding cDNA (cDNA (SEQ ID NO:19), Signal Peptide (SEQ ID NO:299), Peptide B (SEQ ID NO:300), Peptide C (SEQ ID NO:301), Peptide A (SEQ ID NO:302)).

FIGS. 5A–5B. Annotated sequence of C. elegans insulin-like protein ZK75.1 (SEQ ID NO:2) and corresponding cDNA (SEQ ID NO:20).

FIGS. 6A–6B. Annotated sequence of C. elegans insulin-like protein ZK75.2 (SEQ ID NO:3) and corresponding cDNA (SEQ ID NO:21).

FIGS. 7A–7B. Annotated sequence of *C. elegans* insulin-like protein ZK75.3 (SEQ ID NO:4) and corresponding cDNA (SEQ ID NO:22).

FIGS. 8A–8B. Annotated sequence of *C. elegans* insulin-like protein ZK84.6 (SEQ ID NO:5) and corresponding cDNA (SEQ ID NO:23).

FIGS. 9A–9B. Annotated sequence of *C. elegans* insulin-like protein ZK84.N2 (SEQ ID NO:6) and corresponding cDNA (SEQ ID NO:24).

FIGS. 10A–10B. Annotated sequence of *C. elegans* insulin-like protein ZK1251.2 (SEQ ID NO:7) and corresponding cDNA (SEQ ID NO:25).

FIGS. 11A–11B. Annotated sequence of *C. elegans* insulin-like protein ZK1251.N (SEQ ID NO:8) and corresponding cDNA (SEQ ID NO:26).

FIGS. 12A–12B. Annotated sequence of *C. elegans* insulin-like protein CO6E2.N (SEQ ID NO:9) and corresponding cDNA (SEQ ID NO:27).

FIG. 13. Annotated sequence of *C. elegans* insulin-like protein C17C3.4 (SEQ ID NO:10) and corresponding cDNA (SEQ ID NO:28).

FIG. 14. Annotated sequence of *C. elegans* insulin-like protein C17C3.N (SEQ ID NO:11) and corresponding cDNA (SEQ ID NO:29).

FIG. 15. Annotated sequence of *C. elegans* insulin-like protein M04D8.1 (SEQ ID NO:12) and corresponding cDNA (SEQ ID NO:30).

FIG. 16. Annotated sequence of *C. elegans* insulin-like protein M04D8.2 (SEQ ID NO:13) and corresponding cDNA (SEQ ID NO:31).

FIG. 17. Annotated sequence of *C. elegans* insulin-like protein M04D8.3 (SEQ ID NO:14) and corresponding cDNA (SEQ ID NO:32).

FIG. 18. Annotated sequence of *C. elegans* insulin-like protein ZK84.N (SEQ ID NO:15) and corresponding cDNA (SEQ ID NO:33).

FIGS. 19A–19B. Annotated sequence of *C. elegans* insulin-like protein F56F3.6 (SEQ ID NO:16) and corresponding cDNA (SEQ ID NO:34).

FIG. 20. Annotated sequence of *C. elegans* insulin-like protein T28B8.N (SEQ ID NO:17) and corresponding cDNA (SEQ ID NO:35).

FIG. 21. Annotated sequence of *C. elegan* insulin-like protein ZC334.N (SEQ ID NO:18) and corresponding cDNA (SEQ ID NO:36).

FIG. 22. Annotated sequence of *C. elegans* insulin-like protein TO8G5.N (SEQ ID NO:158) and corresponding cDNA (SEQ ID NO:162).

FIG. 23. Annotated sequence of *C. elegans* insulin-like protein F41G3.N (SEQ ID NO:159) and corresponding cDNA (SEQ ID NO:163).

FIG. 24. Annotated sequence of *C. elegans* insulin-like protein F41G3.N2 (SEQ ID NO:160) and corresponding cDNA (SEQ ID NO:164).

FIG. 25. Annotated sequence of *C. elegans* insulin-like protein C17C3 (SEQ ID NO:161) and corresponding cDNA (SEQ ID NO:165).

FIGS. 26A–26B. Annotated sequence of *C. elegans* insulin-like protein ZC334.N2 (SEQ ID NO:198) and corresponding cDNA (SEQ ID NO:207).

FIG. 27. Annotated sequence of *C. elegans* insulin-like protein ZC334.N3 (SEQ ID NO:199) and corresponding cDNA (SEQ ID NO:208).

FIGS. 28A–28B. Annotated sequence of *C. elegans* insulin-like protein ZC334.N4 (SEQ ID NO:200) and corresponding cDNA (SEQ ID NO:209).

FIG. 29. Annotated sequence of *C. elegans* insulin-like protein ZC334.N5 (SEQ ID NO:201) and corresponding cDNA (SEQ ID NO:210).

FIG. 30. Annotated sequence of *C. elegans* insulin-like protein ZC334.N6 (SEQ ID NO:202) and corresponding cDNA (SEQ ID NO:211).

FIGS. 31A–31B. Annotated sequence of *C. elegans* insulin-like protein ZC334.N7 (SEQ ID NO:203) and corresponding cDNA (SEQ ID NO:212).

FIGS. 32A–32C. Annotated sequence of *C. elegans* insulin-like protein T10D4.N (SEQ ID NO:204) and corresponding cDNA (SEQ ID NO:213).

FIGS. 33A–33B. Annotated sequence of *C. elegans* insulin-like protein T10D4.N (SEQ ID NO:205) and corresponding cDNA (SEQ ID NO:214).

FIG. 34. Annotated sequence of *C. elegans* insulin-like protein Y52A1.N (SEQ ID NO:206) and corresponding cDNA (SEQ ID NO:215).

5. DETAILED DESCRIPTION OF THE INVENTION

The present invention relates to proteins encoded by and nucleotide sequences of *C. elegans* insulin-like genes. The invention further relates to fragments and other derivatives and analogs of such insulin-like proteins. Nucleic acids encoding such fragments or derivatives are also within the scope of the invention. Production of the foregoing proteins, e.g., by recombinant methods, is provided.

The invention also relates to insulin-like protein derivatives and analogs which are functionally active, i.e., which are capable of displaying one or more known functional activities associated with a full-length (wild-type) insulin-like protein. Such functional activities include but are not limited to antigenicity (ability to bind, or to compete for binding, to an anti-insulin-like protein antibody), immunogenicity (ability to generate antibody which binds to an insulin-like protein), and ability to bind (or compete for binding) to a receptor for insulin (e.g., the *C. elegans* insulin receptor-like gene daf-2).

The invention further relates to fragments (and derivatives and analogs thereof) of an insulin-like protein which comprise one or more domains of the insulin-like protein.

Antibodies to an insulin-like protein, its derivatives and analogs, are additionally provided.

The invention is illustrated by way of examples set forth in Section 6 below which disclose, inter alia, the cloning and characterization of *C. elegans* insulin-like genes.

For clarity of disclosure, and not by way of limitation, the detailed description of the invention is divided into the subsections which follow.

5.1. Isolation of *C. elegans* Insulin-LIKE Genes

The invention relates to the nucleotide sequences of *C. elegans* insulin-like nucleic acids. In specific embodiments, insulin-like nucleic acids comprise the cDNA sequences of SEQ ID NOs:19–36 or the coding regions thereof, or nucleic acids encoding an insulin-like protein (e.g., a protein having the sequence of SEQ ID NOs:1–18). The invention provides purified nucleic acids consisting of at least 8 nucleotides (i.e., a hybridizable portion) of an insulin-like gene sequence; in other embodiments, the nucleic acids consist of at least 25 (continuous) nucleotides, 50 nucleotides, 100 nucleotides, 150 nucleotides, or 200 nucleotides of an insulin-like sequence, or a full-length insulin-like coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of an insulin-like gene.

5.1.1. Hybridization Conditions

In a specific embodiment, a nucleic acid which is hybridizable to an insulin-like nucleic acid (e.g., having a sequence as set forth in SEQ ID NOs:19–36), or to a nucleic acid encoding an insulin-like derivative, under conditions of low stringency is provided. By way of example and not limitation, procedures using such conditions of low stringency are as follows (see also Shilo and Weinberg, 1981, Proc. Natl. Acad. Sci. U.S.A. 78, 6789–6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another specific embodiment, a nucleic acid which is hybridizable to an insulin-like nucleic acid under conditions of high stringency is provided. By way of example and not limitation, procedures using such conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at. 50° C. for 45 min before autoradiography. Other conditions of high stringency which may be used are well known in the art.

In another specific embodiment, a nucleic acid which is hybridizable to an insulin-like nucleic acid under conditions of moderate stringency is provided. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987–1997 Current Protocols, © 1994–1997 John Wiley and Sons, Inc.).

Nucleic acids encoding derivatives and analogs of insulin-like proteins, and insulin-like antisense nucleic acids are additionally provided. As is readily apparent, as used herein, a "nucleic acid encoding a fragment or portion of an insulin-like protein" shall be construed as referring to a nucleic acid encoding only the recited fragment or portion of the insulin-like protein and not the other contiguous portions of the insulin-like protein as a continuous sequence.

Fragments of insulin-like nucleic acids comprising regions conserved between (i.e., with homology to) other insulin-like nucleic acids, of the same or different species, are also provided. Nucleic acids encoding one or more insulin-like domains are provided.

5.1.2. Cloning Procedures

Specific embodiments for the cloning of an insulin-like gene follow. For expression cloning (a technique well know n in the art), an expression library is constructed by any method known in the art. For example, mRNA is isolated, cDNA is made and ligated into an expression vector (e.g., a bacteriophage derivative) such that it is capable of being expressed by the host cell into which it is then introduced. various screening assays can then be used to select for the expressed insulin-like product. In one embodiment, anti-insulin-like antibodies can be used for selection.

In another embodiment, polymerase chain reaction (PCR) is used to amplify the desired sequence in a genomic or cDNA library, prior to selection. Oligonucleotide primers representing known insulin-like sequences can be used as primers in PCR. In a preferred aspect, the oligonucleotide primers represent at least part of conserved segments of strong homology between insulin-like genes of different species. The synthetic oligonucleotides may be utilized as primers to amplify sequences from a source (RNA or DNA), preferably a cDNA library, of potential interest. PCR can be carried out, e.g., by use of a Perkin-Elmer Cetus thermal cycler and Taq polymerase (e.g., Gene Amp™). The nucleic acid being amplified can include mRNA or cDNA or genomic DNA from any species. One may synthesize degenerate primers for amplifying homologs from other species in the PCR reactions. It is also possible to vary the stringency of hybridization conditions used in priming the PCR reactions, to allow for greater or lesser degrees of nucleotide sequence similarity between the known insulin-like nucleotide sequences and a nucleic acid homolog (or ortholog) being isolated. For cross species hybridization, low stringency conditions are preferred. For same species hybridization, moderately stringent conditions are preferred. After successful amplification of a segment of an insulin-like homolog, that segment may be cloned and sequenced by standard techniques, and utilized as a probe to isolate a complete cDNA or genomic clone. This, in turn, permits the determination of the gene's complete nucleotide sequence, the analysis of its expression, and the production of its protein product for functional analysis, as described below. In this fashion, additional genes encoding insulin-like proteins and insulin-like analogs may be identified.

The above-described methods are not meant to limit the following general description of methods by which clones of insulin-like genes may be obtained.

Any eukaryotic cell potentially can serve as the nucleic acid source for molecular cloning of an insulin-like gene. The nucleic acid sequences encoding insulin-like proteins may be isolated from vertebrate, mammalian, human, porcine, bovine, feline, avian, equine, canine, as well as additional primate sources, insects (e.g., Drosophila), invertebrates (e.g., C. elegans), plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see e.g., Sambrook et al., 1989, Molecular Cloning, A Laboratory. Manual, 2d Ed., Cold Spring Harbor Laboratory Press, Cold Spring Harbor, N.Y.; Glover (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if a portion of an insulin-like gene or its specific RNA or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the desired gene may be detected by assays based on the physical, chemical, or immunological properties of its expressed product. For example, cDNA clones, or DNA clones which hybrid-select the proper mRNAs, can be selected and expressed to produce a protein that has, e.g., similar or identical electrophoretic migration, isoelectric focusing behavior, proteolytic digestion maps, hormonal activity, binding activity, or antigenic properties as known for an insulin-like protein. Using an antibody to a known insulin-like protein, other insulin-like proteins may be identified by binding of the labeled antibody to expressed putative insulin-like proteins, e.g., in an ELISA (enzyme-linked immunosorbent assay)-type procedure. Further, using a binding protein specific to a known insulin-like protein, other insulin-like proteins may be identified by binding to such a protein (see e.g., Clemmons, 1993, "IGF binding proteins and their functions," Mol. Reprod. Dev. 35:368–374; Loddick et al., 1998, "Displacement of insulin-like growth factors from their binding proteins as a potential treatment for stroke," Proc. Natl. Acad. Sci. U.S.A. 95:1894–1898).

An insulin-like gene can also be identified by mRNA selection using nucleic acid hybridization followed by in vitro translation. In this procedure, fragments are used to isolate complementary mRNAs by hybridization. Such DNA fragments may represent available, purified insulin-like DNA of another species (e.g., Drosophila, mouse, human). Immunoprecipitation analysis or functional assays (e.g., aggregation ability in vitro, binding to receptor, etc.) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against insulin-like protein. A radiolabeled insulin-like cDNA can be synthesized using the selected mRNA (from the adsorbed polysomes) as a template. The radiolabeled mRNA or cDNA may then be used as a probe to identify the insulin-like DNA fragments from among other genomic DNA fragments.

Alternatives to isolating the insulin-like genomic DNA include, but are not limited to, chemically synthesizing the gene sequence itself from a known sequence or making cDNA to the mRNA which encodes the insulin-like protein. For example, RNA for cDNA cloning of the insulin-like gene can be isolated from cells which express the gene.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and an insulin-like gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning-vector.

In specific embodiments, transformation of host cells with recombinant DNA molecules that incorporate an isolated insulin-like gene, cDNA, or synthesized DNA sequence enables generation of multiple copies-of the gene. Thus, the gene may be obtained in large quantities by growing transformants, isolating the recombinant DNA molecules from the transformants and, when necessary, retrieving the inserted gene from the isolated recombinant DNA.

The insulin-like sequences provided by the instant invention include those nucleotide sequences encoding substantially the same amino acid sequences as found in native insulin-like proteins, and those encoded amino acid sequences with functionally equivalent amino acids, as well as those encoding other insulin-like derivatives or analogs, as described in below for insulin-like derivatives and analogs.

5.2. Expression of *C. elegans* Insulin-LIKE Genes

The nucleotide sequence coding for an insulin-like protein or a functionally active analog or fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native insulin-like gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In yet another embodiment, a fragment of an insulin-like protein comprising one or more domains of the insulin-like protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding an insulin-like protein or peptide fragment may be regulated by a second nucleic acid sequence so that the insulin-like protein or peptide is expressed in a host transformed with the recombinant DNA molecule. For example, expression of an insulin-like protein may be controlled by any promoter/enhancer element known in the art. Promoters which may be used to control insulin-like gene expression include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff et al., 1978, Proc. Natl. Acad. Sci. U.S.A. 75:3727–3731), or the lac promoter (DeBoer et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter., alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); a gene control region which is active in pancreatic beta cells (Hanahan, 1985, Nature 315:115–122), an immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, a vector is used that comprises a promoter operably linked to an insulin-like gene nucleic acid, one or more origins of replication, and, optionally, one or more selectable markers (e.g., an antibiotic resistance gene).

In a specific embodiment, an expression construct is made by subcloning an insulin-like coding sequence into the EcoRI restriction site of each of the three PGEX vectors (Glutathione S-Transferase expression vectors; Smith and Johnson, 1988, Gene 7:31–40). This allows for the expression of the insulin-like protein product from the subclone in the correct reading frame.

Expression vectors containing insulin-like gene inserts can be identified by three general approaches: (a) nucleic acid hybridization; (b) presence or absence of "marker" gene functions; and (c) expression of inserted sequences. In the first approach, the presence of an insulin-like gene inserted in an expression vector can be detected by nucleic acid hybridization using probes comprising sequences that are homologous to an inserted insulin-like gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of an insulin-like gene in the vector. For example, if the insulin-like gene is inserted within the marker gene sequence of the vector, recombinants containing the insulin-like insert can be identified by the absence of the marker gene function. In the third approach, recombinant expression vectors can be identified by assaying the insulin-like product expressed by the recombinant. Such assays can be based, for example, on the physical or functional properties of the insulin-like protein in in vitro assay systems, e.g., binding with anti-insulin-like protein antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda phage), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered insulin-like protein may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce a non-glycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the insulin-like protein, fragment, analog, or derivative may be expressed as a fusion, or chimeric protein product (comprising the protein, fragment, analog, or derivative joined via a peptide bond to a heterologous protein sequence of a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

5.3. Identification and Purification of Gene Products

In particular aspects, the invention provides amino acid sequences of insulin-like proteins and fragments and derivatives thereof which comprise an antigenic determinant (i.e., can be recognized by an antibody) or which are otherwise functionally active, as well as nucleic acid sequences encoding the foregoing. "Functionally active" insulin-like material as used herein refers to that material displaying one or more functional activities associated with a full-length (wild-type) insulin-like protein, e.g., binding to an insulin-like receptor (e.g., daf-2) or insulin-like protein binding partner, antigenicity (binding to an anti-insulin-like protein antibody), immunogenicity, etc.

In specific embodiments, the invention provides fragments of an insulin-like protein consisting of at least 6 amino acids, 10 amino acids, 20 amino acids, 50 amino acids, or of at least 75 amino acids. In other embodiments, the proteins comprise or consist essentially of an insulin-like B peptide domain, an insulin-like A peptide domain, an insulin-like C peptide domain, or any combination of the foregoing, of an insulin-like protein. Fragments, or proteins comprising fragments, lacking some or all of the foregoing regions of a insulin-like protein are also provided. Nucleic acids encoding the foregoing are provided.

Once a recombinant which expresses the insulin-like gene sequence is identified, the gene product can be analyzed. This is achieved by assays based on the physical or functional properties of the product, including radioactive labeling of the product followed by analysis by gel electrophoresis, immunoassay, etc.

Once the insulin-like protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, once an insulin-like protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller et al., 1984, Nature 310:105–111).

In another alternate embodiment, native insulin-like proteins can be purified from natural sources, by standard methods such as those described above (e.g., immunoaffinity purification).

In a specific embodiment of the present invention, such insulin-like proteins, whether produced by recombinant DNA techniques or by chemical synthetic methods or by purification of native proteins, include but are not limited to those containing, as a primary amino acid sequence, all or part of the amino acid sequence substantially as depicted in FIG. 1 (SEQ ID NOs:1–18), as well as fragments and other derivatives, and analogs thereof, including proteins homologous thereto.

5.4. Structure of Insulin-like Genes and Proteins

The structure of insulin-like genes and proteins of the invention can be analyzed by various methods known in the art. Some examples of such methods are described below.

5.4.1. Genetic Analysis

The cloned DNA or cDNA corresponding to an insulin-like gene can be analyzed by methods including but not limited to Southern hybridization (Southern, 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, 1982, Molecular Cloning, A Laboratory Manual, Cold Spring Harbor Laboratory Press, Cold Spring Harbor, N.Y.), and DNA sequence analysis. Accordingly, this invention provides nucleic acid probes recognizing an insulin-like gene. For example, polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with an insulin-like gene-specific probe can allow the detection of an insulin-like gene in DNA from various cell types. Methods of amplification other than PCR are commonly known and can also be employed. In one embodiment, Southern hybridization can be used to determine the genetic linkage of an insulin-like gene. Northern hybridization analysis can be used to determine the expression of an insulin-like gene. Various cell types, at various states of development or activity can be tested for insulin-like gene expression. The stringency of the hybridization conditions for both Southern and Northern hybridization can be manipulated to ensure detection of nucleic acids with the desired degree of relatedness to the specific insulin-like gene probe used. Modifications of these methods and other methods commonly known in the art can be used.

Restriction endonuclease mapping can be used to roughly determine the genetic structure of an insulin-like gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster city, Calif.).

5.4.2. Protein Analysis

The amino acid sequence of an insulin-like protein can be derived by deduction from the DNA sequence, or alternatively, by direct sequencing of the protein, e.g., with an automated amino acid sequencer.

An insulin-like protein sequence can be further characterized by a hydrophilicity analysis (Hopp and Woods, 1981, Proc. Natl. Acad. Sci. U.S.A. 78:3824). A hydrophilicity profile can be used to identify the hydrophobic and hydrophilic regions of the insulin-like protein and the corresponding regions of the gene sequence which encode such regions.

Secondary, structural analysis (Chou and Fasman, 1974, Biochemistry 13:222) can also be done, to identify regions of an insulin-like protein that assume specific secondary structures.

Manipulation, translation, and secondary structure prediction, open reading frame prediction and plotting, as well as determination of sequence homologies, can also be accomplished using computer software programs available in the art.

Other methods of structural analysis can also be employed. These include but are not limited to X-ray crystallography (Engstom, 1974, Biochem. Exp. Biol. 11:7–13), nuclear magnetic resonance spectroscopy (Clore and Gonenborn, 1989, CRC Crit. Rev. Biochem. 24:479–564) and computer modeling (Fletterick and Zoller (eds.), 1986, Computer Graphics and Molecular Modeling, in Current Communications in Molecular Biology, Cold Spring Harbor Laboratory Press, Cold Spring Harbor, N.Y.).

5.5. Antibodies

According to the invention, insulin-like protein, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In another embodiment, antibodies to a domain. (e.g., an insulin-like receptor binding domain) of an insulin-like protein are produced. In a specific embodiment, fragments of an insulin-like protein identified as hydrophilic are used as immunogens for antibody production.

Various procedures known in the art may be used for the production of polyclonal antibodies to an insulin-like protein or derivative or analog. In a particular embodiment, rabbit polyclonal antibodies to an epitope of an insulin-like protein encoded by a sequence of SEQ ID NOs:1–18, or a subsequence thereof, can be obtained. For the production of antibody, various host animals can be immunized by injection with the native insulin-like protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed to an insulin-like protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (see e.g., PCT/US90/02545). According to the invention, human antibodies may be used and can be obtained by using human hybridomas (Cole et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for an insulin-like protein together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce insulin-like-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for insulin-like proteins, derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent, and Fv fragments.

In the production of antibodies, screening for the desired antibody can be accomplished by techniques known in the art (e.g., enzyme-linked immunosorbent assay or ELISA). For example, to select antibodies which recognize a specific domain of a insulin-like protein, one may assay generated hybridomas for a product which binds to a insulin-like fragment containing such domain. For selection of an antibody that specifically binds a first insulin-like homolog but which does not specifically bind a different insulin-like homolog, one can select on the basis of positive binding to the first insulin-like homolog and a lack of binding to the second insulin-like homolog.

Antibodies specific to a domain of an insulin-like protein are also provided. Antibodies specific to an epitope of an insulin-like protein are also provided.

The foregoing antibodies can be used in methods known in the art relating to the localization and activity of the insulin-like protein sequences of the invention, e.g., for imaging these proteins, measuring levels thereof in appropriate physiological samples, in diagnostic methods, etc.

5.6. Insulin-like Proteins, Derivatives and Analogs

The invention further relates to insulin-like proteins and derivatives (including but not limited to fragments) and analogs of insulin-like proteins. Nucleic acids encoding insulin-like protein derivatives and protein analogs are also provided. In one embodiment, the insulin-like proteins are encoded by the insulin-like nucleic acids described in Section 5.1 above. In particular aspects, the proteins, derivatives, or analogs are of insulin-like proteins of animals, e.g., fly, frog, mouse, rat, pig, cow, dog, monkey, human, worm, or plant.

The production and use of derivatives and analogs related to an insulin-like protein are within the scope of the present invention. In a specific embodiment, the derivative or analog is functionally active, i.e., capable of exhibiting one or more functional activities associated with a full-length, wild-type insulin-like protein. As one example, such derivatives or analogs which have the desired immunogenicity or antigenicity can be used in immunoassays, for immunization, for inhibition of insulin-like activity, etc. As another example, such derivatives or analogs which have the desired binding activity can be used for binding to the daf-2 gene product. As yet another example, such derivatives or analogs which have the desired binding activity can be used for binding to a binding protein specific for a known insulin-like protein (see e.g., Clemmons, 1993, "IGF binding proteins and their functions," Mol. Reprod. Dev. 35:368–374; Loddick et al., 1998, "Displacement of insulin-like growth factors from their binding proteins as a potential treatment for stroke," Proc. Natl. Acad. Sci. U.S.A. 95:1894–1898). Derivatives or analogs that retain, or alternatively lack or inhibit, a desired insulin-like protein property-of-interest (e.g., binding to an insulin-like protein binding partner), can be used as inducers, or inhibitors, respectively, of such property and its physiological correlates. A specific embodiment relates to an insulin-like protein fragment that can be bound by an anti-insulin-like protein antibody. Derivatives or analogs of an insulin-like protein can be tested for the desired activity by procedures known in the art, including but not limited to the assays described in Section 5.7 below.

In particular, insulin-like derivatives can be made by altering insulin-like sequences by substitutions, additions (e.g., insertions.) or deletions that provide for functionally equivalent molecules. Due to the degeneracy of nucleotide coding sequences, other DNA sequences which encode substantially the same amino acid sequence as an insulin-like gene may be used in the practice of the present invention. These include but are not limited to nucleotide sequences comprising all or portions of an insulin-like gene which is altered by the substitution of different codons that encode a functionally equivalent amino acid residue within the sequence, thus producing a silent change. Likewise, the insulin-like derivatives of the invention include, but are not limited to, those containing, as a primary amino acid sequence, all or part of the amino acid sequence of an insulin-like protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In a specific embodiment of the invention, proteins consisting of or comprising a fragment of an insulin-like protein consisting of at least 10 (continuous) amino acids of the insulin-like protein is provided. In other embodiments, the fragment consists of at least 20 or at least 50 amino acids of the insulin-like protein. In specific embodiments, such fragments are not larger than 35, 100 or 200 amino acids. Derivatives or analogs of insulin-like proteins include but are not limited to those molecules comprising regions that are substantially homologous to an insulin-like protein or fragment thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding insulin-like-gene sequence, under high stringency, moderate stringency, or low stringency conditions.

The insulin-like derivatives and analogs of the invention can be produced by various methods known in the art. The manipulations which result in their production can occur at the gene or protein level. For example, a cloned insulin-like gene sequence can be modified by any of numerous strategies known in the art (Sambrook et al., 1989, Molecular Cloning, A Laboratory Manual, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of a modified gene encoding a derivative or analog of an insulin-like protein, care should be taken to ensure that the modified gene remains within the same translational reading frame as the native protein, uninterrupted by translational stop signals, in the gene region where the desired insulin-like protein activity is encoded.

Additionally, an insulin-like nucleic acid sequence can be mutated in vitro or in vivo, to create and/or destroy translation, initiation, and/or termination sequences, or to create variations in coding regions and/or to form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson et al., 1978, J. Biol. Chem. 253:6551), use of TAB® linkers (Pharmacia), etc.

Manipulations of an insulin-like protein sequence may also be made at the protein level. Included within the scope of the invention are insulin-like protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, -acetylation, formylation, oxidation, reduction, metabolic synthesis in the presence of tunicamycin, etc.

In addition, analogs and derivatives of an insulin-like protein can be chemically synthesized. For example, a peptide corresponding to a portion of an insulin-like protein which comprises the desired domain (see Section 5.6.1), or which mediates the desired activity in vitro, can be synthesized by use of a peptide synthesizer. Furthermore, if desired, nonclassical amino acids or chemical amino acid analogs can be introduced as a substitution or addition into the insulin-like sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, an insulin-like protein derivative is a chimeric or fusion protein comprising an insulin-like protein or fragment thereof (preferably consisting of at least a domain or motif of the insulin-like protein, or at least 10 amino acids of the insulin-like protein) joined at its amino- or carboxy-terminus via a peptide bond to an amino acid sequence of a different protein. In one embodiment, such a chimeric protein is produced by recombinant expression of a nucleic acid encoding the protein (comprising an insulin-like-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of an insulin-like gene fused to any heterologous protein-encoding sequences may be constructed. A specific embodiment relates to a chimeric protein comprising a fragment of an insulin-like protein of at least six amino acids.

In another specific embodiment, the insulin-like derivative is a molecule comprising a region of homology with a insulin-like protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art. For example, a molecule can comprise one or more regions homologous to an insulin-like domain (see Section 5.6.1) or a portion thereof.

In a specific embodiment, the invention relates to insulin-like derivatives and analogs, in particular insulin-like fragments and derivatives of such fragments, that comprise, or alternatively consist of, one or more domains of an insulin-like protein, including but not limited to an insulin-like B peptide domain, an insulin-like A peptide domain, or an insulin-like connecting (C) peptide domain.

A specific embodiment relates to molecules comprising specific fragments of an insulin-like protein that are those fragments in the respective insulin-like proteins of the invention most homologous to specific fragments of a human or mouse insulin-like protein. A fragment comprising a domain of an insulin-like homolog can be identified by protein analysis methods well known in the art.

In another specific embodiment, a molecule is provided that comprises one or more domains (or-functional portion thereof) of an insulin-like protein but that also lacks one or more domains (or functional portion thereof) of an insulin-like protein. In particular examples, insulin-like protein derivatives are provided that either an A peptide domain or a B peptide domain. By way of another example, such a protein may retain such domains separated by a peptide spacer. Such spacer may be the same as or different from an insulin-like connecting (C) peptide. In another embodiment, a molecule is provided that comprises one or more domains (or functional portion(s) thereof) of an insulin-like protein, and that has one or more mutant (e.g., due to deletion or point mutation(s)) domains of an insulin-like protein (e.g., such that the mutant domain has decreased function).

5.7. Proteins Which Interact With Insulin-like Proteins

The present invention further provides methods of identifying or screening for proteins which interact with *C. elegans* insulin-like proteins, or derivatives, fragments or analogs thereof. Preferably, the method of identifying or screening is a yeast two hybrid assay system or a variation thereof, as further described below. In this regard, the yeast two-hybrid method has been used to analyze IGF-1-receptor interactions (see Zhu and Kahn, 1997 "Analysis of a peptide hormone-receptor interaction i the yeast two-hybrid system," Proc. Natl. Acad. Sci. U.S.A. 94, 13063–13068). Derivatives (e.g., fragments) and analogs of a protein can also be assayed for binding to a binding partner by any method known in the art, for example, immunoprecipitation with an antibody that binds to the protein in a complex followed by analysis by size fractionation of the immunoprecipitated proteins (e.g., by denaturing or nondenaturing polyacrylamide gel electrophoresis), Western analysis, nondenaturing gel electrophoresis, etc.

One aspect of the present invention provides methods for assaying and screening fragments, derivatives and analogs of *C. elegans* insulin-like protein. interacting proteins (for binding to a *C. elegans* insulin-like peptide). Derivatives, analogs and fragments of proteins that interact with a *C. elegans* insulin-like protein can be identified by means of a yeast two hybrid assay system (Fields and Song, 1989, Nature 340:245–246 and U.S. Pat. No. 5,283,173). Because the interactions are screened for in yeast, the intermolecular protein interactions detected in this system occur under physiological conditions that mimic the conditions in mammalian cells (Chien et al., 1991, Proc. Natl. Acad. Sci. U.S.A. 88:9578–9581). This feature facilitates identification of proteins capable of interaction with a *C. elegans* insulin-like protein from species other than *C. elegans*.

Identification of interacting proteins by the improved yeast two hybrid system is based upon the detection of expression of a reporter gene, the transcription of which is dependent upon the reconstitution of a transcriptional regulator by the interaction of two proteins, each fused to one half of the transcriptional regulator. The "bait" (i.e., *C. elegans* insulin-like protein or derivative or analog thereof) and "prey" (proteins to be tested for ability to interact with the bait) proteins are expressed as fusion proteins to a DNA binding domain, and to a transcriptional regulatory domain, respectively, or vice versa. In various specific embodiments, the prey has a complexity of at least about 50, about 100, about 500, about 1,000, about 5,000, about 100,000, or about 50,000; or has a complexity in the range of about 25 to about 100,000, about 100 to about 10,000, about 50,000 to about 100,000, or about 100,000 to about 500,000. For example, the prey population can be one or more nucleic acids encoding mutants of a protein (e.g., as generated by site-directed mutagenesis or another method of making mutations in a nucleotide sequence.) Preferably, the prey populations are proteins encoded by DNA, e.g., cDNA or genomic DNA or synthetically-generated DNA. For example, the populations can be expressed from:chimeric genes comprising cDNA sequences from an un-characterized sample of a population of cDNA from mRNA.

In a specific embodiment, recombinant biological libraries expressing random peptides can be used as the source of prey nucleic acids.

In another embodiment, the invention provides methods of screening for inhibitors or enhancers of the protein interactants identified herein. Briefly, the protein-protein interaction assay can be carried out as described herein, except that it is done in the presence of one or more candidate molecules. An increase or decrease in reporter gene activity relative to that present when the one or more candidate molecules are absent indicates that the candidate molecule has an effect on the interacting pair. In a preferred method, inhibition of the interaction is selected for (i.e., inhibition of the interaction is necessary for the cells to survive), for example, where the interaction activates the URA3 gene, causing yeast to die in medium containing the chemical 5-fluoroorotic acid (Rothstein, 1983, Meth. Enzymol. 101:167–180). The identification of inhibitors of such interactions can also be accomplished, for example, but not by way of limitation, using competitive inhibitor assays, as described above.

In general, proteins of the bait and prey populations are provided as fusion (chimeric) proteins (preferably by recombinant expression of a chimeric coding sequence) comprising each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor). Accordingly, in the present method of the present invention, binding of a C. elegans insulin-like fusion protein to a prey fusion protein leads to reconstitution of a transcriptional activator (or inhibitor) which activates (or inhibits) expression of the reporter gene. The activation (or inhibition) of transcription of the reporter gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native to the promoter. Thus, for example, one or more tandem copies (e.g., four or five copies) of the appropriate DNA binding site can be introduced upstream of the TATA box in the desired promoter (e.g., in the area of about position −100 to about −400). In a preferred aspect, 4 or 5 tandem copies of the 17 bp UAS (GAL4 DNA binding site) are introduced upstream of the TATA box in the desired promoter, which is upstream of the desired coding sequence for a selectable or detectable marker. In a preferred embodiment, the GAL1-10 promoter is operably fused to the desired nucleotide sequence; the GAL1-10 promoter already contains 5 binding sites for GAL4.

Alternatively, the transcriptional activation binding site of the desired gene(s) can be deleted and replaced with GAL4 binding sites (Bartel et al., 1993, BioTechniques 14:920–924, Chasman et al., 1989, Mol. Cell. Biol. 9:4746–4749). The reporter gene preferably contains the sequence encoding a detectable or selectable marker, the expression of which is regulated by the transcriptional activator, such that the marker is either turned on or off in the cell in response to the presence of a specific interaction. Preferably, the assay is carried out in the absence of background levels of the transcriptional activator (e.g., in a cell that is mutant or otherwise lacking in the transcriptional activator). In one embodiment, more than one reporter gene is used to detect transcriptional activation, e.g., one reporter gene encoding a detectable marker and one or more reporter genes encoding different selectable markers. The detectable marker can be any molecule that can give rise to a detectable signal, e.g., a fluorescent protein or a protein that can be readily visualized or that is recognizable by a specific antibody. The selectable marker can be any protein molecule that confers the ability to grow under conditions that do not support the growth of cells not expressing the selectable marker, e.g., the selectable marker is an enzyme that provides an essential nutrient and the cell in which the interaction assay occurs is deficient in the enzyme and the selection medium lacks such nutrient. The reporter gene can either be under the control of the native promoter that naturally contains a binding site for the DNA binding protein, or under the control of a heterologous or synthetic promoter.

The activation domain and DNA binding domain used in the assay can be from a wide variety of transcriptional activator proteins, as long as these transcriptional activators have separable binding and transcriptional activation domains. For example, the GAL4 protein of S. cerevisiae (Ma et al., 1987, Cell 48:847–853), the GCN4 protein of S. cerevisiae (Hope and Struhl, 1986, Cell 46:885894), the ARD1 protein of S. cerevesiae (Thukral et al., 1989, Mol. Cell. Biol. 9:2360–2369), and the human estrogen receptor (Kumar et al., 1987, Cell 51:941–951), have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg et al., 1988, Genes Dev. 2:730–742) activation domain is employed. In a specific embodiment, amino acids 1–147 of GAL4 (Ma et al., 1987, Cell 48:847–853; Ptashne et al., 1990, Nature 346:329–331) is the DNA binding domain, and amino acids 411–455 of VP16 (Triezenberg et al., 1988, Genes Dev. 2:730–742; Cress et al., 1991, Science 251:87–90) comprise the activation domain.

In a preferred embodiment, the yeast transcription factor GAL4 is reconstituted by protein-protein interaction and the host strain is mutant for GAL4. In another embodiment, the DNA-binding domain is Ace1N and/or the activation domain is Ace1, the DNA binding and activation domains of the Ace1 protein, respectively. Ace1 is a yeast protein that activates transcription from the CUP1 operon in the presence of divalent copper. CUP1 encodes metallothionein, which chelates copper, and the expression of CUP1 protein allows growth in the presence of copper, which is otherwise toxic to the host cells. The reporter gene can also be a CUP1-lacZ fusion that expresses the enzyme beta-galactosidase (detectable by routine chromogenic assay) upon binding of a reconstituted Ace1N transcriptional activator (see Chaudhuri et al., 1995, FEBS Letters 357:221–226). In another specific embodiment, the DNA binding domain of the human estrogen receptor is used, with a reporter gene driven by one or three estrogen receptor response elements (Le Douarin et al., 1995, Nucl. Acids. Res. 23:876–878).

The DNA binding domain and the transcriptional activator/inhibitor domain each preferably has a nuclear localization signal (see Ylikomi et al., 1992, EMBO J. 11:3681–3694, Dingwall and Laskey, 1991, TIBS 16:479–481) functional in the cell in which the fusion proteins are to be expressed.

To facilitate isolation of the encoded proteins, the fusion constructs can further contain sequences encoding affinity tags such as glutathione-S-transferase or maltose-binding protein or an epitope of an available antibody, for affinity purification (e.g., binding to glutathione, maltose, or a particular antibody specific for the epitope, respectively) (Allen et al., 1995, TIBS 20:511–516). In another embodiment, the fusion constructs further comprise bacterial promoter sequences for recombinant production of the fusion protein in bacterial cells.

The host cell in which the interaction assay occurs can be any cell, prokaryotic or eukaryotic, in which transcription of the reporter gene can occur and be detected, including, but not limited to, mammalian (e.g., monkey, mouse, rat, human, bovine), chicken, bacterial, or insect cells, and is preferably a yeast cell. Expression constructs encoding and capable of expressing the binding domain fusion proteins, the transcriptional activation domain fusion proteins, and the reporter gene product(s) are provided within the host cell, by mating of cells containing the expression constructs, or by cell fusion, transformation, electroporation, microinjection, etc. In a specific embodiment in which the assay is carried out in mammalian cells (e.g., hamster cells, HeLa cells), the DNA binding domain is the GAL4 DNA binding domain, the activation domain is the herpes simplex virus VP16 transcriptional activation domain, and the reporter gene contains the desired coding sequence operably linked to a minimal promoter element from the adenovirus E1B gene driven by several GAL4 DNA binding sites (see Fearon et al., 1992, Proc. Natl. Acad. Sci. U.S.A. 89:7958–7962). The host cell used should not express an endogenous transcription factor that binds to the same DNA site as that recognized by the DNA binding domain fusion population. Also, preferably, the host cell is mutant or otherwise lacking in an endogenous, functional form of the reporter gene(s) used in the assay.

Various vectors and host strains for expression of the two fusion protein populations in yeast are known and can be used (see e.g., U.S. Pat. No. 5,1468,614; Bartel et al., 1993, "Using the two-hybrid system to detect protein-protein interactions" In: *Cellular Interactions in Development*, Hartley, ed., Practical Approach Series xviii, IRL Press at Oxford University Press, New York, N.Y., pp. 153–179; Fields and Sternglanz, 1994, Trends In Genetics 10:286–292). By way of example but not limitation, yeast strains or derivative strains made therefrom, which can be used are N105, N106, N1051, N1061, and YULH. Other exemplary strains that can be used in the assay of the invention also include, but are not limited to, the following:

Y190: MATa, ura3-52, his3-200, lys2-801, ade2-101, trp1-901, leu2-3,112, gal4α, gal80α, cyh$^r$2, LYS2::GAL1$_{UAS}$-HIS3$_{TATA}$HIS3, URA3::GAL1$_{UAS}$-GAL1$_{TATA}$-lacZ; Harper et al., 1993, Cell 75:805–816, available from Clontech, Palo Alto, Calif., Y190 contains HIS3 and lacZ reporter genes driven by GAL4 binding sites.

CG-1945: MATa, ura3-52, his3-200, lys2-801, ade2-101, trp1-901, leu2-3,112, gal4-542, gal80-538, cyh$^r$2, LYS2::GAL1$_{UAS}$-HIS3$_{TATA}$HIS3, URA3::GAL1$_{UAS17mers(x3)}$-CYC1$_{TATA}$-lacZ, available from Clontech, Palo Alto, Calif. CG-1945 contains HIS3 and lacZ reporter genes driven by GAL4 binding sites.

Y187: MAT-α, ura3-52, his3-200, ade2-101, trp1-901, leu2-3,112, gal4α, gal80α, URA3::GAL1$_{UAS}$-GAL1$_{TATA}$-lacZ, available from Clontech, Palo Alto, Calif. Y187 contains a lacZ reporter gene driven by GAL4 binding sites.

SFY526: MATa, ura3-52, his3-200, lys2-801, ade2-101, trp1-901, leu2-3,112, gal4-542, gal80-538, can$^r$, URA3::GAL1-lacZ, available from Clontech, Palo Alto, Calif. SFY526 contains HIS3 and lacZ reporter genes driven by GAL4 binding sites.

HF7c: MATa, ura3-52, his3-200, lys2-801, ade2-101, trp1-901, leu2-3,112, gal4-542, gal80-538, LYS2::GAL1-HIS3, URA3::GAL1$_{UAS\ 17MERS(x3)}$-CYC1-lacZ, available from Clontech, Palo Alto, Calif. HF7c contains HIS3 and lacZ reporter genes driven by GAL4 binding sites.

YRG-2: MATa, ura3-52, his3-200, lys2-801, ade2-101, trp1-901, leu2-3,112, gal4-542, gal80-538, LYS2::GAL1$_{UAS}$-GAL1$_{TATA}$-HIS3, URA3::GAL1$_{UAS17mers(x3)}$-CYC1-lacZ, available from Stratagene, La Jolla, Calif. YRG-2 contains HIS3 and lacZ reporter genes driven by GAL4 binding sites.

Many other strains commonly known and available in the art can be used.

If not already lacking in endogenous reporter gene activity, cells mutant in the reporter gene may be selected by known methods, or the cells can be made mutant in the target reporter gene by known gene-disruption methods prior to introducing the reporter gene (Rothstein, 1983, Meth. Enzymol. 101:202–211).

In a specific embodiment, plasmids encoding the different fusion protein populations can be introduced simultaneously into a single host cell (e.g., a haploid yeast cell) containing one or more reporter genes, by co-transformation, to conduct the assay for protein-protein interactions. Or, preferably, the two fusion protein populations are introduced into a single cell either by mating (e.g., for yeast cells) or cell fusions (e.g., of mammalian cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, will deliver both constructs into the same diploid cell. The mating type of a yeast strain may be manipulated by transformation with the HO gene (Herskowitz and Jensen, 1991, Meth. Enzymol. 194:132–146).

In a preferred embodiment, a yeast interaction mating assay is employed using two different types of host cells, strain-type a and alpha of the yeast *Saccharomyces cerevisiae*. The host cell preferably contains at least two reporter genes, each with one or more binding sites for the DNA-binding domain (e.g., of a transcriptional activator). The activator domain and DNA binding domain are each parts of chimeric proteins formed from the two respective populations of proteins. One strain of host cells, for example the a strain, contains fusions of the library of nucleotide sequences with the DNA-binding domain of a transcriptional activator, such as GAL4. The hybrid proteins expressed in this set of host cells are capable of recognizing the DNA-binding site in the promoter or enhancer region in the reporter gene construct. The second set of yeast host cells, for example, the alpha strain, contains nucleotide sequences encoding fusions of a library of DNA sequences fused to the activation domain of a transcriptional activator.

In a preferred embodiment, the fusion protein constructs are introduced into the host cell as a set of plasmids. These plasmids are preferably capable of autonomous replication in a host yeast cell and preferably can also be propagated in *E. coli*. The plasmid contains a promoter directing the transcription of the DNA binding or activation domain fusion genes, and a transcriptional termination signal. The plasmid also preferably contains a selectable marker gene, permitting selection of cells containing the plasmid. The plasmid can be single-copy or multi-copy. Single-copy yeast plasmids that have the yeast centromere may also be used to express the activation and DNA binding domain fusions (Elledge et al., 1988, Gene 70:303–312).

In another embodiment, the fusion constructs are introduced directly into the yeast chromosome via homologous recombination. The homologous recombination for these purposes is mediated through yeast sequences that are not essential for vegetative growth of yeast, e.g., the MER2, MER1, ZIPI, REC102, or ME14 gene.

Bacteriophage vectors can also be used to express the DNA binding domain and/or activation domain fusion proteins. Libraries can generally be prepared faster and more easily from bacteriophage vectors than from plasmid vectors.

In a specific embodiment, the present invention provides a method of detecting one or more protein-protein interactions comprising (a) recombinantly expressing a *C. elegans* insulin-like protein or a derivative or analog thereof in a first population of yeast cells being of a first mating type and comprising a first fusion protein containing the *C. elegans* insulin-like sequence and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) negatively selecting to eliminate those yeast cells in said first population in which said increased transcription of said first nucleotide sequence occurs in the absence of said second fusion protein; (c) recombinantly expressing in a second population of yeast cells of a second mating type different from said first mating type, a plurality of said second fusion proteins, each second fusion protein comprising a sequence of a fragment, derivative or analog of a protein and an activation domain of a transcriptional activator, in which the activation domain is the same in each said second fusion protein; (d) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (e) detecting said increased transcription of said first and/or second nucleotide sequence, thereby detecting an interaction between a first fusion protein and a second fusion protein.

In a preferred embodiment, the bait *C. elegans* insulin-like sequence and the prey library of chimeric genes are combined by mating the two yeast strains on solid media for a period of approximately 6–8 hours. In a less preferred embodiment, the mating is performed in liquid media. The resulting diploids contain both kinds of chimeric genes, i.e., the DNA-binding domain fusion and the activation domain fusion.

Preferred reporter genes include the URA3, HIS3 and/or the lacZ genes (see e.g., Rose and Botstein, 1983, Meth. Enzymol. 101:167–180) operably linked to GAL4 DNA-binding domain recognition elements. Other reporter genes comprise the functional coding sequences for, but not limited to, Green Fluorescent Protein (GFP) (Cubitt et al., 1995, Trends Biochem. Sci. 20:448–455), luciferase, LEU2, LYS2, ADE2, TRP1, CAN1, CYH2, GUS, CUP1 or chloramphenicol acetyl transferase (CAT). Expression of LEU2, LYS2, ADE2 and TRP1 are detected by growth in a specific defined media; GUS and CAT can be monitored by well known enzyme assays; and CAN1 and CYH2 are detected by selection in the presence of canavanine and cycloheximide. With respect to GFP, the natural fluorescence of the protein is detected, or a modified GFP having modified fluorescence is detected.

In a specific embodiment, transcription of the reporter gene is detected by a linked replication assay. For example, as described by Vasavada et al., 1991, Proc. Natl. Acad. Sci. U.S.A. 88:10686–10690, expression of SV40 large T antigen is under the control of the E1B promoter responsive to GAL4 binding sites. The replication of a plasmid containing the SV40 origin of replication, indicates the reconstruction of the GAL4 protein and a protein-protein interaction. Alternatively, a polyoma virus replicon can be employed (Vasavada et al., 1991, Proc. Natl. Acad. Sci. U.S.A. 88:10686–10690).

In another embodiment, the expression of reporter genes that encode proteins can be detected by immunoassay, i.e., by detecting the immunospecific binding of an antibody to such protein, which antibody can be labeled, or alternatively, which antibody can be incubated with a labeled binding partner to the antibody, so as to yield a detectable signal. Alam and Cook (1990, Anal. Biochem. 188:245–254) disclose non-limiting examples of detectable marker genes that can be operably linked to a transcriptional regulatory region responsive to a reconstituted transcriptional activator, and thus used as reporter genes.

The activation of reporter genes like URA3 or HIS3 enables the cells to grow in the absence of uracil or histidine, respectively, and hence serves as a selectable marker. Thus, after mating, the cells exhibiting protein-protein interactions are selected by the ability to grow in media lacking a nutritional component, such as uracil or histidine (referred to as -URA (minus URA) and -HIS (minus HIS) medium, respectively). The -HIS medium preferably contains 3-amino-1,2,4-triazole (3-AT), which is a competitive inhibitor of the HIS3 gene product, and thus, requires higher levels of transcription in the selection (see Durfee et al., 1993, Genes Dev. 7:555–569). Similarly, 6-azauracil, which is an inhibitor of the URA3 gene product, can be included in -URA medium (Le Douarin et al., 1995, Nucl. Acids Res. 23:876–878). URA3 gene activity can also be detected and/or measured by determining the activity of its gene product, orotidine-5'-monophosphate decarboxylase (Pierrat et al., 1992, Gene 119:237–245; Wolcott et al., 1966, Biochem. Biophys. Acta 122:532–534). In other embodiments of the present invention, the activities of the reporter genes like GFP or lacZ are monitored by measuring a detectable signal (e.g., fluorescent or chromogenic, respectively) that results from the activation of these reporter genes. For example, lacZ transcription can be monitored by incubation in the presence of a chromogenic substrate, such as X-gal (5-bromo-4-chloro-3-indolyl-β-D-galactoside), of its encoded enzyme, β-galactosidase. The pool of all interacting proteins isolated by this manner from mating the *C. elegans* insulin-like sequence product and the library identifies the "insulin-like interactive population".

In a preferred embodiment of the present invention, false positives arising from transcriptional activation by the DNA binding domain fusion proteins in the absence of a transcriptional activator domain fusion protein are prevented or reduced by negative selection for such activation within a host cell containing the DNA binding fusion population, prior to exposure to the activation domain fusion population. By way of example, if such cell contains URA3 as a reporter gene, negative selection is carried out by incubating the cell in the presence of 5-fluoroorotic acid (5-FOA, which kills URA+cells (Rothstein, 1983, Meth. Enzymol. 101:167–180). Hence, if the DNA-binding domain fusions by themselves activate transcription, the metabolism of 5-FOA will lead to cell death and the removal of self-activating DNA-binding domain hybrids.

Negative selection involving the use of a selectable marker as a reporter gene and the presence in the cell medium of an agent toxic or growth inhibitory to the host cells in the absence of reporter gene transcription is preferred, since it allows a higher rate of processing than other methods. As will be apparent, negative. selection can also be carried out on the activation domain fusion population prior to interaction with the DNA binding domain fusion population, by similar methods, either alone or in addition to negative selection of the DNA-binding fusion population.

Negative selection can also be carried out on the recovered protein-protein complex by known methods (see e.g., Bartel et al., 1993, BioTechniques 14:920–924) although pre-negative selection (prior to the interaction assay), as described above, is preferred. For example, each plasmid encoding a protein (peptide or polypeptide) fused to the activation domain (one-half of a detected interacting complex) can be transformed back into the original screening strain, either alone or with a plasmid encoding only the DNA-binding domain, the DNA-binding domain fused to the detected interacting protein, or the DNA-binding domain fused to a protein that does not affect transcription or participate in the protein-protein interaction. A positive interaction detected with any plasmid other than that encoding the DNA-binding domain fusion to the detected interacting protein is deemed a false positive and is eliminated from the screen.

In a preferred embodiment, the *C. elegans* insulin-like plasmid population is transformed in a yeast strain of a first mating type (a or alpha), and the second plasmid population (containing the library of DNA sequences) is transformed in a yeast strain of a different mating type.

Both strains are preferably mutant for URA3 and HIS3, and contain HIS3, and optionally lacZ, as reporter genes.

The first set of yeast cells are positively selected for the insulin-like plasmids and are negatively selected for false positives by incubation in medium lacking the selectable marker (e.g., tryptophan) and containing 5-FOA. Yeast cells of the second mating type are transformed with the second plasmid population, and are positively selected for the presence of the plasmids containing the library of fusion proteins. Selected cells are pooled. Both groups of pooled cells are mixed together and mating is allowed to occur on a solid phase. The resulting diploid cells are then transferred to selective media that selects for the presence of each plasmid and for activation of reporter genes.

In a preferred embodiment of the invention, after an interactive population is obtained, the DNA sequences encoding the pairs of interactive proteins are isolated by a method wherein either the DNA-binding domain hybrids or the activation domain hybrids are amplified, in separate respective reactions. Preferably, the amplification is carried out by polymerase chain reaction (PCR) (see U.S. Pat. Nos. 4,683,202; 4,683,195; and 4,889,818; Gyllenstein et al., 1988, Proc. Natl. Acad. Sci. U.S.A. 85:7652–7656; Ochman et al., 1988, Genetics 120:621–623; Toh et al., 1989, Science 243:217–220; Innis et al., 1990, *PCR Protocols*, Academic Press, Inc., San Diego, Calif.) using pairs of oligonucleotide primers specific for either the DNA-binding domain hybrids or the activation domain hybrids. This PCR reaction can also be performed on pooled cells expressing interacting protein complexes, preferably pooled arrays of interactants. Other amplification methods known in the art can be used, including but not limited to ligase chain reaction (see EP 320,308), use of Qβ replicase, or methods listed in Kricka et al., 1995, *Molecular Probing, Blotting, and Sequencing*, Academic Press, New York, Chapter 1 and Table IX.

The plasmids encoding the DNA-binding domain hybrid and the activation domain hybrid proteins can also be isolated and cloned by any of the methods well known in the art. For example, but not by way of limitation, if a shuttle (yeast to *E. coli*) vector is used to express the fusion proteins, the genes can be recovered by transforming the yeast DNA into *E. coli* and recovering the plasmids from *E. coli* (see e.g., Hoffman et al., 1987, Gene 57:267–272). Alternatively, the yeast vector can be isolated, and the insert encoding the fusion protein subcloned into a bacterial expression vector, for growth of the plasmid in *E. coli*.

5.8. Assays of Insulin-like Proteins

The functional activity of insulin-like proteins, derivatives and analogs can be assayed by various methods known to one skilled in the art.

For example, in one embodiment, where one is assaying for the ability to bind to or compete with a wild-type insulin-like protein for binding to an anti-insulin-like protein antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where an insulin-like-binding protein is identified, the binding can be assayed, e.g., by means well-known in the art. In another embodiment, physiological correlates of insulin-like protein binding to its substrates and/or receptors (e.g., signal transduction) can be assayed.

In another embodiment, in insect (e.g., D. melanogaster), worm (e.g., C. elegans), or other model systems, genetic studies can be done to study the phenotypic effect of an insulin-like gene mutant that is a derivative or analog of a wild-type insulin-like gene (see Section 6).

Other such methods will be readily apparent to the skilled artisan and are within the scope of the invention.

5.9. Antisense Regulation of Gene Expression

The invention provides for antisense uses of C. elegans insulin-like genes. In a specific embodiment, an insulin-like protein function is inhibited by use of insulin-like antisense nucleic acids. The present invention provides for use of nucleic acids of at least six nucleotides that are antisense to a gene or cDNA encoding an insulin-like protein or a portion thereof. An insulin-like "antisense" nucleic acid as used herein refers to a nucleic acid-capable of hybridizing to a portion of an insulin-like RNA (preferably mRNA) by virtue of some sequence complementarity. Antisense nucleic acids may also be referred to as inverse complement nucleic acids. The antisense nucleic acid may be complementary to a coding and/or noncoding region of an insulin-like mRNA. Such antisense nucleic acids have utility in inhibiting an insulin-like protein function. For example, such antisense nucleic acids may be useful as pesticides to eradicate parasites in plants, or in animals such as dogs.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous introduced sequences. In a preferred embodiment, the antisense nucleic acids of the invention are double-stranded RNA (see Fire et al., 1998, Nature 391:806–811).

The insulin-like antisense nucleic acids of the invention are preferably oligonucleotides (ranging from 6 to about 50 oligonucleotides). In specific aspects, an oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, or single-stranded or double-stranded. The oligonucleotide can be modified at the base moiety, sugar moiety, or phosphate backbone. The oligonucleotide may include other appending groups such as peptides, or agents facilitating transport across the cell membrane (see e.g., Letsinger et al., 1989, Proc. Natl. Acad. Sci. U.S.A. 86:6553–6556; Lemaitre et al., 1987, Proc. Natl. Acad. Sci. U.S.A. 84:648–652; PCT Publication No. WO 88/09810, published Dec. 15, 1988) or blood-brain barrier (see e.g., PCT Publication No. WO 89/10134, published Apr. 25, 1988), hybridization-triggered cleavage agents (see e.g., Krol et al., 1988, BioTechniques 6:958–976) or intercalating agents (see e.g., Zon, 1988, Pharm. Res. 5:539–549).

In a preferred aspect of the invention, an insulin-like antisense oligonucleotide is provided as single-stranded DNA. In another preferred aspect, such an oligonucleotide comprises a sequence antisense to the sequence encoding a B peptide domain or an A peptide domain of an insulin-like protein. The oligonucleotide may be modified at any position on its structure with substituents generally known in the art.

The insulin-like antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5methylcytosine, N6-adenine, 7-methylguanine, 5methylaminomethyluracil, 5methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2thiouracil, 4thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, a hybridization-triggered cross-linking agent, a transport agent, a hybridization-triggered cleavage agent, etc.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

In a specific embodiment, an insulin-like antisense oligonucleotide comprises catalytic RNA, or a ribozyme (see e.g., PCT International Publication WO 90/11364, published Oct. 4, 1990; Sarver et al., 1990, Science 247:1222–1225). In another embodiment, the oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the insulin-like antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the insulin-like antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the insulin-like antisense RNA can be by any promoter known in the art to act in mammalian cells. Such promoters can be inducible or constitutive. Such promoters include but are not limited to: the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of an insulin-like gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded insulin-like antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an insulin-like RNA it may contain and still form a stable duplex (or triplex, as the case may be). One skilled in the art can ascertain a tolerable degree of mismatch by use of standard procedures to determine the melting point of the hybridized complex.

5.10. Identifying Signaling Pathways and Phenotypes

This invention provides animal models which may be used in the identification and characterization of C. elegans insulin-like protein signaling pathways, and/or phenotypes associated with the mutation or abnormal expression of a C. elegans insulin-like protein. Methods of producing such animal models using novel genes and proteins are well known in the art (see e.g., PCT International Publication No. WO 96/34099, published Oct. 31, 1996, which is incorporated by reference herein in its entirety). Such models include but are not limited to the following three embodiments. Additional specific examples of animal models and their use are described in Section 6 below.

First, animals are provided in which a normal C. elegans insulin-like gene has been recombinantly introduced into the genome of the animal as an additional gene, under the regulation of either an exogenous or an endogenous promoter element, and as either a minigene or a large genomic fragment. Animals are also provided in which a normal gene has been recombinantly substituted for one or both copies of the animal's homologous gene by homologous recombination or gene targeting.

Second, animals are provided in which a mutant C. elegans insulin-like gene has been recombinantly introduced into the genome of the animal as an additional gene, under the regulation of either an exogenous or an endogenous promoter element, and as either a minigene or a large genomic fragment. Animals are also provided in which a mutant gene has been recombinantly substituted for one or both copies of the animal's homologous gene by homologous recombination or gene targeting.

Third, animals are provided in which a mutant version of one of that animal's own genes (bearing, for example, a specific mutation corresponding to, or similar to, a pathogenic mutation of an insulin-like gene from another species) has been recombinantly-introduced into the genome of the animal as an additional gene, under the regulation of either an exogenous or an endogenous promoter element, and as either a minigene or a large genomic fragment.

Finally, equivalents of transgenic animals, including animals with mutated or inactivated genes, may be produced using chemical or x-ray mutagenesis. Using the isolated nucleic acids disclosed or otherwise enabled herein, one of ordinary skill may more rapidly screen the resulting offspring by, for example, direct sequencing, restriction fragment length polymorphism (RFLP) analysis, PCR, or hybridization analysis to detect mutants, or Southern blotting to demonstrate loss of one allele.

Such animal models may be used to identify a C. elegans insulin-like protein signaling pathway by various methods. In one embodiment, this invention provides a method of identifying a C. elegans insulin-like protein signaling pathway comprising: (a) disrupting a C. elegans insulin-like gene; and (b) identifying the effect of the gene disrupted in step (a) in an assay selected from the group consisting of a dauer formation assay, a developmental assay, an energy metabolism assay, a growth rate assay and a reproductive capacity assay. Such assays are well known to those skilled in the art. In one embodiment, the gene is disrupted using EMS chemical deletion mutagenesis. In another embodiment, the gene is disrupted using transposon insertion:mutagenesis. Examples of such mutagenesis are set forth in Section 6 below.

Further, this invention provides a method of identifying a phenotype associated with mutation or abnormal expression of a C. elegans insulin-like protein comprising identifying the effect of a mutated or abnormally expressed C. elegans insulin-like gene in a C. elegans animal. In one embodiment, the effect is determined by an assay selected from the group consisting of a dauer formation assay, a developmental assay, an energy metabolism assay, a growth rate assay and a reproductive capacity assay. Still further, this invention provides a method of identifying a phenotype associated with mutation or abnormal expression of a C. elegans insulin-like protein comprising: (a) mutating or abnormally expressing a C. elegans insulin-like gene in a C. elegans animal; and (b) identifying the effect of the gene mutated or abnormally expressed. In one embodiment, the effect is determined by an assay selected from the group consisting of a dauer formation assay, a developmental assay, an energy metabolism assay, a growth rate assay and a reproductive capacity assay. In another embodiment, the gene is mutated or abnormally expressed using a technique selected from the group consisting of EMS chemical deletion mutagenesis; transposon insertion mutagenesis and double-stranded RNA interference. Abnormal expression can be overexpression, underexpression (e.g., due to inactivation), expression at a developmental time different from wild-type animals, or expression in a cell type different from in wild-type animals.

5.11. Assays for Changes in Gene Expression

This invention provides assays for detecting changes in the expression of the identified C. elegans insulin-like genes and proteins. Assays for changes in gene expression are well known in the art (see e.g., PCT International Publication No. WO 96/34099, published Oct. 31, 1996, which is incorporated by reference herein in its entirety). Such assays may be performed in vitro using transformed cell lines, immortalized cell lines, or recombinant cell lines, or in vivo using animal models.

In particular, the assays may detect the presence of increased or decreased expression of a C. elegans insulin-like gene or protein on the basis of increased or decreased mRNA expression (using, e.g., nucleic acid probes)., increased or decreased levels of related protein products (using, e.g., the antibodies disclosed herein), or increased or decreased levels of expression of a marker gene (e.g., β-galactosidase or luciferase) operably linked to a 5' regulatory region in a recombinant construct.

In yet another series of embodiments, various expression analysis techniques may be used to identify genes which are differentially expressed between two conditions, such as a cell line or animal expressing a normal C. elegans insulin-like gene compared to another cell line or animal expressing a mutant C. elegans insulin-like gene. Such techniques comprise any expression analysis technique known to one skilled in the art, including but not limited to differential display, serial analysis of gene expression (SAGE), nucleic acid array technology, subtractive hybridization, proteome analysis and mass-spectrometry of two-dimensional protein gels. In a specific embodiment, nucleic acid array technology (i.e., gene chips) may be used to determine a global (i.e., genome-wide) gene expression pattern in a normal C. elegans animal for comparison with an animal having a mutation in one or more C. elegans insulin-like genes.

To elaborate further, the various methods of gene expression profiling mentioned above can be used to identify other genes (or proteins) that may have a functional relation to (e.g., may participate in a signaling pathway with) a C. elegans insulin-like gene. Gene identification of such other genes is made by detecting changes in their expression levels following mutation, i.e., insertion, deletion or substitution in, or overexpression, underexpression, misexpression or knock-out, of a C. elegans insulin-like gene, as described in Sections 6.7 through 6.14 below. Expression profiling methods thus provide a powerful approach for analyzing the effects of mutation in a C. elegans insulin-like gene.

Methods of gene expression profiling are well-known in the art, as exemplified by the following references describing subtractive hybridization (Wang and Brown, 1991, "A gene expression screen," Proc. Natl. Acad. Sci. U.S.A. 88:11505–11509), differential display (Liang and Pardee, 1992, "Differential display of eukaryotic messenger RNA by means of the polymerase chain reaction," Science 257:967–971), SAGE (Velculescu et al., 1995, "Serial analysis of gene expression," Science 270:484–487), proteome analysis (Humphery-Smith et al., 1997, "Proteome research: complementarity and limitations with respect to the RNA and DNA worlds," Electrophoresis 18:1217–1242; Dainese et al., 1997, "Probing protein function using a combination of gene knockout and proteome analysis by mass spectrometry," Electrophoresis 18:432–442), and hybridization-based methods employing nucleic acid arrays (Heller et al., 1997, "Discovery and analysis of inflammatory disease-related genes using cDNA microarrays," Proc. Natl. Acad. Sci. U.S.A. 94:2150–2155; Lashkari et al., 1997, "Yeast microarrays for genome wide parallel genetic and gene expression analysis," Proc. Natl. Acad. Sci. U.S.A. 94:13057–13062; Wodicka et al., 1997, "Genome-wide expression monitoring in Saccharomyces cerevisiae," Nature Biotechnol. 15:1259–1267).

5.12. Identification of Compounds With Binding Capacity

This invention provides screening methodologies useful in the identification of proteins and other compounds which bind to, or otherwise directly interact with, the C. elegans insulin-like genes and proteins. Screening methodologies are well known in the art (see e.g., PCT International Publication No. WO 96/34099, published Oct. 31, 1996, which is incorporated by reference herein in its entirety). The proteins and compounds include endogenous cellular components which interact with the identified genes and proteins in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to one of the normal or mutant C. elegans insulin-like genes and proteins. Alternatively, any of a variety of exogenous compounds, both naturally occurring and/or synthetic (e.g., libraries of small molecules or peptides), may be screened for binding capacity.

As will be apparent to one of ordinary skill in the art, there are numerous other methods of screening individual proteins or other compounds, as well as large libraries of proteins or other compounds (e.g., phage display libraries) to identify molecules which bind to C. elegans insulin-like proteins. All of these methods comprise the step of mixing a C. elegans insulin-like protein or fragment with test compounds, allowing time for any binding to occur, and assaying for any bound complexes. All such methods are enabled by the present disclosure of substantially pure C. elegans insulin-like proteins, substantially pure functional domain fragments, fusion proteins, antibodies, and methods of making and using the same.

6. EXAMPLES

The following examples are provided merely as illustrative of various aspects of the invention and shall not be construed to limit the invention in any way.

6.1. Identification of C. elegans Insulin-like Genes

An unexpectedly large family of insulin-like genes has been identified in the model organism C. elegans (i.e., the nematode Caenorhabditis elegans). This invention provides the following examples of identification of eighteen C. elegans insulin-like genes as illustrated in the alignment of FIGS. 3A–3B and described in detail below. The SEQ ID NO for each protein and cDNA corresponding to the eighteen C. elegans insulin-like genes is set forth in Table 1 below.

6.2. Computational Strategy

One advantage of investigating insulin-like genes in C. elegans comes from the tremendous progress made in the genome project for this organism. At the time of this writing, approximately 90% of the C. elegans genome has been sequenced, and that data is publically available in GenBank®, as well as in a specialized database for the *C. elegans* genome referred to as ACEDB (i.e., A C. *elegans* Data Base) (Waterston and Sulston, 1995. "The genome of *Caenorhabditis elegans*", Proc. Natl. Acad. Sci. U.S.A. 92:10836–10840). In spite this wealth of genomic sequence information, the process of identifying authentic insulin superfamily genes in *C. elegans* is not trivial, as evidenced by a lack of reports of such insulin superfamily genes in the recent literature. This point is emphasized by considering the considerable effort required for the identification of putative genes that encode other components of the insulin signaling pathway in *C. elegans*, specifically, insulin receptor (daf-2), PI3K (age-1), and HNF-3 (daf-16) homologs.

TABLE 1

*C. elegans* insulin-like genes and the corresponding sequence identification number (SEQ ID NO:) for each encoded protein and CDNA. See FIG. 4A through FIG. 34 for annotated sequences.

| gene | SEQ ID NO: protein | cDNA |
|---|---|---|
| F13B12.N | 1 | 19 |
| ZK75.1 | 2 | 20 |
| ZK75.2 | 3 | 21 |
| ZK75.3 | 4 | 22 |
| ZK84.6 | 5 | 23 |
| ZK84.N2 | 6 | 24 |
| ZK1251.2 | 7 | 25 |
| ZK1251.N | 8 | 26 |
| C06E2.N | 9 | 27 |
| C17C3.4 | 10 | 28 |
| C17C3.N | 11 | 29 |
| M04D8.1 | 12 | 30 |
| M04D8.2 | 13 | 31 |
| M04D8.3 | 14 | 32 |
| ZK84.N | 15 | 33 |
| F56F3.6 | 16 | 34 |
| T28B8.N | 17 | 35 |
| ZC334.N | 18 | 36 |
| T08G5.N | 158 | 162 |
| F41G3.N | 159 | 163 |
| F41G3.N2 | 160 | 164 |
| C17C3.N2 | 161 | 165 |
| ZC334.N2 | 198 | 207 |
| ZC334.N3 | 199 | 208 |
| ZC334.N4 | 200 | 209 |
| ZC334.N5 | 201 | 210 |
| ZC334.N6 | 202 | 211 |
| ZC334.N7 | 203 | 212 |
| T10D4.N | 204 | 213 |
| T10D4.N2 | 205 | 214 |
| Y52A1.N | 206 | 215 |

There are a number of factors that make identifying insulin-like genes in *C. elegans* genomic data particularly difficult. The insulin superfamily is fairly divergent at the sequence level and the expected degree of sequence homology between vertebrate and *C. elegans* insulin-like proteins is expected to be relatively low. Furthermore, there may be significant structural deviations in *C. elegans* insulin-like proteins that are absent or not common in the well-characterized vertebrate insulin-like proteins. This issue revolves around the potential structural features that were present in an early progenitor of the insulin superfamily that preceded the divergence of invertebrates and vertebrates, as well as the possible elaboration of this ancestral structure with unique features during evolution of the invertebrate branch that led to present-day nematodes.

6.2.1. Search Issues

In view of the above considerations, a prepro-insulin-like hormone in *C. elegans* may have a somewhat different organization and a different pathway of proteolytic processing from that common in vertebrates. This possibility is suggested by the differences between precursor forms of insulins and IGFs, where IGFs do not have an excisable C peptide. Along a similar line of reasoning, it is notable that, for the locust LIRP insulin-like protein, there is an extra peptide between the signal sequence and the beginning of the mature B peptide region which is evidently removed by proteolytic processing (see Lagueux et al., 1990, "cDNAs from neurosecretory cells of brains of *Locusta migratoria* (Insecta, Orthoptera) encoding a novel member of the superfamily of insulins", Eur. J. Biochem. 187:249–254). Yet another variation in the overall processing of prehormones has been suggested from the structure of the MIP-II insulin-like gene of the freshwater snail. The MIP-II of snail has been proposed to contain two tandem C peptides, termed C-alpha and C-beta, that connect the B chain and A chain in the prehormone (Smit et al., 1991, "Characterization of a cDNA clone encoding molluscan insulin-related peptide II of *Lymnaea stagnalis*", Eur. J. Biochem. 199:699–703). There may be other types of structural alterations that are common in *C. elegans* insulin-like proteins, but relatively rare in those characterized to date, as suggested by the occurrence of an extra pair of Cys residues in the MIP insulin-like proteins of the freshwater snail (see FIG. 2).

Another issue germane to searches of genomic sequences is that of exon-intron organization. There is a tendency for intron positions to be conserved within gene families, and exons often have been found to define structurally meaningful modules or domains within proteins. Indeed, most insulin superfamily genes in vertebrates have an intron positioned between the B and A peptide regions (i.e., domains), either within, or at the boundary of, the C peptide coding portion. However, this organizational theme is not entirely universal among the insulin-like superfamily since the bombyxin genes of silkworm appear to lack introns altogether (Kondo et al., 1996, "Multiple gene copies for bombyxin, an insulin-related peptide of the silkmoth *Bombyx mori*: structural signs for gene rearrangement and duplication responsible for generation of multiple molecular forms of bombyxin", J Mol. Biol. 259:926–937). In summary, a successful search strategy to identify insulin-like genes must accommodate a large degree of diversity in gene structure and protein structure.

There are a number of software tools that can aid the process of identifying gene homologs in the *C. elegans* genome, including gene prediction programs (e.g., GeneFinder), sequence homology searching programs (e.g., BLAST, FASTA) and protein motif searching programs (e.g., Prosite, BLOCKS, Markoff models). Nonetheless, identifying insulin-like genes within the *C. elegans* genome can be expected to pose a significant challenge that goes beyond just the straightforward application of any of these programs, due to the expected level of sequence divergence and structural variation described above. These problems are confounded further by the fact that insulins are small genes whose coding regions are often divided into smaller exons. Small genes and exons are the most difficult to reliably predict from genomic sequence data with gene finding programs, and small blocks of divergent sequence are difficult to identify with homology searching programs as authentic sequence matches over those that would occur by chance.

The Prosite sequence matches found in the *C. elegans* genome illustrate the above-described problem. A pattern of specific amino acid residues has been derived from comparison of insulin superfamily proteins, termed an "insulin family signature," that reflects highly-conserved amino acid positions within the A chain of known insulin molecules. There are 27 matches to the Prosite "insulin family signature" identified in the C. elegans genome sequence and listed in ACEDB. Subsequent searches and analysis of insulin-like genes has revealed that only five of the 27 Prosite matches correspond to authentic insulin-like genes (as judged by criteria described below). Furthermore, at least another 17 authentic insulin-like genes in C. elegans did not have matches to the Prosite insulin family signature.

6.2.2. Search Strategy

Given the difficulties in identifying insulin-like genes in the C. elegans genome, we have pursued a strategy of combining several tools to find and evaluate potential insulin superfamily genes. Our search strategy used sequence features of known insulin superfamily genes, but focused initially on identifying matches to either: (1) B peptide region alone; (2) A peptide region alone; or (3) B and A peptide sequences fused together (i.e., artificially). The A and B peptide regions (i.e., domains) of known insulin superfamily proteins were chosen as queries since these are the most highly-conserved regions among the superfamily. The searching programs that were employed for the initial canvassing of the C. elegans genomic sequence included BLAST, FASTA, Markoff model searches, and exact pattern match searches (i.e., regular expression searches). For matches to the B or A peptide alone, the genomic sequence was examined manually, and with the aid of the GeneFinder program, to identify a plausible nearby region encoding the other peptide in the correct relative position (i.e., B peptide region N-terminal to A peptide region).

In most cases, the B and A peptide matches did not form a continuous open reading frame in the genomic DNA, and so the sequence was examined manually, and with the aid of a GeneFinder program, for the presence of likely splice junctions that would join the presumptive B and A peptide coding regions in-frame. Coding sequences N-terminal to presumptive B peptide coding regions were further examined manually, and with the aid of the GeneFinder program, for extended coding regions that might have a characteristic signal sequence for secretion following an initiator methionine (Met) codon. Also, regions upstream of the presumptive B peptide were examined manually, and with the aid of the GeneFinder program, for potential splice sites that might join these segments to mRNA leaders found in trans-spliced mRNAs.

Each genomic match with correctly-oriented B and A peptides was further evaluated as follows to confirm that these regions preserved most of the structural features that are important for the formation of the characteristic insulin secondary and tertiary structure (discussed in detail in Section 2 above): (1) number and spacing of Cys residues involved in inter-chain and intra-chain disulfide bonds; (2) hydrophobic residues that form the "insulin core" at the interface of the A and B chains; (3) presence of Pro and Gly residues that promote characteristic breaks or turns between secondary structure elements; and (4) presence of proteolytic processing signals for maturation of the prehormone, especially removal of a C peptide, or regions preceding the B peptide and following a secretory signal.

The computational strategy described above resulted in the identification of up to 31 possible insulin-like genes. The structure and expression of the coding regions of 22 of these putative C. elegans insulin-like genes have been confirmed using an experimental approach involving reverse transcription of C. elegans mRNA, PCR amplification of specific cDNAs, cloning, and DNA sequencing. The details of the conditions used for each putative insulin-like gene are described below.

6.3. PCR Cloning of C. elegans Insulin-like cDNAs

Twenty-two C. elegans insulin-like genes have been cloned using the polymerase chain reaction (PCR), as described in detail below. See Table 1 for the assigned name of each of the eighteen C. elegans insulin-like genes, and the corresponding sequence identification number for the nucleotide sequence of each cDNA and the amino acid sequence of each protein.

PCR primers were designed for cloning each gene under the following general rationale. For further details specific for each gene, see Sections 6.3.1 through 6.3.18 below.

Genes ZK75.3, ZK75.1, ZK1251.2 and ZK1251.N were all predicted to have an SL1 splice acceptor upstream of the predicted start codon. Therefore, the SL1 sequence was used as the upstream primer for each of these cDNAs. ZK84.6 was predicted to have a splice acceptor upstream of the start codon; however, no PCR product was obtained using SL1 as an upstream primer. Therefore, the sequence immediately following the predicted splice acceptor was used. The downstream primers were chosen to fall downstream of the predicted stop codon.

For M04D8.1, M04D8.2, M04D8.3, C17C3.4, C17C3.N, F13B12.N, T28B8.N, ZC334.N, and ZK84.N, primers had a HindIII site on the end of the 5' primer according to the formula CCC-AAGCTT-N, where N=24 to 26 specific nucleotides; and an XbaI site on the end of the 3' primer according to the formula GC-TCTAGA-N, where N=24 to 26 specific nucleotides.

The engineered restriction sites of these primers were used for cloning. F56F3.6 has an internal XbaI site, so an XhoI site was used instead on the 3' primer. What follows is a list of conditions used for PCR amplification and cloning of each gene.

6.3.1. ZK75.1

The template DNA source was a mixed-stage, C. elegans cDNA library, oligo-dT primed and ligated into Unizap XR (phage lambda) vector available from Stratagene. The library DNA was prepared by Qiagen purification and adjusted to a concentration of 70 ng/µl.

The cDNA was generated by the polymerase chain reaction (PCR) procedure, using the Boehringer Mannheim Expand High Fidelity PCR System. Each reaction was performed in a total volume of 100 µl. The components of the reaction were 1 µl (70 ng) template DNA, 200 µM each dNTP, 300 nM each primer as described below, 1×buffer with $MgCl_2$ as supplied by the manufacturer, and 2.6 U of enzyme.

First, the primers were pooled and denatured at 95° C. for 5:00 (where 0:00 indicates time in minutes:seconds), and stored on ice. The remainder of the reaction mixture was added, and the PCR reaction started as follows:

95° C. for 2:00
35 cycles of:
   95° C. for 0:15
   54° C. for 0:30
   72° C. for 1:00
   72° for 5:00

For the first round of PCR, the primers used were as follows:

75.1 GACGGAGATGGCTTGTTGGACGAC (SEQ ID NO:37)
SL1 GGTTTAATTACCCAAGTTTGAG (SEQ ID NO:38)

The first round of PCR yielded no detectable band as determined by agarose gel electrophoresis, staining with ethidium bromide, and visualization on a long-wave UV light box. Accordingly, a second round of PCR was next performed as described above, except with the following changes. The template DNA was 1 µl of the first round PCR reaction, the reactions were run for 20 cycles only, and different (nested) primers were used as follows:
75.1.5' CAAGAGAATGTTTTCATTCTTTAC (SEQ ID NO:39)
75.1B TTACTTTTCTGGGCAGCAAGCTTG (SEQ ID NO:40)

The second PCR reaction yielded a strong single band of DNA at the predicted size. To subclone this PCR product into a plasmid vector for DNA sequencing, we first isolated the PCR product by agarose gel electrophoresis (90 µl of the second PCR reaction run on a 1.2% gel). We excised the band with a razor blade and purified the product from the gel using the Prep-a-Gene kit from BioRad. We then ligated the PCR product into the plasmid vector PCRII and transformed E. coli using an InVitrogen TA Cloning Kit. We screened bacterial colonies for the correct plasmid by preparing mini-prep DNA using the Primm Labs Mini-Prep kit, and analyzed the mini-prep DNA by EcoRI restriction digest and agarose gel electrophoresis.

We sequenced the subcloned PCR products by thermal cycling, using the Big Dye ready reaction mix sequencing kit. For each sequencing reaction, we added: approximately 100 ng of mini-prep DNA; 0.8 pmol of sequencing primer; 1.5 µl 5×Big Dye ready reaction buffer; 1 µl 80 mM Tris, 2 mM $MgCl_2$ pH 9.0; and adjusted the volume to 10 µl with distilled water. The M13 Forward and M13 Reverse sequencing primers were used. The sequencing reactions were thermal cycled using the following program:

96° for 5:00
25 cycles of:
    96° C. for 0:30
    50° C. for 0:15
    60° C. for 4:00

We precipitated the cycled DNA with 75 µl 70% ethanol/5 mM $MgCl_2$ by incubating at room temperature for 20 minutes. We recovered the precipitated DNA by centrifugation at 15,000×g for 30 minutes, removed the supernatant, and further dried the DNA pellet by vacuum centrifugation for 10 minutes. The sequencing reactions were analyzed and the DNA sequence determined by gel electrophoresis and fluorescent detection of sequencing products.

6.3.2. ZK75.2

The template DNA source was mixed-stage *C. elegans* first strand cDNA, poly-A selected and oligo-dT primed using the Gibco-BRL Superscript kit. The RNA was removed by RNAse digestion, and the cDNA was diluted with TE buffer and adjusted to a final concentration of approximately 70 ng/µl. The cDNA was generated by the polymerase chain reaction (PCR) procedure, using the Boehringer Mannheim Expand High Fidelity PCR System. Each reaction was performed in a total volume of 100 µl. The components of the reaction were 1 µl (70 ng) template DNA, 200 µM each dNTP, 300 nM each primer as described below, 1×buffer with $MgCl_2$ as supplied by the manufacturer, and 2.6 U enzyme.

First, the template was denatured at 95° C. for 5:00 minutes and stored on ice. The remainder of the reaction mixture was added, and the PCR reaction started as follows:

95° C. for 2:00
35 cycles of:
    95° C. for 0:15
    54° C. for 0:30
    72° C. for 1:00
    72° for 5:00

For the first round of PCR, the primers were as follows:
75.2.5' CTACCATGAACGCTATAATCTTCT (SEQ ID NO:41)
75.2.3' ATGATAGTACGATATGTCCATAAC (SEQ ID NO:42)

This reaction yielded a single strong band of the expected size (349 bp) after one round of PCR.

To subclone the PCR product into a plasmid vector for DNA sequencing, we first isolated the PCR product by agarose gel electrophoresis (90 µl of the second PCR reaction run on a 1.2% gel). We excised the band with a razor blade, and purified the product from the gel using the Prep-a-Gene kit from BioRad. We then ligated the PCR product into the plasmid vector PCRII and transformed E. coli using the InVitrogen TA Cloning Kit. We screened bacterial colonies for the correct plasmid by colony PCR, using the following primers:
75.2.5' CTACCATGAACGCTATAATCTTCT (SEQ ID NO:41)
75.2.3' ATGATAGTACGATATGTCCATAAC (SEQ ID NO:42)

To confirm the positive colonies, we prepared miniprep plasmid DNA from positive colonies using the Primm Labs miniprep kit and confirmed the plasmid by EcoR1 restriction digest and agarose gel electrophoresis.

We analyzed the sequence of the PCR product as described for ZK75.1.

6.3.3. ZK75.3

A first round PCR reaction was performed exactly as for ZK75.2, except using primers:
75.3 CCTATTTTCCAGCCACAGCACTCTC (SEQ ID NO:43)
SL1 GGTTTAATTACCCAAGTTTGAG (SEQ ID NO:38)

No band was obtained after the first round of PCR. Strong bands of 426 bp were obtained-after the second round of PCR, which was performed as follows:
    template=2 µl of first round PCR
    same primers as first round
    same PCR conditions as first round Subcloning and sequencing of the second round reaction product was performed exactly as for ZK75.1.

6.3.4. ZK84.6

First round PCR was performed exactly as for ZK75.1, except using primers:
84.3OUTER CCCCGTACTCATTTTCCGTTATCC (SEQ ID NO:44)
84.3 GTATGGTACAGAGACTGATATCGG (SEQ ID NO:45)

A strong single band of 423 bp after the first round of PCR was obtained. Subcloning and sequencing of PCR products was performed exactly as for ZK75.2, except using the following primers for colony PCR screening:
84.3OUTER CCCCGTACTCATTTTCCGTTATCC (SEQ ID NO:44)
84.3.5'B CAAGGAAAATGCACTCGATCGTCG (SEQ ID NO:46)

6.3.5. ZK84.N

The template DNA source was a mixed stage *C. elegans* cDNA library oligo primed and ligated into UniZap XR (phage lambda) vector, purchased-from Stratagene. The library DNA was prepared by Qiagen purification and adjusted to a concentration of 70 ng/µl.

The cDNA was generated by the polymerase chain reaction (PCR) procedure, using the Boehringer Mannheim Expand High Fidelity PCR System. Each reaction was performed in a total volume of 50 µl. The components of the reaction were 0.5 µl (70 ng) template DNA, 100 µM each dNTP, 150 nM each primer as described below, 1×buffer with MgCl$_2$ as supplied by the manufacturer, and 1.3 U enzyme.

First, the template was denatured at 95° C. for 5:00 minutes, and stored on ice. The remainder of the reaction mixture was added, and the PCR reaction started as follows:
95° C. for 2:00
35 cycles of:
95° C. for 0:15
54° C. for 0:30
72° C. for 1:00

For the first round of PCR, the primers were:
84.NF-Hin CCCAAGCTTTGTTATTTAATGATGTGGAGATGG (SEQ ID NO:47)
84.NR-XBA GCTCTAGAATGGTAAATACAGAACATTGGTTC (SEQ ID NO:48)

This reaction yielded a strong single band of DNA at the predicted size. To subclone the PCR product into a plasmid vector for DNA sequencing, we first purified the PCR product with the Geneclean kit (Bio101), then digested the product with HindIII and XbaI and isolated the PCR product by agarose gel electrophoresis (45 µl of the PCR reaction run on a 1.2% gel). We excised the band with a razor blade, and purified the product from the gel using the Geneclean kit. We then ligated the cut PCR product into the plasmid vector pcDNA3.1 (InVitrogen) cut with HindIII/XbaI and transformed *E. coli*. We screened bacterial colonies for the correct plasmid by preparing mini-prep DNA using the Primm Labs MiniPrep kit, and analyzed the mini-prep DNA by PmeI restriction digest and agarose gel electrophoresis.

We sequenced the subcloned PCR products by thermal cycling, using the Big Dye ready reaction mix sequencing kit. For each sequencing reaction, we added approximately 100 ng of mini-prep DNA; 0.8 pmol of sequencing primer; 1 µl 5×Big Dye ready reaction buffer; 1.5 µl 80 mM Tris, 2 mM MgCl$_2$ pH 9.0; and adjusted the volume to 10 µl with distilled water. The sequencing primers used were pcDNA3.1BGHReverse and a T7 promoter primer. The sequencing reactions were thermal cycled using the following program:
96° for 5:00
25 cycles of:
96° C. for 0:30
50° C. for 0:15
60° C. for 4:00

We precipitated the cycled DNA with 75 µl 70% ethanol/5 mM MgCl$_2$ by incubating at room temperature for 20 minutes. We recovered the precipitated DNA by centrifugation at 15,000×g for 30 minutes, removed the supernatant, and further dried the DNA pellet by vacuum centrifugation for 10 minutes. The sequencing reactions were analyzed and the DNA sequence determined by gel electrophoresis and fluorescent detection of sequencing products.

6.3.6. ZK84.N2

PCR was performed exactly as for ZK84.N, except using PCR primers:
ORPR-XBA GCTCTAGAGTGACGGTAGGTGTGTAGATGAAC (SEQ ID NO:49)
84.35' ATCGAAACTCTTCAATCTTCAAGG (SEQ ID NO:50)

This reaction yielded a strong single band of DNA at the predicted size. To subclone the PCR product into a plasmid vector for DNA sequencing, we first isolated the PCR product by agarose gel electrophoresis (45 µl of the PCR reaction run on a 1.2% gel). We excised the band with a razor blade, and purified the product from the gel using the Geneclean kit. We then ligated the PCR product into the plasmid vector PCRII and transformed *E. coli* using the InVitrogen TA Cloning Kit. We screened bacterial colonies for the correct plasmid by preparing mini-prep DNA using the Primm Labs MiniPrep kit, and analyzed the mini-prep DNA by PmeI restriction digest and agarose gel electrophoresis.

We sequenced the subcloned PCR products by thermal cycling, using the Big Dye ready reaction mix sequencing kit. For each sequencing reaction, we added approximately 100 ng of mini-prep DNA; 0.8 pmol of sequencing primer; 1 µl 5×Big Dye ready reaction buffer; 1.5 µl 80 mM Tris, 2 mM MgCl$_2$, pH 9.0; and adjusted the volume to 10 µl with distilled water. The sequencing primers used were pcDNA3.1BGHReverse and a T7 promoter primer. The sequencing reactions were thermal cycled using the following program:
96° for 5:00
25 cycles of:
96° C. for 0:30
50° C. for 0:15
60° C. for 4:00

We precipitated the cycled DNA with 75 µl 70% ethanol/5 mM MgCl$_2$ by incubating at room temperature for 20 minutes. We recovered the precipitated DNA by centrifugation at 15,000×g for 30 minutes, removed the supernatant, and further dried the DNA pellet by vacuum centrifugation for 10 minutes. The sequencing reactions were analyzed and the DNA sequence determined by gel electrophoresis and fluorescent detection of sequencing products.

6.3.7. ZK1251.2

PCR was performed exactly as for ZK75.1, except using primers:
SL1 GGTTTAATTACCCAAGTTTGAG (SEQ ID NO:38)
1251.2 GATAGAAGAAATTAAGGACAGCAC (SEQ ID NO:51)

A single strong band of 351 bp was obtained after one round of PCR. Subcloning and sequencing of PCR products was performed exactly as for ZK75.1.

6.3.8. ZK1251.N

PCR was performed exactly as for ZK75.1, except using primers:
1251.N GTAAACGATTAGATTAAGGACAAC (SEQ ID NO:52)
SL1 GGTTTAATTACCCAAGTTTGAG (SEQ ID NO:38)

No band was obtained after the first round of PCR. A second round was performed using an aliquot of the first round reaction as template, the same reaction mix and primers, and the same PCR conditions. Strong bands of 349 bp were obtained after the second round of PCR. Subcloning and sequencing was performed exactly as for ZK75.1.

6.3.9. C06E2.N

PCR was performed exactly as for ZK75.1, except using primers:
C06E2.5' GAGGAGTGAAACGATGATCGTCAC (SEQ ID NO:53)

C06E2 ATCCAATTGAGAAGACGATTGTTG (SEQ ID NO:54)

No band was obtained after the first round of PCR. A second round of PCR was performed using an aliquot of the first round as template, the same reaction mix and primers, and the same PCR conditions as in the first round, but for 20 cycles rather than 35 cycles.

A single strong band of 404 bp was obtained after the second round of PCR. Subcloning and sequencing of PCR products was performed exactly as ZK75.1.

6.3.10. M04D8.1

PCR was performed exactly as for ZK84.N, except using primers:
8.1F-Hin CCCAAGCTTTTGAACCATGAAAAC-CTACTCATT (SEQ ID NO:55)
8.IR-XBA GCTCTAGAGCTTTTTTTTATTCGGGA-CAGCAA (SEQ ID NO:56)

6.3.11. M04D8.3

PCR was performed exactly as for ZK84.N, except using primers:
8.3F-Hin CCCAAGCTTGGATTTCTGGAATTTC-GATAATG (SEQ ID NO:57)
8.3R-XBA GCTCTAGAGCAGCATAGAATGGCGGAA-GATC (SEQ ID NO:58)

6.3.12. C17C3.4

PCR was performed exactly as for ZK84.N, except using primers:
3.4F-Hin CCCAAGCTTGTGTAGGAATCGT-TAAATATGTCT (SEQ ID NO:59)
3.4R-XBA GCTCTAGAGAGATCATATTATATTACAC-GAAC (SEQ ID NO:60)

6.3.13. P13B12.N

PCR was performed exactly as for ZK84.N, except using primers:
B12F-Hin CCCAAGCTTCCGCTCTCAACAACGGGC-CACACG (SEQ ID NO:61)
B12R-XBA GCTCTAGAGATGAATAAGTTATCAAT-TATCGT (SEQ ID NO:62)

6.3.14. T28B8.N

PCR was performed-exactly as for ZK84.N, except using primers:
SL1-Hin CCCAAGCTTGGTTTAATTAC-CCAAGTTTGAG (SEQ ID NO:63)
B8.2R-XBA GCTCTAGATGATGCGTATTTTGTGGGCG-GTAC (SEQ ID NO:64)

6.3.15. ZC334.N

PCR was performed exactly as for ZK84.N, except using primers:
SL1-Hin CCCAAGCTTGGTTTAATTAC-CCAAGTTTGAG (SEQ ID NO:63)
34.NR-XBA GCTCTAGACTCATCAGTTGAAAAT-GAATTAAG (SEQ ID NO:65)

6.3.16. F36F3.6

PCR was performed exactly as for ZK84.N, except using primers:
F3.6F-Hin CCCAAGCTTGGCATAAGCGAGTATCTGT-GATCC (SEQ ID NO:66)
F3.6R-XHO CCGCTCGAGGTAAAGCGAGGGTAAAG-TAGATCG (SEQ ID NO:67)

6.3.17. M04D8.2

PCR was performed exactly as for ZK84.N, except using primers:
8.2F-Hin CCCAAGCTTCTAACCAACAAAAATGCA-CACTAC (SEQ ID NO:68)
8.2R-XBA GCTCTAGACACGTGAACAATCTT-TATCTTTAT (SEQ ID NO:69)

6.3.18. C17C3.N

PCR was performed exactly as for ZK84.N, except using primers:
3.NF-Hin CCCAAGCTTCACAGCCAAAAACAAAAAT-GCAATC (SEQ ID NO:70)
3.NR-XBA GCTCTAGACACAGTATTTTAATGAAG-GAGATC (SEQ ID NO:71)

6.3.19. T08G5.N

PCR was performed exactly as for ZK84.N, except using 0.5 µl (35 ng) of template DNA and PCR primers:
SL1-Hin CCCAAGCTTGGTTTAATTAC-CCAAGTTTGAG (SEQ ID NO:144)
G5.NR-XBA GCTCTAGATAATTCAATGAAAAG-GCAAAACGACG (SEQ ID NO:145)

This reaction yielded four bands after one round of PCR. The cDNA was contained within an approximately 315 bp DNA fragment. Subcloning and sequencing of PCR products was performed exactly as for ZK75.1 except with the following sequencing primers:
pcDNA3.1BGH Reverse TAGAAGGCACAGTCGAGG (SEQ ID NO:146)
T7 promoter primer TAATACGACTACTATAGGG (SEQ ID NO:147)

6.3.20. F41G3.N

PCR was performed exactly as for T08G5.N, except using PCR primers:
G3.NF-Hin CCCAAGCTTCTTCATTTGGGCTTCATTT-TACCAC (SEQ ID NO:148)
G3.NR-XBA GCTCTAGAGAAACAATGTTTTTAT-TCAACATG (SEQ ID NO:149)

This reaction yielded a band of the expected size after one round of PCR. The PCR product was cloned into pcDNA3.1 and sequenced exactly as described for ZK75.1.

6.3.21. F41G3.N2

PCR was performed exactly as for T08G5.N, except using PCR primers:
G3.N2F-OUT CCCAAGCTTGGACTTTATCACAATTTC-CAGCAC (SEQ ID NO:154)
G3.N2R-XBA GCTCTAGAGTTTCTAGATTTTTA-GATTTCGTG (SEQ ID NO:155) No band was visualized after the first round of PCR. A second PCR was performed as described above with the following changes: the template DNA was 1 of the first round PCR reacton, the reactions were run for 20 cycles only, and a different (nested) 3' primer was used. The primers were:
G3.N2F-XHO CCGCTCGAGATAATGAAGCTTCTTCT-TCTCATTG (SEQ ID NO:156)
G3.N2R-XBA GCTCTAGAGTTTCTAGATTTTTA-GATTTCGTG (SEQ ID NO:157)

This reaction yielded a band of the expected size. The PCR product was subcloned into pcDNA3.1 and sequenced exactly as described for T085G.N, except the restriction enzymes used to digest the PCR product and vector were XbaI and XhoI.

6.3.22. C17C3.N2

PCR was performed exactly as for T08G5.N, except using PCR primers:
C3.N2F-XHO CCGCTCGAGCTCGACGTTCTTCAATC-TATATTTC (SEQ ID NO:150)
C3.N2R-XBA GCTCTAGACAAACACCATTAAATCTG-TATTTAAAC (SEQ ID NO:151)

No band appeared after the first round of PCR. A second round of PcR was performed exactly as before using the following primers:
C3N2F-XHO CCGCTCGAGCTCGACGTTCTTCAATC-TATATTTC (SEQ ID NO:164)
C3.N2R-INN GCTCTAGAGTTCACAAAT-TCATTTTCAAATACG (SEQ ID NO:165)

This reaction yield a single strong band of the expected size. The PCR product was subcloned into pcDNA3.1 and sequenced exactly as described for T08G5.N, except the restriction enzymes used to digest the PCR product and vector were XbaI and XhoI.

6.3.23. Y52A1.N

The template DNA source was mixed-stage *C. elegans* first-strand cDNA, poly-A selected and oligo-dT primed using the Gibco-BRL Superscript kit. The RNA was removed by RNAse digestion, and the cDNA was diluted with TE buffer and adjusted to a final concentration of approximately 70 ng/μl.

The cDNA was generated by the polymerase chain reaction (PCR) procedure, using the Boehringer Mannheim Expand High Fidelity PCR System. Each reaction was performed in a total volume of 50 μl. The components of the reaction were 0.5 μl (35 ng) template DNA, 100 μM each dNTP, 150 nM each primer as described below, 1×buffer with MgCl₂ as supplied by the manufacturer, and 1.3 units of enzyme.

First, the template was denatured at 95° C. for 5:00 minutes, and stored on ice. The remainder of the reaction mixture was added, and the PCR reaction started as follows:
95° C. for 2:00
35 cycles of:
  95° C. for 0:15
  54° C. for 0:30
  72° C. for 1:00
For the first round of PCR, the primers were:
SL1-Hin CCCAAGCTTGGTTTAATTAC-CCAAGTTTGAG (SEQ ID NO:166)
A1.1R-XBA GCTCTAGACAATTTTGATAT-TAAATTTTGTCG (SEQ ID NO:167)

The first round of PCR yielded no detectable band as determined by agarose gel electrophoresis, staining with ethidium bromide, and visualization on a UV light box.

A second round of PCR was performed as described above, with the following changes: the template DNA was 1 μl of the 1st round PCR reaction, the reactions were run for 20 cycles only, and a different (nested) 3' primer was used. The primers were:
SL1-Hin CCCAAGCTTTGGTTTAATTAC-CCAAGTTTGAG (SEQ ID NO:168)
1.1R-INN GCTCTAGATAAATTTTGTC-GATTTTCAAGTTG (SEQ ID NO:169)

This reaction yielded a strong single band of DNA at approximately 1.3 kb.

To subclone the PCR product into a plasmid vector for DNA sequencing, we first isolated the PCR product by agarose gel electrophoresis (45 μl of the second PCR reaction run on a 1.2% gel). We excised the band with a razor blade, and purified the product from the gel using the Geneclean (Bio101). We then ligated the PCR product into the plasmid vector pCRII and transformed *E. coli* using the InVitrogen TA Cloning Kit. We screened bacterial colonies for the correct plasmid by preparing mini-prep DNA (Biotechniques 8, 172–3), and analyzed the mini-prep DNA by EcoRI restriction digest and agarose gel electrophoresis.

We sequenced the subcloned PCR products by thermal cycling, using the Big Dye ready reaction mix sequencing kit. For each sequencing reaction, we added: approximately 100 ng of mini-prep DNA; 0.8 pmol of sequencing primer; 1 μl 5×BigDye ready reaction buffer; 1.5 μl 80 mM Tris, 2 mM MgCl₂, pH 9.0; and adjusted the volume to 10 μl with distilled water. The following sequencing primers were used:
M13 Forward GTTTTCCCAGTCACG (SEQ ID NO:170)
M13 Reverse CAGGAAACAGCTATGAC (SEQ ID NO:171)

The sequencing reactions were thermal cycled using the following program:
96° for 5:00
25 cycles of:
  96° C. for 0:30
  50° C. for 0:15
  60° C. for 4:00

We precipitated the cycled DNA with 75 μl 70% ethanol/5 mM MgCl₂ by incubating at room temperature for 20 minutes. We recovered the precipitated DNA by centrifugation at 15,000×g for 30 minutes, removed the supernatant, and further dried the DNA pellet by vacuum centrifugation for 10 minutes. The sequencing reactions were analyzed and the DNA sequence determined by gel electrophoresis and fluorescent detection of sequencing products. The resulting DNA sequence for the Y52A1-derived product indicated that there were in fact two opening reading frames in this cDNA. The open reading frame closest to the 5'-end of the message corresponding to this cDNA was not related to the insulin family. Instead, the insulin-like sequences predicted from the search of genomic DNA were found to correspond to the second open reading frame of this mRNA. Comparison of this Y52A1-derived cDNA sequence with the genomic sequence suggested that the likely explanation for this configuration of two open reading frames was that they correspond to an operon where multiple mRNAs are derived from the same transcription unit through different patterns of trans-splicing (see Zorio et al., 1994, Operons as a common form of chromosomal organization in *C. elegans*, Nature 372, 270–272). Thus, it was assumed that the insulin-like open reading frame in the Y52A1-derived product is actually translated from an mRNA that may be generated using an alternative trans-spliced leader such as SL2 or other leaders related to SL2.

PCR was used to amplify the presumptive insulin-like coding region from the larger cDNA product derived above. PCR was performed as above, with the following changes: the template was 1 μl of mini-prep DNA, and the following program was used:
95° C. for 2:00
10 cycles of:
  95° C. for 0:30
  54° C. for 0:30
  72° C. for 1:00

The primers were:
Y52A1-i CCCAAGCTTGAGCATTTTGTTGCTCTG-CAAAATG (SEQ ID NO:172)
1.1R-INN GCTCTAGATTAAATTTTGTC-GATTTCAAGTTG (SEQ ID NO:173)
This reaction yielded a 268 bp product.

To subclone the PCR product into a plasmid vector for DNA sequencing, we first purified the PCR product with the Geneclean kit (Bio101), then digested the product with HindIII and XbaI and isolated the PCR product by agarose gel electrophoresis (45 µl of the PCR reaction run on a 1.2% gel). We excised the band with a razor blade, and purified the product from the gel using the Geneclean kit. We then ligated the cut PCR product into the plasmid vector pcDNA3.1 (InVitrogen) cut with HindIII/XbaI and transformed E. coli. We screened bacterial colonies for the correct plasmid by preparing mini-prep DNA (Biotechniques 8, 172–3), and analyzed the mini-prep DNA by PmeI restriction digest and agarose gel electrophoresis.

We sequenced the subcloned PCR products exactly as above, except with the following sequencing primers:
pcDNA3.1BGH Reverse TAGAAGGCACAGTCGAGG (SEQ ID NO:174)
T7 promoter primer TAATACGACTACTATAGGG (SEQ ID NO:175)

6.3.24. ZC334.N2

The cloning sites, HindIII and XbaI were used for many of the cDNAs except ZC334.N2, which has internal HindIII and XbaI sites. The 5' primer contains a BamHI restriction site on the 5' end: CG-GGATCC-N=24; and the 3' primer contains an EcoRI site on the end: CG-GAATTC-N=25.

The template DNA source was mixed stage C. elegans first strand cDNA, poly-A selected and oligo-dT primed using the Gibco-BRL Superscript kit. The RNA was removed by RNAse digestion, and the cDNA was diluted with TE buffer and adjusted to a final concentration of approximately 70 ng/µl.

The cDNA was generated by the polymerase chain reaction (PCR) procedure, using the Boehringer Mannheim Expand High Fidelity PCR System. Each reaction was performed in a total volume of 50 µl. The components of the reaction were 50 µl (210 ng) template DNA, 200 µM each dNTP, 300 nM each primer as described below, 1×buffer with MgCl$_2$ as supplied by the manufacturer, and 2.6 units of enzyme.

The reaction mixture was assembled with the above components, except for the first strand cDNA template. The first strand cDNA template was added subsequently, and the PCR reaction started as follows:
95° C. for 2:00
35 cycles of:
95° C. for 0:15
54° C. for 0:30
72° C. for 1:00
For the first round of PCR, the primers were:
R334N2-L1BAM CGGGATCCCCGCACAAACTTATAT-GACAACTC (SEQ ID NO:176)
R334N2-R1ECORI CGGAATTCGGTGTCTCATAATGG-TAGTGGATAC (SEQ ID NO:177)

The first round of PCR yielded no detectable band as determined by agarose gel electrophoresis, staining with ethidium bromide, and visualization on a UV light box.

A second round of PCR was performed as described above, with the following changes: the template DNA was 0.5 µl of the 1st round PCR reaction, and a different (nested) 3' primer was used. The primers were:
R334N2-L1BAM CGGGATCCCCGCACAAACTTATAT-GACAACTC (SEQ ID NO:178)
R334N2-R2ECORI CGGAATTCGCAAAAGAGAGG-TATAGGGATAAAG (SEQ ID NO:179)

This reaction yielded a strong single band of DNA at approximately 400 bp.

To subclone the PCR product into a plasmid vector for DNA sequencing, we first purified the PCR reaction using the Promega Wizard PCR preps DNA purification system kit, according to the manufacturer's instructions, except the purified DNA was eluted from the column using 25 µl of distilled water. The purified DNA was digested with BamHI and EcoRI and the digested PCR product was isolated by agarose gel electrophoresis on a 1% agarose gel. The DNA product was eluted by electrophoresis into 1% low-melting temperature agarose. The product was purified from the gel by digestion of the low-melting temperature agarose with 5 units of B-agarase I (New England Biolabs) for 1 hour at 40° C. in 1×B-agarase buffer provided by the manufacturer, followed by precipitation of the DNA with ¹⁄₁₀ volumes of 3M sodium acetate, pH 5.2 and 2 volumes of isopropanol. Following incubation of this mixture at −20° C. for 30 minutes, the precipitated DNA was recovered by centrifugation at 13,500×g for 15 minutes, the supernatant was removed, the DNA pellet was air-dried for 10 minutes and resuspended in 10–20 µl of distilled water. We then ligated the PCR product into the plasmid vector pcDNA3.1 (InVitrogen), cut with BamHI and EcoRI and transformed E. coli. We screened bacterial colonies for the correct plasmid by preparing mini-prep DNA using the Primm Labs Mini-Prep kit, and analyzed the miniprep DNA by BamHI and EcoRI restriction digestion and agarose gel electrophoresis.

We sequenced the subcloned PCR products by thermal cycling, using the Big Dye ready reaction mix sequencing kit. For each sequencing reaction, we added: approximately 100–200 ng of mini-prep DNA; 0.8 pmol of sequencing primer; 1 µl 1×BigDye ready reaction buffer (80 mM Tris, 2 mM MgCl$_2$, pH 9.0) and adjusted the volume to 5 µl with distilled water. The following sequencing primers were used:
pcDNA3.1BGH Reverse TAGAAGGCACAGTCGAGG (SEQ ID NO:180)
T7 promoter primer TAATACGACTACTATAGGG (SEQ ID NO:181)

The sequencing reactions were thermal cycled using the following program:
96° for 4:00
25 cycles of:
96° C. for 0:30
50° C. for 0:15
60° C. for 4:00
We purified the cycled DNA by centrifugation through Centriflex gel filtration cartridge spin columns (Edge Biosystems), according to the manufacturer's instructions. The purified DNA was dried by vacuum centrifugation for 30 minutes. The sequencing reactions were analyzed and the DNA sequence determined by gel electrophoresis and fluorescent detection of sequencing products.

6.3.25. ZC334.N3

The first round PCR was performed exactly as ZC334.N2, except the 5' primer contains an HindIII site, and the 3' primer contains and XbaI site, as the Y52A1.N primers. First round primers:
334N3-LIH3 CCCAAGCTTAAAGGCTTAGATGCA-GAAAGACC (SEQ ID NO:182)
334N3-RXBA GCTCTAGAGGGATTAAAATCACTCT-GTGATTAAG (SEQ ID NO:183)

The first round of PCR yielded no detectable band as determined by agarose gel electrophoresis, staining with ethidium bromide, and visualization on a UV light box.

A second round of PCR was performed as described above; a different (nested) 5' primer was used. The primers were:
334N3-L2H3 CCCAAGCTTTAAAGGTGGACATTGTAGAAGGTTG (SEQ ID NO:184)
334N3-RXBA GCTCTAGAGGGATTAAAATCACTCTGTGATTAAG (SEQ ID NO:185)

This reaction yielded several different sized DNA products, including a strong band of DNA at the predicted size of approximately 350 bp. This 350 bp product was subcloned and sequenced exactly as described for ZC334.N2.

6.3.26. ZC334.N4

The first round PCR was performed exactly as ZC334.N2. Primers contain HindIII and XbaI sites as ZC334.N3. First round primers:
R334N4-LIH3 CCCAAGCTTCCTTCACTTCTCAGCGAAGGAAATG (SEQ ID NO:186)
R334N4-RXBA GCTCAGAGTGCTCATGCTCCGTTATTTGTGC (SEQ ID NO:187)

This reaction yielded a strong single band of DNA at approximately 380 bp after one round of PCR. This product was subcloned and sequenced exactly as described for ZC334.N2.

6.3.27. ZC334.N5

The first round PCR was performed exactly as ZC334.N2. The 5' primer contains a EcoRI restriction site on the 5' end, i.e. CG-GAATTC-N=26; and the 3' primer contains an XhoI site on the end, i.e. CCG-CTCGAG-N=24 for cloning; the HindIII and XbaI sites, which were used as cloning sites for many of the cDNAs, were not used in this case since ZC334.N5 has both internal HindIII and XbaI sites. First round primers:
R334N5-L1ECORI CGGAATTCCTAGAATTTTCACCCCAAATGTTCAG (SEQ ID NO:188)
R334N5-RXHO CCGCTCGAGAAATGTAAGTGATTGGCAAGTTGG (SEQ ID NO:189)

This reaction yielded a strong single band of DNA at approximately 300 bp after one round of PCR. This product was subcloned and sequenced exactly as described for ZC334.N2.

6.3.28. ZC334.N6

The first round PCR was performed exactly as ZC334.N2. Primers contain HindIII and XbaI sites as ZC334.N3. First round primers:
334N6-L1H3 CCCAAGCTTAGAGACTTAGACGCAAAGAGGACC (SEQ ID NO:190)
334N6-RXBA GCTCTAGAGCAGGAAATTAGCTAAAACATAATG (SEQ ID NO:191)

The first round of PCR yielded no detectable band as determined by agarose gel electrophoresis, staining with ethidium bromide, and visualization on a UV light box.

A second round of PCR was performed using the same two primers that were used in the ZC334.N6 first round reaction, as described above. This reaction yielded several products, including a strong band of DNA at the predicted size of approximately 450 bp.

This 450 bp product was subcloned and sequenced exactly as described for ZC334.N2.

6.3.29. ZC334.N7

The first round PCR was performed exactly as ZC334.N2. The 5' primer contains a EcoRI restriction site on the 5' end, i.e. CG-GAATTC-N=24; and the 3' primer contains an XhoI site on the end, i.e. CCG-CTCGAG-N=25 for cloning; the HindIII and XbaI sites, which were used as cloning sites for many of the cDNAs, were not used in this case since ZC334.N7 has both internal HindIII and XbaI sites. First round primers:
R334N7-L1ECORI CGGAATTCGGCGAAACACTTCCGCCAACTCAC (SEQ ID NO:192)
R334N7-R1XHO CCGCTCGAGACCTACCTCAACTTGGAGGATAAC (SEQ ID NO:193)

The first round of PCR yielded no detectable band as determined by agarose gel electrophoresis, staining with ethidium bromide, and visualization on a UV light box.

A second round of PCR was performed using the same two primers that were used in the ZC334.N7 first round reaction, as described above. This reaction yielded several products, including a band of DNA at the predicted size of approximately 650 bp. This 650 bp product was subcloned and sequenced exactly as described for ZC334.N2.

6.3.30. T10D4.N

The first round PCR was performed exactly as ZC334.N2. Primers contain HindIII and XbaI sites as ZC334.N3. First round primers:
D4N-L2H3 CCCAAGCTTCCTTGCACCTGCCTTCAACCATCAC (SEQ ID NO:194)
D4N-RXBA GCTCTAGATATTCTGACCCCAAAATGACAATC (SEQ ID NO:195)

This reaction yielded a single band of DNA at approximately 700 bp after one round of PCR. This product was subcloned and sequenced exactly as described for ZC334.N2.

6.3.31. T10D4.N2

The first round PCR was performed exactly as ZC334.N2. Primers contain HindIII and XbaI sites as ZC334.N3. First round primers:
RD4N2-L1H3 CCCAAGCTTTTCTGCAGACTTGCAAGGTTAGTTC (SEQ ID NO:196)
RD4N2-R1XBA GCTCTAGAATTCACAAAATAATCAAGACAATC (SEQ ID NO:197)

The first round of PCR yielded no detectable band as determined by agarose gel electrophoresis, staining with ethidium bromide, and visualization on a UV light box.

A second round of PCR was performed using the same two primers that were used in the T10D4.N2 first round reaction, as described above. This reaction yielded a strong band of DNA at approximately 400 bp. This product was subcloned and sequenced exactly as described for ZC334.N2.

6.4. Expression Analysis

Analysis of expression patterns of C. elegans insulin-like genes was carried out by fusing the transcriptional control regions identified for each gene to a reporter gene encoding green fluorescent protein (GFP), a protein whose expression is easily detected by its fluorescence in vivo (see Chalfie et al., 1994, "Green fluorescent protein as a marker for gene expression", Science 263:802–805). Each reporter gene so constructed was then expressed as a transgene in transgenic nematodes. Table 2 entitled "Expression Data" sets forth the results.

6.4.1. Expression Analysis Strategy

For each C. elegans insulin-like gene, putative promoter/enhancer regions were identified in the adjacent genomic sequence (GenBank®, *C. elegans* Genome Project) as regions extending from the predicted start codon of each insulin-like gene to the next gene upstream, identified using the GeneFinder program. If the putative promoter/enhancer region was 6 kilobase pairs (kbp) or less in size, synthetic oligonucleotide primers were designed to amplify the entire region by PCR. For F13B12.N, ZK75.2 and M04D8.1, and the putative promoter/enhancer region was more than 6 kbp or was unbounded (see Table 2) by a clearly-defined upstream gene. In these instances, a 2 to 6 kbp segment of upstream region was arbitrarily chosen for amplification, based on available genomic sequence information and favorable primer annealing sites. In addition to the gene-specific sequences incorporated into the PCR primers, each primer also contained restriction enzyme cleavage sites to allow easy insertion into the GFP reporter vector system (pPD117.01): Asc I cleavage sites where incorporated in primers positioned upstream of each enhancer/promoter region, and either Age I or Kpn I sites incorporated into each primer position downstream of the promoter/enhancer. The specific primer pair sequences used to amplify the promoter/enhancer regions of each gene are listed below.

TABLE 2

Expression Data

| Class | Chromosome | Gene | Enhancer (Kb) | Duplicate | stages | cell bodies in NR (per side) | sensory processes | other processes/ neurons | non-neuronal cells | starved plates |
|---|---|---|---|---|---|---|---|---|---|---|
| I | IV | F13B12.N | 5.2 (not bounded) | independent | embryo–adult | many | amphid | ventral, lateral, tail | | same |
| II | II | ZK75.2 | 3.7 (not bounded) | independent | embryo (bean), L1 (weak L2, L3?) | many | amphid, IL (2?) | ventral, tail | weak pharynx, vulva | absent/ weak |
| | | ZK75.3 | 5.7 (bounded) | independent | L1–adult | 4? | amphid, IL (2?) | ventral, lateral, dorsal, circum-ferential | | same |
| | | ZK75.1 | 5.7 (bounded) | same PCR | embryo (2X)–adult | 4? | amphid, IL (2?) | ventral, dorsal, tail | hypodermis (L2/3-adult) | same |
| | | ZK84.N2 | 1.7 (bounded) | | | | | | | |
| | | ZK84.6 | 3.7 (bounded) | independent | L1–adult | 2 | amphid, IL (2) | ventral, tail | | same |
| | IV | ZK1251.2 | 0.6 (bounded) | independent | embryo–adult | 4? | amphid, IL (2) | ventral, tail | weak cuticle? | same |
| | | ZK1251.N | 1.3 (bounded) | same PCR | embryo–adult | 4? | amphid, IL (2) | ventral, tail | vulva, weak cuticle? | same |
| | X | C06E2.N | 3.0 (bounded) | same PCR | L1–adult | 2 | amphid | | | same |
| III | II | C17C3.N | 2.3 (bounded) | | | | | | | |
| | | C17C3.4 | 1.4 (bounded) | independent | | | | | | |
| IV | II | ZK84.N | 2.1 (bounded) | | | | | | | |
| | III | M04D8.1 | 3.0 (not bounded) | | embryo–adult | 2 | amphid | ventral, weak tail | | same |
| | | M04D8.2 | 2.2 (bounded) | independent | | | | | | |
| | | M04D8.3 | 1.6 (bounded) | independent | | | | | | |
| daf-2 | | | 3.4 (not bounded) | same PCR | embryo–adult | many | amphid, IL (2) | ventral, lateral, circumferential, vulval, tail | BW muscle, hypodermis (embryo-L4) | same + intestine |

6.4.2. List of Primers for Promoter/Enhancer Amplification

| Gene (PCR product size in kbp) | |
|---|---|
| Sense and antisense primers | |
| F13B12.N (5.2) | |
| TTGGGCGCGCCGTCTTGCATGCAGTTGTCACG | (SEQ ID NO:72) |
| CCAACCGGTATCATTGCGTACTGTCGTAGCGTGTG | (SEQ ID NO:73) |
| ZK75.2 (3.7) | |
| TTGGGCGCGCCTGCTACCGTGGGAATTTTACAAG | (SEQ ID NO:74) |
| CCAACCGGTATCATGGTAGATTTTAGAATGGAAAG | (SEQ ID NO:75) |
| ZK75.3 (5.7) | |
| TTGGGCGCGCCGGAGTTCATCTGGAGGTCACATC | (SEQ ID NO: 76) |

-continued

| Gene (PCR product size in kbp) | |
|---|---|
| CCAACCGGTATCATTATTCAGAACAGGAATTGATAAATG | (SEQ ID NO:77) |
| ZK75.1 (5.7) | |
| TTGGGCGCCAGATAAATACAGAATGGGCGGAG | (SEQ ID NO:78) |
| CCAACCGGTATCATTCTCTTGGAGCTTTTGAAAAAC | (SEQ ID NO:79) |
| ZK84.N2 (1.7) | |
| TTGGGCGCGCCAGTCGTCCAACAAGCCATCTCC | (SEQ ID NO:80) |
| CCAACCGGTTGCATTTTCCTTGAAGATTGAAG | (SEQ ID NO:81) |
| ZK84.6 (3.7) | |
| TTGGGCGCGCCTAGATTTTCTCCATTCACAAAC | (SEQ ID NO:82) |
| CCAACCGGTATCATTATAATGATATGGATAACGG | (SEQ ID NO:83) |
| ZK1251.2 (0.6) | |
| TTGGGCGCGCCAATCGTTTTCATCATTTTGCTTC | (SEQ ID NO:84) |
| CCAACCGGTATCATCTGGAAAAGTAATATTATAT | (SEQ ID NO:85) |
| ZK1251.N (1.3) | |
| TTGGGCGCGCCTGAAATCTTTATATCCTCTTCAC | (SEQ ID NO:86) |
| CCAACCGGTATCATCTGGAAATAATTAATATCAG | (SEQ ID NO:87) |
| C06E2.N (3.0) | |
| TTGGGCGCGCCTAACACGTGCATTGGAGGCGGAG | (SEQ ID NO:88) |
| CCAACGGTATCATCGTTTCACTCCTCGAATTATTTG | (SEQ ID NO:89) |
| C17C3.N (2.3) | |
| TTGGGCGCGCCATTGGTATCACAAGGATCAAGC | (SEQ ID NO:90) |
| CCAACCGGCATTTTTGTTTTTGGCTGTGATTA | (SEQ ID NO:91) |
| C17C3.4 (1.4) | |
| TTGGGCGCGCCAATTTTGACGACGATCTCCTTC | (SEQ ID NO:92) |
| CCAACCGGTATCATATTTAACGATTCCTACACAAACC | (SEQ ID NO:93) |
| ZK84.N (2.1) | |
| TTGGGCGCGCCGTGTGGAGGTGGTGAATCC | (SEQ ID NO:94) |
| CGGGGTACCCTCATTTCAAAGAAATGTTGAATA | (SEQ ID NO:95) |
| M04D8.1 (3.0) | |
| TTGGGCGCGCCGGAGCCGAACAAGAAAAACCTAC | (SEQ ID NO:96) |
| CCAACCGGTTTCATGGTTCAACTCAAAAAGGAA | (SEQ ID NO:97) |
| M04D8.2 (2.2) | |
| TTGGGCGCGCCAGTTCGTCTCAGCATCATCTTGC | (SEQ ID NO:98) |
| CCAACCGGTTTCATGGTTCAACTCAAAAAGGAA | (SEQ ID NO:99) |
| M04D8.3 (1.6) | |
| TTGGGCGCGCCATGGGATTTTCAGACTCTCAG | (SEQ ID NO:100) |
| CCAACCGGTAACATTATCGAAATTCCAGAAATCCG | (SEQ ID NO:101) |

The following PCR conditions were used: 95° C. for 2 min; either 15 cycles (genomic DNA templates) or 10 cycles (cosmid DNA templates) of the following steps, (1) 95° C. for 15 sec, (2) 50° C. for 30 sec, and (3) 68° C. for a time equivalent to 1 min per kbp of expected product length, and additional cycles with 20 sec added per cycle at step (3). N2genomic DNA was used as template, except for ZK75.2, ZK75.3, ZK75.1, and ZK84.6, for which cosmid DNA was used. The PCR products were digested with either AscI-AgeI or AscI-KpnI, ligated into similarly-digested PPD117.01 GFP fusion vector, and transformed into E. coli. DNA from the resulting clones was prepared using a Qiagen kit, and the correct structure and reading frame of fusion between promoter region and GFP coding region was checked by DNA sequencing.

6.4.3. GFP Fusion Construct Injection

Each GFP fusion construct was injected into wild type worms using a standard protocol for C. elegans transformation (see Mello et al., 1991, "Efficient gene transfer in C. elegans : extrachromosomal maintenance and integration of transforming sequences", EMBO J. 10:3959–3970) at a concentration of 100 µg/ml each GFP fusion plasmid plus 100 µg/ml pRF4 rol-6(d) transformation marker. Stably transformed strains exhibiting a Roller phenotype were established and examined for fluorescence by inspection using an Axioplan microscope (Zeiss). For each GFP fusion construct, two transformant lines which exhibited the highest levels of fluorescence were chosen for further analysis.

Duplicate constructs were analyzed for all promoter/enhancer region-GFP fusions, and the patterns of GFP expression were found to be identical for all duplicates (see Table 2). Duplicate constructs were derived from independent PCR reactions for all genes except ZK75.1, ZK1251.N, and C06E2.N.

6.5. Structural Categories of Genes

Comparison of the predicted coding regions of C. elegans insulin-like genes reveals a remarkable and unexpected diversity of structures, which are nonetheless clear variations on the common theme that characterizes the insulin superfamily discussed in Section 2 above. Structural domains within each predicted C. elegans insulin-like protein are annotated in the sequences set forth in FIG. 4A through FIG. 34. In FIGS. 3A–3B, the sequences of predicted mature forms of the proteins are aligned to one another to highlight features that tend to be conserved compared with the insulin superfamily (discussed in detail in Section 2 above), as well as to emphasize features that distinguish different Classes of C. elegans insulin-like proteins.

We have divided the currently-characterized C. elegans insulin-like genes into four Classes based on the protein primary structural characteristics as set forth below.

6.5.1. Class I

One C. elegans insulin-like gene, F13B12.N has been assigned to Class I. Class I is characterized as having a cleavable C peptide separating the B and A chains. This C peptide possesses processing sites for prohormone convertases, similar to that of vertebrate insulin. Ends generated by proteolytic removal of the C peptide are indicated by the symbols "<<" and ">>" in FIGS. 3A–3B for the B and A peptides. Further, Class I is characterized as having an extra pair of Cys residues present which is not found in vertebrate insulins. One Cys residue is located in the B chain and the other Cys residue is located in the A chain. This unique extra pair of Cys residues presumably form an extra inter-chain disulfide bond.

6.5.2. Class II

Nine *C. elegans* insulin-like genes, ZK75.1, ZK75.2, ZK75.3, ZK84.6, ZK84.N2, ZK1251.2, ZK1251.N, C06E2.N and TO85G.N have been assigned to Class II. Class II is characterized by the absence of a C peptide. Further, Class II is characterized as having an extra pair of Cys residues. Still further, Class II is characterized as having a "Pro peptide," which is presumably removed by proteolytic processing from the mature hormone. This Pro peptide is located between the signal sequence and the beginning of the B domain (i.e., similar to the Pro peptide of locust LIRP insulin-like protein). The B and A regions or domains presumably are not cleaved into separate chains in this Class II and the following Classes III-IV.

TO8G5.N is unique in that there is a repositioning of one of the Cys residues in the B domain. In this case, the second Cys residue appears to be moved by four amino acid residues from the end of the presumptive central helix of the B domain towards the middle of the central helix. The repositioning places the Cys residue such that it would project from the same side of the presumptive B domain helix and remain available for disulfide bond formation with the normal partner Cys residue at the end of the second helix of the A domain. Although the spacing of Cys residues in the B domain is unique to insulin-like protein TO8G5.N, it is anticipated that this Cys residue repositioning can be accommodated with relatively small changes in the tertiary structure typical of the insulin superfamily, and no significant changes in secondary structure motifs.

6.5.3. Class III

Ten *C. elegans* insulin-like genes, C17C3.4, C17C3.N, C17C3.N2, F41G3.N, F41G3.N2, F56F3.6, Y52A1.N, T28B8.N, T10D4.N and T10D4.N2, have been assigned to Class III. Class III is characterized by the absence of a C peptide. Further, Class III is characterized as having the same number of Cys residues in the B and A domains as found in vertebrate insulin. Some members of this Class lack an intron positioned between the B and A domains within the genomic sequence. FIGS. 3A–3B denotes the lack of an intron in this position by the symbol "--" at the C-terminus of the B domain and N-terminus of the A domain for C17C3.N2, F41G3.N2, and F56F3.6, and the most N-terminal of the three insulin-like modules of T10D4.N, designated as T10D4.Na, as indicated in FIGS. 3A–3B.

6.5.4. Class IV

Eleven *C. elegans* insulin-like genes, M04D8.1, M04D8.2, M04D8.3, ZK84.N, ZC334.N, ZC334.N2, ZC334.N3, ZC334.N4, ZC334.N5, ZC334.N6 and ZC334.N7, have been assigned to Class IV. Class IV is characterized by the absence of a C peptide. Further, Class IV is characterized as having an extra pair of Cys residues, as in Classes I and II. Still further, Class IV is characterized by the absence of a Cys pair in the A domain; the missing Cys pair in most cases is replaced by hydrophobic residues.

6.6. Structural Comparison With Known Genes

With respect to the well-characterized structures of previously-known insulin superfamily proteins, each of the *C. elegans* insulin-like proteins identified herein has at least one novel and significant structural feature which is not typical of the previously-characterized insulin superfamily proteins. These features include: absence of a C peptide; presence of an extra inter-chain Cys pair; absence of a Cys pair in the A chain domain; altered spacing of Cys residues; and/or multiple B domain and A domain pairs in the same polypeptide. However, these primary structural differences can be accommodated within the overall secondary and tertiary structural framework that is common to the insulin superfamily, as described below.

6.6.1. Peptide Domains

Only one of the *C. elegans* insulin-like genes possesses a "connecting" or C peptide between the A and B chain domains (i.e., F13B12.N, Class I). Since the C-terminus of the B chain and the C-terminus of the A chain are relatively close in space within the tertiary structure of insulin, it is quite possible that a continuous main chain could connect presumptive B and A domains without grossly disturbing the overall insulin fold. There is an intriguing aspect of the gene organization of the *C. elegans* insulin-like genes that supports the notion of structural motifs corresponding to the B and A peptides of the insulin superfamily, despite the lack of a C peptide. All *C. elegans* insulin-like genes have introns, and nearly all genes encoding proteins that lack an identifiable C peptide (Classes II through IV) have an intron positioned between the B domain and A domain as indicated in FIGS. 3A–3B (the only exceptions are F56F3.6, C17C3.N2, F41G3.N2, and the most N-terminal insulin-like module of T10D4.N indicated as T10D4.Na). Indeed, even the Class I *C. elegans* insulin-like gene, which has a C peptide, also has an intron positioned at the boundary of the B and C peptides. In vertebrates, the most common exon-intron structure of insulin-like genes is that with an intron position either at the boundary or within the C peptide coding region.

One of the *C. elegans* insulin-like genes, T10D4.N, is especially remarkable in terms of domain organization as this gene encodes a single polypeptide which possesses three tandem pairs of B and A domains, or insulin-like "modules", in effect producing a trimeric insulin. Multiple insulin-like modules within the same polypeptide have not been observed previously in any organism. The sequences of the three insulin-like modules within the T10D4.N polypeptide are labeled in FIGS. 3A–3B as T10D4.Na, T10D4.Nb, and T10D4.Nc, extending in order from the N-terminus to the C-terminus of the polypeptide. The symbol "-" at the C-terminus of sequences for modules T10D4.Na and T10D4.Nb signifies that the polypeptide sequence continues with the first residue of the sequence in the line below. It is noteworthy that the tandem insulin-like modules in T10D4.N are connected by hydrophobic spacers at the end of the A domain of each module T10D4.Na and T10D4.Nb. Further, the C-terminal module T10D4.Nc contains a tail extending the end of the A domain of the same length and hydrophobic character as the connecting spacer regions. It is also intriguing that immediately adjacent to the T10D4.N gene within genomic DNA is another insulin-like gene, T10D4.N2, oriented in the opposite direction which consists of the typical single insulin module. T10D4.N2is very closely related in primary sequence to the individual modules that comprise T10D4.N (see sequence alignments in FIGS. 3A–3B) and also possesses the tail extending at the end of the A domain that is similar in size and character to the tail and connecting spacers in the trimeric T10D4.N.

6.6.2. CYS Residues

Most *C. elegans* insulin-like proteins possess an extra pair of Cys residues (Classes I, II and IV) and it is striking that there is a consistent spatial positioning of them (see the alignment of FIGS. 3A–3B). One extra Cys is found toward the C-terminal end of the B chain (i.e., B region or domain) and the other extra Cys is found toward the C-terminal end of the A chain (i.e., A region or domain). These two positions are expected to be very close in space within the known tertiary structure of insulin superfamily proteins. Thus, it is quite possible that the extra Cys residues in the *C. elegans* insulin-like proteins form a disulfide bond that further stabilizes the structure. This situation is reminiscent of that previously noted for extra Cys residues within the MIP family of insulin-like proteins from freshwater snail. However, in the case of the MIP proteins, the extra Cys residues are positioned at the N-terminal regions of the A and B chains (see FIG. 2).

Some *C. elegans* insulin-like proteins (i.e. Class IV) are missing a pair of Cys residues in the A domain that are invariably found in the previously-characterized insulin superfamily members and which form an intra-chain disulfide bond that stabilizes a bend in the A chain structure. It is notable that, in many of the *C. elegans* Class IV proteins, there appears to be a concerted replacement of these two Cys residues with either aromatic or aliphatic residues. Such substitutions are consistent with the normal placement of this disulfide linkage within the hydrophobic core between the A and B chains. It seems that in these *C. elegans* Class IV insulin-like proteins, a strong covalent linkage has been substituted with a weaker stacking or hydrophobic interaction between side chains in these positions. It is relevant that all *C. elegans* insulin-like proteins that are "missing" a pair of Cys residues within the A domain also have an "extra pair" of Cys residues at the ends of the B and A domains, as described above.

Several *C. elegans* insulin-like proteins are highly unusual by virtue of having an abnormal spacing between conserved Cys positions (T08G5.N, Y52A1.N, F56F3.6, T28B8.N, T10D4.N, T10D4.N2 and ZC334.N. see FIGS. 3A–3B). Nonetheless, as indicated in the sequence alignment of FIGS. 3A–3B, the changes in spacing can be viewed as relatively small alterations which are not expected to cause large-scale changes in structure that would deviate from that typical of the insulin superfamily. The "repositioning" of one Cys residue within the B domain of T08G5.N was discussed previously. For other insulin-like genes with altered spacing of Cys residues, the changes in spacing can be viewed as small insertions or deletions within structural transitions of the typical insulin fold. Thus, Y52A1.N can be viewed as having a deletion of three residues (symbolized by "---" in FIGS. 3A–3B) that shortens the loop connecting the two helices of the A domain. Conversely, ZC334.N and insulin-like modules T10D4.Nb and T10D4.Nc of T10D4.N can all be viewed as having an insertion of a dipeptide of either "Ser Gly", "Pro Glu", or "Ser Ala", respectively, within the loop connecting the two helices of the A domain. Also, T10D4.N2and modules T10D4.Na, T10D4.Nb, and T10D4.Nc of T10D4.N can each be viewed as having an insertion of a single residue, either "Ile", "Phe", "Val", or "Val", respectively, at the end of the second helix of the A domain. Finally, F56F3.6 and T28B8.N can be viewed as having an insertion of a tripeptide having the sequence "Pro Pro Gly" within the turn that immediately precedes central helix of the B domain. It is particularly intriguing that the presence of both insertions and deletions of this sort within the *C. elegans* insulin-like proteins points to an ability to accommodate more variation within the insulin protein structure than had been appreciated from sequences of previously described insulin superfamily proteins.

6.7. Generation and Genetic Analysis of Nematodes With Altered Insulin-like Genes

*C. elegans* insulin-like genes are important tools for creating genetically-engineered nematodes, as exemplified in this Section 6.7 and subsequent Sections 6.8 through 6.14. Genetically-engineered nematodes may harbor: (a) deletions or insertions in an insulin-like gene or genes; (b) interfering RNAs derived from such genes; (c) and/or transgenes for misexpression of wild-type or mutant forms of such genes. Such *C. elegans* strains with laboratory-generated alterations in insulin-like genes are useful for many purposes. Examples of such purposes include: (a) identification of insulin-like genes that participate in biochemical and/or genetic pathways that constitute possible pesticide targets, as judged by phenotypes such as non-viability, block of normal development, defective feeding, defective movement, or defective reproduction; (b) identification of insulin-like genes that participate in genetic and/or biochemical pathways that relate to therapeutic applications associated with the insulin superfamily hormones, such as metabolic control, growth regulation, differentiation, reproduction, and aging, through the generation of phenotypes associated with those functions in the altered *C. elegans* strains; and (c) as substrates for large-scale genetic modifier screens aimed at systematic identification of other components of these genetic and/or biochemical pathways that serve as novel drug targets, diagnostics, prognostics, therapeutic proteins, pesticide targets or protein pesticides.

Methods for creation and analysis of *C. elegans* strains having modified expression of insulin-like genes are described in the Sections below. Expression modification methods include any method known to one skilled in the art. Specific examples include but are not limited to EMS chemical mutagenesis, Tc1 transposon mutagenesis, double-stranded RNA interference, and transgene-mediated misexpression. In the creation of transgenic animals, it is preferred that heterologous (i.e., non-native) promoters be used to drive transgene expression.

6.8. EMS Chemical Deletion Mutagenesis

Ethyl methanesulfonate (EMS) is a commonly-used chemical mutagen for creating loss-of-function mutations in genes-of-interest in *C. elegans*. Approximately 13% of mutations induced by EMS are small deletions. With the methods described herein, there is approximately a 95% probability of identifying a deletion-of-interest by screening $4 \times 10^6$ EMS-mutagenized genomes. Briefly, this procedure involves creating a library of several million mutagenized *C. elegans* which are distributed in small pools in 96-well plates, each pool composed of approximately 400 haploid genomes. A portion of each pool is used to generate a corresponding library of genomic DNA derived from the mutagenized nematodes. The DNA library is screened with a PCR assay to identify pools that carry genomes with deletions-of-interest, and mutant worms carrying the desired deletions are recovered from the corresponding pools of the mutagenized animals. Although EMS is a preferred mutagen to generate deletions, other mutagens can be used that also provide a significant yield of deletions, such as X-rays, gamma-rays, diepoxybutane, formaldehyde and trimethylpsoralen with ultraviolet light.

Nematodes may be mutagenized with EMS using any procedure known to one skilled in the art, such as the procedure described by Sulston and Hodgkin (1988, Methods, pp. 587–606, in The nematode *Caenorhabditis elegans*, Wood, Ed., Cold Spring Harbor Laboratory Press, Cold Spring Harbor, N.Y.). Following exposure to the mutagen, nematodes are dispensed into petri dishes, incubated one to two days, and embryos isolated by hypochlorite treatment (Id.) Embryos are allowed to hatch and L1 larvae are collected following overnight incubation. The larvae are distributed in petri plates at an average density of 200 animals per plate and incubated for 5 to 7 days until just starved. A sample of nematodes is collected from each plate by washing with a solution of distilled water, and the nematodes washed from each plate are placed in one well of a 96-well plate. Worms are lysed by addition of an equal volume of lysis buffer (100 mM FCl, 20 mM Tris-HCl pH 8.3, 5 mM $MgCl_2$, 0.9% Nonidet P-40, 0.9% Tween-20, 0.02% gelatin, and 400 µg/ml proteinase K) followed by incubation at –80° C. for 15 minutes, 60° C. for 3 hours, and 95° C. for 15–30 minutes. The DNA-containing lysates are kept by storage of plates at –80° C. until analyzed further. Live nematodes from each plate are aliquoted into tubes within racks for storage at –80° C., such that the physical arrangement of tubes of live animals is the same as the arrangement of corresponding DNA lysates in the 96-well plates.

A pooling strategy is used to allow efficient PCR screening of the DNA lysates. The pools are made from each 96-well plate by mixing 10 µl of lysate from 8 wells comprising each column of wells in a plate. The pooled lysates for each column are used for screening with PCR. PCR primers are designed for each locus-of-interest to be about 1.5 to 12 kb apart, depending on the size of the locus, such that deletions encompassing the entire coding regions of insulin-like genes can be detected following a previously-described procedure (see Plasterk, 1995, Reverse genetics: from gene sequence to mutant worm, Methods in Cell Biology 48:59–80). For each region, two sets of primer pairs are chosen for carrying out a nested PCR strategy such that an outside set is used for the first round of PCR and an inside set is used for the second round of PCR. The second round of PCR is performed to achieve greater specificity in the reaction. Examples of primers which have been used is set forth in Section 6.8.7 below.

The first round PCR reactions are performed in duplicate for each pool with reactions carried out in a 96-well plate. Each reaction contains 18 µl of the following mixture and 2 µl of each pooled lysate:

reaction buffer provided by the manufacturer (e.g., Boehringer Mannheim Biochemicals)
2.5 mM $MgCl_2$
0.2 mM each dNTP
0.5 µM each gene-specific primer
1.7 units Expand Hi Fidelity enzyme mix (Boehringer Mannheim Biochemicals)
to 18 µl per reaction with $dH_2O$ The reactions are carried out using the same general temperature cycling parameters except that the extension time is varied depending on the normal distance between the primer pairs as follows:

4 kb wild-type product or shorter: 1 minute extension time
4–6 kb wild-type product: 2 minute extension time
6–12 kb wild-type product: 4 minute extension time The temperature cycling conditions used are 94° C. for 3 minutes, then 35 cycles of the following: 94° C. for 40 seconds, 55° C. for 1 minute, and 72° C. for the number of minutes of extension time described above.

The second round of PCR is performed essentially as above, except that 15 µl of mixture containing the following was aliquoted to each reaction:

reaction buffer provided by the manufacturer
1.5 mM $MgCl_2$
0.2 mM each dNTP
0.5 µM each gene-specific primer
1.7 units of Expand Hi fidelity enzyme mix to 15 µl per reaction with $dH_2O$ A small amount of first-round reaction products is transferred to the second-round reaction mixtures using a 96-pin replicator. The same temperature cycling sequence is used for the second round as described for the first round.

Products of the second round of PCR may be analyzed by electrophoresis in 1% agarose gels. If a potential deletion product is observed in at least one of the two reactions, two rounds of PCR are performed as described above on lysates from each individual well derived from the column corresponding to the positive pool. This results in the identification of a positive "address," i.e., a specific well within an individual plate, containing a deletion mutant. The positive address is re-tested in quadruplicate using two rounds of PCR as described above, and the-product is gel purified and sequenced directly to confirm the presence of the desired deletion.

For example, two deletions have been identified and characterized by DNA sequencing, using the procedures described above, that remove the *C. elegans* insulin-like gene ZK75.1.

Once a positive address has been identified and confirmed by sequence analysis, approximately 300 individual worms from the relevant plate are cloned onto separate, fresh plates. When F1 animals are present on the plate, the parent nematodes are placed into buffer and lysed as described above. The same primer pairs and cycling conditions used to identify the deletion are used to perform PCR on these animals. Once a single animal carrying the deletion has been identified, its progeny are cloned and examined using the same conditions described above, until a homozygous population of deletion animals is obtained.

Detailed protocols which may be used for EMS mutagenesis of the genes identified herein are set forth below in Sections 6.8.1 through 6.8.12.

6.8.1. Mutagenizing Nematodes

Plates crowded with L4 hermaphrodite worms are washed off with M9 buffer into 15 ml tubes and centrifuged. The worms are washed 2×with M9 buffer and resuspended in 9 ml of M9 buffer and transferred to a 50 ml tube.

In a chemical fume hood, 1 ml of M9 buffer and 62 µl of EMS are added to a microfuge tube. Close tube and shake to mix M9 and EMS. The EMS/M9 mixture is then added to the 9 ml of worms. This is a concentration of 50 mM EMS in 10 ml of worms in suspension. Rotate suspension on a rotation device (e.g., Nutator) for 4 hours. After the incubation, wash worms with M9 buffer 3×.

Plate animals to plates with thick lawns of bacteria and place them at 20° C. for about 24 hours until they become full of eggs as adults. Hypochlorite treat worms to kill adults and isolate embryos (see below).

6.8.2. Isolating Worm Embryos

The following protocol may be used to isolate mutagenized worm embryos following the above EMS chemical treatment:
1. wash worms off plates into a 15 ml tube in a total of 15 ml sterile water
2. spin down worms 30 sec at about 15K rpm and wash 2× in water 3. rinse worms briefly in 4 ml hypochlorite solution (6.6 ml water, 400 μl 5 M KOH, 1 ml 10% Na hypochlorite) and spin down
5. add remaining 4 ml hypochlorite solution and transfer a drop to a watch glass to observe the reaction under a dissecting microscope
6. as soon as adults start to burst at vulva and release embryos, adults are broken open by passage through a 21 gauge needle 2–3×
7. quickly fill tube with M9 buffer and spin down eggs
8. rinse 3× with M9 buffer
9. filter embryos through 52 μm mesh in 30 ml M9 into a 50 ml tube (if volume of embryos <0.5 ml, embryos are resuspend in 8 ml M9 buffer in a 15 ml tube)
10. rotate embryos on nutator at 15° C. overnight
11. spin down L1 larvae and plate on 3–8 large NGM plates seeded with concentrated *E. coli*

A typical library may contain 6668 lysates representing 2.18 million haploid genomes.

6.8.3. Lists of Primers for EMS Analysis (EMS Table)

6.8.4. Results of an Example EMS Screen

The following results were obtained in an example EMS screen.

| | |
|---|---|
| C06E2.N region: | 2.3 million haploid genomes screened |
| ZK75.2/.3 region: | 1.2 million haploid genomes screened |
| ZK1251.2/.N region: | 1.2 million haploid genomes screened |

-continued

| | |
|---|---|
| ZK75.1 region: | 800,000 haploid genomes screened |
| Two confirmed deletions have been obtained in the ZK75.1 region, as follows: | |
| (1) ZK75.1Δ1 deletes nucleotides 15,182–17,369 of cosmid ZK75.1 | |
| (2) ZK75.1Δ2 deletes nucleotides 15,430–17,879 of cosmid ZK75.1 | |
| ZK75.2/.3/.1/84.N2/84.6 region: | 875,000 haploid genomes screened |
| ZK75.1/84.N2/84.6 region: | 2.1 million haploid genomes screened |
| M04D8.1/.2/.3 region: | 460,000 haploid genomes screened |
| F13B12.N region: | 1.9 million haploid genomes screened |

6.9. Tc1 Transposon Insertion Mutagenesis

The transposable element Tc1 may also be used as a mutagen in *C. elegans* since insertion of the transposable element into a gene-of-interest can result in the inactivation of gene function. Starting with a strain that contains a high copy number of the Tc1 transposable element in a mutator background (i.e., a strain in which the transposable element is highly mobile), a Tc1 library containing approximately 3,000 individual cultures is created as previously described (Id.). The library is screened for Tc1 insertions in the region of interest using the polymerase chain reaction with one set of primers specific for Tc1 sequence and one set of gene-specific primers. Because Tc1 exhibits a preference for insertion within introns, it is sometimes necessary to carry out a secondary screen of populations of insertion animals for imprecise excision of the transposable element, which can result in deletion of part or all of the gene of interest

| Genes screened-(product size) | primer name | | primer sequence | |
|---|---|---|---|---|
| C06E2.N (X)-(2.1 kb) | C06E2-1 | (round 1 forward) | CAAACAGTTGTAGCTCAAAGGC | (SEQ ID NO:104) |
| | C06E2-4 | (round 1 reverse) | GCATACGGTACCTATTCGTTTC | (SEQ ID NO:105) |
| | C06E2-2 | (round 2 forward) | AGCTCAAAGGCCAAATGTGTG | (SEQ ID NO:106) |
| | C06E2-3 | (round 2 reverse) | AACAAACCCTACAGTTACTGGG | (SEQ ID NO:107) |
| ZK75.2/75.3(II)-(3.6 kb) | ZK75-31 | (round 1 forward) | GCTATCCACCTGTCCAACCTAC | (SEQ ID NO:108) |
| | ZK75-35 | (round 1 reverse) | GGAGGCTCTTTACTCGCCTTAC | (SEQ ID NO:109) |
| | ZK7S-32 | (round 2 forward) | TACAGGCTGTCCTTCTGTTACG | (SEQ TD NO:110) |
| | ZK75-34 | (round 2 reverse) | TCCACTATTCCGGTAATACCTC | (SEQ ID NO:111) |
| ZK1251.N/ZK1251.2 (IV)-(3.5 kb) | ZK1251-W1 | (round 1 forward) | GTAAGAAATCGAGAGTCACGCC | (SEQ ID NO:112) |
| | ZK1251-W4 | (round 1 reverse) | GTCTTCACTATCAAACGGGAGG | (SEQ ID NO:113) |
| | ZK1251-W2 | (round 2 forward) | CTGCCTCAAGGAGGAGTTACAC | (SEQ ID NO:114) |
| | ZK12S1-W3 | (round 2 reverse) | ATTTATCCCCACGTGAGAGAGG | (SEQ ID NO:115) |
| ZK75.2/.3/.1/84.N 2/84.6 (II)-(12.7 kb) | ZK75-31 | (round 1 forward) | see above | |
| | ZK75-W4 | (round 1 reverse) | CACTGGGATGACAGATTTGATG | (SEQ ID NO:116) |
| | ZK75-32 | (round 2 forward) | see above | |
| | ZK84-3B | (round 2 reverse) | TGATGAGACACGGGTGAAACG | (SEQ ID NO:117) |
| ZK75.1/84.N2/84.6 (II)-(4.7 kb) | ZK75-1F | (round 1 forward) | GAACGGATAAAAAGGCGGAGC | (SEQ.ID NO:118) |
| | ZK75-W4 | (round 1 reverse) | see above | |
| | ZK75-2A | (round 2 forward) | TTGATGTGACCTCCAGATGAAC | (SEQ ID NO:119) |
| | ZK84-3B | (round 2 reverse) | see above | |
| M04D8.1/.2/.3 (III)-(5 kb) | M04D8-1 | (round 1 forward) | GCAGCACACTCTTGTTTTCAGC | (SEQ ID NO:120) |
| | M04D8-4 | (round 1 reverse) | CAAATCACTCACTITCCTGCG | (SEQ ID NO:121) |
| | M04D8-2 | (round 2 forward) | TTCAAGTGTCCTTGTATCCGTG | (SEQ ID NO:122) |
| | M04D8-3 | (round 2 reverse) | GCATAGAATGGCGGAAGATCAC | (SEQ ID NO:123) |
| F13B12.N (IV)-(2.1 kb) | F13B12-1 | (round 1 forward) | CTTCCAAATTTGTCCTGACTGC | (SEQ ID NO:124) |
| | F13B12-4 | (round 1 reverse) | AATTGCAGGAGTCGAAGTTTCC | (SEQ ID NO:125) |
| | F13B12-2 | (round 2 forward) | AACGAGCAGACAGGAAATCATC | (SEQ ID NO:126) |
| | F13B12-3 | (round 2 reverse) | TGTGACAGCATGTTTGAACGTC | (SEQ ID NO:127) |
| ZK75.1 (II)-(3.7 kb) | ZK75-11 | (round 1 forward) | AGTTGTCAAGAAGTGCGTCAAG | (SEQ ID NO:128) |
| | ZK75-1B | (round 1 reverse) | GAGATGGCTTGTTGGACGAC | (SEQ ID NO:129) |
| | ZK75-12 | (round 2 forward) | GACAAAATCACGTCACGAAGT | (SEQ ID NO:130) |
| | ZK75-13 | (round 2 reverse) | TTACTTTTCTGGGCAGCAAGC | (SEQ ID NO:131) |

(generally, 1–2 kb of genomic sequence is deleted). The screen for Tc1 deletions is performed and deletion animals are recovered in the same manner as for the EMS screen described above.

Using such procedures, C. elegans strains have been isolated that contain Tc1 transposon insertions within or neighboring the following insulin-like genes: ZK1251.1/ZK1251.N, C06E2.N, and F13B12.N. Detailed methods are set forth in Sections 6.9.1 to 6.9.8 below.

6.9.1. Tc1 Library Construction

A Tc1 transposon insertion library was constructed according to published protocols by Zwaal et al., 1993, Proc. Natl. Acad. Sci. U.S.A. 90:7431–7435; and Plasterk, 1995, Reverse Genetics: From Gene Sequence to Mutant Worm, in Caenorhabditis elegans: Modern Biological Analysis of an Organism (Epstein and Shakes, Eds.) pp. 59–80.

| | |
|---|---|
| Size of typical library: | 3 sets of 960 cultures |
| Analysis of library: | By sets of 960 cultures |
| Dimensions of set: | 10 racks of 8 × 12 as follows: |
| | Row (8): A–H |
| | Column (12): 1–12 |
| | Plate (10): p1–p10 |

6.9.2. Culturing Worms

POUR 100-mm NGM (2×peptone) plates—2880 plates total
SEED with E. coli in sterile hood CULTURE 5–10 non-synchronized mut-2 (MT3126) animals per plate—250 plates/day for 12 days:
PREPARE suspension of MT3126 in M9 buffer in dish
TRANSFER 5 $\mu$l of suspension onto plates
COUNT# worms on first few plates
INCUBATE @20° C. for 11–12 days
ADD 4 ml M9 buffer to plate
SHAKE plates O/N @18–20° C.

6.9.3. Storage of Worms

PREPARE Costar racks (3 racks required per 96 cultures)—90 racks total:
MARK racks clearly on front, side, and top
MARK individual tubes in each rack ALIQUOT each culture into 3 racks (8×12)—240 cultures/day for 12 days:
ADD few drops of fresh M9 buffer if <1 ml suspension on plate
TRANSFER 400 $\mu$l suspension to identical positions on 2 racks (for freezing) and remaining suspension to identical position on 3RD RACK (for DNA analysis)
FREEZE 2 racks for survival:
  ADD 400 $\mu$l freezing solution to each tube:
    30% glycerol (v/v)
    25 mM $KPO_4$, pH 6.6
    50 mM NaCl
    2.5 $\mu$g/ml cholesterol
  CLOSE tubes with sterile caps (8 caps on a strip, Costar)
  COVER rack with lid
  MIX M9 buffer and freezing solution by inverting rack several times
  WRAP racks in cotton wool and 2 towels for slow freezing O/N @80° C.
UNWRAP racks and store in separate freezers @80° C.

6.9.4. Lysate Preparation (3RD Rack)

REMOVE M9 buffer supernatant from sedimented worm suspension WASH 1×with cold $H_2$—960 cultures/day for 3 days
CENTRIFUGE for 3 minutes to pellet worms and ice for 30 sec REMOVE supernatant
(FREEZE worm pellets or LYSE directly) ADD 200 $\mu$l Cell Lysis Solution (Gentra Kit) and 2 $\mu$l Proteinase K (10 mg/ml) to each pellet
CLOSE tubes with sterile caps (8 caps on a strip, Costar) COVER rack with lid
INCUBATE @55° C. for 3 hrs—O/N (invert. occasionally) STORE @=20 or −80° C.

6.9.5. DNA Preparation

POOL lysates in 3-D matrix: Pool Rows (individual A–H by plate)
240 pools total
8 pools/plate
12 lysates/pool
pool=240 $\mu$l
TRANSFER 20 $\mu$l of each lysate/row to a pool—80 pools/day for 3 days
VORTEX

| 1-D Address: Row | 2-D Address: Plate |
|---|---|
| Pool Rows (cumulative A–H) | 240 pools total |
| 24 pools total | 8 pools/plate |
| 0 mixed lysates/pool | 12 lysates/pool |
| 120 lysates (total)/pool | pool = 60 $\mu$l | pool = 1.8 ml (180 $\mu$l of each mixed lysate)

TRANSFER 180 $\mu$l of each mixed lysate/row to a pool
PURIFY DNA by Gentra kit—24 DNA preps
RESUSPEND in TE: 10 mM Tris-HCl 1 mM EDTA, pH 7.6
STORE @ −20° C.
88 DNA preps/day for 3 days
(This stock may be used for many searches: 10×–50× dilutions used.)

6.9.6. Library Screening

A library is screened in individual Tiers, each library having three Tiers. Each Tier is composed of 1,000 lysates or 200,000 haploid genomes. Lysates are pooled according to above references. First dimension screen involves PCR on 8 samples of pooled DNA from 10 96-well plates. Second dimension screen determines on which of the 10 96-well plates the mutant resides (involves screening of 10 DNA pools). Third dimension. screen determines the "address" of a particular mutant (i.e., in which column and row a particular mutant resides—via screening of 12 individual lysates from a single row). First dimension reactions are done in quadruplicate; second and third are done in triplicate.

Two rounds of PCR are performed; PCR is performed with a pair of gene-specific primers and a pair of Tc1-specific primers. Two different pairs of Tc1 primers are used: one pair points outward from the left of the transposon, and the other pair points outward from the right (these primer pairs are described in the references cited above).

The first and second round PCR for each dimension is performed in 15 µl using the following in each reaction:

1×PCR buffer provided by the manufacturer (Perkin Elmer)
1.5 mM MgCl$_2$
0.2 mM dNTPs
0.5 µM of the Tc1 and the gene-specific primer
0.5 units of Perkin Elmer Taq Polymerase
H$_2$O to 13 µl for the first round reactions, and to 15 µl for the second round First and Second dimension: 2 µl of 1:20 DNA is added; 1:10 DNA is added to the third dimension reactions. A small amount of first round reaction is transferred to the second round using a pin replicator. PCR cycling conditions are: 94 for 3 minutes; then 94 for 40 seconds, 58 for 1 minute, 72 for 2 minutes for 35 cycles; then 72 for 2 minutes.

6.9.7. Lists of Primers for Tc1 Analysis (Tc1 Table)

| Genes screened | Oligo name | | oligo sequence | |
|---|---|---|---|---|
| All | *Tc1 L1 | (round 1 left) | CGTGGGTATTCCTTGTTCGAAGCCAGCTAC | (SEQ ID NO:132) |
| | *Tc1 L2 | (round 2 left) | TCAAGTCAAATGGATGCTTGAGA | (SEQ ID NO:133) |
| | *Tc1 R1 | (round 1 right) | TCACAAGCTGATCGACTCGATGCCACGTCG | (SEQ ID NO:134) |
| | *Tc1 R2 | (round 2 right) | GATTTTGTGAACACTGTGGTGAAGT | (SEQ ID NO:135) |
| ZK75.2/.3/.1/84.N2/84.6 | ZK75-31 | (round 1) | SEE EMS TABLE | |
| | ZK75-32 | (round 2) | SEE EMS TABLE | |
| | ZK7S-35 | (round 1) | SEE EMS TABLE | |
| | ZK75-34 | (round 2) | SEE EMS TABLE | |
| | ZK75-1F | (round 1) | SEE EMS TABLE | |
| | ZK75-2A | (round 2) | SEE EMS TABLE | |
| | ZK75-W4 | (round 1) | SEE EMS TABLE | |
| | ZK84-3B | (round 2) | SEE EMS TABLE | |
| | ZK75-M4 | (round 1) | TTATTACATCCGTCACTGCGTC | (SEQ ID NO:136) |
| | ZK75-M3 | (round 2) | GCGTCCTTATTCAGAATTCCAG | (SEQ ID NO:137) |
| ZK1251.N/ZK1251.2 (IV) | ZK1251-W4 | (round 1) | SEE EMS TABLE | |
| | ZK1251-W3 | (round 2) | SEE EMS TABLE | |
| | ZK12S1-24 | (round 1) | CTTGTGACTTCAAGCCCACTTC | (SEQ ID NO:138) |
| | ZK1251-23 | (round 2) | GGTTATGAACCGATTAGGCTCC | (SEQ ID NO:139) |
| | ZK1251-N1 | (round 1) | GTAGCCTTCCGGGGTTAAAATC | (SEQ ID NO:140) |
| | ZK1251-N2 | (round 2) | GATCTCGCGCTATGTTTTGAG | (SEQ ID NO:141) |
| C0632.N (X) | C06E2-1A | (round 1) | GACAGCTGAAGCTGACCAAAC | (SEQ ID NO:142) |
| | C06E2-2A | (round 2) | CAGGAGTTAAACGTGGTCACTG | (SEQ ID NO:143) |
| | C06E2-4 | (round 1) | SEE EMS TABLE | |
| F13B12.N (IV) | F13B12-1 | (round 1) | SEE EMS TABLE | |
| | F13B12-2 | (round 2) | SEE EMS TABLE | |
| | F13B12-4 | (round 1) | SEE EMS TABLE | |
| | F13B12-3 | (round 2) | SEE EMS TABLE | |
| M04D8.1/.2/.3 (III) | M04D8-1 | (round 1) | SEE EMS TABLE | |
| | M04D8-4 | (round 1) | SEE EMS TABLE | |
| | M04D8-2 | (round 2) | SEE EMS TABLE | |
| | M04D8-3 | (round 2) | SEE EMS TABLE | |

6.9.8. Results of Tc1 Screen

Five confirmed Tc1 insertions have been found in or near the following C. elegans insulin-like genes: one insertion near ZK1251.2/.N; two insertions near C06E2.N; and two insertions in F13B12.N.

6.10. Double-stranded RNA Interference Analysis

The function of the C. elegans insulin-like genes identified herein may be characterized and/or determined using a method based on the interfering properties of double-stranded RNAs derived from the coding regions of the identified genes (see Fire et al., 1998, Potent and specific genetic interference by double-stranded RNA in Caenorhabditis elegans, Nature 391:806–811). In this method, sense and antisense RNAs derived from a substantial portion of a C. elegans insulin-like gene are synthesized in vitro from phagemid DNA templates containing cDNA clones of insulin-like genes which are inserted between opposing promoters for T3 and T7 phage RNA polymerases, or from PCR products amplified from coding regions of insulin-like genes, where the primers used for the PCR reactions are modified by the addition of phage T3 and T7 promoters. The resulting sense and antisense RNAs are annealed in an injection buffer and the double-stranded RNA injected into C. elegans hermaphrodites.

Progeny of the injected hermaphrodites are inspected for phenotypes-of-interest.

Other methods can also been employed for generating mutant phenotypes in nematodes using single-stranded antisense DNA or RNA species, as described in Section 5.8 above. However, single-stranded methods may be less effective in nematodes than that of double-stranded RNA interference (see Guo and Kemphues, 1995, par-1, a gene required for establishing polarity in C. elegans embryos, encodes a putative Ser/Thr kinase that is asymmetrically distributed, Cell 81:611–620; see also Fire, 1991, Production of antisense RNA leads to effective and specific inhibition of gene expression in C. elegans muscle, Development 113:503–514).

6.11. Mis-expression Analysis

Mis-expression (i.e., ectopic expression, abnormal expression) of wild-type and/or mutant C. elegans insulin-like genes so as to create transgenic animals is another useful method for the analysis of gene function in nematodes (Mello and Fire, 1995, DNA transformation, Methods in Cell Biology 48:451–482). Such transgenic animals may be created to contain gene fusions of the coding regions of insulin-like genes joined (i.e., operably linked) to a specific promoter whose regulation has been well characterized.

Such a specific promoter may be used as a heterologous promoter (i.e., a promoter which is not naturally linked to the gene). Examples of promoters that can be used to drive such mis-expression of insulin-like genes include but are not limited to: the heat shock gene promoters hsp 16-2 and hsp 16-41, useful for temperature-induced expression; the myo-2 gene promoter, useful for pharyngeal muscle-specific expression; the hlh-1 gene promoter, useful for body-muscle-specific expression; and the mec-3 gene promoter, useful for touch-neuron-specific gene expression. Gene fusions for directing the mis-expression of insulin-like genes are incorporated into a transformation vector which is injected into nematodes along with a plasmid containing a dominant selectable marker, such as rol-6. Transgenic animals are identified as those exhibiting a roller phenotype, and the transgenic animals are inspected for additional phenotypes of interest created by mis-expression of the insulin-like gene.

6.12. Analysis of Mutant Phenotypes

After isolation of nematodes carrying mutated or mis-expressed insulin-like genes, or inhibitory RNAs, animals are carefully examined for phenotypes-of-interest. For the situations involving deletions or Tc1 insertions in insulin-like genes, nematodes are generated that are homozygous and heterozygous for the mutant insulin-like genes.

Examples of specific phenotypes that may be investigated include but are not limited to: lethality, sterility, reduction in brood size, egg-laying defects, dauer constitutive, dauer defective, increased life span, decreased life span, defective locomotion, defective chemotaxis, defective thermotaxis, abnormal body shape, abnormal body size, and alterations in the morphogenesis of specific organs, such as the vulva, nervous system, gut, or musculature (see Hodgkin, 1997, Appendix I: Genetics, pp. 882–1047, in *C. elegans* II, Riddle et al., Eds., Cold Spring Harbor Laboratory Press, Cold Spring Harbor, N.Y.).

6.13. Analysis of Genetic Interactions and Multiple Mutants

Yet another approach that may be used to probe the biological function of the insulin-like genes identified herein is by using tests for genetic interactions with other genes that may participate in the same, related, interacting, or modifying genetic or biochemical pathways. In particular, since it is evident that there are closely-linked clusters of insulin-like genes in the *C. elegans* genome, this raises the possibility of functional redundancy of one or more genes. Consequently, it is of interest to investigate the phenotypes of nematodes containing mutations (such as deletions or Tc1 insertions as described above) that knock-out the function of more than one insulin-like gene. Such strains carrying mutations in multiple genes can be generated by cross breeding animals carrying the individual mutations, followed by selection of progeny that carry the desired multiple mutations. Alternatively, multiple insulin-like genes can be inactivated by the simultaneous injection of double-stranded RNAs derived from each gene using the method of double-stranded RNA interference described above.

One specific question-of-interest is genetic analysis of interactions of insulin-like genes with other well-characterized *C. elegans* genes and pathways. Thus, double mutant nematodes may be constructed that carry mutations in an insulin-like gene and another gene-of-interest. It is of particular interest to test the interaction of the insulin-like genes with other genes involved in the dauer formation and life span pathway, especially those that exhibit homology to insulin signaling components in vertebrates. For example, nematodes carrying mutations in insulin-like genes and either a loss-of-function mutation of daf-16, a hypomorphic allele of daf-2, a hypomorphic allele of age-1, would be of use in investigating the involvement of different insulin-like genes in the dauer formation and life span pathways. Also, transgenic animals mis-expressing insulin-like genes which further carry mutations in daf-2 are of interest, e.g., for examining genetic interactions between the insulin-like genes and the dauer formation and life span pathways. Other genetic interactions may be tested based on the phenotypes observed for alterations of the insulin-like genes alone. For example, if alteration of insulin-like genes produces an abnormal body size, mutations in these insulin-like genes could be tested for interactions with other genes that also affect body size, such as daf-4, sma-2 and sma-3.

6.14. Genetic Modifier Screens

The initial characterization of phenotypes created by mutations in single or multiple insulin-like genes is expected to lead to the identification of nematode strains that exhibit phenotypes appropriate for large-scale genetic modifier screens aimed at discovering other components of the same pathway. For example, it is of particular interest to identify those insulin-like genes that encode ligands of the daf-2 receptor. As discussed in Section 2 above, the daf-2 receptor is involved in controlling dauer formation and aging. Potential daf-2 ligands (agonists) might be revealed by the genetic interaction analysis described above as those insulin-like genes which, when mutated alone or in combination, exhibit the following properties: (a) a dauer constitutive phenotype similar to that observed in daf-2 mutant animals; and (b) suppression of the dauer constitutive phenotype when insulin-like gene mutations are tested in combination with mutations in the daf-16 gene (an antagonist of the pathway). There are, however, many other phenotypes that could be suitable starting points for large-scale genetic modifier screens, including a defective egg-laying phenotype, an abnormal lipid accumulation phenotype (e.g., as revealed by staining with lipid-specific dyes), and decreased or increased life span phenotypes.

The procedures involved in a typical genetic modifier screen are described below (see also Huang and Sternberg, 1995, Genetic discussion of developmental pathways, Methods in Cell Biology 48:97–122). In general, hermaphrodites carrying mutations in insulin-like genes are exposed to a mutagen, such as EMS or trimethylpsoralen with ultraviolet radiation. The descendants of such animals are then screened for the rare individuals that display suppressed or enhanced versions of the original phenotype, and any new mutations detected are presumed to alter other genes that participate in the same phenotype-generating pathway. In a pilot-scale genetic screen, 10,000 or fewer mutagenized nematodes would be inspected; in a moderate-scale genetic screen, about 30,000 to 100,000 mutagenized animals would be inspected; and in a large-scale genetic screen, more than 100,000 mutagenized animals would be inspected.

Next, nematodes identified with suppressor or enhancer mutations are isolated, and populations of descendants of these animals are expanded. The newly-identified "modifier" genes that are altered by these suppressor or enhancer mutations are mapped using a combination of genetic and molecular methods. Such newly-identified modifier mutations may also be isolated away from the mutations in the insulin-like genes by genetic crosses; the intrinsic phenotypes caused by the modifier mutations themselves may thus be assessed in isolation.

Also, such newly-identified modifier mutations may be tested for genetic interactions with other genes-of-interest using methods described above. In particular, modifier genes may be placed into so-called complementation groups, using genetic crosses, for subsequent examination of the phenotypes of progeny that contain two or more modifier mutations. Two modifier mutations are said to fall within the same complementation group if nematodes carrying both mutations exhibit essentially the same phenotype as nematodes carrying each mutation alone. Generally, individual complementation groups defined in this way correspond to individual genes. The precise location and sequence of the modifier gene in the genomic DNA is confirmed by: (a) identifying sequence changes specific to. the modifier mutations within the gene in question; and (b) in most cases, demonstrating reversion of the phenotype caused by the modifier mutation upon injection of a limited DNA fragment containing the wild-type form of the modifier gene.

An alternative mutagenesis-and-screening strategy that is especially useful for the rapid identification of modifier genes has also been described (see Anderson, 1995, Mutagenesis, Methods in Cell Biology 4:31–58) which is based on the use of transposable elements as mutagens. Because the mutated modifier gene becomes tagged with sequences derived from the transposable element, such as Tc1 as described above, this strategy allows for easy identification of the modifier gene through PCR amplification of sequences adjacent to the insertion site of the transposon. Mutagenesis may be carried out by introduction of a mutator locus, termed mut-2, which promotes mobility of transposons. In this case, the mutator locus is introduced into strains carrying mutations in insulin-like genes, and the progeny examined for suppression or enhancement of the original phenotype, as described above.

Once nematode modifier genes that participate in the same pathway as insulin-like genes have been identified using genetic screens, homologous genes in other species-of-interest can be isolated using procedures based on cross-hybridization with *C. elegans* modifier gene DNA probes, PCR-based strategies with primer sequences derived from those of *C. elegans* modifier genes, and/or computer searches of sequence databases. For therapeutic applications related to the function of insulin superfamily hormones, human and rodent homologs of the nematode modifier genes are of particular interest. For pesticide applications, homologs of nematode modifier genes in agriculturally-important pest species, beneficial insects, and other invertebrate model organisms are of particular interest and include the following: *D. melanogaster*, Anopheles, *Heliothis virescens, Plodia interpunctella, Spodoptera frugiperda, Pectinophora gosypiella, Plutella xylostella, Tribolium castaneum*, Diabrotica spp., *Leptinotarsa decemlineata, Anthonomus grandis, Bemisia tabaci, Myzus persicae, Blattella germanica, Apis mellifera, Ctenocephalites felis, Amblyoma americanum*, Meloidogyne spp., *Heterodera glycinii*, etc.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims.

Various references are cited herein above, the disclosures of which are hereby incorporated by reference in their entireties.

SEQUENCE LISTING

<160> NUMBER OF SEQ ID NOS: 298

<210> SEQ ID NO 1
<211> LENGTH: 109
<212> TYPE: PRT
<213> ORGANISM: Caenorhabditis elegans

<400> SEQUENCE: 1

Met Tyr Trp Phe Arg Gln Val Tyr Arg Pro Ser Phe Phe Gly Phe
1               5                   10                  15

Leu Ala Ile Leu Leu Leu Ser Ser Pro Thr Pro Ser Asp Ala Ser Ile
                20                  25                  30

Arg Leu Cys Gly Ser Arg Leu Thr Thr Thr Leu Leu Ala Val Cys Arg
            35                  40                  45

Asn Gln Leu Cys Thr Gly Leu Thr Ala Phe Lys Arg Ser Ala Asp Gln
        50                  55                  60

Ser Tyr Ala Pro Thr Thr Arg Asp Leu Phe His Ile His His Gln Gln
65                  70                  75                  80

Lys Arg Gly Gly Ile Ala Thr Glu Cys Cys Glu Lys Arg Cys Ser Phe
                85                  90                  95

Ala Tyr Leu Lys Thr Phe Cys Cys Asn Gln Asp Asp Asn
            100                 105

<210> SEQ ID NO 2

```
<211> LENGTH: 106
<212> TYPE: PRT
<213> ORGANISM: Caenorhabditis elegans

<400> SEQUENCE: 2
```

| | | | | | | | | | | | | | | | |
|---|---|---|---|---|---|---|---|---|---|---|---|---|---|---|---|
| Met | Phe | Ser | Phe | Phe | Thr | Tyr | Phe | Leu | Leu | Ser | Ala | Leu | Leu | Leu | Ser |
| 1 | | | | 5 | | | | | 10 | | | | | 15 | |
| Ala | Ser | Cys | Arg | Gln | Pro | Ser | Met | Asp | Thr | Ser | Lys | Ala | Asp | Arg | Ile |
| | | | 20 | | | | | 25 | | | | | 30 | | |
| Leu | Arg | Glu | Ile | Glu | Met | Glu | Thr | Glu | Leu | Glu | Asn | Gln | Leu | Ser | Arg |
| | | | 35 | | | | | 40 | | | | | 45 | | |
| Ala | Arg | Arg | Val | Pro | Ala | Gly | Glu | Val | Arg | Ala | Cys | Gly | Arg | Arg | Leu |
| | | 50 | | | | | 55 | | | | | 60 | | | |
| Leu | Leu | Phe | Val | Trp | Ser | Thr | Cys | Gly | Glu | Pro | Cys | Thr | Pro | Gln | Glu |
| 65 | | | | | 70 | | | | | 75 | | | | | 80 |
| Asp | Met | Asp | Ile | Ala | Thr | Val | Cys | Cys | Thr | Thr | Gln | Cys | Thr | Pro | Ser |
| | | | | 85 | | | | | 90 | | | | | 95 | |
| Tyr | Ile | Lys | Gln | Ala | Cys | Cys | Pro | Glu | Lys | | | | | | |
| | | | | 100 | | | | | 105 | | | | | | |

```
<210> SEQ ID NO 3
<211> LENGTH: 106
<212> TYPE: PRT
<213> ORGANISM: Caenorhabditis elegans

<400> SEQUENCE: 3
```

| | | | | | | | | | | | | | | | |
|---|---|---|---|---|---|---|---|---|---|---|---|---|---|---|---|
| Met | Asn | Ala | Ile | Ile | Phe | Cys | Leu | Leu | Phe | Thr | Thr | Val | Thr | Ala | Thr |
| 1 | | | | 5 | | | | | 10 | | | | | 15 | |
| Tyr | Glu | Val | Phe | Gly | Lys | Gly | Ile | Glu | His | Arg | Asn | Glu | His | Leu | Ile |
| | | | 20 | | | | | 25 | | | | | 30 | | |
| Ile | Asn | Gln | Leu | Asp | Ile | Ile | Pro | Val | Glu | Ser | Thr | Pro | Thr | Pro | Asn |
| | | | 35 | | | | | 40 | | | | | 45 | | |
| Arg | Ala | Ser | Arg | Val | Gln | Lys | Arg | Leu | Cys | Gly | Arg | Arg | Leu | Ile | Leu |
| | | 50 | | | | | 55 | | | | | 60 | | | |
| Phe | Met | Leu | Ala | Thr | Cys | Gly | Glu | Cys | Asp | Thr | Asp | Ser | Ser | Glu | Asp |
| 65 | | | | | 70 | | | | | 75 | | | | | 80 |
| Leu | Ser | His | Ile | Cys | Cys | Ile | Lys | Gln | Cys | Asp | Val | Gln | Asp | Ile | Ile |
| | | | | 85 | | | | | 90 | | | | | 95 | |
| Arg | Val | Cys | Cys | Pro | Asn | Ser | Phe | Arg | Lys | | | | | | |
| | | | | 100 | | | | | 105 | | | | | | |

```
<210> SEQ ID NO 4
<211> LENGTH: 107
<212> TYPE: PRT
<213> ORGANISM: Caenorhabditis elegans

<400> SEQUENCE: 4
```

| | | | | | | | | | | | | | | | |
|---|---|---|---|---|---|---|---|---|---|---|---|---|---|---|---|
| Met | Lys | Leu | Ser | Val | Val | Leu | Ala | Leu | Phe | Ile | Ile | Phe | Gln | Leu | Gly |
| 1 | | | | 5 | | | | | 10 | | | | | 15 | |
| Ala | Ala | Ser | Leu | Met | Arg | Asn | Trp | Met | Phe | Asp | Phe | Glu | Lys | Glu | Leu |
| | | | 20 | | | | | 25 | | | | | 30 | | |
| Glu | His | Asp | Tyr | Asp | Asp | Ser | Glu | Ile | Gly | Phe | His | Asn | Ile | His | Ser |
| | | | 35 | | | | | 40 | | | | | 45 | | |
| Leu | Met | Ala | Arg | Ser | Arg | Arg | Gly | Asp | Lys | Val | Lys | Ile | Cys | Gly | Thr |
| | | 50 | | | | | 55 | | | | | 60 | | | |
| Lys | Val | Leu | Lys | Val | Met | Val | Met | Val | Met | Cys | Gly | Gly | Glu | Cys | Ser |
| 65 | | | | | 70 | | | | | 75 | | | | | 80 |

```
Thr Asn Glu Asn Ile Ala Thr Glu Cys Cys Glu Lys Met Cys Thr Met
                85                  90                  95

Glu Asp Ile Thr Thr Lys Cys Cys Pro Ser Arg
            100                 105

<210> SEQ ID NO 5
<211> LENGTH: 112
<212> TYPE: PRT
<213> ORGANISM: Caenorhabditis elegans

<400> SEQUENCE: 5

Met Asn Ser Val Phe Thr Ile Ile Phe Val Leu Cys Ala Leu Gln Val
1               5                   10                  15

Ala Ala Ser Phe Arg Gln Ser Phe Gly Pro Ser Met Ser Glu Ser
                20                  25                  30

Ala Ser Met Gln Leu Leu Arg Glu Leu Gln His Asn Met Met Glu Ser
            35                  40                  45

Ala His Arg Pro Met Pro Arg Ala Arg Val Pro Ala Pro Gly Glu
        50                  55                  60

Thr Arg Ala Cys Gly Arg Lys Leu Ile Ser Leu Val Met Ala Val Cys
65                  70                  75                  80

Gly Asp Leu Cys Asn Pro Gln Glu Gly Lys Asp Ile Ala Thr Glu Cys
                85                  90                  95

Cys Gly Asn Gln Cys Ser Asp Asp Tyr Ile Arg Ser Ala Cys Cys Pro
                100                 105                 110

<210> SEQ ID NO 6
<211> LENGTH: 100
<212> TYPE: PRT
<213> ORGANISM: Caenorhabditis elegans

<400> SEQUENCE: 6

Met His Ser Ile Val Ala Leu Met Leu Ile Gly Thr Ile Leu Pro Ile
1               5                   10                  15

Ala Ala Leu His Gln Lys His Gln Gly Phe Ile Leu Ser Ser Ser Asp
                20                  25                  30

Ser Thr Gly Asn Gln Pro Met Asp Ala Ile Ser Arg Ala Asp Arg His
            35                  40                  45

Thr Asn Tyr Arg Ser Cys Ala Leu Arg Leu Ile Pro His Val Trp Ser
        50                  55                  60

Val Cys Gly Asp Ala Cys Gln Pro Gln Asn Gly Ile Asp Val Ala Gln
65                  70                  75                  80

Lys Cys Cys Ser Thr Asp Cys Ser Ser Asp Tyr Ile Lys Glu Ile Cys
                85                  90                  95

Cys Pro Phe Asp
            100

<210> SEQ ID NO 7
<211> LENGTH: 105
<212> TYPE: PRT
<213> ORGANISM: Caenorhabditis elegans

<400> SEQUENCE: 7

Met Pro Pro Ile Ile Leu Val Phe Phe Leu Val Leu Ile Pro Ala Ser
1               5                   10                  15

Gln Gln Tyr Pro Phe Ser Leu Glu Ser Leu Asn Asp Gln Ile Ile Asn
                20                  25                  30

Glu Glu Val Ile Glu Tyr Met Leu Glu Asn Ser Ile Arg Ser Ser Arg
```

```
                35                  40                  45
Thr Arg Arg Val Pro Asp Glu Lys Lys Ile Tyr Arg Cys Gly Arg Arg
            50                  55                  60
Ile His Ser Tyr Val Phe Ala Val Cys Gly Lys Ala Cys Glu Ser Asn
 65                  70                  75                  80
Thr Glu Val Asn Ile Ala Ser Lys Cys Cys Arg Glu Glu Cys Thr Asp
                85                  90                  95
Asp Phe Ile Arg Lys Gln Cys Cys Pro
                100             105

<210> SEQ ID NO 8
<211> LENGTH: 104
<212> TYPE: PRT
<213> ORGANISM: Caenorhabditis elegans

<400> SEQUENCE: 8

Met Ser Pro Ile Ile Leu Ile Phe Phe Leu Val Phe Ile Pro Phe Ser
 1               5                  10                  15
Gln Gln His Thr Ser Leu Glu Glu Ser Leu Asn Asp Arg Ile Ile Ser
                20                  25                  30
Glu Glu Val Val Glu Met Leu Ser Glu Lys Glu Ile Arg Pro Ser Arg
                35                  40                  45
Val Arg Arg Val Pro Glu Gln Lys Asn Lys Leu Cys Gly Lys Gln Val
            50                  55                  60
Leu Ser Tyr Val Met Ala Leu Cys Glu Lys Ala Cys Asp Ser Asn Thr
 65                  70                  75                  80
Lys Val Asp Ile Ala Thr Lys Cys Cys Arg Asp Ala Cys Ser Asp Glu
                85                  90                  95
Phe Ile Arg His Gln Cys Cys Pro
                100

<210> SEQ ID NO 9
<211> LENGTH: 118
<212> TYPE: PRT
<213> ORGANISM: Caenorhabditis elegans

<400> SEQUENCE: 9

Met Ile Val Thr Leu Ile Val Phe Leu Val Ile Gly Leu Gln Met Ala
 1               5                  10                  15
His Leu Ser Gln Val Ser Gly Asn Asn Glu Asn Gly Phe Leu Asn Pro
                20                  25                  30
Phe Asp Leu Ser Gln Trp Ser Glu Glu Ile Leu His Arg Gln Tyr His
                35                  40                  45
His His His His His His Gly Asn Arg Ala Arg Arg Thr Leu Glu
            50                  55                  60
Thr Glu Lys Ile Tyr Arg Cys Gly Arg Lys Leu Tyr Thr Asp Val Leu
 65                  70                  75                  80
Ser Ala Cys Asn Gly Pro Cys Glu Pro Gly Thr Glu Gln Asp Leu Ser
                85                  90                  95
Lys Leu Cys Cys Gly Asn Gln Cys Thr Phe Val Glu Ile Arg Lys Ala
                100             105                 110
Cys Cys Ala Asp Lys Leu
            115

<210> SEQ ID NO 10
<211> LENGTH: 91
<212> TYPE: PRT
```

<213> ORGANISM: Caenorhabditis elegans

<400> SEQUENCE: 10

```
Met Ser Ser Tyr Arg Gln Thr Leu Phe Ile Leu Ile Leu Ile Val
1               5                   10                  15

Ile Ile Leu Phe Val Asn Glu Gly Gln Gly Ala Pro His His Asp Lys
                20                  25                  30

Arg His Thr Ala Cys Val Leu Lys Ile Phe Lys Ala Leu Asn Val Met
                35                  40                  45

Cys Asn His Glu Gly Asp Ala Asp Val Leu Arg Arg Thr Ala Ser Asp
        50                  55                  60

Cys Cys Arg Glu Ser Cys Ser Leu Thr Glu Met Leu Ala Ser Cys Thr
65                  70                  75                  80

Leu Thr Ser Ser Glu Glu Ser Thr Arg Asp Ile
                85                  90
```

<210> SEQ ID NO 11
<211> LENGTH: 86
<212> TYPE: PRT
<213> ORGANISM: Caenorhabditis elegans

<400> SEQUENCE: 11

```
Met Gln Ser Asn Ile Thr Ala Ser Leu Phe Ile Ala Leu Leu Ile Phe
1               5                   10                  15

Gly Val Ile Ser Ala Ala Pro Ser His Glu Lys Thr His Lys Lys Cys
                20                  25                  30

Ser Asp Lys Leu Tyr Leu Ala Met Lys Ser Leu Cys Ser Tyr Arg Gly
                35                  40                  45

Tyr Ser Glu Phe Leu Arg Asn Ser Ala Thr Lys Cys Cys Gln Asp Asn
        50                  55                  60

Cys Glu Ile Ser Glu Met Met Ala Leu Cys Val Val Ala Pro Asn Phe
65                  70                  75                  80

Asp Asp Asp Leu Leu His
                85
```

<210> SEQ ID NO 12
<211> LENGTH: 76
<212> TYPE: PRT
<213> ORGANISM: Caenorhabditis elegans

<400> SEQUENCE: 12

```
Met Lys Thr Tyr Ser Phe Phe Val Leu Phe Ile Val Phe Ile Phe Phe
1               5                   10                  15

Ile Ser Ser Ser Lys Ser His Ser Lys Lys His Val Arg Phe Leu Cys
                20                  25                  30

Ala Thr Lys Ala Val Lys His Ile Arg Lys Val Cys Pro Asp Met Cys
                35                  40                  45

Leu Thr Gly Glu Glu Val Glu Val Asn Glu Phe Cys Lys Met Gly Tyr
        50                  55                  60

Ser Asp Ser Gln Ile Lys Tyr Ile Cys Cys Pro Glu
65                  70                  75
```

<210> SEQ ID NO 13
<211> LENGTH: 83
<212> TYPE: PRT
<213> ORGANISM: Caenorhabditis elegans

<400> SEQUENCE: 13

-continued

Met His Thr Thr Thr Ile Leu Ile Cys Phe Phe Ile Phe Leu Val Gln
1               5                   10                  15

Val Ser Thr Met Asp Ala His Thr Asp Lys Tyr Val Arg Thr Leu Cys
            20                  25                  30

Gly Lys Thr Ala Ile Arg Asn Ile Ala Asn Leu Cys Pro Pro Lys Pro
            35                  40                  45

Glu Met Lys Gly Ile Cys Ser Thr Gly Glu Tyr Pro Ser Ile Thr Glu
        50                  55                  60

Tyr Cys Ser Met Gly Phe Ser Asp Ser Gln Ile Lys Phe Met Cys Cys
65                  70                  75                  80

Asp Asn Gln

<210> SEQ ID NO 14
<211> LENGTH: 76
<212> TYPE: PRT
<213> ORGANISM: Caenorhabditis elegans

<400> SEQUENCE: 14

Met Phe Val Leu Leu Ile Ile Leu Ser Ile Ile Leu Ala Gln Val Thr
1               5                   10                  15

Asp Ala His Ser Glu Leu His Val Arg Arg Val Cys Gly Thr Ala Ile
            20                  25                  30

Ile Lys Asn Ile Met Arg Leu Cys Pro Gly Val Pro Ala Cys Glu Asn
            35                  40                  45

Gly Glu Val Pro Ser Pro Thr Glu Tyr Cys Ser Met Gly Tyr Ser Asp
        50                  55                  60

Ser Gln Val Lys Tyr Leu Cys Cys Pro Thr Ser Gln
65                  70                  75

<210> SEQ ID NO 15
<211> LENGTH: 80
<212> TYPE: PRT
<213> ORGANISM: Caenorhabditis elegans

<400> SEQUENCE: 15

Met Asp Lys Pro Ser Tyr Leu Ser Ser Lys Glu Ala Trp Lys Met Leu
1               5                   10                  15

Asn Glu Leu Leu Lys Glu Pro Lys His His His His His Arg His
            20                  25                  30

Lys Gly Tyr Cys Gly Val Lys Ala Val Lys Lys Leu Lys Gln Ile Cys
            35                  40                  45

Pro Asp Leu Cys Ser Asn Val Asp Asp Asn Leu Leu Met Glu Met Cys
        50                  55                  60

Ser Lys Asn Leu Thr Asp Asp Asp Ile Leu Gln Arg Cys Cys Pro Glu
65                  70                  75                  80

<210> SEQ ID NO 16
<211> LENGTH: 108
<212> TYPE: PRT
<213> ORGANISM: Caenorhabditis elegans

<400> SEQUENCE: 16

Met Phe Ser Thr Arg Gly Val Leu Leu Leu Ser Leu Met Ala Ala
1               5                   10                  15

Val Ala Ala Phe Gly Leu Phe Ser Arg Pro Ala Pro Ile Thr Arg Asp
            20                  25                  30

Thr Ile Arg Pro Pro Arg Ala Lys His Gly Ser Leu Lys Leu Cys Pro
            35                  40                  45

-continued

Pro Gly Gly Ala Ser Phe Leu Asp Ala Phe Asn Leu Ile Cys Pro Met
            50                  55                  60

Arg Arg Arg Arg Arg Ser Val Ser Glu Asn Tyr Asn Asp Gly Gly
65                  70                  75                  80

Ser Leu Leu Gly Arg Thr Met Asn Met Cys Cys Glu Thr Gly Cys Glu
                85                  90                  95

Phe Thr Asp Ile Phe Ala Ile Cys Asn Pro Phe Gly
            100                 105

<210> SEQ ID NO 17
<211> LENGTH: 95
<212> TYPE: PRT
<213> ORGANISM: Caenorhabditis elegans

<400> SEQUENCE: 17

Met Val His Arg Leu Phe Ile Val Leu Ile Ala Ile Ile Leu Val Ala
1               5                   10                  15

Lys Ser Thr Ala Ile Ser Leu Gln Gln Ala Asp Gly Arg Met Lys Met
                20                  25                  30

Cys Pro Pro Gly Gly Ser Thr Phe Thr Met Ala Trp Ser Met Ser Cys
            35                  40                  45

Ser Met Arg Arg Arg Lys Arg Asp Val Gly Arg Tyr Phe Glu Lys Arg
        50                  55                  60

Ala Leu Ile Ala Pro Ser Ile Arg Gln Leu Gln Thr Ile Cys Cys Gln
65                  70                  75                  80

Val Gly Cys Asn Val Glu Asp Leu Leu Ala Tyr Cys Ala Pro Ile
                85                  90                  95

<210> SEQ ID NO 18
<211> LENGTH: 83
<212> TYPE: PRT
<213> ORGANISM: Caenorhabditis elegans

<400> SEQUENCE: 18

Met Lys Phe Phe Arg Leu Ile Leu Leu Cys Ala Leu Val Leu Thr Thr
1               5                   10                  15

Met Ala Phe Leu Ala Pro Ser Thr Ala Ala Lys Arg Arg Cys Gly Arg
                20                  25                  30

Arg Leu Ile Pro Tyr Val Tyr Ser Ile Cys Gly Gly Pro Cys Glu Asn
            35                  40                  45

Gly Asp Ile Ile Ile Glu His Cys Phe Ser Gly Thr Thr Pro Thr Ile
        50                  55                  60

Ala Glu Val Gln Lys Ala Cys Cys Pro Glu Leu Ser Glu Asp Pro Thr
65                  70                  75                  80

Phe Ser Ser

<210> SEQ ID NO 19
<211> LENGTH: 321
<212> TYPE: DNA
<213> ORGANISM: Caenorhabditis elegans

<400> SEQUENCE: 19
atgttttcat tctttacata tttccttctc tccgcacttc ttctctccgc ttcatgtcga      60
caaccttcca tggacaccag caaagccgat cgtattctac gagagatcga atggaaaca     120 gaactcgaaa atcaactctc ccgagcacga cgagtcccag ctggagaggt tcgtgcctgt     180
ggaagacgac ttcttctctt tgtctggtca acctgtggag aaccatgcac gccacaagag     240

```
gacatggaca ttgccacagt ttgctgcaca acacagtgca ctccatcata tataaaacaa    300
gcttgctgcc cagaaaagta a                                              321
```

<210> SEQ ID NO 20
<211> LENGTH: 321
<212> TYPE: DNA
<213> ORGANISM: Caenorhabditis elegans

<400> SEQUENCE: 20

```
atgttttcat tctttacata tttccttctc tccgcacttc ttctctccgc ttcatgtcga    60
caaccttcca tggacaccag caaagccgat cgtattctac gagagatcga aatggaaaca    120
gaactcgaaa atcaactctc ccgagcacga cgagtcccag ctggagaggt tcgtgcctgt    180
ggaagacgac ttcttctctt tgtctggtca acctgtggag aaccatgcac gccacaagag    240
gacatggaca ttgccacagt ttgctgcaca acacagtgca ctccatcata tataaaacaa    300
gcttgctgcc cagaaaagta a                                              321
```

<210> SEQ ID NO 21
<211> LENGTH: 321
<212> TYPE: DNA
<213> ORGANISM: Caenorhabditis elegans

<400> SEQUENCE: 21

```
atgaacgcta taatcttctg tctcctcttc acaactgtca ctgccactta tgaagttttc    60
ggaaaaggaa tagaacacag aaatgaacat ttgatcatca atcaacttga tatcatacca    120
gttgagtcaa ctccaactcc aaaccgtgcc tcaagagtcc agaaacgtct atgcggaaga    180
cgtcttattt tattcatgct tgcaacatgt ggagaatgtg atacagattc atcagaagac    240
ctttcgcata tttgctgcat aaaacaatgt gacgttcaag atatcatcag agtctgctgc    300
ccgaattcat ttagaaaata g                                              321
```

<210> SEQ ID NO 22
<211> LENGTH: 324
<212> TYPE: DNA
<213> ORGANISM: Caenorhabditis elegans

<400> SEQUENCE: 22

```
atgaaactct ccgttgttct tgcacttttc attattttcc aacttggagc tgcaagtctt    60
atgcgtaact ggatgttcga ttttgagaaa gaattggaac acgattatga tgattcggaa    120
attggattcc ataacattca ctccctgatg gccagatcaa aagaggaga caaagtgaag    180 atttgtggta caaaagttct gaaaatggtg atggtaatgt gtggaggaga atgttcatca    240
acgaatgaga acatcgctac agaatgctgt gaaaaaatgt gcacaatgga agatataact    300
actaagtgct gcccttcaag atga                                           324
```

<210> SEQ ID NO 23
<211> LENGTH: 339
<212> TYPE: DNA
<213> ORGANISM: Caenorhabditis elegans

<400> SEQUENCE: 23

```
atgaactctg tctttactat catcttcgtt ttgtgcgcac tccaagtcgc tgcaagtttc    60
cgtcaatcct tcggtccttc aatgtctgaa gaatcagcaa gcatgcaact tctccgtgaa    120
cttcaacaca acatgatgga atcagctcac cgaccaatgc cacgagcaag acgtgttcca    180
```

```
gcaccaggag aaactcgtgc ctgcggaaga aaactcatct ctttagtcat ggctgtctgt    240
ggagatcttt gcaacccaca agaaggaaag gacattgcga ctgaatgctg cggaaatcag    300
tgttctgatg actacataag atctgcttgt tgtccatga                          339

<210> SEQ ID NO 24
<211> LENGTH: 303
<212> TYPE: DNA
<213> ORGANISM: Caenorhabditis elegans

<400> SEQUENCE: 24
atgcactcga tcgtcgcctt gatgctcatc ggaacaattc tcccaatcgc tgctcttcac     60
cagaagcatc aaggcttcat cctgtcgtca tccgattcaa ccggaaacca accaatggat    120
gcgatctcaa gagccgaccg tcacaccaac taccgatcat gcgcattgcg gctcatcccg    180
catgtctggt cggtgtgcgg tgacgcctgc aaccacaaa acggaatcga tgtcgctcaa    240
aaatgttgct ccactgattg cagctccgat tacatcaaag aaatctgctg cccatttgac    300
taa                                                                 303

<210> SEQ ID NO 25
<211> LENGTH: 318
<212> TYPE: DNA
<213> ORGANISM: Caenorhabditis elegans

<400> SEQUENCE: 25
atgccaccaa taattttggt tttcttttg gttttaatcc ctgcttctca acaatatcct      60
ttttcactgg agtccttaaa tgatcaaata atcaatgaag aagtaatcga atatatgctt    120
gaaaattcaa ttaggtccag cagaaccaga agagtccctg acgagaaaaa aatttatcgt    180
tgtggaagaa gaatacattc gtatgtgttt gcggtttgtg aaaagcatg cgaatcgaat    240 actgaagtta atattgcatc aaaatgttgc cgtgaagaat gcaccgacga cttcattcga    300
aaacagtgct gtccttaa                                                 318

<210> SEQ ID NO 26
<211> LENGTH: 315
<212> TYPE: DNA
<213> ORGANISM: Caenorhabditis elegans

<400> SEQUENCE: 26
atgtcgccaa tcattttgat tttcttttg gttttcattc cgttttctca acaacacaca     60
tctttagagg agtccttaaa tgatcgaata atcagtgaag aagtagtcga aatgctatca    120
gagaaagaaa ttagacccag cagagtaaga agagtccctg aacaaaaaaa taattgtgc    180 ggaaagcaag tcttatccta cgttatggca cttttgtgaaa aagcatgcga ttcaaataca    240
aaagtcgata ttgcgacaaa atgttgccgc gatgcatgct cagacgaatt cattcgacat    300
caatgttgtc cttaa                                                    315

<210> SEQ ID NO 27
<211> LENGTH: 357
<212> TYPE: DNA
<213> ORGANISM: Caenorhabditis elegans

<400> SEQUENCE: 27
atgatcgtca ctttgattgt ctttcttgtc attggacttc aaatggcaca cctttctcaa     60
gtatctggaa acaacgaaaa tggattctta aatccatttg atttgtctca atggagcgaa    120
gaaatcctcc accgtcagta tcatcatcac caccaccatc accatggaaa tcgggcgaga    180
```

```
agaaccttgg aaaccgaaaa aatctaccgc tgtggaagaa aactctacac tgatgtgcta      240
tcagcgtgca acgggccatg tgaaccgggt acggaacagg atctctctaa gctgtgctgt      300
ggaaaccaat gtactttcgt tgaaatcagg aaagcatgct gtgccgacaa attgtaa         357
```

<210> SEQ ID NO 28
<211> LENGTH: 276
<212> TYPE: DNA
<213> ORGANISM: Caenorhabditis elegans

<400> SEQUENCE: 28

```
atgtctagtt accgtcaaac attgttcatt cttattattc ttattgtaat tattctcttc      60
gtcaatgagg gtcaaggagc gcctcaccat gacaaacggc acactgcatg cgtcctaaag     120
attttcaagg cgctaaacgt tatgtgtaat catgaaggtg atgcagatgt tctgaggaga     180
acagcatccg actgctgtcg ggagagctgc tcgctaacag aaatgttagc gagctgcacc     240
ctcaccagct cagaagagtc aactcgggac atttaa                              276
```

<210> SEQ ID NO 29
<211> LENGTH: 261
<212> TYPE: DNA
<213> ORGANISM: Caenorhabditis elegans

<400> SEQUENCE: 29

```
atgcaatcaa acatcaccgc ttcattattc atagcgttgc ttatatttgg agtaatcagt      60
gcagctccat ctcatgaaaa aacacacaaa aaatgctctg ataaattata tttggcgatg     120
aagtcgttgt gtagttatcg aggttatagt gaattcttaa gaaattctgc aactaagtgt     180
tgccaagaca attgtgagat ttcggaaatg atggcgttgt gtgttgttgc tcccaatttt     240
gacgacgatc tccttcatta a                                               261
```

<210> SEQ ID NO 30
<211> LENGTH: 231
<212> TYPE: DNA
<213> ORGANISM: Caenorhabditis elegans

<400> SEQUENCE: 30

```
atgaaaacct actcattttt cgtgcttttt attgtattca tcttttttat ttcttcatca      60
aaatctcatt caaagaaaca tgttcgtttc ctttgtgcaa caaaagcggt caaacacatt     120
cggaaagtat gccctgatat gtgtctcact ggagaagaag tcgaagtcaa tgagttttgc     180
aagatggggt actcggattc tcaaatcaag tacatttgct gtcccgaata a              231
```

<210> SEQ ID NO 31
<211> LENGTH: 252
<212> TYPE: DNA
<213> ORGANISM: Caenorhabditis elegans

<400> SEQUENCE: 31

```
atgcacacta caactattct catatgcttt ttcatctttc ttgttcaagt ctccacaatg      60
gatgctcaca ctgacaaata cgtcagaact ctgtgtggaa aaactgcaat cagaaatatt     120
gccaaccttt gcccgccaaa gccagaaatg aagggtatct gttctaccgg agagtatcca     180
agcatcaccg aatactgttc catgggattt tcagactctc agatcaagtt tatgtgctgt     240
gataaccaat ga                                                         252
```

<210> SEQ ID NO 32

<211> LENGTH: 231
<212> TYPE: DNA
<213> ORGANISM: Caenorhabditis elegans

<400> SEQUENCE: 32

| | |
|---|---|
| atgttcgttc ttcttattat tctctctatc attctggctc aagtcactga tgctcattca | 60 |
| gagcttcacg ttcgtagggt gtgcggaact gctatcataa agaacataat gcgattgtgc | 120 |
| ccaggggtac cggcttgcga aaatggagaa gttccaagtc caaccgagta ctgttcaatg | 180 |
| gggtactcag acagccaggt aaaataccta tgctgtccaa cttctcagtg a | 231 |

<210> SEQ ID NO 33
<211> LENGTH: 243
<212> TYPE: DNA
<213> ORGANISM: Caenorhabditis elegans

<400> SEQUENCE: 33

| | |
|---|---|
| atggacaaac catcctacct gtcatccaaa gaagcatgga aaatgctaaa tgagctgctg | 60 |
| aaagagccga acatcatca tcatcatcac aggcacaaag atattgtgg agttaaagct | 120 |
| gtaaagaaat taaacaaat ctgtccagat ctttgctcga atgttgatga taaccttctc | 180 |
| atggaaatgt gctcaaaaaa cctgacggat gatgatattt gcaacggtg ctgtccagaa | 240 |
| tga | 243 |

<210> SEQ ID NO 34
<211> LENGTH: 327
<212> TYPE: DNA
<213> ORGANISM: Caenorhabditis elegans

<400> SEQUENCE: 34

| | |
|---|---|
| atgttctcga ccagaggggt actccttta ctgtctttga tggctgctgt agccgcattc | 60 |
| gggctgtttt ctagaccggc tccaatcact cgggacacta tccgaccacc acgtgccaaa | 120 |
| cacggttcgc tgaaattatg cccaccaggt ggtgcctcat tccttgacgc tttcaacttg | 180 |
| atttgcccaa tgcgccgtcg acgcaggagt gtttcagaaa actacaacga cggcggtggc | 240 |
| agccttttgg gacggacaat gaatatgtgc tgtgagacgg gatgtgaatt cactgacatt | 300 |
| ttcgcaatct gcaatccttt tggataa | 327 |

<210> SEQ ID NO 35
<211> LENGTH: 288
<212> TYPE: DNA
<213> ORGANISM: Caenorhabditis elegans

<400> SEQUENCE: 35

| | |
|---|---|
| atggtccacc gactttcat cgtccttatt gcaattattc ttgtcgcaaa atcaactgca | 60 |
| atctcacttc aacaagctga cggacgcatg aaaatgtgcc caccaggtgg ttcaacattc | 120 |
| acaatggcat ggtcaatgtc gtgttcgatg cgcaggagaa aacgagatgt tggacgatat | 180 |
| ttcgaaaaac gtgctctgat cgccccatca atccgtcaac ttcaaacaat ttgctgtcaa | 240 |
| gttggttgca acgtggaaga tcttcttgcc tactgtgccc caatttaa | 288 |

<210> SEQ ID NO 36
<211> LENGTH: 252
<212> TYPE: DNA
<213> ORGANISM: Caenorhabditis elegans

<400> SEQUENCE: 36

| | |
|---|---|
| atgaaattct tccgcttaat cttgctctgc gcccttgtcc tgaccaccat ggctttttg | 60 |

```
gctccaagta cggcagccaa gaggcgttgt ggccgccgct taattcccta tgtctattca      120
atatgcggcg gcccgtgcga gaatggagat attatcatcg agcactgctt ctccggaaca      180
actcccacca ttgccgaagt ccaaaaggct tgctgtcctg aactatctga agacccaact      240
ttctcatctt aa                                                          252
```

```
<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 37
gacggagatg gcttgttgga cgac                                              24

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 38
ggtttaatta cccaagtttg ag                                                22

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 39
caagagaatg ttttcattct ttac                                              24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 40
ttacttttct gggcagcaag cttg                                              24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 41
ctaccatgaa cgctataatc ttct                                              24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 42
```
atgatagtac gatatgtcca taac    24

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 43
cctattttcc agccacagca ctctc    25

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 44
ccccgtactc attttccgtt atcc    24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 45
gtatggtaca gagactgata tcgg    24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 46
caaggaaaat gcactcgatc gtcg    24

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 47
cccaagcttt gttatttaat gatgtggaga tgg    33

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 48
gctctagaat ggtaaataca gaacattggt tc    32

<210> SEQ ID NO 49
<211> LENGTH: 32
<212> TYPE: DNA
<213> ORGANISM: Artificial Sequence

```
<220> FEATURE:
<223> OTHER INFORMATION: Description of Artificial Sequence: PCR Primer

<400> SEQUENCE: 49
gctctagagt gacggtaggt gtgtagatga ac                              32

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 50
atcgaaactc ttcaatcttc aagg                                       24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 51
gatagaagaa attaaggaca gcac                                       24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 52
gtaaacgatt agattaagga caac                                       24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 53
gaggagtgaa acgatgatcg tcac                                       24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 54
atccaattga gaagacgatt gttg                                       24

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 55
cccaagcttt tgaaccatga aaacctactc att                             33
```

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 56
gctctagagc tttttttat tcgggacagc aa        32

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 57
cccaagcttg gatttctgga atttcgataa tg        32

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: PCR Primer

<400> SEQUENCE: 58
gctctagagc agcatagaat ggcggaagat c        31

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 59
cccaagcttg tgtaggaatc gttaaatatg tct        33

<210> SEQ ID NO 60
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 60
gctctagaga gatcatatta tattacacga ac        32

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 61
cccaagcttc cgctctcaac aacgggccac acg        33

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 62
gctctagaga tgaataagtt atcaattatc gt                              32

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: PCR Primer

<400> SEQUENCE: 63
cccaagcttg gtttaattac ccaagtttga g                               31

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 64
gctctagatg atgcgtattt tgtgggcggt ac                              32

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 65
gctctagact catcagttga aaatgaattt aag                             33

<210> SEQ ID NO 66
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 66
cccaagcttg gcataagcga gtatctgtga tcc                             33

<210> SEQ ID NO 67
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 67
ccgctcgagg taaagcgagg gtaaagtaga tcg                             33

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 68
cccaagcttc taaccaacaa aaatgcacac tac                             33

<210> SEQ ID NO 69

<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 69
gctctagaca cgtgaacaat ctttatcttt at                                     32

<210> SEQ ID NO 70
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 70
cccaagcttc acagccaaaa acaaaaatgc aatc                                   34

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 71
gctctagaca cagtatttta atgaaggaga tc                                     32

<210> SEQ ID NO 72
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 72
ttgggcgcgc cgtcttgcat gcagttgtca cg                                     32

<210> SEQ ID NO 73
<211> LENGTH: 35
<212> TYPE: DNA
<213> ORGANISM: Artificial Sequence
<220> FEATURE:
<223> OTHER INFORMATION: Description of Artificial Sequence: PCR Primer

<400> SEQUENCE: 73
ccaaccggta tcattgcgta ctgtcgtagc gtgtg                                  35

<210> SEQ ID NO 74
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 74
ttgggcgcgc ctgctaccgt gggaatttta caag                                   34

<210> SEQ ID NO 75
<211> LENGTH: 35
<212> TYPE: DNA
<213> ORGANISM: Artificial Sequence
<220> FEATURE:
<223> OTHER INFORMATION: Description of Artificial Sequence: PCR Primer

<400> SEQUENCE: 75

-continued ccaaccggta tcatggtaga ttttagaatg gaaag                35

<210> SEQ ID NO 76
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 76
ttgggcgcgc cggagttcat ctggaggtca catc                 34

<210> SEQ ID NO 77
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 77
ccaaccggta tcattattca gaacaggaat tgataaatg            39

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 78
ttgggcgcca gataaataca gaatgggcgg ag                   32

<210> SEQ ID NO 79
<211> LENGTH: 36
<212> TYPE: DNA
<213> ORGANISM: Artificial Sequence
<220> FEATURE:
<223> OTHER INFORMATION: Description of Artificial Sequence: PCR Primer

<400> SEQUENCE: 79
ccaaccggta tcattctctt ggagcttttg aaaaac               36

<210> SEQ ID NO 80
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 80
ttgggcgcgc cagtcgtcca acaagccatc tcc                  33

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 81
ccaaccggtt gcattttcct tgaagattga ag                   32

<210> SEQ ID NO 82
<211> LENGTH: 33
<212> TYPE: DNA

```
<213> ORGANISM: Artificial Sequence
<220> FEATURE:
<223> OTHER INFORMATION: Description of Artificial Sequence: PCR Primer

<400> SEQUENCE: 82
ttgggcgcgc ctagattttc tccattcaca aac                           33

<210> SEQ ID NO 83
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 83
ccaaccggta tcattataat gatatggata acgg                          34

<210> SEQ ID NO 84
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 84
ttgggcgcgc caatcgtttt catcattttg cttc                          34

<210> SEQ ID NO 85
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 85
ccaaccggta tcatctggaa aagtaatatt atat                          34

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 86
ttgggcgcgc ctgaaatctt tatatcctct tcac                          34

<210> SEQ ID NO 87
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 87
ccaaccggta tcatctggaa ataattaata tcag                          34

<210> SEQ ID NO 88
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 88
ttgggcgcgc ctaacacgtg cattggaggc ggag                          34
```

```
<210> SEQ ID NO 89
<211> LENGTH: 36
<212> TYPE: DNA
<213> ORGANISM: Artificial Sequence
<220> FEATURE:
<223> OTHER INFORMATION: Description of Artificial Sequence: PCR Primer

<400> SEQUENCE: 89
ccaacggtat catcgtttca ctcctcgaat tatttg                                36

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 90
ttgggcgcgc cattggtatc acaaggatca agc                                   33

<210> SEQ ID NO 91
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 91
ccaaccggca tttttgtttt tggctgtgat ta                                    32

<210> SEQ ID NO 92
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 92
ttgggcgcgc caattttgac gacgatctcc ttc                                   33

<210> SEQ ID NO 93
<211> LENGTH: 37
<212> TYPE: DNA
<213> ORGANISM: Artificial Sequence
<220> FEATURE:
<223> OTHER INFORMATION: Description of Artificial Sequence: PCR Primer

<400> SEQUENCE: 93
ccaaccggta tcatatttaa cgattcctac acaaacc                               37

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 94
ttgggcgcgc cgtgtggagg tggtgaatcc                                       30

<210> SEQ ID NO 95
<211> LENGTH: 33
<212> TYPE: DNA
<213> ORGANISM: Artificial Sequence
<220> FEATURE:
```

<223> OTHER INFORMATION: Description of Artificial Sequence: PCR Primer

<400> SEQUENCE: 95
cggggtaccc tcatttcaaa gaaatgttga ata                    33

<210> SEQ ID NO 96
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 96
ttgggcgcgc cggagccgaa caagaaaaac ctac                   34

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 97
ccaaccggtt tcatggttca actcaaaaag gaa                    33

<210> SEQ ID NO 98
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 98
ttgggcgcgc cagttcgtct cagcatcatc ttgc                   34

<210> SEQ ID NO 99
<211> LENGTH: 33
<212> TYPE: DNA
<213> ORGANISM: Artificial Sequence
<220> FEATURE:
<223> OTHER INFORMATION: Description of Artificial Sequence:  PCR Primer

<400> SEQUENCE: 99
ccaaccggtt tcatggttca actcaaaaag gaa                    33

<210> SEQ ID NO 100
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 100
ttgggcgcgc catgggattt tcagactctc ag                     32

<210> SEQ ID NO 101
<211> LENGTH: 35
<212> TYPE: DNA
<213> ORGANISM: Artificial Sequence
<220> FEATURE:
<223> OTHER INFORMATION: Description of Artificial Sequence: PCR Primer

<400> SEQUENCE: 101
ccaaccggta acattatcga aattccagaa atccg                  35

```
<210> SEQ ID NO 102
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 102
ttgggcgcgc cacttcggac agatgtgaca cg                              32

<210> SEQ ID NO 103
<211> LENGTH: 35
<212> TYPE: DNA
<213> ORGANISM: Artificial Sequence
<220> FEATURE:
<223> OTHER INFORMATION: Description of Artificial Sequence: PCR Primer

<400> SEQUENCE: 103
cggggtacct gcattgtaaa agtgattttg aaaat                           35

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 104
caaacagttg tagctcaaag gc                                         22

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 105
gcatacggta cctatrcgtt tc                                         22

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 106
agctcaaagg ccaaatgtgt g                                          21

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 107
aacaaaccct acagttactg gg                                         22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: PCR Primer
```

```
<400> SEQUENCE: 108
gctatccacc tgtccaacct ac                                          22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 109
ggaggctctt tactcgcctt ac                                          22

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 110
tacaggctgt ccttctgtta cg                                          22

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 111
tccactattc cggtaatacc tc                                          22

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 112
gtaagaaatc gagagtcacg cc                                          22

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 113
ctgcctcaag gaggagttac ac                                          22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 114
ctgcctcaag gaggagttac ac                                          22

<210> SEQ ID NO 115
<211> LENGTH: 22
```

```
<212> TYPE: DNA
<213> ORGANISM: Artificial Sequence
<220> FEATURE:
<223> OTHER INFORMATION: Description of Artificial Sequence: PCR Primer

<400> SEQUENCE: 115
atttatcccc acgtgagaga gg                                              22

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 116
cactggatga cagatttgat g                                               21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 117
tgatgagaca cgggtgaaac g                                               21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 118
gaacggataa aaaggcggag c                                               21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 119
ttgatgtgac ctccagatga ac                                              22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 120
gcagcacact cttgttttca gc                                              22

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 121
```

```
caaatcactc acttcctgcg                                              20

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 122
ttcaagtgtc cttgtatccg tg                                           22

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 123
gcatagaatg gcggaagatc ac                                           22

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 124
cttccaaatt tgtcctgact gc                                           22

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 125
aattgcagga gtcgaagttt cc                                           22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 126
aacgagcaga caggaaatca tc                                           22

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 127
tgtgacagca tgtttgaacg tc                                           22

<210> SEQ ID NO 128
<211> LENGTH: 22
<212> TYPE: DNA
<213> ORGANISM: Artificial Sequence
```

```
<220> FEATURE:
<223> OTHER INFORMATION: Description of Artificial Sequence: PCR Primer

<400> SEQUENCE: 128
agttgtcaag aagtgcgtca ag                                          22

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 129
gagatggctt gttggacgac                                             20

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 130
gacaaaatca cgtcacgaag t                                           21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 131
ttacttttct gggcagcaag c                                           21

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 132
cgtgggtatt ccttgttcga agccagctac                                  30

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 133
tcaagtcaaa tggatgcttg aga                                         23

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 134
tcacaagctg atcgactcga tgccacgtcg                                  30
```

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 135
gattttgtga acactgtggt gaagt                                   25

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 136
ttattacatc cgtcactgcg tc                                      22

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 137
gcgtccttat tcagaattcc ag                                      22

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 138
cttgtgactt caagcccact tc                                      22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 139
ggttatgaac cgattaggct cc                                      22

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 140
gtagccttcc ggggtaaaat c                                       21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 141
gatctcgcgc tatgttttga g                                                    21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 142
gacagctgaa gctgaccaaa c                                                    21

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 143
caggagttaa acgtggtcac tg                                                   22

<210> SEQ ID NO 144
<211> LENGTH: 31
<212> TYPE: DNA
<213> ORGANISM: Artificial Sequence
<220> FEATURE:
<223> OTHER INFORMATION: Description of Artificial Sequence: PCR Primer

<400> SEQUENCE: 144
cccaagcttg gtttaattac ccaagtttga g                                         31

<210> SEQ ID NO 145
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 145
gctctagata attcaatgaa aaggcaaaac gacg                                      34

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 146
tagaaggcac agtcgagg                                                        18

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 147
taatacgact actataggg                                                       19

<210> SEQ ID NO 148

```
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 148
cccaagcttc ttcatttggg cttcattta ccac                                34

<210> SEQ ID NO 149
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 149
gctctagaga aacaatgttt ttattcaaca tg                                 32

<210> SEQ ID NO 150
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 150
ccgctcgagc tcgacgttct tcaatctata tttc                               34

<210> SEQ ID NO 151
<211> LENGTH: 35
<212> TYPE: DNA
<213> ORGANISM: Artificial Sequence
<220> FEATURE:
<223> OTHER INFORMATION: Description of Artificial Sequence: PCR Primer

<400> SEQUENCE: 151
gctctagaca aacaccatta aatctgtatt taaac                              35

<210> SEQ ID NO 152
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 152
ccgctcgagc tcgacgttct tcaatctata tttc                               34

<210> SEQ ID NO 153
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 153
gctctagagt tcacaaattc ataaacaaat acg                                33

<210> SEQ ID NO 154
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 154
```
cccaagcttg gactttatca caatttccag cac                                    33

<210> SEQ ID NO 155
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 155
gctctagagt ttctagattt ttagatttcg tg                                     32

<210> SEQ ID NO 156
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 156
ccgctcgaga taatgaagct tcttcttctc attg                                   34

<210> SEQ ID NO 157
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 157
gctctagagt ttctagattt ttagatttcg tg                                     32

<210> SEQ ID NO 158
<211> LENGTH: 85
<212> TYPE: PRT
<213> ORGANISM: Caenorhabditis elegans

<400> SEQUENCE: 158

Met Ser Leu His Phe Ser Thr Ile Gln Lys Thr Ile Leu Leu Ile Ser
1               5                   10                  15

Phe Leu Leu Leu Val Thr Leu Ala Pro Arg Thr Ser Ala Ala Phe Pro
                20                  25                  30

Phe Gln Ile Cys Val Lys Lys Met Glu Lys Met Cys Arg Ile Ile Asn
            35                  40                  45

Pro Glu Gln Cys Ala Gln Val Asn Lys Ile Thr Glu Ile Gly Ala Leu
        50                  55                  60

Thr Asp Cys Cys Thr Gly Leu Cys Ser Trp Glu Glu Ile Arg Ile Ser
65                  70                  75                  80

Cys Cys Ser Val Leu
                85

<210> SEQ ID NO 159
<211> LENGTH: 81
<212> TYPE: PRT
<213> ORGANISM: Caenorhabditis elegans

<400> SEQUENCE: 159

Met Leu Thr His Leu Lys Phe Leu Leu Leu Val Ser Leu Phe Ile Asn
1               5                   10                  15

Phe Ala Val Ser Ser Glu Asp Ile Lys Cys Asp Ala Lys Phe Ile Ser
                20                  25                  30

-continued

Arg Ile Thr Lys Leu Cys Ile His Gly Ile Thr Glu Asp Lys Leu Val
           35                  40                  45

Arg Leu Leu Thr Arg Cys Cys Thr Ser His Cys Ser Lys Ala His Leu
        50                  55                  60

Lys Met Phe Cys Thr Leu Lys Pro His Glu Glu Pro His His Glu
65                  70                  75                  80

Ile

<210> SEQ ID NO 160
<211> LENGTH: 83
<212> TYPE: PRT
<213> ORGANISM: Caenorhabditis elegans

<400> SEQUENCE: 160

Met Lys Leu Leu Pro Leu Ile Val Val Phe Ala Leu Leu Ala Val Ile
1               5                   10                  15

Ser Glu Ser Tyr Ser Gly Asn Asp Phe Gln Pro Arg Asp Asn Lys His
            20                  25                  30

His Ser Tyr Arg Ser Cys Gly Glu Ser Leu Ser Arg Arg Val Ala Phe
        35                  40                  45

Leu Cys Asn Gly Gly Ala Ile Gln Thr Glu Ile Leu Arg Ala Leu Asp
    50                  55                  60

Cys Cys Ser Thr Gly Cys Thr Asp Lys Gln Ile Phe Ser Trp Cys Asp
65                  70                  75                  80

Phe Gln Ile

<210> SEQ ID NO 161
<211> LENGTH: 73
<212> TYPE: PRT
<213> ORGANISM: Caenorhabditis elegans

<400> SEQUENCE: 161

Met Lys Leu Leu His Ile Phe Ile Ile Phe Leu Leu Phe Gln Ser Cys
1               5                   10                  15

Ser Asn Lys Met Cys Gln Tyr Ser Lys Lys Tyr Lys Ile Cys Gly
            20                  25                  30

Val Arg Ala Leu Lys His Met Lys Val Tyr Cys Thr Arg Gly Met Thr
        35                  40                  45

Arg Asp Tyr Gly Lys Leu Leu Val Thr Cys Cys Ser Lys Gly Cys Asn
    50                  55                  60

Ala Ile Asp Ile Gln Arg Ile Cys Leu
65                  70

<210> SEQ ID NO 162
<211> LENGTH: 258
<212> TYPE: DNA
<213> ORGANISM: Caenorhabditis elegans

<400> SEQUENCE: 162
atgtcactgc atttctccac tattcaaaaa acaattcttc taatctcatt cttgctcctc        60
gtaacattgg ctcccagaac aagtgcagct tttccattcc aaatttgtgt caaaaaaatg       120
gaaaaaatgt gcagaatcat caatccagag cagtgtgcac aagtaaataa aatcactgag       180
attggagcat tgacagactg ttgcaccgga ctgtgctcct gggaagaaat ccggatctcc       240
tgctgctccg ttttataa                                                    258

<210> SEQ ID NO 163

<211> LENGTH: 246
<212> TYPE: DNA
<213> ORGANISM: Artificial Sequence
<220> FEATURE:
<223> OTHER INFORMATION: Description of Artificial Sequence: PCR Primer

<400> SEQUENCE: 163

```
atgctcacac atctgaaatt cttgcttcta gtgagccttt ttatcaactt cgccgtaagc      60
tctgaagaca tcaaatgcga tgcaaagttc atttcgagaa tcacgaaact ctgtattcac     120
ggaattactg aagataaact tgttcgtctt ctcacaagat gctgcacatc tcactgctcc     180
aaagctcatc tgaaaatgtt ctgcaccctg aaacctcacg aagaagaacc acatcacgaa     240
atctaa                                                                246
```

<210> SEQ ID NO 164
<211> LENGTH: 249
<212> TYPE: DNA
<213> ORGANISM: Caenorhabditis elegans

<400> SEQUENCE: 164

```
atgaagcttc ttctcattgt ggttttgct cttttggcag tcatatcaga atcatattct      60
ggaaatgact tccaacctcg tgacaataaa catcattcct atcgttcatg tggggaatcg     120
ttgagccgac gagttgcatt tctgtgtaat ggtggagcta ttcaaacaga aatactaaga     180
gctctggatt gttgttccac tggttgtacg gacaaacaga tcttttcttg gtgtgatttt     240
caaatttga                                                             249
```

<210> SEQ ID NO 165
<211> LENGTH: 222
<212> TYPE: DNA
<213> ORGANISM: Caenorhabditis elegans

<400> SEQUENCE: 165

```
atgaagcttt tacatatttt tattattttt ctgttattcc aatcgtgctc taataaaatg      60
tgtcaatatt caaagaaaaa gtacaagatt tgtggagtta gagctattaa gcatatgaaa     120
gtctattgta cacgtggaat gacaagagat tatggaaaat tactcgtgac ttgttgttcg     180
aaaggatgta atgcaataga tatccaacgt atttgtttat ga                        222
```

<210> SEQ ID NO 166
<211> LENGTH: 31
<212> TYPE: DNA
<213> ORGANISM: Artificial Sequence
<220> FEATURE:
<223> OTHER INFORMATION: Description of Artificial Sequence: PCR Primer

<400> SEQUENCE: 166

```
cccaagcttg gtttaattac ccaagtttga g                                    31
```

<210> SEQ ID NO 167
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 167

```
gctctagaca attttgatat taaattttgt cg                                   32
```

<210> SEQ ID NO 168
<211> LENGTH: 31

```
<212> TYPE: DNA
<213> ORGANISM: Artificial Sequence
<220> FEATURE:
<223> OTHER INFORMATION: Description of Artificial Sequence: PCR Primer

<400> SEQUENCE: 168
cccaagcttg gtttaattac ccaagtttga g                                    31

<210> SEQ ID NO 169
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 169
gctctagatt aaattttgtc gattttcaag ttg                                  33

<210> SEQ ID NO 170
<211> LENGTH: 15
<212> TYPE: DNA
<213> ORGANISM: Artificial Sequence
<220> FEATURE:
<223> OTHER INFORMATION: Description of Artificial Sequence: PCR Primer

<400> SEQUENCE: 170
gttttcccag tcacg                                                      15

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: PCR Primer

<400> SEQUENCE: 171
caggaaacag ctatgac                                                    17

<210> SEQ ID NO 172
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 172
cccaagcttg agcattttgt tgctctgcaa aatg                                 34

<210> SEQ ID NO 173
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 173
gctctagatt aaattttgtc gattttcaag ttg                                  33

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 174
```

```
tagaaggcac agtcgagg                                                   18

<210> SEQ ID NO 175
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 175
taatacgact actataggg                                                  19

<210> SEQ ID NO 176
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 176
cgggatcccc gcacaaactt atatgacaac tc                                   32

<210> SEQ ID NO 177
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 177
cggaattcgg tgtctcataa tggtagtgga tac                                  33

<210> SEQ ID NO 178
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 178
cgggatcccc gcacaaactt atatgacaac tc                                   32

<210> SEQ ID NO 179
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 179
cggaattcgc aaaagagagg tagggata aag                                    33

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 180
tagaaggcac agtcgagg                                                   18

<210> SEQ ID NO 181
<211> LENGTH: 19
<212> TYPE: DNA
<213> ORGANISM: Artificial Sequence
```

```
<220> FEATURE:
<223> OTHER INFORMATION: Description of Artificial Sequence: PCR Primer

<400> SEQUENCE: 181
taatacgact actataggg                                                    19

<210> SEQ ID NO 182
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 182
cccaagctta aaggcttaga tgcagaaaga cc                                     32

<210> SEQ ID NO 183
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 183
gctctagagg gattaaaatc actctgtgat taag                                   34

<210> SEQ ID NO 184
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 184
cccaagctta aggtggaca ttgtagaagg ttg                                     33

<210> SEQ ID NO 185
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 185
gctctagagg gattaaaatc actctgtgat taag                                   34

<210> SEQ ID NO 186
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 186
cccaagcttc cttcacttct cagcgaagga aatg                                   34

<210> SEQ ID NO 187
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 187
gctctagagt gctcatgctc cgttattttg tgc                                    33
```

<210> SEQ ID NO 188
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 188
cggaattcct agaattttca ccccaaatgt tcag                           34

<210> SEQ ID NO 189
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 189
ccgctcgaga aatgtaagtg attggcaagt tgg                            33

<210> SEQ ID NO 190
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 190
cccaagctta gagacttaga cgcaaagagg acc                            33

<210> SEQ ID NO 191
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 191
gctctagagc aggaaaatta gctaaaacat aatg                           34

<210> SEQ ID NO 192
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 192
cggaattcgg cgaaacactt ccgccaactc ac                             32

<210> SEQ ID NO 193
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 193
ccgctcgaga cctaccgtca acttggagga taac                           34

<210> SEQ ID NO 194
<211> LENGTH: 34
<212> TYPE: DNA
<213> ORGANISM: Artificial Sequence
<220> FEATURE:
<223> OTHER INFORMATION: Description of Artificial Sequence: PCR Primer

```
<400> SEQUENCE: 194
cccaagcttc cttgcacctg ccttcaacca tcac                              34

<210> SEQ ID NO 195
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 195
gctctagata ttctgacccc aaaatgacaa tc                                32

<210> SEQ ID NO 196
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 196
cccaagcttt tctgcagact tgcaaggtta gttc                              34

<210> SEQ ID NO 197
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 197
gctctagaat tcacaaaata atcaagacaa tc                                32

<210> SEQ ID NO 198
<211> LENGTH: 103
<212> TYPE: PRT
<213> ORGANISM: Caenorhabditis elegans

<400> SEQUENCE: 198
```

Met Arg Ser Pro Thr Leu Phe Leu Leu Leu Leu Val Pro Leu Ala
1               5                   10                  15

Leu Cys His Val Phe Ser Glu Pro Ala Asp Leu Glu Leu Lys Ser Tyr
                20                  25                  30

Gln Ala Leu Glu Lys Ser Leu Lys Glu Met Gly Leu Ile Arg Ala Asn
            35                  40                  45

Gln Gly Pro Gln Lys Ala Cys Gly Arg Ser Met Met Met Lys Val Gln
        50                  55                  60

Lys Leu Cys Ala Gly Gly Cys Thr Ile Gln Asn Asp Asp Leu Thr Ile
65                  70                  75                  80

Lys Ser Cys Ser Thr Gly Tyr Thr Asp Ala Gly Phe Ile Ser Ala Cys
                85                  90                  95

Cys Pro Ser Gly Phe Val Phe
            100

```
<210> SEQ ID NO 199
<211> LENGTH: 72
<212> TYPE: PRT
<213> ORGANISM: Caenorhabditis elegans

<400> SEQUENCE: 199
```

Met Leu Phe Lys Ile Ile Ile Leu Phe Phe Leu Leu Leu Gln Leu Ser

```
              1               5                  10                 15
    Glu Ala Lys Pro Glu Ala Gln Arg Arg Cys Gly Arg Tyr Leu Ile Arg
                        20                  25                  30

Phe Leu Gly Glu Leu Cys Asn Gly Pro Cys Ser Gly Val Ser Ser Val
                35                  40                  45

Asp Ile Ala Thr Ile Ala Cys Ala Thr Ala Val Pro Ile Glu Asp Leu
                50                  55                  60

Lys Asn Met Cys Cys Pro Asn Leu
    65                  70

<210> SEQ ID NO 200
    <211> LENGTH: 110
    <212> TYPE: PRT
    <213> ORGANISM: Caenorhabditis elegans

<400> SEQUENCE: 200

Met Arg Ala Leu Val Ala Ile Leu Cys Leu Met Ala Leu Cys His Ala
    1               5                  10                  15

Ala Met Leu Asp Glu Leu Glu Met Gln Lys Glu Val Gln Glu Phe His
                    20                  25                  30

His Met Asn Gly Met Leu Gln Glu Phe Met Asn Lys Gly Leu Ile Gly
                35                  40                  45

Asn His His Gly Thr Lys Ala Gly Leu Thr Cys Gly Met Asn Ile
            50                  55                  60

Ile Glu Arg Val Asp Lys Leu Cys Asn Gly Gln Cys Thr Arg Asn Tyr
    65                  70                  75                  80

Asp Ala Leu Val Ile Lys Ser Cys His Arg Gly Val Ser Asp Met Glu
                    85                  90                  95

Phe Met Val Ala Cys Cys Pro Thr Met Lys Leu Phe Ile His
                100                 105                 110

<210> SEQ ID NO 201
    <211> LENGTH: 67
    <212> TYPE: PRT
    <213> ORGANISM: Caenorhabditis elegans

<400> SEQUENCE: 201

Met Met Arg Ser Phe Phe Val Leu Leu Ala Leu Leu Ala Ile Val Thr
    1               5                  10                  15

Ser Thr Ala Ser Pro Thr Cys Gly Arg Ala Leu Leu His Arg Ile Gln
                    20                  25                  30

Ser Val Cys Gly Leu Cys Thr Ile Asp Ala His His Glu Leu Ile Ala
                35                  40                  45

Ile Ala Cys Ser Arg Gly Leu Gly Asp Lys Glu Ile Glu Met Cys
            50                  55                  60

Cys Pro Ile
    65

<210> SEQ ID NO 202
    <211> LENGTH: 76
    <212> TYPE: PRT
    <213> ORGANISM: Caenorhabditis elegans

<400> SEQUENCE: 202

Met Phe Cys Lys Phe Val Phe Leu Ile Phe Leu Leu Ile Ser Leu Ser
    1               5                  10                  15

Val Ala Thr Ala Asp Phe Gly Ala Gln Arg Arg Cys Gly Arg His Leu
                    20                  25                  30
```

```
Val Asn Phe Leu Glu Gly Leu Cys Gly Pro Cys Ser Glu Ala Pro
        35                  40                  45

Thr Val Glu Leu Ala Ser Trp Ala Cys Ser Ser Ala Val Ser Ile Gln
 50                  55                  60

Asp Leu Glu Lys Leu Cys Cys Pro Ser Asn Leu Ala
65                  70                  75

<210> SEQ ID NO 203
<211> LENGTH: 120
<212> TYPE: PRT
<213> ORGANISM: Caenorhabditis elegans

<400> SEQUENCE: 203

Met Ser Ser His Ala Leu Val Leu Phe Leu Leu Phe Leu Leu Pro
 1               5                  10                  15

Val Ala Leu Gly His Phe Leu Ser Lys Pro Ala Pro Asp Pro Arg Ile
                20                  25                  30

Thr Phe Asn Arg Lys Leu Ala Glu Thr Leu Lys Glu Leu Gln Asp Met
            35                  40                  45

Gly Leu Ile Gln Ala Pro Arg Glu Pro Val Val Ala Ala Gln Gly Ala
 50                  55                  60

Lys Lys Thr Cys Gly Arg Ser Leu Leu Ile Lys Ile Gln Gln Leu Cys
65                  70                  75                  80

His Gly Ile Cys Thr Val His Ala Asp Asp Leu His Glu Thr Ala Cys
                85                  90                  95

Met Lys Gly Leu Thr Asp Ser Gln Leu Ile Asn Ser Cys Cys Pro Pro
                100                 105                 110

Ile Pro Gln Thr Pro Phe Val Phe
                115                 120

<210> SEQ ID NO 204
<211> LENGTH: 218
<212> TYPE: PRT
<213> ORGANISM: Caenorhabditis elegans

<400> SEQUENCE: 204

Met Lys Met Pro Leu Ile Leu Leu Leu Val Ala Ala Ala Ser Ala
 1               5                  10                  15

Phe Val His His Phe Asp His Ser Met Phe Ala Arg Pro Glu Lys Thr
                20                  25                  30

Cys Gly Gly Leu Leu Ile Arg Arg Val Asp Arg Ile Cys Pro Asn Leu
            35                  40                  45

Asn Tyr Thr Tyr Lys Ile Glu Trp Glu Leu Met Asp Asn Cys Cys Glu
 50                  55                  60

Val Val Cys Glu Asp Gln Trp Ile Lys Glu Thr Phe Cys Arg Ala Pro
65                  70                  75                  80

Arg Phe Asn Phe Phe Gly Pro Ser Phe Lys Ala Leu Glu Arg Ser Cys
                85                  90                  95

Gly Pro Lys Leu Phe Thr Arg Val Lys Thr Val Cys Gly Glu Asp Ile
                100                 105                 110

Asn Val Asp Asn Lys Val Lys Ile Ser Asp His Cys Cys Thr Pro Glu
                115                 120                 125

Gly Gly Cys Thr Asp Asp Trp Ile Lys Glu Asn Val Cys Lys Gln Thr
            130                 135                 140

Arg Phe Asn Phe Phe Arg Gln Phe Leu Asp Ser Pro Gln Arg Ser Cys
145                 150                 155                 160
```

Gly Pro Gln Leu Phe Lys Arg Val Asn Thr Leu Cys Asn Glu Asn Ile
            165                 170                 175

Asn Val Glu Asn Asn Val Ser Val Ser Lys Ser Cys Cys Glu Ser Ala
        180                 185                 190

Ala Gly Cys Thr Asp Asp Trp Ile Lys Lys Asn Val Cys Thr Gln His
        195                 200                 205

Lys Pro Phe Val Phe Arg Pro Gly Phe Tyr
    210                 215

<210> SEQ ID NO 205
<211> LENGTH: 107
<212> TYPE: PRT
<213> ORGANISM: Caenorhabditis elegans

<400> SEQUENCE: 205

Met Ile Phe Tyr Leu Thr Thr Tyr Leu Val Thr Met Ser Pro Leu Phe
1               5                   10                  15

Leu Ile Leu Leu Leu Val Ser Thr Thr Tyr Pro Tyr Ile Ile Asp
            20                  25                  30

Ser Ser Glu Ser Tyr Glu Val Leu Met Leu Phe Gly Tyr Lys Arg Thr
        35                  40                  45

Cys Gly Arg Arg Leu Met Asn Arg Ile Asn Arg Val Cys Val Lys Asp
    50                  55                  60

Ile Asp Pro Ala Asp Ile Asp Pro Lys Ile Lys Leu Ser Glu His Cys
65                  70                  75                  80

Cys Ile Lys Gly Cys Thr Asp Gly Trp Ile Lys Lys His Ile Cys Ser
                85                  90                  95

Glu Glu Val Leu Asn Phe Gly Phe Phe Glu Asn
            100                 105

<210> SEQ ID NO 206
<211> LENGTH: 77
<212> TYPE: PRT
<213> ORGANISM: Caenorhabditis elegans

<400> SEQUENCE: 206

Met Gln Ser Leu Pro Ile Leu Ala Cys Leu Leu Thr Leu Ser Val Phe
1               5                   10                  15

Ala Pro Glu Ile His Gly Arg Glu Leu Lys Arg Cys Ser Val Lys Leu
            20                  25                  30

Phe Asp Ile Leu Ser Val Ile Cys Gly Thr Glu Ser Asp Ala Glu Ile
        35                  40                  45

Leu Gln Lys Val Ala Val Lys Cys Cys Gln Glu Gln Cys Gly Phe Glu
    50                  55                  60

Glu Met Cys Gln His Ala Asn Leu Lys Ile Asp Lys Ile
65                  70                  75

<210> SEQ ID NO 207
<211> LENGTH: 312
<212> TYPE: DNA
<213> ORGANISM: Caenorhabditis elegans

<400> SEQUENCE: 207
atgagatctc ccaccttgtt tcttcttctg ctcctagtgc ccctggcact atgccatgtc      60
ttctcggagc ccgcggattt ggagctcaaa agctaccaag cgcttgaaaa aagcctcaag     120
gagatgggac tcattcgagc caaccaggga cctcaaaaag cgtgcggacg atcaatgatg     180

-continued

| | |
|---|---|
| atgaaggtgc agaagctttg cgcgggcgga tgcacaattc agaacgacga tcttaccatc | 240 |
| aaatcctgca gtactgggta caccgatgcc ggcttcatct cggcctgctg cccatctggc | 300 |
| ttcgttttct aa | 312 |

<210> SEQ ID NO 208
<211> LENGTH: 216
<212> TYPE: DNA
<213> ORGANISM: Caenorhabditis elegans

<400> SEQUENCE: 208

| | |
|---|---|
| atgttgttca aaatcatcat tttatttttc ctgctccagc tttctgaagc caaaccggaa | 60 |
| gcccagaggc gctgcggccg gtatttaatt cgttttttgg gggaactgtg taatggtccc | 120 |
| tgctcaggag tttcaagcgt tgacattgcc acaattgcct gtgcaaccgc cgtcccaatc | 180 |
| gaagatctga agaatatgtg ttgcccaaat ttgtga | 216 |

<210> SEQ ID NO 209
<211> LENGTH: 333
<212> TYPE: DNA
<213> ORGANISM: Caenorhabditis elegans

<400> SEQUENCE: 209

| | |
|---|---|
| atgagagctc tcgtcgctat tctctgcctt atggcactat gccatgcagc aatgctcgat | 60 |
| gagctggaga tgcagaagga ggttcaggag ttccatcaca tgaacggcat gctccaagag | 120 |
| ttcatgaata aggggctcat cgggaatcat caccatggta ccaaggccgg cctcacctgc | 180 |
| gggatgaaca tcatcgagag agtcgacaag ctgtgcaatg gcagtgcac tcggaactat | 240 |
| gatgcactcg tcatcaagtc ctgccaccgc ggagtctcgg acatggagtt catggtggca | 300 |
| tgctgcccaa ccatgaagct attcattcac taa | 333 |

<210> SEQ ID NO 210
<211> LENGTH: 204
<212> TYPE: DNA
<213> ORGANISM: Caenorhabditis elegans

<400> SEQUENCE: 210

| | |
|---|---|
| atgatgcgct cattctttgt gctcttggct ctgctcgcaa tagtcaccag caccgctagt | 60 |
| cccacttgtg gcagggctct tctacaccgg atccagtcgg tttgcggtct ctgtaccatc | 120 |
| gacgctcacc acgaactgat tgccattgcc tgctcaaggg gactgggcga taaggaaatc | 180 |
| attgaaatgt gctgtccaat ctaa | 204 |

<210> SEQ ID NO 211
<211> LENGTH: 231
<212> TYPE: DNA
<213> ORGANISM: Caenorhabditis elegans

<400> SEQUENCE: 211

| | |
|---|---|
| atgttctgta aatttgtatt cctgatcttt ctactcatct ctctgtcagt ggccaccgct | 60 |
| gactttggcg cccagcgccg ttgtgggcgc cacttggtga acttcctcga gggactctgc | 120 |
| ggtggcccgt gctctgaagc tccgactgtt gaactagctt cgtgggcatg ttcatcagca | 180 |
| gtctcaattc aggatctcga aaaattgtgc tgtccttcaa atcttgcttg a | 231 |

<210> SEQ ID NO 212
<211> LENGTH: 363
<212> TYPE: DNA
<213> ORGANISM: Caenorhabditis elegans

<400> SEQUENCE: 212

| | | | | |
|---|---|---|---|---|
| atgagttctc | acgccctggt | tcttttcctt | ctccttttcc | tcctaccagt ggcactgggc | 60 |
| cacttcctct | ccaagcctgc | accggatcca | aggatcacat | tcaaccgtaa gcttgcggag | 120 |
| acactcaagg | agcttcagga | catgggactc | atccaggccc | ccgtgagcc ggtagtggcg | 180 |
| gctcagggag | ccaagaagac | ttgcggaagg | agtttgttga | taaagatcca acaactctgc | 240 |
| catggaatct | gcacagttca | cgctgatgac | ctccacgaaa | cggcatgcat gaaaggtctc | 300 |
| accgactctc | agctgatcaa | ctcctgctgc | ccaccaatcc | cccagacacc attcgtcttc | 360 |
| tga | | | | | 363 |

<210> SEQ ID NO 213
<211> LENGTH: 657
<212> TYPE: DNA
<213> ORGANISM: Caenorhabditis elegans

<400> SEQUENCE: 213

| | | | | |
|---|---|---|---|---|
| atgaagatgc | ccttgatctt | gctgcttctc | gtcgccgccg | catcggcgtt cgtccaccac | 60 |
| tttgaccatt | caatgtttgc | cagaccggag | aaaacgtgtg | gaggactact cattcgtcgt | 120 |
| gtcgatagaa | tttgcccgaa | tctaaattat | acatataaaa | ttgactggga acttatggac | 180 |
| aactgttgcg | aagtggtttg | cgaggaccag | tggattaagg | aaacctttg cagagcgccc | 240 |
| aggttcaact | ttttcggacc | ttcattcaaa | gcccttgaaa | gatcgtgtgg accaaaactg | 300 |
| ttcacaaggg | ttaaaactgt | gtgcggtgaa | gacatcaatg | ttgataataa agtcaagatt | 360 |
| tcggatcact | gctgcacacc | agagggagga | tgcacagacg | actggatcaa ggagaacgtc | 420 |
| tgcaaacaga | ccagattcaa | cttttttccga | caatttctcg | attcccctca agatcatgt | 480 |
| ggacccccagt | tgttcaaaag | agtgaatact | ttgtgtaatg | aaaatatcaa tgttgaaaat | 540 |
| aatgtaagcg | tgtcgaaaag | ctgttgcgaa | tcagcggcag | gatgcacgga tgattggatt | 600 |
| aagaagaatg | tctgcacaca | gcataagcct | tttgttttcc | gtccagcctt ttactga | 657 |

<210> SEQ ID NO 214
<211> LENGTH: 324
<212> TYPE: DNA
<213> ORGANISM: Caenorhabditis elegans

<400> SEQUENCE: 214

| | | | | |
|---|---|---|---|---|
| atgattttct | atctgacaac | ctacctagta | actatgtcac | ctctcttcct gatcctgttg | 60 |
| cttctagtct | ctaccactta | cccttacatc | attgactctt | cggagagtta tgaagttcta | 120 |
| atgctattcg | ggtataagag | aacatgtgga | cgacgcttga | tgaacaggat taatagagta | 180 |
| tgcgtgaagg | atatagatcc | agcagatatc | gatccgaaga | tcaaattatc ggagcactgt | 240 |
| tgtatcaagg | gatgcacaga | tggatggatc | aagaagcata | tttgcagtga ggaagttctg | 300 |
| aattttggat | ttttgaaaa | ttga | | | 324 |

<210> SEQ ID NO 215
<211> LENGTH: 234
<212> TYPE: DNA
<213> ORGANISM: Caenorhabditis elegans

<400> SEQUENCE: 215

| | | | | |
|---|---|---|---|---|
| atgcaaagcc | taccaattct | tgcctgcctc | ctcacactgt | cagttttgc gccggaaatt | 60 |
| catggccggg | agctcaaacg | ttgttctgtg | aaacttttg | atattctaag cgtaatttgt | 120 |

```
ggaactgaaa gtgatgcaga aattctacaa aaagtcgcag tgaaatgctg ccaggagcag      180
tgtgggtttg aggaaatgtg ccagcatgcc aacttgaaaa tcgacaaaat ttaa            234
```

<210> SEQ ID NO 216
<211> LENGTH: 30
<212> TYPE: PRT
<213> ORGANISM: Homo sapiens

<400> SEQUENCE: 216

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 217
<211> LENGTH: 21
<212> TYPE: PRT
<213> ORGANISM: Homo sapiens

<400> SEQUENCE: 217

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 218
<211> LENGTH: 68
<212> TYPE: PRT
<213> ORGANISM: Homo sapiens
<220> FEATURE:
<221> NAME/KEY: misc_feature
<222> LOCATION: (30)..(37)
<223> OTHER INFORMATION: Xaa = Any amino Acid

<400> SEQUENCE: 218

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Xaa Xaa Xaa
            20                  25                  30

Xaa Xaa Xaa Xaa Xaa Gln Thr Gly Ile Val Asp Glu Cys Cys Phe Arg
        35                  40                  45

Ser Cys Asp Leu Arg Arg Leu Glu Met Tyr Cys Ala Pro Leu Lys Pro
    50                  55                  60

Ala Lys Ser Ala
65
```

<210> SEQ ID NO 219
<211> LENGTH: 28
<212> TYPE: PRT
<213> ORGANISM: Homo sapiens

<400> SEQUENCE: 219

```
Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25
```

<210> SEQ ID NO 220
<211> LENGTH: 23
<212> TYPE: PRT
<213> ORGANISM: Homo sapiens

```
<400> SEQUENCE: 220

Arg Pro Tyr Val Ala Leu Phe Glu Lys Cys Cys Leu Ile Gly Leu Thr
1               5                   10                  15

Lys Arg Ser Leu Lys Tyr Cys
            20

<210> SEQ ID NO 221
<211> LENGTH: 32
<212> TYPE: PRT
<213> ORGANISM: Homo sapiens

<400> SEQUENCE: 221

Pro Ala Gln Glu Ala Pro Glu Lys Leu Cys Gly His His Phe Val Arg
1               5                   10                  15

Ala Leu Val Arg Leu Cys Gly Gly Pro Arg Trp Ser Pro Glu Asp Gly
            20                  25                  30

<210> SEQ ID NO 222
<211> LENGTH: 26
<212> TYPE: PRT
<213> ORGANISM: Homo sapiens

<400> SEQUENCE: 222

Ala Ala Ala Thr Asn Pro Ala Arg His Cys Cys Leu Ser Gly Cys Thr
1               5                   10                  15

Arg Gln Asp Leu Leu Thr Leu Cys Pro His
            20                  25

<210> SEQ ID NO 223
<211> LENGTH: 41
<212> TYPE: PRT
<213> ORGANISM: Homo sapiens

<400> SEQUENCE: 223

Gln Leu Leu Arg Glu Ser Leu Ala Ala Glu Leu Arg Gly Cys Gly Pro
1               5                   10                  15

Arg Phe Gly Lys His Leu Leu Ser Tyr Cys Pro Met Pro Glu Lys Thr
            20                  25                  30

Phe Thr Thr Thr Pro Gly Gly Trp Leu
            35                  40

<210> SEQ ID NO 224
<211> LENGTH: 25
<212> TYPE: PRT
<213> ORGANISM: Homo sapiens

<400> SEQUENCE: 224

Ser Gly Arg His Arg Phe Asp Pro Phe Cys Cys Glu Val Ile Cys Asp
1               5                   10                  15

Asp Gly Thr Ser Val Lys Leu Cys Thr
            20                  25

<210> SEQ ID NO 225
<211> LENGTH: 28
<212> TYPE: PRT
<213> ORGANISM: Silkworm

<400> SEQUENCE: 225

Gln Gln Pro Gln Ala Val His Thr Tyr Cys Gly Arg His Leu Ala Arg
1               5                   10                  15

Thr Leu Ala Asp Leu Cys Trp Glu Ala Gly Val Asp
```

```
                        20                  25

<210> SEQ ID NO 226
<211> LENGTH: 20
<212> TYPE: PRT
<213> ORGANISM: Silkworm

<400> SEQUENCE: 226

Gly Ile Val Asp Glu Cys Cys Leu Arg Pro Cys Ser Val Asp Val Leu
1               5                  10                  15

Leu Ser Tyr Cys
            20

<210> SEQ ID NO 227
<211> LENGTH: 38
<212> TYPE: PRT
<213> ORGANISM: Freshwater Snail

<400> SEQUENCE: 227

Gln Phe Ser Ala Cys Asn Ile Asn Asp Arg Pro His Arg Arg Gly Val
1               5                  10                  15

Cys Gly Ser Ala Leu Ala Asp Leu Val Asp Phe Ala Cys Ser Ser Ser
                20                  25                  30

Asn Gln Pro Ala Met Val
            35

<210> SEQ ID NO 228
<211> LENGTH: 25
<212> TYPE: PRT
<213> ORGANISM: Freshwater Snail

<400> SEQUENCE: 228

Gln Gly Thr Thr Asn Ile Val Cys Glu Cys Cys Met Lys Pro Cys Thr
1               5                  10                  15

Leu Ser Glu Leu Arg Gln Tyr Cys Pro
            20                  25

<210> SEQ ID NO 229
<211> LENGTH: 31
<212> TYPE: PRT
<213> ORGANISM: Locust

<400> SEQUENCE: 229

Ser Gly Ala Pro Gln Pro Val Ala Arg Tyr Cys Gly Glu Lys Leu Ser
1               5                  10                  15

Asn Ala Leu Lys Leu Val Cys Arg Gly Asn Tyr Asn Thr Met Phe
            20                  25                  30

<210> SEQ ID NO 230
<211> LENGTH: 24
<212> TYPE: PRT
<213> ORGANISM: Locust

<400> SEQUENCE: 230

Thr Arg Gly Val Phe Asp Glu Cys Cys Cys Arg Lys Thr Cys Ser Ile
1               5                  10                  15

Ser Glu Leu Gln Thr Tyr Cys Gly
            20

<210> SEQ ID NO 231
<211> LENGTH: 29
<212> TYPE: PRT
```

```
<213> ORGANISM: Homo sapiens

<400> SEQUENCE: 231

Phe Val Gln His Ile Cys Gly Ser His Ile Val Glu Ala Leu Tyr Leu
1               5                   10                  15
Val Cys Gly Glu Arg Gly Phe Phe Tyr Thr Pro Lys Thr
            20                  25

<210> SEQ ID NO 232
<211> LENGTH: 21
<212> TYPE: PRT
<213> ORGANISM: Homo sapiens

<400> SEQUENCE: 232

Gly Ile Val Glu Gln Cys Cys Thr Ser Ile Cys Ser Leu Tyr Gln Leu
1               5                   10                  15
Glu Asn Tyr Cys Asn
            20

<210> SEQ ID NO 233
<211> LENGTH: 27
<212> TYPE: PRT
<213> ORGANISM: Caenorhabditis elegans

<400> SEQUENCE: 233

Ser Ile Arg Cys Gly Ser Arg Leu Thr Thr Thr Leu Leu Ala Val Cys
1               5                   10                  15
Arg Asn Gln Leu Cys Thr Gly Leu Thr Ala Phe
            20                  25

<210> SEQ ID NO 234
<211> LENGTH: 27
<212> TYPE: PRT
<213> ORGANISM: Caenorhabditis elegans

<400> SEQUENCE: 234

Gly Gly Ile Ala Thr Glu Cys Cys Glu Lys Arg Cys Ser Phe Ala Tyr
1               5                   10                  15
Leu Lys Thr Phe Cys Cys Asn Gln Asp Asp Asn
            20                  25

<210> SEQ ID NO 235
<211> LENGTH: 28
<212> TYPE: PRT
<213> ORGANISM: Caenorhabditis elegans

<400> SEQUENCE: 235

Val Pro Ala Gly Glu Val Arg Ala Cys Gly Arg Arg Leu Leu Leu Phe
1               5                   10                  15
Val Trp Ser Thr Cys Gly Glu Phe Cys Thr Pro Gln
            20                  25

<210> SEQ ID NO 236
<211> LENGTH: 27
<212> TYPE: PRT
<213> ORGANISM: Caenorhabditis elegans

<400> SEQUENCE: 236

Glu Asp Met Asp Ile Ala Thr Val Cys Cys Thr Thr Gln Cys Thr Pro
1               5                   10                  15
Ser Tyr Ile Lys Gln Ala Cys Cys Pro Glu Lys
            20                  25
```

<210> SEQ ID NO 237
<211> LENGTH: 24
<212> TYPE: PRT
<213> ORGANISM: Caenorhabditis elegans

<400> SEQUENCE: 237

Val Gln Lys Arg Ile Cys Gly Arg Arg Leu Ile Leu Phe Met Leu Ala
1               5                   10                  15

Ile Cys Gly Glu Cys Asp Thr Asp
            20

<210> SEQ ID NO 238
<211> LENGTH: 30
<212> TYPE: PRT
<213> ORGANISM: Caenorhabditis elegans

<400> SEQUENCE: 238

Ser Ser Glu Asp Leu Ser His Ile Cys Cys Ile Lys Gln Cys Asp Val
1               5                   10                  15

Gln Asp Ile Ile Arg Met Cys Cys Pro Asn Ser Phe Arg Lys
            20                  25                  30

<210> SEQ ID NO 239
<211> LENGTH: 26
<212> TYPE: PRT
<213> ORGANISM: Caenorhabditis elegans

<400> SEQUENCE: 239

Gly Asp Lys Val Lys Ile Cys Gly Thr Lys Leu Ile Ser Leu Val Met
1               5                   10                  15

Ala Val Cys Gly Asp Ile Cys Asn Pro Gln
            20                  25

<210> SEQ ID NO 240
<211> LENGTH: 27
<212> TYPE: PRT
<213> ORGANISM: Caenorhabditis elegans

<400> SEQUENCE: 240

Thr Asn Glu Asn Ile Ala Thr Glu Cys Cys Glu Lys Met Cys Thr Met
1               5                   10                  15

Glu Asp Ile Thr Thr Lys Cys Cys Pro Ser Arg
            20                  25

<210> SEQ ID NO 241
<211> LENGTH: 29
<212> TYPE: PRT
<213> ORGANISM: Caenorhabditis elegans

<400> SEQUENCE: 241

Val Pro Ala Pro Gly Glu Thr Arg Ala Cys Gly Arg Lys Leu Ile Ser
1               5                   10                  15

Leu Val Met Ala Ala Cys Gly Asp Leu Cys Asn Pro Gln
            20                  25

<210> SEQ ID NO 242
<211> LENGTH: 25
<212> TYPE: PRT
<213> ORGANISM: Caenorhabditis elegans

<400> SEQUENCE: 242

```
Glu Gly Lys Asp Ile Ala Thr Glu Cys Cys Gly Asn Gln Cys Ser Asp
1               5                   10                  15

Asp Tyr Ile Arg Ser Ala Cys Cys Pro
            20              25

<210> SEQ ID NO 243
<211> LENGTH: 26
<212> TYPE: PRT
<213> ORGANISM: Caenorhabditis elegans

<400> SEQUENCE: 243

Ala Asp Arg His Thr Asn Tyr Arg Glu Cys Ala Leu Arg Leu Ile Pro
1               5                   10                  15

His Val Cys Gly Asp Ala Cys Gln Pro Gln
            20              25

<210> SEQ ID NO 244
<211> LENGTH: 27
<212> TYPE: PRT
<213> ORGANISM: Caenorhabditis elegans

<400> SEQUENCE: 244

Asn Gly Ile Asp Val Ala Gln Lys Cys Cys Ser Thr Asp Cys Ser Ser
1               5                   10                  15

Asp Tyr Ile Lys Glu Ile Cys Cys Pro Phe Asp
            20              25

<210> SEQ ID NO 245
<211> LENGTH: 29
<212> TYPE: PRT
<213> ORGANISM: Caenorhabditis elegans

<400> SEQUENCE: 245

Val Pro Asp Glu Lys Lys Ile Tyr Phe Cys Gly Arg Arg Ile His Ser
1               5                   10                  15

Tyr Val Phe Ala Val Cys Gly Lys Ala Cys Glu Ser Asn
            20              25

<210> SEQ ID NO 246
<211> LENGTH: 25
<212> TYPE: PRT
<213> ORGANISM: Caenorhabditis elegans

<400> SEQUENCE: 246

Thr Glu Val Asn Ile Ala Ser Lys Cys Cys Arg Glu Glu Cys Thr Asp
1               5                   10                  15

Asp Phe Ile Arg Lys Gln Cys Cys Pro
            20              25

<210> SEQ ID NO 247
<211> LENGTH: 28
<212> TYPE: PRT
<213> ORGANISM: Caenorhabditis elegans

<400> SEQUENCE: 247

Val Pro Glu Gln Lys Asn Lys Leu Cys Gly Lys Gln Val Leu Ser Tyr
1               5                   10                  15

Val Met Ala Ile Cys Glu Lys Ala Cys Asp Ser Asn
            20              25

<210> SEQ ID NO 248
<211> LENGTH: 25
```

```
<212> TYPE: PRT
<213> ORGANISM: Caenorhabditis elegans

<400> SEQUENCE: 248

Thr Lys Val Asp Ile Ala Thr Lys Cys Cys Arg Asp Ala Cys Ser Asp
1               5                   10                  15

Glu Phe Ile Arg His Gln Cys Cys Pro
            20                  25

<210> SEQ ID NO 249
<211> LENGTH: 29
<212> TYPE: PRT
<213> ORGANISM: Caenorhabditis elegans

<400> SEQUENCE: 249

Thr Leu Glu Thr Glu Lys Ile Tyr Arg Cys Gly Arg Lys Leu Tyr Thr
1               5                   10                  15

Asp Val Leu Ser Ala Cys Asn Gly Pro Cys Glu Pro Gly
            20                  25

<210> SEQ ID NO 250
<211> LENGTH: 28
<212> TYPE: PRT
<213> ORGANISM: Caenorhabditis elegans

<400> SEQUENCE: 250

Thr Glu Gln Asp Ile Ser Lys Leu Cys Cys Gly Met Gln Cys Thr Phe
1               5                   10                  15

Val Glu Ile Arg Lys Ala Cys Cys Ala Asp Lys Leu
            20                  25

<210> SEQ ID NO 251
<211> LENGTH: 32
<212> TYPE: PRT
<213> ORGANISM: Caenorhabditis elegans

<400> SEQUENCE: 251

Ala Phe Pro Phe Gln Ile Cys Val Lys Lys Met Glu Lys Met Cys Arg
1               5                   10                  15

Ile Ile Asn Pro Glu Gln Cys Ala Gln Val Asn Lys Ile Thr Glu Ile
            20                  25                  30

<210> SEQ ID NO 252
<211> LENGTH: 24
<212> TYPE: PRT
<213> ORGANISM: Caenorhabditis elegans

<400> SEQUENCE: 252

Gly Ala Leu Thr Asp Cys Cys Thr Gly Leu Cys Ser Trp Glu Glu Ile
1               5                   10                  15

Arg Ile Ser Cys Cys Ser Val Leu
            20

<210> SEQ ID NO 253
<211> LENGTH: 30
<212> TYPE: PRT
<213> ORGANISM: Caenorhabditis elegans

<400> SEQUENCE: 253

Ala Pro His His Asp Lys Arg His Thr Ala Cys Val Leu Lys Ile Phe
1               5                   10                  15

Lys Ala Ile Asn Val Met Cys Asn His Glu Gly Asp Ala Asp
```

```
                        20                  25                  30

<210> SEQ ID NO 254
<211> LENGTH: 35
<212> TYPE: PRT
<213> ORGANISM: Caenorhabditis elegans

<400> SEQUENCE: 254

Val Leu Arg Arg Thr Ala Ser Asp Cys Cys Arg Glu Ser Cys Ser Leu
1               5                  10                  15

Thr Glu Met Leu Ala Ser Cys Thr Leu Thr Ser Ser Glu Glu Ser Thr
            20                  25                  30

Arg Asp Ile
        35

<210> SEQ ID NO 255
<211> LENGTH: 30
<212> TYPE: PRT
<213> ORGANISM: Caenorhabditis elegans

<400> SEQUENCE: 255

Ala Pro Ser His Glu Lys Thr His Lys Lys Cys Ser Asp Lys Leu Tyr
1               5                  10                  15

Leu Ala Met Lys Ser Leu Cys Ser Tyr Arg Gly Tyr Ser Glu
            20                  25                  30

<210> SEQ ID NO 256
<211> LENGTH: 35
<212> TYPE: PRT
<213> ORGANISM: Caenorhabditis elegans

<400> SEQUENCE: 256

Phe Leu Arg Asn Ser Ala Thr Lys Cys Cys Gln Asp Asn Cys Glu Ile
1               5                  10                  15

Ser Glu Met Met Ala Leu Cys Val Val Ala Pro His Phe Asp Asp Asp
            20                  25                  30

Leu Leu His
        35

<210> SEQ ID NO 257
<211> LENGTH: 33
<212> TYPE: PRT
<213> ORGANISM: Caenorhabditis elegans
<220> FEATURE:
<221> NAME/KEY: misc_feature
<222> LOCATION: (32)..(33)
<223> OTHER INFORMATION: Xaa = any amino acid

<400> SEQUENCE: 257

Asn Lys Cys Gln Tyr Ser Lys Lys Tyr Lys Ile Cys Gly Val Arg
1               5                  10                  15

Ala Leu Lys His Met Lys Val Cys Thr Arg Gly Met Thr Arg Asp Xaa
            20                  25                  30

Xaa

<210> SEQ ID NO 258
<211> LENGTH: 23
<212> TYPE: PRT
<213> ORGANISM: Caenorhabditis elegans
<220> FEATURE:
<221> NAME/KEY: misc_feature
<222> LOCATION: (1)..(2)
<223> OTHER INFORMATION: Xaa = any amino acid
```

```
<400> SEQUENCE: 258

Xaa Xaa Tyr Gly Lys Leu Leu Val Thr Cys Cys Ser Lys Gly Cys Asn
1               5                   10                  15

Ile Asp Gln Arg Thr Cys Leu
            20

<210> SEQ ID NO 259
<211> LENGTH: 25
<212> TYPE: PRT
<213> ORGANISM: Caenorhabditis elegans

<400> SEQUENCE: 259

Ser Glu Asp Ile Lys Cys Asp Ala Lys Phe Ile Ser Arg Ile Thr Lys
1               5                   10                  15

Leu Cys Ile His Gly Ile Thr Glu Asp
            20                  25

<210> SEQ ID NO 260
<211> LENGTH: 35
<212> TYPE: PRT
<213> ORGANISM: Caenorhabditis elegans

<400> SEQUENCE: 260

Lys Leu Val Arg Leu Thr Arg Cys Cys Thr Ser His Cys Ser Lys
1               5                   10                  15

Ala His Leu Lys Met Phe Cys Thr Leu Pro His Glu Glu Pro His
            20                  25                  30

His Glu Ile
        35

<210> SEQ ID NO 261
<211> LENGTH: 38
<212> TYPE: PRT
<213> ORGANISM: Caenorhabditis elegans
<220> FEATURE:
<221> NAME/KEY: misc_feature
<222> LOCATION: (37)..(38)
<223> OTHER INFORMATION: Xaa = any amino acid

<400> SEQUENCE: 261

Gly Asn Asp Phe Gln Pro Arg Asp Asn Lys His His Ser Tyr Arg Ser
1               5                   10                  15

Cys Gly Glu Ser Leu Ser Arg Arg Val Ala Phe Ile Cys Asn Gly Gly
            20                  25                  30

Ile Ala Gln Thr Xaa Xaa
        35

<210> SEQ ID NO 262
<211> LENGTH: 28
<212> TYPE: PRT
<213> ORGANISM: Caenorhabditis elegans
<220> FEATURE:
<221> NAME/KEY: misc_feature
<222> LOCATION: (1)..(2)
<223> OTHER INFORMATION: Xaa = any amino acid

<400> SEQUENCE: 262

Xaa Xaa Glu Ile Leu Arg Ala Leu Asp Cys Cys Ser Thr Gly Cys Thr
1               5                   10                  15

Asp Lys Gln Ile Phe Ser Trp Cys Asp Phe Gln Ile
            20                  25
```

```
<210> SEQ ID NO 263
<211> LENGTH: 25
<212> TYPE: PRT
<213> ORGANISM: Caenorhabditis elegans

<400> SEQUENCE: 263

Arg Glu Leu Lys Phe Cys Ser Val Lys Leu Phe Asp Ile Leu Ser Val
1               5                   10                  15

Ile Cys Gly Thr Glu Ser Asp Ala Glu
            20                  25

<210> SEQ ID NO 264
<211> LENGTH: 33
<212> TYPE: PRT
<213> ORGANISM: Caenorhabditis elegans
<220> FEATURE:
<221> NAME/KEY: misc_feature
<222> LOCATION: (16)..(18)
<223> OTHER INFORMATION: Xaa = any amino acid

<400> SEQUENCE: 264

Ile Leu Gln Lys Met Ala Val Lys Cys Cys Gln Glu Gln Cys Gly Xaa
1               5                   10                  15

Xaa Xaa Phe Glu Glu Met Cys Gln His Ala Asn Leu Lys Ile Asp Lys
            20                  25                  30

Ile

<210> SEQ ID NO 265
<211> LENGTH: 37
<212> TYPE: PRT
<213> ORGANISM: Caenorhabditis elegans
<220> FEATURE:
<221> NAME/KEY: misc_feature
<222> LOCATION: (36)..(37)
<223> OTHER INFORMATION: Xaa = any amino acid

<400> SEQUENCE: 265

Gly Ser Leu Lys Leu Cys Pro Pro Gly Gly Ala Ser Phe Leu Asp Ala
1               5                   10                  15

Phe Asn Leu Ile Cys Pro Met Arg Arg Arg Arg Ser Val Ser Glu
            20                  25                  30

Asn Tyr Asn Xaa Xaa
        35

<210> SEQ ID NO 266
<211> LENGTH: 33
<212> TYPE: PRT
<213> ORGANISM: Caenorhabditis elegans
<220> FEATURE:
<221> NAME/KEY: misc_feature
<222> LOCATION: (1)..(2)
<223> OTHER INFORMATION: Xaa = any amino acid

<400> SEQUENCE: 266

Xaa Xaa Asp Gly Gly Ser Leu Leu Gly Arg Ile Met Asn Met Cys
1               5                   10                  15

Cys Glu Thr Gly Cys Glu Phe Thr Asp Ile Phe Ala Cys Asn Pro Phe
            20                  25                  30

Gly

<210> SEQ ID NO 267
<211> LENGTH: 42
<212> TYPE: PRT
```

<213> ORGANISM: Caenorhabditis elegans

<400> SEQUENCE: 267

Ile Ser Leu Gln Gln Ala Asp Gly Arg Met Lys Met Cys Pro Pro Gly
1               5                   10                  15

Gly Ser Thr Phe Thr Met Ala Trp Ser Met Ser Cys Ser Met Arg Arg
            20                  25                  30

Arg Lys Arg Asp Val Gly Arg Tyr Phe Glu
        35                  40

<210> SEQ ID NO 268
<211> LENGTH: 34
<212> TYPE: PRT
<213> ORGANISM: Caenorhabditis elegans

<400> SEQUENCE: 268

Lys Arg Ala Leu Ile Ala Pro Ser Ile Arg Gln Leu Gln Thr Ile Cys
1               5                   10                  15

Cys Gln Val Gly Cys Asn Val Glu Asp Asp Leu Leu Ala Tyr Cys Ala
            20                  25                  30

Pro Ile

<210> SEQ ID NO 269
<211> LENGTH: 36
<212> TYPE: PRT
<213> ORGANISM: Caenorhabditis elegans
<220> FEATURE:
<221> NAME/KEY: misc_feature
<222> LOCATION: (35)..(36)
<223> OTHER INFORMATION: Xaa = any amino acid

<400> SEQUENCE: 269

Phe Val His His Phe Asp His Ser Met Phe Ala Arg Pro Glu Lys Ile
1               5                   10                  15

Cys Gly Gly Leu Leu Ile Arg Arg Val Asp Arg Ile Cys Pro Asn Leu
            20                  25                  30

Asn Tyr Xaa Xaa
        35

<210> SEQ ID NO 270
<211> LENGTH: 41
<212> TYPE: PRT
<213> ORGANISM: Caenorhabditis elegans
<220> FEATURE:
<221> NAME/KEY: misc_feature
<222> LOCATION: (1)..(2)
<223> OTHER INFORMATION: Xaa = any amino acid
<220> FEATURE:
<221> NAME/KEY: misc_feature
<222> LOCATION: (41)..(41)
<223> OTHER INFORMATION: Xaa = any amino acid

<400> SEQUENCE: 270

Xaa Xaa Thr Tyr Lys Ile Glu Trp Glu Leu Met Asp Asn Cys Cys Glu
1               5                   10                  15

Val Val Cys Glu Asp Gln Trp Ile Lys Glu Thr Phe Cys Arg Pro Arg
            20                  25                  30

Phe Asn Phe Phe Gly Pro Ser Phe Xaa
        35                  40

<210> SEQ ID NO 271
<211> LENGTH: 21
<212> TYPE: PRT

<213> ORGANISM: Caenorhabditis elegans

<400> SEQUENCE: 271

Lys Ala Leu Glu Arg Ser Cys Gly Pro Lys Leu Phe Thr Arg Val Lys
1               5                   10                  15

Thr Val Cys Gly Glu
            20

<210> SEQ ID NO 272
<211> LENGTH: 44
<212> TYPE: PRT
<213> ORGANISM: Caenorhabditis elegans
<220> FEATURE:
<221> NAME/KEY: misc_feature
<222> LOCATION: (44)..(44)
<223> OTHER INFORMATION: Xaa = any amino acid

<400> SEQUENCE: 272

Asp Ile Asn Val Asp Asn Lys Val Lys Ile Ser Asp His Cys Cys Thr
1               5                   10                  15

Pro Glu Gly Gly Cys Thr Asp Asp Trp Ile Lys Glu Asn Val Cys Lys
            20                  25                  30

Gln Thr Arg Phe Asn Phe Phe Arg Gln Phe Leu Xaa
        35                  40

<210> SEQ ID NO 273
<211> LENGTH: 21
<212> TYPE: PRT
<213> ORGANISM: Caenorhabditis elegans

<400> SEQUENCE: 273

Asp Ser Pro Gln Arg Ser Cys Gly Pro Gln Leu Phe Lys Arg Val Asn
1               5                   10                  15

Thr Leu Cys Asn Glu
            20

<210> SEQ ID NO 274
<211> LENGTH: 44
<212> TYPE: PRT
<213> ORGANISM: Caenorhabditis elegans

<400> SEQUENCE: 274

Asn Ile Asn Val Glu Asn Asn Val Ser Val Ser Lys Ser Cys Cys Glu
1               5                   10                  15

Ser Ala Ala Gly Cys Thr Asp Asp Trp Ile Lys Lys Asn Val Cys Thr
            20                  25                  30

Gln His Lys Pro Phe Val Phe Arg Pro Gly Phe Tyr
        35                  40

<210> SEQ ID NO 275
<211> LENGTH: 38
<212> TYPE: PRT
<213> ORGANISM: Caenorhabditis elegans
<220> FEATURE:
<221> NAME/KEY: misc_feature
<222> LOCATION: (1)..(7)
<223> OTHER INFORMATION: Xaa = any amino acid

<400> SEQUENCE: 275

Xaa Xaa Xaa Xaa Xaa Xaa Xaa Ser Tyr Glu Val Leu Met Leu Phe Gly
1               5                   10                  15

Tyr Lys Arg Thr Cys Gly Arg Arg Leu Met Asn Arg Ile Asn Arg Val
            20                  25                  30

Cys Val Lys Asp Ile Asp
          35

<210> SEQ ID NO 276
<211> LENGTH: 41
<212> TYPE: PRT
<213> ORGANISM: Caenorhabditis elegans

<400> SEQUENCE: 276

Pro Ala Asp Ile Asp Pro Lys Ile Lys Leu Ser Glu His Cys Cys Ile
1               5                   10                  15

Lys Gly Cys Thr Asp Gly Trp Ile Lys His Ile Cys Ser Glu Glu
            20                  25                  30

Val Leu Asn Phe Gly Phe Phe Glu Asn
            35                  40

<210> SEQ ID NO 277
<211> LENGTH: 33
<212> TYPE: PRT
<213> ORGANISM: Caenorhabditis elegans

<400> SEQUENCE: 277

Ser Lys Ser His Ser Lys Lys His Val Arg Phe Ile Cys Ala Thr Lys
1               5                   10                  15

Ala Val Lys His Ile Arg Lys Val Cys Pro Asp Met Cys Leu Thr Gly
            20                  25                  30

Glu

<210> SEQ ID NO 278
<211> LENGTH: 25
<212> TYPE: PRT
<213> ORGANISM: Caenorhabditis elegans

<400> SEQUENCE: 278

Glu Val Glu Val Asn Glu Phe Cys Lys Met Cys Gly Tyr Ser Asp Ser
1               5                   10                  15

Gln Ile Lys Tyr Ile Cys Cys Pro Glu
            20                  25

<210> SEQ ID NO 279
<211> LENGTH: 39
<212> TYPE: PRT
<213> ORGANISM: Caenorhabditis elegans

<400> SEQUENCE: 279

Met Asp Ala His Thr Asp Lys Tyr Val Arg Thr Leu Cys Gly Lys Thr
1               5                   10                  15

Ala Ile Arg Asn Ile Ala Asn Leu Cys Pro Pro Lys Pro Glu Met Lys
            20                  25                  30

Gly Ile Cys Ser Thr Gly Glu
            35

<210> SEQ ID NO 280
<211> LENGTH: 25
<212> TYPE: PRT
<213> ORGANISM: Caenorhabditis elegans

<400> SEQUENCE: 280

Tyr Pro Ser Ile Thr Glu Tyr Cys Ser Met Gly Phe Ser Asp Ser Gln
1               5                   10                  15

```
Ile Lys Phe Met Cys Cys Asp Asn Gln
        20              25
```

<210> SEQ ID NO 281
<211> LENGTH: 37
<212> TYPE: PRT
<213> ORGANISM: Caenorhabditis elegans

<400> SEQUENCE: 281

```
Gln Val Thr Asp Ala His Ser Glu Leu His Val Arg Arg Val Cys Gly
1               5                   10                  15

Thr Ala Ile Ile Lys Asn Ile Met Arg Ile Cys Pro Gly Val Pro Ala
            20                  25                  30

Cys Glu Asn Gly Glu
        35
```

<210> SEQ ID NO 282
<211> LENGTH: 25
<212> TYPE: PRT
<213> ORGANISM: Caenorhabditis elegans

<400> SEQUENCE: 282

```
Val Ser Pro Thr Glu Tyr Cys Ser Met Gly Tyr Ser Asp Ser Gln Val
1               5                   10                  15

Lys Tyr Leu Cys Cys Pro Thr Ser Gln
            20                  25
```

<210> SEQ ID NO 283
<211> LENGTH: 37
<212> TYPE: PRT
<213> ORGANISM: Caenorhabditis elegans

<400> SEQUENCE: 283

```
Lys Glu Pro Lys His His His His His Arg His Lys Gly Tyr Cys
1               5                   10                  15

Gly Val Lys Ala Val Lys Lys Leu Lys Gln Ile Cys Pro Asp Leu Cys
            20                  25                  30

Ser Asn Val Asp Asp
        35
```

<210> SEQ ID NO 284
<211> LENGTH: 23
<212> TYPE: PRT
<213> ORGANISM: Caenorhabditis elegans

<400> SEQUENCE: 284

```
Asn Leu Leu Met Glu Met Cys Ser Lys Asn Leu Thr Asp Asp Ile
1               5                   10                  15

Leu Gln Arg Cys Cys Pro Glu
            20
```

<210> SEQ ID NO 285
<211> LENGTH: 32
<212> TYPE: PRT
<213> ORGANISM: Caenorhabditis elegans

<400> SEQUENCE: 285

```
Phe Leu Glu Pro Ser Thr Ala Ala Lys Arg Phe Cys Gly Arg Arg Leu
1               5                   10                  15

Ile Pro Tyr Val Tyr Ser Ile Cys Gly Gly Pro Cys Glu Asn Gly Asp
            20                  25                  30
```

```
<210> SEQ ID NO 286
<211> LENGTH: 33
<212> TYPE: PRT
<213> ORGANISM: Caenorhabditis elegans

<400> SEQUENCE: 286

Ile Ile Ile Glu His Cys Phe Ser Gly Thr Thr Pro Thr Ile Ala Glu
1               5                   10                  15

Val Gln Lys Ala Cys Cys Pro Glu Leu Ser Glu Asp Pro Thr Phe Ser
            20                  25                  30

Ser

<210> SEQ ID NO 287
<211> LENGTH: 59
<212> TYPE: PRT
<213> ORGANISM: Caenorhabditis elegans
<220> FEATURE:
<221> NAME/KEY: misc_feature
<222> LOCATION: (1)..(24)
<223> OTHER INFORMATION: Xaa = any amino acid

<400> SEQUENCE: 287

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Met Gly Leu Ile Arg Ala Asn Gln Gly
            20                  25                  30

Pro Gln Lys Ala Cys Gly Arg Ser Met Met Met Lys Val Gln Lys Leu
        35                  40                  45

Cys Ala Gly Gly Cys Thr Ile Gln Asn Asp Asp
    50                  55

<210> SEQ ID NO 288
<211> LENGTH: 26
<212> TYPE: PRT
<213> ORGANISM: Caenorhabditis elegans

<400> SEQUENCE: 288

Leu Thr Ile Lys Ser Cys Ser Thr Gly Tyr Thr Asp Ala Gly Phe Ile
1               5                   10                  15

Ser Ala Cys Cys Pro Ser Gly Phe Val Phe
            20                  25

<210> SEQ ID NO 289
<211> LENGTH: 31
<212> TYPE: PRT
<213> ORGANISM: Caenorhabditis elegans

<400> SEQUENCE: 289

Lys Pro Glu Ala Gln Arg Phe Cys Gly Arg Tyr Leu Ile Arg Phe Leu
1               5                   10                  15

Gly Glu Leu Cys Asn Gly Pro Cys Ser Gly Val Ser Ser Val Asp
            20                  25                  30

<210> SEQ ID NO 290
<211> LENGTH: 23
<212> TYPE: PRT
<213> ORGANISM: Caenorhabditis elegans

<400> SEQUENCE: 290

Ile Ala Thr Ile Ala Cys Ala Thr Ala Val Pro Ile Glu Asp Leu Lys
1               5                   10                  15
```

Asn Met Cys Cys Pro Asn Leu
            20

<210> SEQ ID NO 291
<211> LENGTH: 66
<212> TYPE: PRT
<213> ORGANISM: Caenorhabditis elegans
<220> FEATURE:
<221> NAME/KEY: misc_feature
<222> LOCATION: (1)..(30)
<223> OTHER INFORMATION: Xaa = any amino acid

<400> SEQUENCE: 291

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Ile Gly
                20                  25                  30

Asn His His His Gly Thr Lys Ala Gly Leu Thr Cys Gly Met Asn Ile
            35                  40                  45

Ile Glu Arg Val Asp Lys Leu Cys Asn Gly Gln Cys Thr Arg Asn Tyr
        50                  55                  60

Asp Ala
65

<210> SEQ ID NO 292
<211> LENGTH: 28
<212> TYPE: PRT
<213> ORGANISM: Caenorhabditis elegans

<400> SEQUENCE: 292

Leu Val Ile Lys Ser Cys His Arg Gly Val Ser Asp Met Glu Phe Met
1               5                   10                  15

Val Ala Cys Cys Pro Thr Met Lys Leu Phe Ile His
            20                  25

<210> SEQ ID NO 293
<211> LENGTH: 27
<212> TYPE: PRT
<213> ORGANISM: Caenorhabditis elegans

<400> SEQUENCE: 293

Ala Ser Pro Thr Cys Gly Arg Ala Leu Leu His Arg Ile Gln Ser Val
1               5                   10                  15

Cys Gly Leu Cys Thr Ile Asp Ala His His Glu
            20                  25

<210> SEQ ID NO 294
<211> LENGTH: 22
<212> TYPE: PRT
<213> ORGANISM: Caenorhabditis elegans

<400> SEQUENCE: 294

Leu Ile Ala Ile Ala Cys Ser Arg Gly Leu Gly Asp Lys Glu Ile Ile
1               5                   10                  15

Glu Met Cys Cys Pro Ile
            20

<210> SEQ ID NO 295
<211> LENGTH: 31
<212> TYPE: PRT
<213> ORGANISM: Caenorhabditis elegans

<400> SEQUENCE: 295

```
Asp Phe Gly Ala Gln Arg Phe Cys Gly Arg His Leu Val Asn Phe Leu
1               5                   10                  15

Glu Gly Leu Cys Gly Gly Pro Cys Ser Glu Ala Pro Thr Val Glu
            20                  25                  30

<210> SEQ ID NO 296
<211> LENGTH: 25
<212> TYPE: PRT
<213> ORGANISM: Caenorhabditis elegans

<400> SEQUENCE: 296

Leu Ala Ser Trp Ala Cys Ser Ser Ala Val Ser Ile Gln Asp Leu Glu
1               5                   10                  15

Lys Leu Cys Cys Pro Ser Asn Leu Ala
            20                  25

<210> SEQ ID NO 297
<211> LENGTH: 70
<212> TYPE: PRT
<213> ORGANISM: Caenorhabditis elegans
<220> FEATURE:
<221> NAME/KEY: misc_feature
<222> LOCATION: (1)..(34)
<223> OTHER INFORMATION: Xaa = any amino acid

<400> SEQUENCE: 297

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Arg Glu Pro Val Val Ala Ala Gln Gly Ala Lys Lys Ile Cys
        35                  40                  45

Gly Arg Ser Leu Leu Ile Lys Ile Gln Gln Ile Cys His Gly Ile Cys
        50                  55                  60

Thr Val His Ala Asp Asp
65                  70

<210> SEQ ID NO 298
<211> LENGTH: 29
<212> TYPE: PRT
<213> ORGANISM: Caenorhabditis elegans

<400> SEQUENCE: 298

Asp His Glu Thr Cys Met Lys Gly Leu Thr Asp Ser Gln Leu Ile Asn
1               5                   10                  15

Ser Cys Cys Pro Pro Ile Pro Gln Thr Pro Phe Val Phe
            20                  25
```

What is claimed is:

1. An isolated nucleic acid comprising a nucleotide sequence encoding an insulin-like protein comprising SEQ ID NO:1.

2. The isolated nucleic acid of claim 1 comprising the nucleotide sequence of SEQ ID NO:19.

* * * * *

UNITED STATES PATENT AND TRADEMARK OFFICE
CERTIFICATE OF CORRECTION

PATENT NO.    : 6,627,746 B1  
DATED         : September 30, 2003  
INVENTOR(S)   : Doberstein et al.

Page 1 of 1

It is certified that error appears in the above-identified patent and that said Letters Patent is hereby corrected as shown below:

<u>Columns 117-119,</u>
SEQ ID NO:19, should read:

```
-- <210>  SEQ ID NO 19
   <211>  LENGTH:  330
   <212>  TYPE:  DNA
   <213>  ORGANISM:  Caenorhabditis elegans

<400>  SEQUENCE:  19 atgtactggt ttcgtcaagt ttacagaccc tcgttcttct ttggctttct cgcgatcctt   60
ctcctctcgt cgccgacgcc ttcagacgca tcgattcgac tatgtggatc acgtctcaca  120
acaacccttt tagcagtatg ccggaatcag ctgtgcactg gattaaccgc tttcaaacgt  180
tccgccgacc aatcctatgc accaacaact cgcgatcttt ttcacattca ccaccaacaa  240
aagcgaggcg gaattgcgac agaatgttgt gagaagcgat cttcatttgc atatctcaaa  300
acattctgct gcaatcagga cgataattga                                   330 --
```

<u>Column 222,</u>
After line 56, please add the following:

3. The isolated nucleic acid of claim 1, consisting of a nucleotide sequence encoding an insulin-like protein comprising SEQ ID NO:1.

4. The isolated nucleic acid of claim 2, consisting of the nucleotide sequence of SEQ ID NO:19

Signed and Sealed this

First Day of June, 2004

JON W. DUDAS  
*Acting Director of the United States Patent and Trademark Office*